(12) United States Patent
Garst et al.

(10) Patent No.: US 11,268,061 B2
(45) Date of Patent: *Mar. 8, 2022

(54) DETECTION OF NUCLEASE EDITED SEQUENCES IN AUTOMATED MODULES AND INSTRUMENTS

(71) Applicant: Inscripta, Inc., Boulder, CO (US)

(72) Inventors: Andrew Garst, Boulder, CO (US); Michael Graige, Boulder, CO (US); Richard Fox, Boulder, CO (US); Eileen Spindler, Boulder, CO (US); Amy Hiddessen, Boulder, CO (US); Phillip Belgrader, Pleasanton, CA (US); Don Masquelier, Boulder, CO (US); Bruce Chabansky, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/401,362

(22) Filed: Aug. 13, 2021

(65) Prior Publication Data
US 2021/0371799 A1    Dec. 2, 2021

Related U.S. Application Data

(63) Continuation of application No. 16/536,049, filed on Aug. 8, 2019, now Pat. No. 11,142,740.
(Continued)

(51) Int. Cl.
*C12M 3/00* (2006.01)
*C12M 1/00* (2006.01)
(Continued)

(52) U.S. Cl.
CPC ............ *C12M 35/08* (2013.01); *C12M 23/44* (2013.01); *C12M 33/14* (2013.01); *C12N 15/11* (2013.01);
(Continued)

(58) Field of Classification Search
CPC ...... C12M 35/00; C12M 35/04; C12M 35/02; B01L 2200/04; B01L 2200/06; B01L 2200/18
See application file for complete search history.

(56) References Cited

U.S. PATENT DOCUMENTS

| 4,833,080 A | 5/1989 | Brent et al. |
| 4,959,317 A | 9/1990 | Sauer et al. |

(Continued)

FOREIGN PATENT DOCUMENTS

| CN | 2397122 Y | 9/2000 |
| EP | 2135626 A1 | 12/2009 |

(Continued)

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).
(Continued)

*Primary Examiner* — Nathan A Bowers
(74) *Attorney, Agent, or Firm* — Sarah Brashears

(57) ABSTRACT

The present disclosure provides automated modules and instruments for improved detection of nuclease genome editing of live cells. The disclosure provides improved modules—including high throughput modules—for screening cells that have been subjected to editing and identifying and selecting cells that have been properly edited.

20 Claims, 52 Drawing Sheets

Related U.S. Application Data

(60) Provisional application No. 62/841,213, filed on Apr. 30, 2019, provisional application No. 62/781,112, filed on Dec. 18, 2018, provisional application No. 62/779,119, filed on Dec. 13, 2018, provisional application No. 62/769,805, filed on Nov. 20, 2018, provisional application No. 62/735,365, filed on Sep. 24, 2018, provisional application No. 62/718,449, filed on Aug. 14, 2018.

(51) Int. Cl.
  *B01L 3/00* (2006.01)
  *C12M 1/42* (2006.01)
  *C12N 15/11* (2006.01)
  *C12N 15/90* (2006.01)
  *C12M 1/26* (2006.01)

(52) U.S. Cl.
  CPC ........ *C12N 15/902* (2013.01); *C12N 2310/20* (2017.05)

(56) References Cited

U.S. PATENT DOCUMENTS

| | | |
|---|---|---|
| 5,464,764 A | 11/1995 | Capecchi et al. |
| 5,487,992 A | 1/1996 | Capecchi et al. |
| 5,627,059 A | 5/1997 | Capecchi et al. |
| 5,631,153 A | 5/1997 | Capecchi et al. |
| 5,654,182 A | 8/1997 | Wahl et al. |
| 5,677,177 A | 10/1997 | Wahl et al. |
| 5,710,381 A | 1/1998 | Atwood et al. |
| 5,792,943 A | 8/1998 | Craig |
| 5,885,836 A | 3/1999 | Wahl et al. |
| 5,888,732 A | 3/1999 | Hartley et al. |
| 6,074,605 A | 6/2000 | Meserol et al. |
| 6,127,141 A | 10/2000 | Kopf |
| 6,143,527 A | 11/2000 | Pachuk et al. |
| 6,150,148 A | 11/2000 | Nanda et al. |
| 6,204,061 B1 | 3/2001 | Capecchi et al. |
| 6,277,608 B1 | 8/2001 | Hartley et al. |
| 6,391,582 B2 | 5/2002 | Ying et al. |
| 6,482,619 B1 | 11/2002 | Rubinsky et al. |
| 6,509,156 B1 | 1/2003 | Stewart et al. |
| 6,654,636 B1 | 11/2003 | Dev et al. |
| 6,689,610 B1 | 2/2004 | Capecchi et al. |
| 6,746,441 B1 | 6/2004 | Hofmann et al. |
| 6,774,279 B2 | 8/2004 | Dymecki |
| 6,837,995 B1 | 1/2005 | Vassarotti et al. |
| 6,916,632 B2 | 7/2005 | Chesnut et al. |
| 6,956,146 B2 | 10/2005 | Wahl et al. |
| 7,029,916 B2 | 4/2006 | Dzekunov et al. |
| 7,112,715 B2 | 9/2006 | Chambon et al. |
| 7,141,425 B2 | 11/2006 | Dzekunov et al. |
| 7,166,443 B2 | 1/2007 | Walker et al. |
| 7,422,889 B2 | 9/2008 | Sauer et al. |
| 8,110,122 B2 | 2/2012 | Alburty et al. |
| 8,110,360 B2 | 2/2012 | Serber et al. |
| 8,153,432 B2 | 4/2012 | Church et al. |
| 8,332,160 B1 | 12/2012 | Platt et al. |
| 8,569,041 B2 | 10/2013 | Church et al. |
| 8,584,535 B2 | 11/2013 | Page et al. |
| 8,584,536 B2 | 11/2013 | Page et al. |
| 8,667,839 B2 | 3/2014 | Kimura |
| 8,667,840 B2 | 3/2014 | Lee et al. |
| 8,677,839 B2 | 3/2014 | Page et al. |
| 8,677,840 B2 | 3/2014 | Page et al. |
| 8,697,359 B1 | 4/2014 | Zhang et al. |
| 8,726,744 B2 | 5/2014 | Alburty et al. |
| 8,758,623 B1 | 6/2014 | Alburty et al. |
| 8,921,332 B2 | 12/2014 | Choulika et al. |
| 8,926,977 B2 | 1/2015 | Miller et al. |
| 8,932,850 B2 | 1/2015 | Chang et al. |
| 9,029,109 B2 | 5/2015 | Hur et al. |
| D731,634 S | 6/2015 | Page et al. |
| 9,063,136 B2 | 6/2015 | Talebpour et al. |
| 9,175,259 B2 | 11/2015 | Nankervis |
| 9,260,505 B2 | 2/2016 | Weir et al. |
| 9,361,427 B2 | 6/2016 | Hillson |
| 9,499,855 B2 | 11/2016 | Hyde et al. |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,179,898 B2 | 1/2019 | Khan |
| 10,227,576 B1 | 3/2019 | Cameron et al. |
| 10,240,117 B2 | 3/2019 | Dahlberg et al. |
| 10,266,851 B2 | 4/2019 | Chen |
| 10,294,447 B2 | 5/2019 | Reif et al. |
| 10,370,629 B2 | 8/2019 | Mietzner et al. |
| 10,577,576 B2 | 3/2020 | Nankervis et al. |
| 10,633,625 B2 | 4/2020 | Nankervis et al. |
| 10,669,519 B2 | 6/2020 | Stanton, IV et al. |
| 10,704,033 B1 | 7/2020 | Kim et al. |
| 10,724,021 B1 | 7/2020 | Kim et al. |
| 10,745,678 B1 | 8/2020 | Kim et al. |
| 10,767,169 B1 | 9/2020 | Kim et al. |
| 10,837,021 B1 | 11/2020 | Tian et al. |
| 10,927,385 B2 | 2/2021 | Kannan et al. |
| 2002/0139741 A1 | 10/2002 | Kopf |
| 2003/0059945 A1 | 3/2003 | Dzekunov et al. |
| 2003/0073238 A1 | 4/2003 | Dzekunov et al. |
| 2003/0104588 A1 | 6/2003 | Orwar et al. |
| 2004/0110253 A1 | 6/2004 | Kappler et al. |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2005/0118705 A1 | 6/2005 | Rabbitt et al. |
| 2006/0001865 A1 | 1/2006 | Bellalou et al. |
| 2006/0014137 A1 | 1/2006 | Ghosh et al. |
| 2006/0224192 A1 | 10/2006 | Dimmer et al. |
| 2007/0020761 A1 | 1/2007 | Yu et al. |
| 2007/0042427 A1 | 2/2007 | Gerdes et al. |
| 2007/0105206 A1 | 5/2007 | Lu et al. |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2010/0055790 A1 | 3/2010 | Simon |
| 2010/0076057 A1 | 3/2010 | Sontheimer et al. |
| 2011/0002812 A1 | 1/2011 | Asogawa et al. |
| 2011/0003303 A1 | 1/2011 | Pagano et al. |
| 2011/0009807 A1 | 1/2011 | Kjeken et al. |
| 2011/0065171 A1 | 3/2011 | Dzekunov et al. |
| 2011/0213288 A1 | 9/2011 | Choi et al. |
| 2011/0236962 A1 | 9/2011 | Loebbert et al. |
| 2011/0294217 A1 | 12/2011 | McConnell-Smith et al. |
| 2012/0156786 A1 | 6/2012 | Bebee |
| 2013/0005025 A1 | 1/2013 | Church et al. |
| 2013/0196441 A1 | 8/2013 | Rubinsky et al. |
| 2013/0236970 A1 | 9/2013 | Anneren et al. |
| 2014/0068797 A1 | 3/2014 | Doudna et al. |
| 2014/0121728 A1 | 5/2014 | Dhillon et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2014/0350456 A1 | 11/2014 | Caccia |
| 2015/0024464 A1 | 1/2015 | Lippow et al. |
| 2015/0071898 A1 | 3/2015 | Liu et al. |
| 2015/0072413 A1 | 3/2015 | Zenhausern et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0297887 A1 | 10/2015 | Dhillon et al. |
| 2015/0344549 A1 | 12/2015 | Muir et al. |
| 2016/0024529 A1 | 1/2016 | Carstens et al. |

(56) References Cited

U.S. PATENT DOCUMENTS

| | | |
|---|---|---|
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0130608 A1 | 5/2016 | Doudna et al. |
| 2016/0168592 A1 | 6/2016 | Church et al. |
| 2016/0264981 A1 | 9/2016 | Yang et al. |
| 2016/0272961 A1 | 9/2016 | Lee |
| 2016/0281047 A1 | 9/2016 | Chen et al. |
| 2016/0281053 A1 | 9/2016 | Sorek et al. |
| 2016/0289673 A1 | 10/2016 | Huang et al. |
| 2016/0298074 A1 | 10/2016 | Dai |
| 2016/0298134 A1 | 10/2016 | Chen et al. |
| 2016/0310943 A1 | 10/2016 | Woizenko et al. |
| 2016/0313306 A1 | 10/2016 | Ingber et al. |
| 2016/0354487 A1 | 12/2016 | Zhang et al. |
| 2016/0367991 A1 | 12/2016 | Cepheid |
| 2017/0002339 A1 | 1/2017 | Barrangou et al. |
| 2017/0022499 A1 | 1/2017 | Lu et al. |
| 2017/0029805 A1 | 2/2017 | Li et al. |
| 2017/0051310 A1 | 2/2017 | Doudna et al. |
| 2017/0073705 A1 | 3/2017 | Chen et al. |
| 2017/0218355 A1 | 3/2017 | Buie et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0283761 A1 | 10/2017 | Corso |
| 2017/0307606 A1 | 10/2017 | Hallock |
| 2017/0349874 A1 | 12/2017 | Jaques et al. |
| 2017/0369870 A1 | 12/2017 | Gill et al. |
| 2018/0023045 A1 | 1/2018 | Hallock et al. |
| 2018/0028567 A1 | 2/2018 | Li et al. |
| 2018/0051327 A1 | 2/2018 | Blainey et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0142196 A1 | 5/2018 | Coppeta et al. |
| 2018/0155665 A1 | 6/2018 | Zenhausern et al. |
| 2018/0169148 A1 | 6/2018 | Adair et al. |
| 2018/0179485 A1 | 6/2018 | Borenstein et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2018/0284125 A1 | 10/2018 | Gordon et al. |
| 2019/0017072 A1 | 1/2019 | Ditommaso et al. |
| 2019/0085324 A1 | 3/2019 | Regev et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0071660 A1 | 3/2020 | Spindler et al. |
| 2020/0095533 A1 | 3/2020 | Garst et al. |
| 2020/0216794 A1 | 7/2020 | Belgrader et al. |
| 2020/0263197 A1 | 8/2020 | Cheng et al. |
| 2020/0270632 A1 | 8/2020 | Roy et al. |

FOREIGN PATENT DOCUMENTS

| | | |
|---|---|---|
| EP | 2240238 | 10/2010 |
| EP | 2395087 | 12/2011 |
| EP | 3030652 | 6/2016 |
| EP | 1766004 | 8/2016 |
| EP | 3199632 | 8/2017 |
| EP | 2459696 | 11/2017 |
| WO | WO 2003/057819 | 7/2001 |
| WO | WO2002/010183 | 2/2002 |
| WO | WO 2003/087341 | 10/2003 |
| WO | WO 2009/091578 | 7/2009 |
| WO | WO 2010/079430 | 7/2010 |
| WO | WO 2011/072246 | 6/2011 |
| WO | WO2011/143124 | 11/2011 |
| WO | WO 2012/012779 A3 | 1/2012 |
| WO | WO2013/142578 | 9/2013 |
| WO | WO 2013/176772 | 11/2013 |
| WO | WO2014/018423 | 1/2014 |
| WO | WO2014/143381 | 9/2014 |
| WO | WO2014/144495 | 9/2014 |
| WO | WO 201/5021270 | 2/2015 |
| WO | WO 2016/003485 | 1/2016 |
| WO | WO 2016/054939 | 4/2016 |
| WO | WO 2016/110453 | 7/2016 |
| WO | WO 2016/145290 | 9/2016 |
| WO | WO2017/053902 | 3/2017 |
| WO | WO2017/075265 | 5/2017 |
| WO | WO 2017/078631 | 5/2017 |
| WO | WO2017/083722 | 5/2017 |
| WO | WO 2017/106414 | 6/2017 |
| WO | WO2017/161371 | 9/2017 |
| WO | WO2017/174329 | 10/2017 |
| WO | WO2017/186718 | 11/2017 |
| WO | WO2017/212400 | 12/2017 |
| WO | WO 2017/216392 | 12/2017 |
| WO | WO 2017/223330 | 12/2017 |
| WO | WO 2018/015544 | 1/2018 |
| WO | WO2018/031950 | 2/2018 |
| WO | WO2018/071672 | 4/2018 |
| WO | WO2018/083339 | 5/2018 |
| WO | WO2018/152325 | 8/2018 |
| WO | WO2018/172556 | 9/2018 |
| WO | WO 2018/191715 | 10/2018 |
| WO | WO2019/006436 | 1/2019 |
| WO | WO2019/028047 | 2/2019 |
| WO | WO2019/046766 | 3/2019 |
| WO | WO2019/055878 | 3/2019 |
| WO | WO2019/200004 | 10/2019 |
| WO | WO2019/209926 | 10/2019 |
| WO | WO2020/005383 | 1/2020 |
| WO | WO2020/021045 | 1/2020 |
| WO | WO2020/074906 | 4/2020 |

OTHER PUBLICATIONS

Dicarlo, et al., "Genome engineering in *Saccharomyces cervisiae* using CRISPR-Case systems", Nucleic Acids Research, 41(7):4336-43 (2013).

Eklund, et al., "Altered target site specificity variants of the I-Ppol His-Cys bis homing endonuclease" Nucleic Acids Research, 35(17):5839-50 (2007).

Garst, et al., "Genome-wide mapping of mutations at single-nucleotide resolution for protein, metabolic and genome engineering", Nature Biotechnology, 35(1):48-59 (2017).

Boles, et al., "Digital-to-biological converter for on-demand production of biologies", Nature Biotechnology, doi:10.1038/nbt.3859 (May 29, 2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems". Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Pines, et al., "Codon Compression Algorithms for Saturation Mutagenesis", ACS Synthetic Biology, 4:604-14 (2015).

Verwaal, et al., "CRISPR/Cpfl enables fast and simple genome editing of *Saccaramyces cerevisiae*", Yeast, 35:201-11 (2018).

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

Roy, et cl., "Multiplexed precision genome editing with trackable genomic barcodes in yeast", Nature Biotechnolgy, doi:10.1038/nbt. 4137, pp. 1-16 (2018).

Bessa et al., "Improved gap repair cloning in yeast: treatment of the gapped vector with Taq DNA polymerase avoids vector self-ligation," Yeast, 29(10):419-23 (2012).

Boch, "TALEs of genome targeting," Nature Biotechnology vol. 29, pp. 135-136 (2011).

Campbell et al., "Targeting protein function: the expanding toolkit for conditional disruption," Biochem J., 473(17):2573-2589 (2016).

(56) References Cited

OTHER PUBLICATIONS

Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Cramer et al., "Functional association between promoter structure and transcript alternative splicing," PNAS USA, 94(21):11456-60 (1997).
Dalphin et al., "Transterm: A Database of Translational Signals," Nucl. Acids Res., 24(1): 216-218 (1996).
Datsenko and Wanner, "One-step inactivation of chromosomal genes in *Escherichia coli* K-12 using PCR products", PNAS USA, 97(12):6640-5 (2000).
De Kok et al., "Rapid and reliable DNA assembly via ligase cycling reaction," ACS Synth Biol., 3(2):97-106 (2014).
Desmet et al., "Human Splicing Finder: an online bioinformatics tool to predict splicing signals," Nucleic Acids Res., 37(9):e67 (2009).
Divina et al., "Ab Initio prediction of mutation-induced cryptic splice-site activation and exon skipping," European Journal of Human Genetics, 17:759-765 (2009).
Dong, "Establishment of a highly efficient virus-inducible CRISPR/Cas9 system in insect cells," Antiviral Res., 130:50-7(2016).
Durai et al., "Zinc finger nucleases: custom-designed molecular scissors for genome engineering of plant and mammalian cells", Nucleic Acids Res., 33(18):5978-90 (2005).
Engler et al., "PLoS One, A One Pot, One Step, Precision Cloning Method with High Throughput Capability," 3(ll):e3647 (2008).
Epinat et al., "A novel engineered meganuclease induces homologous recombination in eukaryotic cells, e.g., yeast and mammalian cells", Nucleic Acids Research, 31(11): 2952-2962.
Faber et al., "Genome-wide prediction of splice-modifying SNPs in human genes using a new analysis pipeline called AASsites," BMC Bioinformatics, 12(suppl 4):S2 (2011).
Farasat et al., "A Biophysical Model of CRISPR/Cas9 Activity for Rational Design of Genome Editing and Gene Regulation," PLoS Comput Biol., 29:12(1):el004724 (2016).
Adamo, et al., "Flow-through comb electroporation device for delivery of macromolecules", Analytical Chemistry, 85(3):1637-41 (2015).
Greger et al., "Balancing transcriptional interference and initiation on the GAL7 promoter of *Saccharomyces cerevisiae*," PNAS, 97(15):8415-20 (2000).
Juan et al., "Histone deacetylases specifically down-regulate p53-dependent gene activation," Journal of Biological Chemistry 275.27 (2000): 20436-20443.
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Lefevre et al., "Alanine-stretch scanning mutagenesis: a simple and efficient method to probe protein structure and function," Nucleic Acids Research, vol. 25(2):447-448 (1997).
Liu et al., "A chemical-inducible CRISPR-Cas9 system for rapid control of genome editing", Nature Chemical Biology, 12:980-987(2016).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Mullick et al., "The cumate gene-switch: a system for regulated expression in mammalian cells", BMC Biotechnology, 6:43 (2006).
Nalla et al., "Automated splicing mutation analysis by information theory," Hum. Mutat., 25:334-342 (2005).
No et al., "Ecdysone-inducible gene expression in mammalian cells and transgenic mice," PNAS, 93(8):3346-3351 (1996).
Ohtsuka, "Lantibiotics: mode of action, biosynthesis and bioengineering," Curr Pharm Biotechnol, 10(2):244-51 (2009).
Patron, "DNA assembly for plant biology: techniques and tools," Curr Opinion Plant Biol., 19:14-9 (2014).
Sands et al., "Overview of Post Cohen-Boyer Methods for Single Segment Cloning and for Multisegment DNA Assembly," Curr Protoc Mol Biol., 113:3.26.1-3.26.20 (2016).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
West et al., "Molecular Dissection of Mammalian RNA Polymerase II Transcriptional Termination," Mol Cell. 29(5):600-10 (2008).
West et al., "Transcriptional Termination Enhances Protein Expression in Human Cells," Mol Cell.; 33(3-9); 354-364 (2009).
International Search Report and Written Opinion for International Application No. PCT/US2018/040519, dated Sep. 26, 2018, p. 1-8.
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Nov. 23, 2018, p. 1-12.
International Search Report and Written Opinion for International Application No. PCT/US2019/023342 dated Jun. 6, 2019, p. 1-12.
International Search Report and Written Opinion for International Application No. PCT/US2019/026836 dated Jul. 2, 2019, p. 1-10.
International Search Report and Written Opinion for International Application No. PCT/US2019/028821 dated Aug. 2, 2019, p. 1-14.
International Search Report and Written Opinion for Interational Application No. PCT/US2019/028883 dated Aug. 16, 2019, p. 1-12.
International Search Report and Written Opinion for International Application No. PCT/US2019/030085 dated Jul. 23, 2019, p. 1-14.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication for U.S. Appl. No. 16/024,831, dated Feb. 12, 2019, p. 1-37.
First Office Action Interview Pilot Program Pre-Interview Communication for U.S. Appl. No. 16/360,404 dated Jul. 1, 2019, p. 1-27.
First Office Action Interview Pilot Program Pre-Interview Communication for U.S. Appl. No. 16/360,423 dated Jul. 1, 2019, p. 1-27.
Non Final Office Action for U.S. Appl. No. 16/399,988 dated Jul. 31, 2019, p. 1-20.
First Office Action Interview Pilot Program Pre-Interview Communication for U.S. Appl. No. 16/454,865 dated Aug. 16, 2019, p. 1-36.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
Yoshioka, et al., "Development for a mono-promoter-driven CRISPR/CAS9 system in mammalian cells", Scientific Reports, Jul. 3, 2015, p. 1-8.
Remaut, et al., "Plasmid vectors for high-efficiency expression controlled by the PL promoter of coliphage lambda", Laboratory of Molecular Biology, Apr. 15, 1981, p. 81-93.
International Search Report and Written Opinion for International Application No. PCT/US19/46515, dated Oct. 28, 2019, p. 1-11.
International Search Report and Written Opinion for International Application No. PCT/US19/49735, dated Nov. 18, 2019, p. 1-13.
International Search Report and Written Opinion for International Application No. PCT/US19/46526, dated Dec. 18, 2019, p. 1-17.
International Search Report and Written Opinion for International Application No. PCT/US18/34779, dated Nov. 26, 2018, p. 1-39.

(56) References Cited

OTHER PUBLICATIONS

International Search Report and Written Opinion for International Application No. PCT/US19/57250, dated Feb. 25, 2020, p. 1-16.
International Search Report and Written Opinion for International Application No. PCT/US20/24341, dated Jun. 19, 2020, p. 1-9.
International Search Report and Written Opinion for International Application No. PCT/US19/47135, dated Jun. 11, 2020, p. 1-15.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.
Anzalone et al., "Search-and-replace genome editing without doubles-strand breaks or donor DNA," Nature, Oct. 21, 2019, vol. 576, No. 7785, pp. 149-157.
International Search Report and Written Opinion for International Application No. PCT/US2020/038345, dated Nov. 23, 2020, p. 1-13.
International Search Report and Written Opinion for International Application No. PCT/US21/12867, dated May 12, 2021, p. 1-17.
International Search Report and Written Opinion for International Application No. PCT/US2020/064727, dated Apr. 28, 2021, p. 1-13.
International Search Report and Written Opinion for International Application No. PCT/US21/15054, dated Apr. 13, 2021, p. 1-15.
International Search Report and Written Opinion for International Application No. PCT/US21/29008, dated Aug. 24, 2021, p. 1-19.
International Search Report and Written Opinion for International Application No. PCT/US21/29011, dated Aug. 24, 2021, p. 1-20.
Borger, et al. "Novel Strategy for microsphere-mediated DNA transfection", Supporting Information for PCT/US2021/015054; Apr. 13, 2021, p. 1-6.
Bauer, et al., "Cell-microcarrier Adhesion to Gas-Liquid Interfaces and Foam", Biotechnol. Prog. 2000, 16, 125-132, Oct. 19, 1999.
Datlinger, et al., "Pooled CRISPR screening with single-cell transcriptome readout", Nature Methods, Jan. 10, 2017; p. 1-10, doi:10.1038/nmeth.4177.
Dixit, et al., "Perturb-Seq: Dissecting Molecular Circuits with Scalable Single-Cell RNA Profiling of Pooled Genetic Screens", Cell 167, p. 1853-1866, Dec. 15, 2016.
GE Healthcare Life Sciences, "Microcarrier Cell Culture Principles and Methods", 18-1140-62 AC, p. 1-23, Nov. 2013.
Jacobi, et al., "Simplified CRISPR tools for efficient genome editing and streamlined protocols for their delivery into mammalian cells and mouse zygotes", Methods 121-122, p. 16-28, Mar. 23, 2017.
Jaitin, et al., "Dissecting Immune Circuits by Linking CRISPR-Pooled Screens with Single-Cell RNA-Seq" Cell 167, p. 1883-1896, Dec. 15, 2016.
Kim, et al., "Formation of Thermoresponsive Poly(N-isopropylacrylamide)/Dextran Particles by Atom Transfer Radical Polymerization", Macromol. Rapid Commun., 24, p. 517-521, 2003.
Kimple, et al., "Overview of Affinity Tags for Protein Purification", Curr Protoc Protein Sci.; 73: Unit-9-9. Doi:10.1002/0471140864. ps0909s73, p. 1-26, Aug. 6, 2015.
Nienow, et al., "A potentially scalable method for the harvesting of hMSCs from microcarriers", Biochemical Engineering Journal 85, p. 79-88, Feb. 4, 2014.
Replogle, et al., "Direct capture of CRISPR quides enables scalable, multiplexed, and multi-omic Perturb-Seq", bioRxiv; doi:http://dx.doi.org/10.1101/503367, p. 1-26, Dec. 21, 2018.

Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.
Filsinger, et al., "Characterizing the portability of RecT-mediated oligonucleotide recombination", bioRxiv, Apr. 15, 2020, doi:org/10.1101/2020.04.14.041095, p. 1-25.
Nelson, et al., "Engineered pegRNAs improve prime editing efficiency", Nature Biotechnology, Jul. 25, 2021, doi.org/10.1038/s41587-021-01039-7, p. 1-14.
Yu, et al., "Improved delivery of Cas9 protein/gRNA complexes using lipofectamine CRISPRMAX", Biotechnol Ltt, Feb. 18, 2016, doi 10.1007/sl0529-016-2064-9, p. 919-929.
Bengali, et al., "Gene Delivery Through Cell Culture Substrate Adsorbed DNA Complexes", Biotechnol Bioeng., May 5, 2005, doi:10.1002/bit.20393, p. 1-23.
Segura, et al., "Substrate-mediated DNA delivery: role of the cationic polymer structure and extent of modification", Journal of Controlled Release, Aug. 9, 2003, doi:10.1016/j.jconrel.2003.08.003, p. 69-84.
Takahashi, et al., "Integration of CpG-free DNA induces de novo methylation of CpG islands in pluripotent stem cells," Science, May 5, 2017, vol. 356, No. 6337, pp. 1-7.
Chen, et al., "Human Pluripotent Stem Cell Culture: Considerations for Maintenance, Expansion, and Therapeutics", Cell Stem Cell, Jan. 2, 2014, doi.org/10.1016/j.stem.2013.12.005, p. 13-26.
Fayazpour, F., "Exploring New Applications For Photophysically Encoded Mircrocarriers", Ghent University Faculty of Pharmaceutical Sciences, Thesis Submission, Sep. 2008, 169 pages.
Chueng, et al., "Unlinking the methylome pattern from nucleotide sequence, revealed by large-scale in vivo genome engineering and methylome editing in medaka fish," PLoS Genetics, Dec. 21, 2017, vol. 13, No. 12, pp. 1-25.
Elvin, et al., "Modified bacteriophage lambda promoter vectors for overproduction of proteins in *Escherichia coli*", Gene, 87, Sep. 15, 1989, p. 123-126.
Segall-Shapiro, et al., "Engineered promoters enable constant gene expression at any copy number in bacteria", Nature Biotechology, vol. 36, No. 4, Mar. 19, 2018, p. 352-363.
Xing, et al., "A CRISPR/Cas9 toolkit for multiplex genome editing in plants", BMC Plant Biology, 2014, p. 1-12.
Sun, et al., "A Single Multiplex crRNA Array for FnCpfl-Mediated Human Genome Editing," Molecular Therapy, Aug. 1, 2018, vol. 26, No. 8, pp. 2070-2076.
Kurata, et al., "Highly multiplexed genome engineering using CRISPR/Cas9 gRNA arrays," PLoS ONE, Sep. 17, 2018, vol. 13, No. 9, pp. 1-17.
Hubmann, et al., "Natural and Modified Promoters for Tailored Metabolic Engineering of the Yeast *Saccharomyces cerevisiae*", Methods in Molecular Biology, vol. 1152, doi10.1007/978-1-4939-0563-8_2, p. 17-42.
Unciti-Broceta, et al., "Combining Nebulization-Mediated Transfection and Polymer Microarrays for the Rapid Determination of Optimal Transfection Substrates", Journal of Combinatorial Chemistry, vol. 10, No. 2, Feb. 5, 2008, p. 179-184.
Fayazpour, et al., "Evaluation of Digitally Encoded Layer-by-layer Coated Microparticles as Cell Carriers", Advanced Functional Materials, Sep. 1, 2008, p. 2716-2723.
UniProtKB/TrEMBL, "A0A1G4WF58_9FIRM", Nov. 22, 2017, rerieved from Internet: https://www.uniprot.org/uniprot/A0A1G4WF58.txt, pp. 1-3.
Natsume, et al., "Conditional Degrons for Controlling Protein Expression at the Protein Level", Annual Review of Genetics, vol. 51, 2017, doi.org/10.1146/annurev-genet-120116-024656, p. 83-104.
Chen, et al., "Enhancing the copy number of episomal plasmids in *Saccharomyces cerevisiae* for improved protein production", FEMS Yeast Research, Apr. 25, 2012, doi:10.1111/j.1567-1364.2012.00809.x; p. 598-607.
Price, et al., "Expanding and understanding the CRISPR toolbox for Bacillus subtilis with MAD7 and dMAD7", Biotechnology and Bioengineering, Feb. 19, 2020, doi:10.1002/bit.27312 p. 1805-1816.

(56) References Cited

OTHER PUBLICATIONS

International Search Report and Written Opinion for International Application No. PCT/US21/43534, dated Nov. 10, 2021, p. 1-16.
International Search Report and Written Opinion for International Application No. PCT/US20/26095, dated Jul. 17, 2020, p. 1-10.
International Search Report and Written Opinion for International Application No. PCT/US21/35807, dated Nov. 24, 2021, p. 1-21.
International Search Report and Written Opinion for International Application No. PCT/US21/50338, dated Dec. 10, 2021, p. 1-17.
International Search Report and Written Opinion for International Application No. PCT/US21/43097, dated Nov. 19, 2021, p. 1-12.
International Search Report and Written Opinion for International Application No. PCT/US21/39872, dated Oct. 27, 2021, p. 1-14.
International Search Report and Written Opinion for International Application No. PCT/US21/48566, dated Dec. 10, 2021, p. 1-10.

|  | Clonality >50% | Clonality >90% | Unique edits |
|---|---|---|---|
| v0.5.0 - SPP | 65/91 | 57/91 | 59/65 |
| v0.5.0 - SPP Cherry | 87/96 | 75/96 | 78/87 |
| v0.5.0 - SPP replated | 8/96 | 5/96 | 7/8 |
| v0.6.0 - Bulk Gel | 44/95 | 39/95 | 42/44 |

Digital growth of E.coli in microwells
Low magnification

Darker microwells = growth

Top view of microwells
Medium magnification

Darker microwells = growth

Microwells with membrane removed
High magnification

Steps 7-11

Steps 12-13

Step 14

Steps 15-18

DETECTION OF NUCLEASE EDITED SEQUENCES IN AUTOMATED MODULES AND INSTRUMENTS

RELATED APPLICATIONS

This application is a continuation of U.S. Ser. No. 16/536,049, filed Aug. 8, 2019; which claims priority to U.S. Provisional Application Nos: 62/718,449, filed Aug. 14, 2018; 62/769,805, filed Nov. 20, 2018; 62/735,365, filed Sep. 24, 2018; 62/781,112, filed Dec. 18, 2018; 62/779,119, filed Dec. 13, 2018; 62/841,213, filed Apr. 30, 2019. This application is also related to U.S. Ser. No. 16/399,988, filed Apr. 30, 2019; and Ser. No. 16/454,865, filed Jun. 26, 2019, all of which are incorporated herein in their entirety.

FIELD OF THE INVENTION

This invention relates to automated modules and instruments for screening, identifying, and selecting live cells that have nuclease-directed edits.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have been identified that allow manipulation of gene sequence, and hence gene function. The nucleases include nucleic acid-guided nucleases, which enable researchers to generate permanent edits in live cells. Editing efficiencies in cell populations can be high; however, in pooled or multiplex formats there tends to be selective enrichment of cells that have not been edited due to the lack of the double-strand DNA breaks that occur during the editing process. Double-strand DNA breaks dramatically negatively impact viability thereby leading to the enhanced survival of unedited cells and making it difficult to identify edited cells in the background of unedited cells. In addition, cells with edits that confer growth advantages or disadvantages can lead to skewed representations for different edits in the population.

There is thus a need in the art of nucleic acid-guided nuclease gene editing for improved methods for enriching, identifying and selecting cells that have been edited. The present invention satisfies this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides methods, modules and instruments for automated high-throughput and extremely sensitive enrichment and selection of cells edited by a nucleic acid-guided nuclease. Some embodiments of the methods take advantage of isolation or substantial isolation, e.g., separating individual cells, providing conditions for editing, and growing the individual cells into clonal colonies. Isolation overcomes growth bias from unedited cells, growth effects from differential editing rates, and growth bias resulting from fitness effects of different edits. Indeed, it has been determined that removing growth rate bias via isolation and growing colonies from the isolated cells to saturation or terminal colony size improves the observed editing efficiency by up to 4× or more over conventional methods. Other embodiments of the methods utilize "cherry picking" or direct selection of edited colonies, determined by the differential growth rate of edited and unedited cell colonies. Cherry picking colonies using the methods described herein more than doubles the observed editing efficiency as the result of isolation. Thus, the combination of isolation and cherry picking improves observed editing efficiency by up to 98% over conventional methods.

The present disclosure provides instruments, modules and methods to enable automated high-throughput and extremely sensitive screening to identify edited cells in populations of cells that have been subjected to nucleic acid-guided nuclease editing. The instruments, modules, and methods take advantage of isolation or substantial isolation, where the term "isolation" in this context refers to the process of separating cells and growing them into clonally-isolated formats. The term "substantial isolation" refers to the process of separating cells in a population of cells into "groups" of 2 to 100, or 2 to 50, and preferably 2 to 10 cells. Isolation (or substantial isolation), followed by an initial period of growth (e.g., incubation), editing, and growth normalization leads to enrichment of edited cells. Further, certain of the instruments, modules, and methods described herein facilitate "cherry picking" of edited cell colonies, allowing for direct selection of edited cells.

Isolation or substantial isolation assists in overcoming the growth bias from unedited cells that occurs under competitive growth regimes such as in bulk liquid culture. Indeed, it has been determined that removing growth rate bias via isolation or substantial isolation, incubation, editing and normalization improves the observed editing efficiency by up to 4× (from, e.g., 10% to 40% absolute efficiency at population scale) or more over conventional methods, and further that cherry-picking colonies using the methods described herein brings the observed editing efficiency up to 8× (from, e.g., 10% to 80% absolute efficiency at population scale) over conventional methods. In some embodiments—particularly in bacteria—the compositions and methods employ inducible guide RNA (gRNA) constructs leading to increased observed transformation efficiency and automation-friendly control over the timing and duration of the editing process.

One particularly facile module or device for isolation or substantial isolation is a solid wall device where cells are substantially isolated, grown in a clonal (or substantially clonal) format, edited, and either normalization or cherry picking is employed. The solid wall devices or modules and the uses thereof are described in detail herein. The instruments, modules and methods in some embodiments allow for normalization of edited and unedited cell colonies. Normalization refers to growing colonies of cells—whether edited or unedited—to terminal size; that is, growing the cells until the cells in the colonies enter senescence due to, e.g., nutrient exhaustion or constrained space for further growth. Since unedited cells grow more quickly, unedited cell colonies will reach terminal size (e.g., senescence) before edited cell colonies; however, the unedited cell colonies eventually "catch up" in size and senescence. Thus, normalization of cell colonies enriches for edited cells as edited cells get "equal billing" with unedited cells. Additionally, certain of the modules as described herein facilitate "cherry picking" of colonies. Cherry picking allows for direct selection of edited cells by taking advantage of edit-induced growth delay in edited colonies. Cherry picking can be performed by selecting slow-growing cell colonies, or cherry picking can be performed by eliminating faster-growing cell colonies by, e.g., irradiating the faster-growing cell colonies in the wells in which they are growing. Cherry picking colonies using the instruments, modules, and methods described herein may more than double the observed editing efficiency as the result of isolation or substantial isolation alone.

Certain embodiments of the instruments, modules, and methods provide for enriching for edited cells during nucleic acid-guided nuclease editing, where the methods comprise transforming cells with one or more vectors comprising a promoter driving expression of a nuclease, a promoter driving transcription of a guide nucleic acid and a donor DNA sequence; diluting the transformed cells to a cell concentration sufficient to substantially isolate the transformed cells on a substrate; growing (e.g., incubating) the substantially isolated cells on the substrate; providing conditions for editing; and either 1) growing the cell colonies to colonies of terminal size (e.g., normalizing the cell colonies) and harvesting (pooling) the normalized cell colonies; or 2) monitoring the growth of cells colonies on the substrate and selecting slow-growing colonies (or eliminating faster-growing colonies). In some aspects at least the gRNA is optionally under the control of an inducible promoter.

Thus in some embodiments there is provided: a solid wall isolation, induction and normalization (SWIIN) module comprising: a retentate member comprising: an upper surface and a lower surface and a first and second end, an upper portion of a serpentine channel defined by raised areas on the lower surface of the retentate member, wherein the upper portion of the serpentine channel traverses the lower surface of the retentate member for about 50% to about 90% of the length and width of the lower surface of the retentate member; at least one port fluidically connected to the upper portion of the serpentine channel; and a reservoir cover at the first end of the retentate member; a permeate member disposed under the retentate member comprising: an upper surface and a lower surface and a first and second end, a lower portion of a serpentine channel defined by raised areas on the upper surface of the permeate member, wherein the lower portion of the serpentine channel traverses the upper surface of the permeate member for about 50% to about 90% of the length and width of the upper surface of the permeate member, and wherein the lower portion of the serpentine channel is configured to mate with the upper portion of the serpentine channel to form a mated serpentine channel; at least one port fluidically connected to the lower portion of the serpentine channel; and a first and second reservoir at the first end of the permeate member, wherein the first reservoir is fluidically connected to the at least one port in the retentate member and the second reservoir is fluidically connected to the at least one port in the permeate member; a perforated member comprising at least 25,000 perforations disposed under and adjacent to the retentate member; a filter disposed under and adjacent to the perforated member and above and adjacent to the permeate member; and a gasket disposed on top of the reservoir cover of the retentate member, wherein the gasket comprises a reservoir access aperture and a pneumatic access aperture for each reservoir.

In some aspects of this embodiment, the permeate member further comprises ultrasonic tabs disposed on the raised areas on the upper surface of the permeate member and at the first and second end of the permeate member, the retentate member further comprises recesses for the ultrasonic tabs disposed in the raised areas on the lower surface and at the first and second end of the retentate member, the ultrasonic tabs are configured to mate with the recesses for the ultrasonic tabs, and the permeate member, retentate member, where the perforated member and the filter are coupled together by ultrasonic welding. In other aspects of this embodiment, the permeate member, retentate member, the perforated member and the filter are coupled together by solvent bonding.

In some aspects, the first and second reservoirs are each fluidically coupled to a reservoir port into which fluids and/or cells flow from the first retentate reservoir into the first retentate port and from the first permeate reservoir into the first permeate port and into the serpentine channels in the retentate and permeate members.

In some aspects of this embodiment, the SWIIN module further comprises a third and a fourth reservoir, wherein the third reservoir is 1) fluidically coupled to a second port in the retentate member, 2) fluidically coupled to a reservoir access aperture into which fluids and/or cells flow from outside the SWIIN module into the third reservoir, and 3) pneumatically coupled to a pressure source; and wherein the fourth reservoir is 1) fluidically coupled to a second port in the permeate member, 2) fluidically coupled to a reservoir access aperture into which fluids and/or cells flow from outside the SWIIN module into the fourth reservoir, and 3) pneumatically coupled to a pressure source.

In some aspects of this embodiment, the perforated member comprises at least 100,000 perforations, or at least 200,000 perforations, or at least 250,000 perforations, or at least 300,000 perforations, or at least 350,000 perforations or at least 400,000 perforations, or at least 500,000 perforations or more. The volume of the wells formed by the perforations is from 1 nL to 50 nL, or from 2 nL to 40 nL, or from 3 nL to 25 nL, or from 2 nL to 10 nL.

In some aspects, the retentate member is fabricated from polycarbonate, cyclic olefin co-polymer, or poly(methyl methylacrylate). In some aspects of the SWIIN module, a serpentine channel portion of each of the retentate and permeate members is from 75 mm to 350 mm in length, from 50 mm to 250 mm in width, and from 2 mm to 15 mm in thickness, and from 150 mm to 250 mm in length, from 100 mm to 150 mm in width, and from 4 mm to 8 mm in thickness. In some aspects, the volume of the mated serpentine channel is from 4 to 40 mL, or from 6 mL to 30 mL, or from 10 mL to 20 mL. In some aspects, the volume of the first and second reservoir is from 5 to 50 mL, or from 8 to 30 mL, or from 10 to 20 mL.

In some aspects of the SWIIN module, there is a support on each end of the permeate member configured to elevate the permeate and retentate members above the at least one port in the in retentate member and the at least one port in the permeate member. Certain embodiments of the SWIIN module further comprise imaging means to detect cells growing in the wells, and in some aspects, the imaging means is a camera with means to backlight the serpentine channel portion of the SWIIN. In some aspects, the SWIIN module is part of a SWIIN assembly comprising a heated cover, a heater, a fan, and a thermoelectric control device.

In yet another embodiment there is provided a method for performing enrichment of cells edited by a nucleic acid-guided nuclease, comprising: providing transformed cells at a dilution resulting in substantially cells in an appropriate liquid growth medium comprising 0.25%-6% alginate, wherein the cells comprise nucleic acid-guided nuclease editing components where the gRNA optionally is under the control of an inducible promoter; solidifying the alginate-containing medium with a divalent cation; allowing the isolated cells to grow for 2 to 50 doublings to establish cell colonies; optionally inducing transcription of the gRNA; allowing the cell colonies to grow to become normalized; and liquefying the alginate-containing medium with a divalent cation chelating agent. In some aspects, the nucleic acid-guided nuclease editing components are provided to the cells on two separate vectors and in some aspects, the nucleic acid-guided nuclease editing components are provided to the cells on a single vector, and in some aspects, the cells are bacterial cells, yeast cells, or mammalian cells.

In some aspects of this method embodiment, the percentage of alginate in the growth medium is 1%-4%, and in some aspects, the percentage of alginate in the growth medium is 2%-3%.

In some aspects, the inducible promoter driving the gRNA is a promoter that is activated upon an increase in temperature, and in some aspects, the inducible promoter is a pL promoter, the cells are transformed with a coding sequence for the CI857 repressor, and transcription of the one or more nucleic acid-guided nuclease editing components is induced by raising temperature of the cells to 42° C.

In some aspects, solidifying the alginate-containing medium is performed with divalent cations except $Mg^{+2}$, and in some embodiments, the divalent cation is $Ca^{+2}$. In some aspects, the divalent cation chelating agent (e.g., liquefying agent) is citrate, ethylenediaminetetraacetic acid (EDTA), or hexametaphosphate.

Other embodiments provide an automated stand-alone multi-module cell editing instrument comprising: a housing configured to house all or some of the modules; a receptacle configured to receive cells; a receptacle configured to receive editing nucleic acids; a growth module for growing cells; a filtration module for concentrating and rendering cells electrocompetent; a transformation module configured to introduce the editing nucleic acids into the cells; a singulation and editing module configured to isolate the transformed cells and allow the editing nucleic acids to edit nucleic acids in the cells wherein the singulation and editing module comprises a device for emulsion formation, comprising: a microfluidic device having an emulsion formation unit including a sample well configured to receive cells in aqueous medium; a carrier fluid well configured to receive a fluid that is immiscible with the cells in aqueous medium; a collection substrate to collect aqueous droplets formed in the immiscible fluid; a sample channel extending from the sample well to a channel intersection; a carrier fluid channel extending from the carrier fluid well to the channel intersection; a droplet channel extending from the channel intersection to the collection substrate; and a pneumatic assembly having a pressure source and a pressure sensor, wherein the pneumatic assembly is configured (a) to apply pressure to the emulsion formation unit to drive generation of droplets at the channel intersection of the emulsion formation unit and collect droplets in the collection substrate, (b) to monitor the pressure with the pressure sensor, and (c) to stop application of the pressure to the emulsion formation unit when the pressure sensor detects a change in pressure indicative of air entering the sample channel from the sample well; a processor configured to operate the automated multi-module cell editing instrument based on user input and/or selection of a pre-programmed script; and an automated liquid handling system to move liquids from the cell receptacle to the growth module, from the growth module to the filtration module, from the filtration module to the transformation module, from the nucleic acid receptacle to the transformation module, and from the transformation module to the singulation and editing module without user intervention.

In some aspects of this embodiment the singulation and editing module further comprises a detection station downstream from the channel intersection and before the collection substrate, in some aspects, the detection station comprises a camera. In some aspects, the singulation and editing module further comprises a temperature-controlled editing reservoir positioned between the channel intersection and the detection station. In some aspects, the detection station detects the optical density of cells in the aqueous droplets, and in some aspects the singulation and editing module further comprises a droplet sorter positioned between the detection station and the collection substrate where the aqueous droplets are sorted into two receptacles in the collection substrate. In other aspects, the collection substrate comprises wells, and is configured to collect one droplet per well. In some aspects, the collection substrate is temperature-controlled, and in some aspects, the singulation and editing module further comprises a detection station configured to detect droplets in the collection substrate.

Yet other embodiments provide a method for isolating and editing cells in the automated stand-alone multi-module cell editing instrument having a microfluidic device, comprising the steps of: providing live cells in the receptacle configured to receive the live cells; providing editing nucleic acids the receptacle configured to receive editing nucleic acids; growing the live cells in a growth module to a desired optical density to produce grown cells; filtering and rendering electrocompetent the grown cells to produce filtered cells; transforming the filtered cells in a transformation module configured to introduce the editing nucleic acids into the filtered cells to produce transformed cells; generating droplets in the microfluidic device by providing the transformed cells in an aqueous medium in the sample well; providing the fluid immiscible with the cells in the aqueous medium in the carrier fluid well; flowing the immiscible fluid from the carrier fluid well through the carrier channel to the channel intersection; flowing the cells in aqueous medium from the sample well through the sample channel to the channel intersection; generating aqueous droplets in the immiscible fluid; and collecting the aqueous droplets in wells in the collection substrate; incubating the aqueous droplets in the collection substrate to allow the editing nucleic acids to edit the transformed cells; pooling the aqueous droplets; and using an automated liquid handling system to 1) transfer the editing nucleic acids from receptacle configured to receive nucleic acids to the transformation module, 2) transfer the live cells from the receptacle configured to receive the live cells to the growth module, 3) transfer the grown cells from the growth module to the filtration module; 4) transfer the filtered cells from the filtration module to the transformation module, 5) transfer the transformed cells to the sample well, and 6) transfer the cells from the collection substrate to a vessel without user intervention.

An additional embodiment provides a method for isolating and editing cells in the automated stand-alone multi-module cell editing instrument having a microfluidic device, comprising the steps of: providing live cells in the receptacle configured to receive the live cells; providing editing nucleic acids the receptacle configured to receive editing nucleic acids; growing the live cells in a growth module to a desired optical density to produce grown cells; filtering and rendering electrocompetent the grown cells to produce filtered cells; transforming the filtered cells in a transformation module configured to introduce the editing nucleic acids into the filtered cells to produce transformed cells; generating droplets in the microfluidic device by providing the transformed cells in an aqueous medium in the sample well; providing the fluid immiscible with the cells in the aqueous medium in the carrier fluid well; flowing the immiscible fluid from the carrier fluid well through the carrier channel to the channel intersection; flowing the cells in aqueous medium from the sample well through the sample channel to the channel intersection; generating aqueous droplets in the immiscible fluid; and collecting the aqueous droplets one at a time in wells in the collection substrate; incubating the aqueous droplets in the collection substrate to allow the editing nucleic acids to edit the transformed cells; monitoring cell growth in the droplets via the detection station; sorting the aqueous droplets based on rapidity of cell growth; pooling the aqueous droplets with slow-growing cells in a vessel; and using an automated liquid handling system to 1) transfer the editing nucleic acids from receptacle configured to receive nucleic acids to the transformation module, 2) transfer the live cells from the receptacle configured to receive the live cells to the growth module, 3) transfer the grown cells from the growth module to the filtration module; 4) transfer the filtered cells from the filtration module to the transformation module, 5) transfer the transformed cells to the sample well, and 6) transfer the cells from the collection substrate to a vessel without user intervention.

In some aspects of these method embodiments, the fluid immiscible with the cells in the aqueous medium is decane, and in some aspects, the generated aqueous droplets comprise cells in a Poisson distribution. In some aspects, after the pooling step, filtering the edited cells in the filtration module.

Also provided herein is an automated multi-module cell editing instrument comprising: an isolation or singulation module, a housing configured to house all of some of the modules; a receptacle configured to receive cells; one or more receptacles configured to receive nucleic acids; a growth module; a transformation module configured to introduce the nucleic acids into the cells; and a processor configured to operate the automated multi-module cell editing instrument based on user input and/or selection of a pre-programmed script.

In some aspects of the automated multi-module cell editing instrument, the transformation module comprises a flow-through electroporation device; and in some aspects the automated multi-module cell editing instrument further comprises a cell concentration module. In some aspects the cell concentration module is a tangential flow filtration module. In some aspects a liquid handling system transfers liquids between the modules. And in some aspects, the automated multi-module cell processing system performs the processes of growing cells, concentrating and rendering the cells electrocompetent, transforming the cells with nucleic acid-guided nuclease editing components, isolating the transformed cells, inducing editing in the isolated cells, and growing and enriching the cells, all without human intervention.

Other embodiments provide a method for enriching edited cells during nucleic acid-guided nuclease editing comprising: transforming cells with one or more vectors comprising a promoter driving transcription of a coding sequence for a nuclease, a promoter driving transcription of a guide nucleic acid and a DNA donor sequence; diluting the transformed cells to a cell concentration to substantially isolate the transformed cells on a substrate; growing the cells and initiating editing; growing the induced cells into colonies; and selecting cells from the substantially isolated colonies from the substrate or pooling cells from the substantially isolated colonies from the substrate, wherein the substantially isolated colonies are enriched for edited cells. In optional aspects of this method, the gRNA is under the control of an inducible promoter and 1) the cells are allowed to grow from 2-200 doublings after isolation, and 2) there is an inducing step after the growth step and prior to the editing step.

Other embodiments provide a method for enriching edited cells during nucleic acid-guided nuclease editing comprising: transforming cells with one or more vectors comprising a promoter driving transcription of a coding sequence for a nuclease, a promoter driving transcription of a guide nucleic acid and a DNA donor sequence; diluting the transformed cells to a cell concentration to substantially isolate the transformed cells on a substrate; growing the cells and allowing the cells to edit; growing the cells to form colonies; and selecting small colonies from the substantially isolated colonies from the substrate, wherein the substantially isolated colonies are enriched for edited cells. In optional aspects of this method, the gRNA is under the control of an inducible promoter and 1) the cells are allowed to grow from 2-200 doublings after singulation, and 2) there is an inducing step after the growth step and prior to the editing step.

These aspects and other features and advantages of the invention are described below in more detail.

DETAILED DESCRIPTION

Figure 1A:
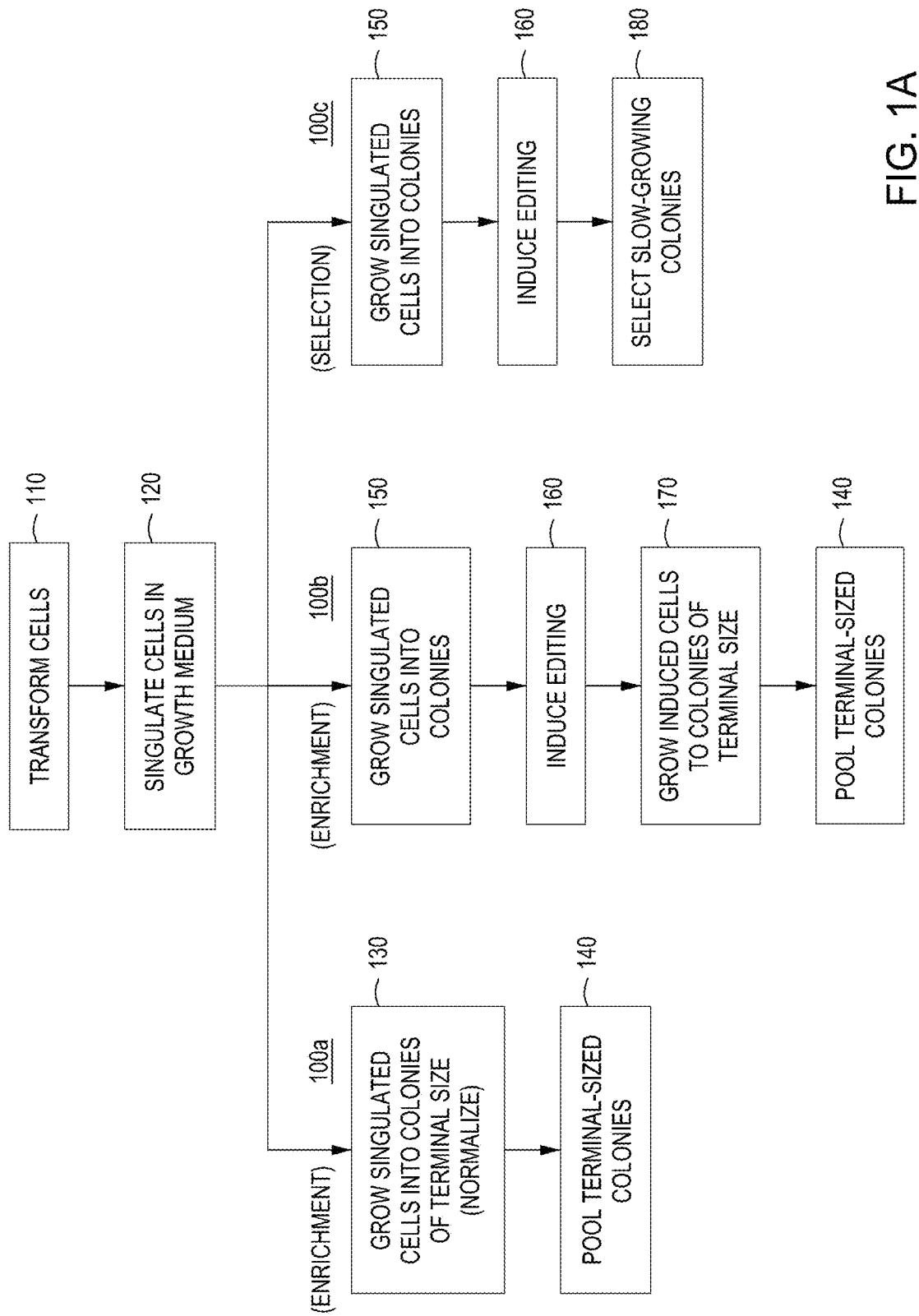
FIG. 1A is a simplified flow chart of exemplary enrichment methods (100a and 100b) and a selection method (100c) that may be performed by an automated module, either as a stand-alone instrument or as part of an automated multi-module cell processing instrument.

All of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., eds., *Genome Analysis: A Laboratory Manual Series* (Vols. I-IV) (1999); Weiner, Gabriel, Stephens, eds., *Genetic Variation: A Laboratory Manual* (2007); Dieffenbach, Dveksler, eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); Stryer, *Biochemistry* (4th Ed.) W. H. Freeman, New York N.Y. (1995); Gait, "*Oligonucleotide Synthesis: A Practical Approach*" (1984), IRL Press, London; Nelson and Cox, *Lehninger, Principles of Biochemistry* $3^{rd}$ Ed., W. H. Freeman Pub., New York, N.Y. (2000); Berg et al., *Biochemistry*, $5^{th}$ Ed., W. H. Freeman Pub., New York, N.Y. (2002); Doyle & Griffiths, eds., *Cell and Tissue Culture: Laboratory Procedures in Biotechnology*, Doyle & Griffiths, eds., John Wiley & Sons (1998); G. Hadlaczky, ed. *Mammalian Chromosome Engineering—Methods and Protocols*, Humana Press (2011); and Lanza and Klimanskaya, eds., *Essential Stem Cell Methods*, Academic Press (2011), all of which are herein incorporated in their entirety by reference for all purposes. CRISPR-specific techniques can be found in, e.g., Appasani and Church, *Genome Editing and Engineering From TAL-ENs and CRISPRs to Molecular Surgery* (2018); and Lindgren and Charpentier, *CRISPR: Methods and Protocols* (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," and/or "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Additionally, the terms "approximately," "proximate," "minor," and similar terms generally refer to ranges that include the identified value within a margin of 20%, 10% or preferably 5% in certain embodiments, and any values therebetween.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, features and procedures well known to those skilled in the art have not been described in order to avoid obscuring the invention.

The term "complementary" as used herein refers to Watson-Crick base pairing between nucleotides and specifically refers to nucleotides that are hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TTAGCTGG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. For example, the donor DNA will have at least one region of sequence homology (e.g., one homology arm) to the genomic target locus. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell-will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 35, 40, 50, 75, 100, 150, 200, 300, 400, or 500 or more base pairs of the target sequence. The donor DNA optionally further includes an alteration to the target sequence, e.g., a PAM mutation, that prevents binding of the nuclease at the PAM or spacer in the target sequence after editing has taken place.

As used herein, "enrichment" refers to enriching for edited cells by isolation or substantial isolation of cells, initial growth of cells into cell colonies (e.g., incubation), editing (optionally induced, particularly in bacterial systems), and growing the cell colonies into terminal-sized colonies (e.g., saturation or normalization of colony growth). As used herein, "cherry picking" or "selection of edited cells" refers to the process of using a combination of isolation or substantial isolation, initial growth of cells into colonies (incubation), editing (optionally induced, particularly in bacterial systems), then using cell growth—measured by colony size, concentration of metabolites or waste products, or other characteristics that correlate with the rate of growth of the cells—to select for cells that have been edited based on editing-induced growth delay. Selection may entail picking or selecting slow-growing cell colonies; alternatively, selection may entail eliminating (by, e.g., eradicating or removing) the faster-growing cell colonies.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

As used herein, the terms "isolation" or "isolate" (and "singulation" or "singulate") mean to separate individual cells so that each cell (and the colonies formed from each cell) will be separate from other cells; for example, a single cell in a single microwell, or 100 single cells each in its own microwell. "Isolation" or "isolated cells" result in one embodiment, from a Poisson distribution in arraying cells. The terms "substantially isolated", "largely isolated", and "substantial isolation" (and "substantially singulated") mean cells are largely separated from one another, in small groups or batches. That is, when 2, 3, 4, 5, 6, 7, 8, 9, 10, 11, 12, 13, 14, 15, 16, 17, 18, 19, 20, 21, 22, 23, 24, 25, 26, 27, 28, 29, 30 or up to 50—but preferably 10 or less cells—are delivered to a microwell. "Substantially isolated" or "largely isolated" result, in one embodiment, from a "substantial Poisson distribution" in arraying cells. With more complex libraries of edits—or with libraries that may comprise lethal edits or edits with greatly-varying fitness effects—it is preferred that cells be isolated via a Poisson distribution.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible. In the methods described herein optionally the promoters driving transcription of the gRNAs is inducible.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA 1; conjugates glutathione to the stem cell selective alkylator busulfan; chemoprotective selectable marker in CD34+ cells); CD24 cell surface antigen in hematopoietic stem cells; rhamnose; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by MAb-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, YACs, BACs, mammalian synthetic chromosomes, and the like. As used herein, the phrase "engine vector" comprises a coding sequence for a nuclease—optionally under the control of an inducible promoter—to be used in the nucleic acid-guided nuclease systems and methods of the present disclosure. The engine vector may also comprise, in a bacterial system, the λ Red recombineering system or an equivalent thereto, as well as a selectable marker. As used herein the phrase "editing vector" comprises a donor nucleic acid, including an alteration to the target sequence which prevents nuclease binding at a PAM or spacer in the target sequence after editing has taken place, and a coding sequence for a gRNA optionally under the control of an inducible promoter (and preferably under the control of an inducible promoter in bacterial systems). The editing vector may also comprise a selectable marker and/or a barcode. In some embodiments, the engine vector and editing vector may be combined; that is, the contents of the engine vector may be found on the editing vector.

Editing in Nucleic Acid-Guided Nuclease Genome Systems Generally

The present disclosure provides instruments, modules and methods for nucleic acid-guided nuclease genome editing that provide 1) enhanced observed editing efficiency of nucleic acid-guided nuclease editing methods, and 2) improvement in screening for and detecting cells whose genomes have been properly edited, including high-throughput screening techniques. In current protocols employing nuclease systems, bulk culture of cells with constitutively-expressed nuclease components typically are used to drive high-efficiency editing. However, pooled or multiplex formats can lead to selective enrichment of cells that are not edited due to the lack of double-strand DNA breaks that occur during editing.

Presented herein are methods that take advantage of isolation (separating cells and growing them into clonal colonies) and either normalization of cell colonies or cherry picking of slow-growing colonies. Isolation or substantial isolation, incubation, followed by editing (optionally with transcription of a gRNA under the control of an inducible promoter) and normalization overcomes growth bias from unedited cells, and substituting cherry picking for normalization allows for direct selection of edited cells. The instruments, modules, and methods may be applied to all cell types including, archaeal, prokaryotic, and eukaryotic (e.g., yeast, fungal, plant and animal) cells.

The instruments, modules, and methods described herein employ editing cassettes comprising a guide RNA (gRNA) sequence covalently linked to a donor DNA sequence where, particularly in bacterial systems, the gRNA optionally is under the control of an inducible promoter (e.g., the editing cassettes are CREATE cassettes; see U.S. Pat. No. 9/982,278 issued May 29, 2019 and Ser. No. 10/240,167, issued Mar. 26, 2019; Ser. No. 10/266,849, issued Apr. 23, 2019; and U.S. Publication Ser. No. 15/948,785, filed Apr. 9, 2018; Ser. No. 16/275,439, filed Feb. 14, 2019; and Ser. No. 16/275,465, filed Feb. 14, 2019 all of which are incorporated by reference in their entirety). The disclosed methods allow for cells to be transformed, substantially isolated, grown for several to many doublings (e.g., incubation), after which editing is allowed. The isolation process effectively negates the effect of unedited cells taking over the cell population. The combination of substantially isolating cells, then allowing for initial growth followed by optionally inducing transcription of the gRNA (and optionally the nuclease) and either normalization of cell colonies or cherry picking cells leads to 2-250×, 10-225×, 20-200×, 30-175×, 4.0-150×, 50-100×, or 10-100× gains in identifying edited cells over prior art methods and allows for generation of arrayed or pooled edited cells comprising cell libraries with edited genomes. Additionally, the methods may be leveraged to create iterative editing systems to generate combinatorial libraries of cells with two to many edits in each cellular genome. Optionally using inducible gRNA constructs (and in some embodiments, inducible nuclease constructs) provides "pulsed" exposure of the cells to active editing components, which 1) allows for the cells to be arrayed (e.g., largely isolated) prior to initiation of the editing procedure, 2) decreases off-target activity, 3) allows for identification of rare cell edits, and 4) enriches for edited cells or permit high-throughput screening applications to identify editing activity using cell growth as a proxy for editing, by, e.g., measuring optical density, colony size, or metabolic by-products or other characteristics thereby enriching the edited cell population.

The instruments, compositions and methods described herein improve editing systems in which nucleic acid-guided nucleases (e.g., RNA-guided nucleases) are used to edit specific target regions in an organism's genome. A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects, the guide nucleic acid may be a single guide nucleic acid that includes both the crRNA and tracrRNA sequences or a single guide nucleic acid that does not require a tracrRNA.

In general, a guide nucleic acid (e.g., gRNA) complexes with a compatible nucleic acid-guided nuclease and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA is encoded by a DNA sequence on a polynucleotide molecule such as a plasmid, linear construct, or resides within an editing cassette and is optionally-particularly in bacterial systems—under the control of an inducible promoter.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence (the portion of the guide nucleic acid that hybridizes with the target sequence) is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acid is provided as a sequence to be transcribed from a plasmid or vector and comprises both the guide sequence and the scaffold sequence as a single transcript. Alternatively, the guide nucleic acids may be transcribed from two separate sequences. The guide nucleic acid can be engineered to target a desired target DNA sequence by altering the guide sequence so that the guide sequence is complementary to the target DNA sequence, thereby allowing hybridization between the guide sequence and the target DNA sequence. In general, to generate an edit in the target DNA sequence, the gRNA/nuclease complex binds to a target sequence as determined by the guide RNA, and the nuclease recognizes a protospacer adjacent motif (PAM) sequence adjacent to the target sequence. The target sequence can be any polynucleotide (either DNA or RNA) endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) and/or a non-coding sequence (e.g., a regulatory polynucleotide, an intron, a PAM, or "junk" DNA).

The guide nucleic acid may be part of an editing cassette that encodes the donor nucleic acid; that is, the editing cassette may be a CREATE cassette (see, e.g., U.S. Pat. No. 9,982,278, issued May 29, 2019 and Ser. No. 10/240,167, issued Mar. 26, 2019; Ser. No. 10/266,849, issued Apr. 23, 2019; and U.S. Publication Ser. No. 15/948,785, filed Apr. 9, 2018; Ser. No. 16/275,439, filed Feb. 14, 2019; and Ser. No. 16/275,465, filed Feb. 14, 2019, all of which are incorporated by reference in their entirety). The guide nucleic acid and the donor nucleic acid may be and typically are under the control of a single (optionally inducible) promoter. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid. In other cases, the donor nucleic acid can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments and preferably, the sequence encoding the guide nucleic acid and the sequence encoding the donor nucleic acid are both included in the editing cassette.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, and increase the versatility of a nucleic acid-guided nuclease. In certain embodiments, the genome editing of a target sequence both introduces a desired DNA change to a target sequence, e.g., the genomic DNA of a cell, and removes, mutates, or renders inactive a proto-spacer (PAM) region in the target sequence; that is, the donor DNA often includes an alteration to the target sequence that prevents binding of the nuclease at the PAM in the target sequence after editing has taken place. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

The range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because the methods disclosed herein allow for identification of edited cells in a large background of unedited cells, the methods allow for identification of edited cells where the PAM is less than optimal; that is, the methods for identifying edited cells herein allow for identification of edited cells even if editing efficiency is very low. Additionally, the present methods expand the scope of target sequences that may be edited since edits are more readily identified, including cells where the genome edits are associated with less functional PAMs.

As for the nuclease component of the nucleic acid-guided nuclease editing system, the polynucleotide sequence encoding the nucleic acid-guided nuclease can be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammal including non-human primate. The choice of nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12/CpfI, MAD2, or MAD7 or other MADzymes. As with the guide nucleic acid, the nuclease may be encoded by a DNA sequence on a vector (e.g., the engine vector) and be under the control of a constitutive or an inducible promoter. Again, at least one of and preferably both of the nuclease and guide nucleic acid are under the control of an inducible promoter.

Another component of the nucleic acid-guided nuclease system is the donor nucleic acid. In some embodiments, the donor nucleic acid is on the same polynucleotide (e.g., vector or editing (CREATE) cassette) as the guide nucleic acid. The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 30, 35, 40, 45, 50, 75, 100, 150, 200, 500, 1000, 2500, 5000 nucleotides or more in length. In certain preferred aspects, the donor nucleic acid can be provided as an oligonucleotide of between 40-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 10, 15, 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the donor nucleic acid. Moreover, there may be more than one, e.g., two, three, four, or more guide nucleic acid/donor nucleic acid cassettes inserted into an engine vector, where the guide nucleic acids are under the control of separate, different promoters, separate, like promoters, or where all guide nucleic acid/donor nucleic acid pairs are under the control of a single promoter. (See, e.g., U.S. Ser. No. 16/275,465, filed Feb. 14, 2019, drawn to multiple CREATE cassettes.) The promoter driving transcription of the gRNA and the donor nucleic acid (or driving more than one gRNA/donor nucleic acid pair) is optionally an inducible promoter (and in bacterial systems is preferably an inducible promoter) and the promoter driving transcription of the nuclease is optionally an inducible promoter as well.

Inducible editing is advantageous in that substantially or largely isolated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells (e.g., the process of "normalization" or growing colonies to "terminal size"; see, e.g., FIG. 1B described infra).

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

Also, as described above, the donor nucleic acid may comprise—in addition to the at least one mutation relative to a target sequence—one or more PAM sequence alterations that mutate, delete or render inactive the PAM site in the target sequence. The PAM sequence alteration in the target sequence renders the PAM site "immune" to the nucleic acid-guided nuclease and protects the target sequence from further editing in subsequent rounds of editing if the same nuclease is used.

The editing cassette also may comprise a barcode. A barcode is a unique DNA sequence that corresponds to the donor DNA sequence such that the barcode can identify the edit made to the corresponding target sequence. The barcode can comprise greater than four nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid design is associated with a different barcode, or, alternatively, each different cassette molecule is associate with a different barcode.

Additionally, in some embodiments, an expression vector or cassette encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination.

Exemplary Workflows for Editing, Enrichment, and Selection of Edited Cells

The methods described herein provide enhanced observed editing efficiency of nucleic acid-guided nuclease editing methods as the result of a combination of isolation or substantial isolation, initial cell growth (incubation), editing, and either normalization of the resulting cell colonies or cherry picking slow-growing cell colonies. The combination of the isolation or substantial isolation, initial cell growth, editing and normalization processes overcomes the growth bias in favor of unedited cells—and the fitness effects of editing (including differential editing rates)—thus allowing all cells "equal billing" with one another. The combination of isolation or substantial isolation, initial cell growth, editing, and cherry picking allows for direct selection of edited colonies of cells. The result of the methods described herein is that even in nucleic acid-guided nuclease systems where editing is not optimal—such as in systems where non-canonical PAMs are targeted—there is an increase in the observed editing efficiency; that is, edited cells can be identified even in a large background of unedited cells. Observed editing efficiency can be improved up to 80% or more. Isolating, incubating, editing, and normalization of cell colonies or cherry picking of cell colonies leads to 2-250×, 10-225×, 25-200×, 40-175×, 50-150×, 60-100×, or 5400× gains in identifying edited cells over prior art methods and allows for the generation of arrayed or pooled edited cells comprising genome libraries. Additionally, the instruments, modules and methods may be leveraged to create iterative editing systems to generate combinatorial libraries, identify rare cell edits, and enable high-throughput enrichment applications to identify editing activity.

FIG. 1A shows simplified flow charts for three exemplary methods described herein, two for enrichment 100a and 100b, and one for selection 100c. Looking at FIG. 1A, method 100a begins by transforming cells 110 with the components necessary to perform nucleic acid-guided nuclease editing. For example, the cells may be transformed simultaneously with separate engine and editing vectors; the cells may already be expressing the nuclease (e.g., the cells may have already been transformed with an engine vector or the coding sequence for the nuclease may be stably integrated into the cellular genome) such that only the editing vector needs to be transformed into the cells; or the cells may be transformed with a single vector comprising all components required to perform nucleic acid-guided nuclease genome editing, which is advantageous when employing curing and recursive rounds of editing.

A variety of delivery systems can be used to introduce (e.g., transform or transfect) nucleic acid-guided nuclease editing system components into a host cell 110. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Ser. No. 16/147,120, filed Sep. 28, 2019; Ser. No. 16/147,353, filed Sep. 28, 2019; 16/426,310, filed May 30, 2019; and Ser. No. 16/147,871, filed Sep. 30, 2018; and U.S. Pat. No. 10,323,258, issued Jun. 18, 2019, all of which are incorporated by reference in their entirety. If the screening/selection module is one module in an automated multi-module cell editing system, the cells are likely transformed in an automated cell transformation module.

After the cells are transformed with the components necessary to perform nucleic acid-guided nuclease editing, the cells are isolated (e.g., singulated) 120; that is, the cells are diluted (if necessary) and plated, arrayed, or otherwise arranged so that cells are sequestered or separated from one another. Isolation can be performed by, e.g., plating cells at a dilution that separates cells (and the clonal colonies that grow) from one another. In some embodiments, isolation itself may act as a partition; in other embodiments, cells are diluted so that they may be flowed into wells where the cells are deposited at an average of one-half cell per well (that is, using solid walls as a partition); in still other embodiments, the cells may be sequestered or separated from one another in emulsion droplets (that is, using liquid "walls" as a partition); in yet another exemplary embodiment, the cells may be sequestered or separated from one another in a three-dimensional gel (that is, e.g., suspending the cells in liquid, causing the liquid to solidify into a gel) or by puncture into an agar; and in another embodiment the cells may be arrayed on functionalized "islands" on a substrate (that is, using "virtual wells", e.g., separated culture areas to culture cells). In addition to selecting a mode for isolated growth, one may select a mode for attaining isolated growth such as random (i.e., Poisson) loading of cells using dilution to assure isolation, or one may use specific cell loading or placement techniques (i.e., super-Poisson) for loading cells.

Once the cells have been isolated in 100a, the cells are grown into colonies of terminal size 130; that is, the colonies arising from the isolated cells are grown into colonies to a point where cell growth has peaked and is normalized or saturated for both edited and unedited cells. In the embodiment 100a shown in FIG. 1A, the editing components are under the control of a constitutive promoter; thus, editing begins immediately (or almost immediately) upon transformation. However, in other embodiments such as shown in 100*b*, at least the guide nucleic acid may be under the control of an inducible promoter, in which case editing may be induced after, e.g., a number of cell doublings. Colony normalization may be effected by physical constraint (e.g., well walls or functionalized islands) or nutrient constraint (e.g., as occurs on solid agar). At this point, the terminal-size colonies are pooled 140 by, e.g., scraping colonies from a solid agar plate, or pooling colonies in liquid medium from wells. Again, because isolation overcomes growth bias from unedited cells or cells exhibiting fitness effects as the result of edits made, isolation alone enriches the total population of cells with cells that have been edited; that is, isolation and, preferably, normalization (e.g., growing colonies to terminal size) allows for high-throughput screening of edited cells.

The method 100*b* shown in FIG. 1A is similar to the method 100*a* in that cells of interest are transformed 110 with the components necessary to perform nucleic acid-guided nuclease editing. As described above, the cells may be transformed simultaneously with both the engine and editing vectors, the cells may already be expressing the nuclease (e.g., the cells may have already been transformed with an engine vector or the coding sequence for the nuclease may be stably integrated into the cellular genome) such that only the editing vector needs to be transformed into the cells, or the cells may be transformed with a single vector comprising all components required to perform nucleic acid-guided nuclease genome editing. Further, if the enrichment/selection module is one module in an automated multi-module cell editing instrument, cell transformation may be performed in an automated transformation module (e.g., a flow-through electroporation device) as described in relation to FIGS. 3C and 3D below.

After the cells are transformed with the components necessary to perform nucleic acid-guided nuclease editing, the cells are isolated 120; that is, the cells are diluted (if necessary) and plated, arrayed, or otherwise arranged so that cells are sequestered or separated from one another. Isolation can be performed by, e.g., plating cells at a dilution that separates cells (and the colonies that grow) from one another, diluting cells so that they may be flowed into wells where the cells are deposited at an average of one-half cell per well, or the cells may be sequestered or separated from one another in emulsion droplets, or on functionalized islands. Further, depending on the device or method used to isolated cells, the cells can be loaded according to a Poisson or super-Poisson distribution.

Once the cells have been isolated 120, the cells are allowed to grow to, e.g., between 2 and 50, or between 5 and 40, or between 10 and 30 doublings, establishing clonal colonies 150. After colonies are grown, editing is induced 160 by, e.g., activating one or more inducible promoters that control transcription of one or more of the components needed for nucleic acid-guided nuclease editing, such as transcription of the gRNA or nuclease. Once editing is induced 160, many of the edited cells in the clonal colonies die due to the double-strand DNA breaks that occur during the editing process and are not repaired; however, in a percentage of edited cells, the genome is edited and the double strand break is properly repaired. These edited cells then start growing and re-establish colonies and the colonies are allowed to grow to terminal size 170. Once the colonies have reached terminal size, the colonies are pooled 140. Thus, methods 100*a* and 100*b* both allow for enrichment of edited cells. Method 100*c* is drawn to selection of edited cells by cherry picking edited colonies.

The method 100*c* shown in FIG. 1A is similar to the methods 100*a* and 100*b* in that cells of interest are transformed 110 with the components necessary to perform nucleic acid-guided nuclease editing. As described above, the cells may be transformed simultaneously with both the engine and editing vectors, the cells may already be expressing the nuclease (e.g., the cells may have already been transformed with an engine vector or the coding sequence for the nuclease may be stably integrated into the cellular genome) such that only the editing vector needs to be transformed into the cells, or the cells may be transformed with a single vector comprising all components required to perform nucleic acid-guided nuclease genome editing. Further, if the enrichment/selection module is one module in an automated multi-module cell editing instrument, cell transformation may be performed in an automated transformation module as described in relation to FIGS. 3C and 3D below.

After the cells are transformed with the components necessary to perform nucleic acid-guided nuclease editing, the cells are isolated 120; that is, the cells are diluted (if necessary) and plated, arrayed, or otherwise arranged so that cells are sequestered or separated from one another. Isolation can be performed by, e.g., plating cells at a dilution that separates cells (and the colonies that grow) from one another, diluting cells so that they may be flowed into wells where the cells are deposited at an average of one-half cell per well, or the cells may be sequestered or separated from one another in emulsion droplets, or on functionalized islands. Further, depending on the device or method used to isolate cells, the cells can be loaded according to a Poisson or super-Poisson distribution.

Once the cells have been isolated 120, the cells are allowed to grow to, e.g., between 3 and 200, or between 5 and 150, or between 10 and 100 doublings, establishing clonal colonies 150. Again, after colonies are grown, editing is induced 160 by, e.g., activating one or more inducible promoters that control transcription of one or more of the components needed for nucleic acid-guided nuclease editing, such as transcription of the gRNA or nuclease. Once editing is induced 160, many of the edited cells in the clonal colonies die due to the double strand DNA breaks that occur during the editing process that are not repaired; however, in a percentage of edited cells the genome is edited and the double strand break is properly repaired. These cells in which the break is properly repaired then start growing and re-establish colonies and the colonies are allowed to grow until colonies form. In method 100*c*, the growth of the cell colonies is monitored via, e.g., size, OD, the concentration of cell metabolites, etc. to identify colonies of cells where growth lags behind other, more rapidly-growing colonies. Once small colonies have been identified, the small colonies optionally can be selected or cherry picked 180 to directly select for edited cells. In one alternative to this general method 100*c*, an inducible promoter is not used and editing is not induced; instead, editing essentially begins immediately upon transformation. Still, cells are allowed to establish colonies, and the slow-growing colonies can be cherry picked.

Another alternative exemplary workflow, cells are transformed first with the editing vector, then isolated by, e.g., growing colonies and picking or by going directly into, e.g., microtiter plates. Once isolated, the cells are allowed to build cell mass to survive cutting. At this juncture, the engine vector (expressing the nuclease) is transformed into the cells and the cells are allowed to grow as described above and pooled, or, alternatively, cherry picked. Because isolation eliminates the bias of non-editing cells and fitness effects from editing as well as effects from differential editing rates, isolation alone enriches for editing cells such that all isolated colonies—not only the slow-growing colonies—may be pooled into an "enriched" edited pool of cells.

Figure 1B:
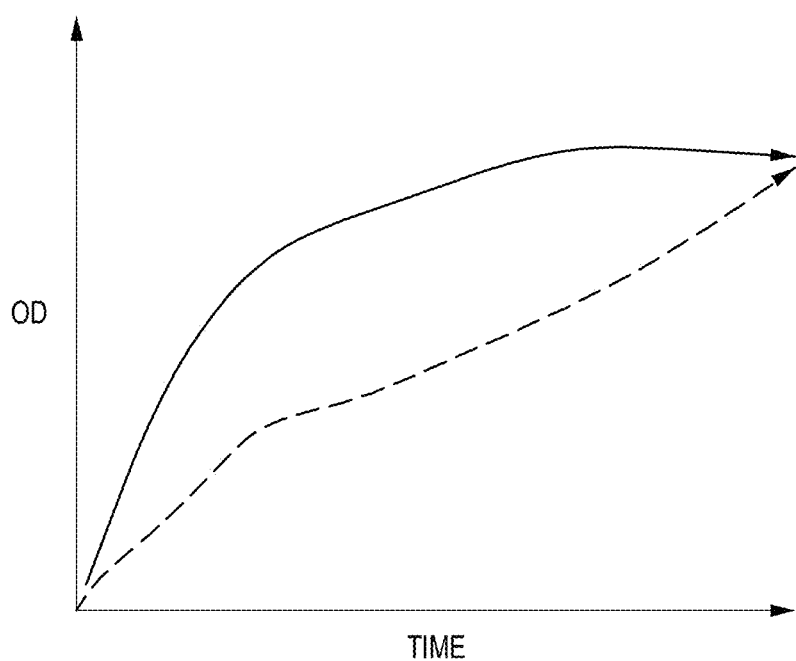
FIG. 1B is a plot of optical density vs. time showing the growth curves for edited cells (dotted line) and unedited cells (solid line).

FIG. 1B is a plot of optical density versus time showing the growth curves for edited cells (dotted line) and unedited cells (solid line). Note that there is a growth lag for edited cells; however, eventually the growth of the edited cells catches up with the growth of the unedited cells. Herein, this phenomenon is referred to as growth of cell colonies to "terminal size", "saturation", or "normalization."

Exemplary Workflows for Screening and Selection

The methods described herein provide enhanced observed editing efficiency of nucleic acid-guided nuclease editing methods, and improvement in enrichment (including high-throughput enrichment) and selection for cells whose genomes have been properly edited. The exemplary workflows described herein employ the concept of isolation. Isolation overcomes the growth bias in favor of unedited cells—and the fitness effects of editing (including differential editing rates)—thus allowing all cells "equal billing" with one another. Further, selection (e.g., cherry picking) may be performed by taking advantage of the growth lag of colonies of edited cells in comparison to colonies of non-edited cells. The result of the methods is that even in nucleic acid-guided nuclease systems where editing is not optimal (such as in systems where non-canonical PAMs are targeted), there is an increase in the observed editing efficiency; that is, edited cells can be identified even in a large background of unedited cells. Observed editing efficiency can be improved up to 98%.

Figure 2A:
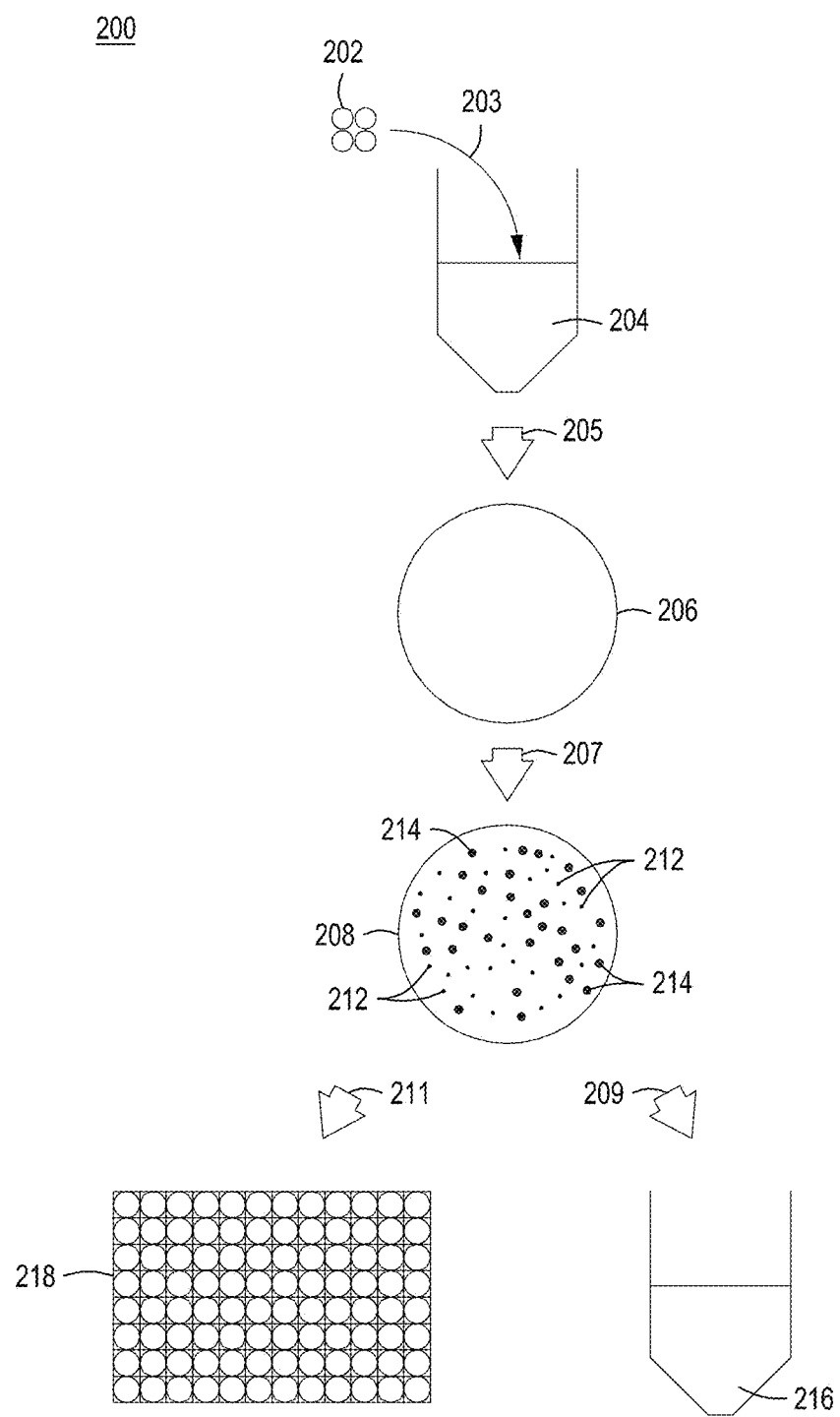
FIGS. 2A-2K depict workflows for enriching, and optionally identifying and selecting edited cells after nucleic acid-guided nuclease genome editing where the workflows are performed in an automated module, and, optionally, as part of an automated instrument.

FIGS. 2A-2K depict improved workflows for enrichment and, in some embodiments, identifying and selecting edited cells after nucleic acid-guided nuclease genome editing. FIG. 2A depicts a protocol for high-throughput selection using colony morphology to identify edited cells. In edited cells, cell viability is compromised in the period after editing begins. The workflow depicted in FIG. 2A takes advantage of the growth lag in colonies of edited cells to identify edited cells. In some embodiments, the colony size of the edited cells is 20% smaller than colonies of non-edited cells once the colonies of edited cells begin to appear to the naked eye. In some aspects, the colony size of the edited cells is 30%, 40%, 50%, 60%, 70%, 80% or 90% smaller than the colonies of non-edited cells once the colonies of edited cells begin to appear to the naked eye. In many embodiments, the colony size of the edited cells is 30-80% smaller than colonies of non-edited cells, and in some embodiments, the colony size of the edited cells is 40-70% smaller than colonies of non-edited cells once the colonies of edited cells begin to appear to the naked eye.

In FIG. 2A, a library or collection of editing vectors 202 is introduced 203 (e.g., electroporated) into cultured cells 204 that comprise a coding sequence for a nuclease under the control of a constitutive or inducible promoter, 1) contained on an "engine plasmid" (most often along with a selectable marker) that has already been transformed into the cells; 2) integrated into the genome of the cells being transformed; or 3) contained or located on the editing vector 202 (e.g., a single vector system). The "introduction" of nucleic acids into the cells (e.g., transformation or transfection) may be accomplished manually before transferring the cells to an enrichment and selection module, or "introducing" the nucleic acids into the cells may take place in an automated transformation module as described below in relation to FIGS. 3A-3D. The editing vectors 202 comprise a donor nucleic acid editing sequence, a PAM-altering sequence (most often a sequence that disables the PAM or spacer at the target site in the genome), a coding sequence for a gRNA, and a selectable marker. In some embodiments, the gRNA, donor nucleic acid, and optional PAM-altering sequence are all contained on an editing cassette, and are all under the control of (e.g., are operably linked to) a single promoter; preferably, the single promoter is an inducible promoter.

At step 205, the transformed cells are diluted and plated (e.g., isolated) onto selective medium 206 (in this case nutrient agar) that selects for both the engine and editing vectors if two plasmids are used (e.g., medium containing chloramphenicol (engine) and carbenicillin (editing)), or a selective medium 206 for the single combined engine/editing plasmid if a single plasmid system is used. Once plated, the cells are grown 207 at 30° C. for approximately 2-12 hours so that the cells grow to form colonies on plate 208. Once colonies appear, there are large 214 and small 212 colonies. The large colonies 214 likely represent cells that have not been edited due to, e.g., an inactive gRNA or nuclease. The colonies with small size 212 are likely colonies of cells that have been edited as the double-strand cuts caused by active editing without repair are largely toxic to the cells. This toxicity results both in cell death in the edited colonies, as well as a lag in growth for the edited cells that do survive but must repair and recover following editing. Here, the small colonies (edited cells) are cherry picked 211 and are arrayed on a 96-well plate 218. Cells in the 96-well plate 218 can be cultured, and aliquots from this 96-well plate 218 can be sequenced and edited colonies identified. This 96-well plate may be kept as a "cell hotel" or cell repository, and once cells that have been properly edited are identified by, e.g., sequence verification, one can retrieve the cells with the desired edit from "cell hotel" plate 218.

Alternatively, small colonies 212 may be picked and pooled 209 for additional rounds of editing (without sequence verification), as the population of cells that goes through the next round of editing has enriched and selected for edited cells from the first round of editing by virtue of isolation and cherry picking. The method depicted in FIG. 2A employs isolation and cherry picking and thus allows for a high-throughput method to identify cells that have a high likelihood to be edited. Screening out a large proportion of the cells with non-functional gRNAs or nucleases allows for identification of edited cells more readily. It has been determined that removing growth rate bias via isolation (screening) and growing colonies to terminal size improves the observed editing efficiency by up to 2×, 3×, 4×, 5×, 6×, 7×, 8×, 9×, 10× or more over conventional methods where isolation is not employed, and further that cherry picking (e.g., selection) colonies using the methods described herein increases by 1.5×, 1.75×, 2.0×, or 2.5× or more the observed editing efficiency due to isolation only. The combination of isolation and cherry-picking results in an increase of up to 98% in observed editing efficiency. Example 1 below provides materials and methods for this embodiment.

An additional feature of the method depicted in FIG. 2A is that in some embodiments at least the gRNA is under the control of an inducible promoter, particularly in bacterial systems and in other cells that divide rapidly. In this instance, isolation is carried out in the same manner (e.g., here, plating 205); however, instead of growing the cells for 12 hours with continuous editing, the cells are allowed to double approximately to between 2 and 200, or between 5 and 150, or between 10 and 100 times to form clonal colonies, then editing is induced by, e.g., temperature or inducer chemicals (e.g., sugars, antibiotics). This method is discussed in relation to FIG. 1 at method 100c. After induction of editing, the cells are allowed to grow to continue to establish colonies. Again, once colonies appear, there are large 214 and small 212 colonies. The large colonies 214 represent cells that have not been edited due to, e.g., an inactive gRNA or nuclease (e.g., "escapees"). The colonies with small size 212 are likely colonies of cells that have been edited as the double-strand cuts caused by active editing that are not repaired are largely toxic to the cells. This toxicity results both in cell death for many of the cells in the edited colonies, as well as a possible lag in growth for the edited cells that do survive but must repair and recover following editing. The small colonies (edited cells) may be cherry picked 211 and are arrayed on a 96-well plate 218.

Figure 2B:
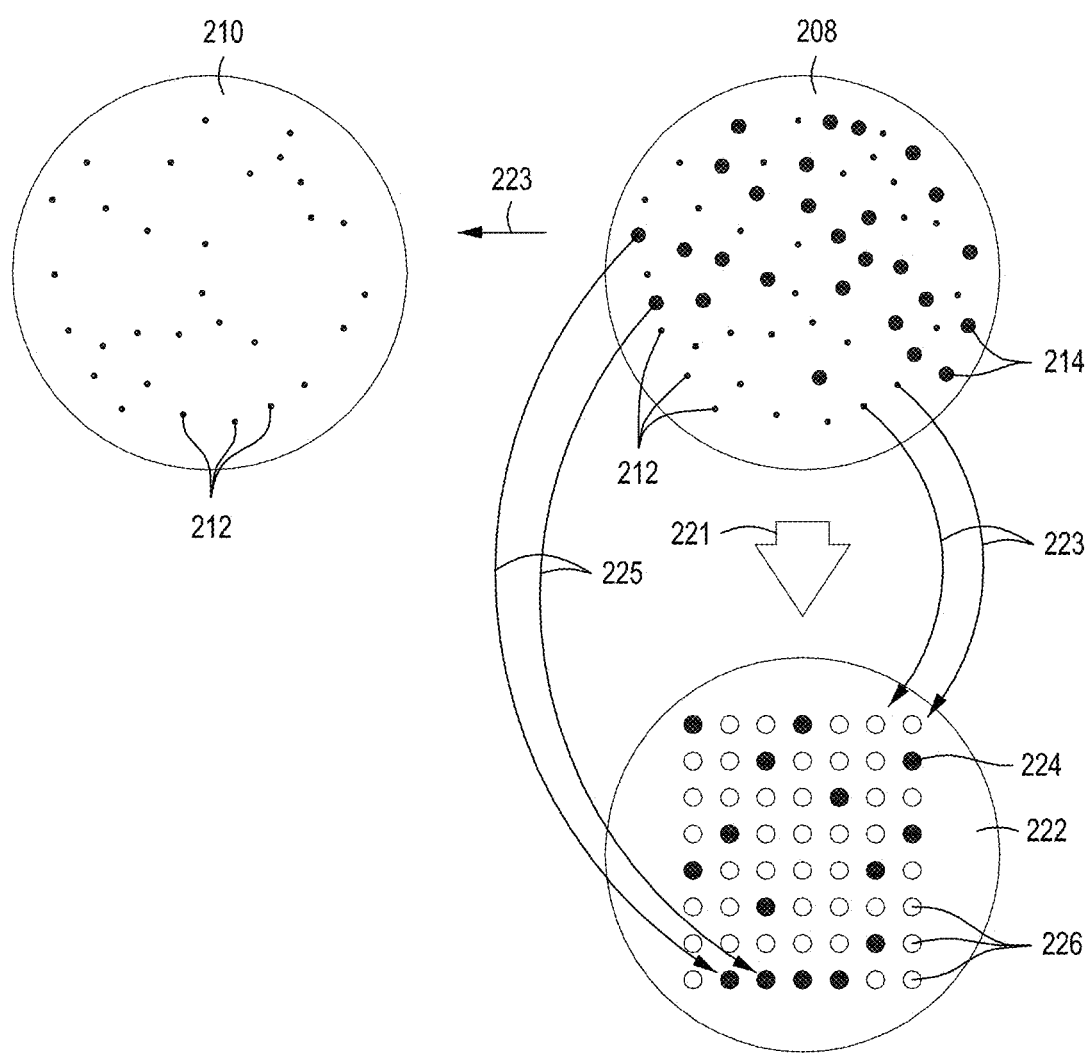

The modules implementing the workflow described in FIG. 2A—as well as the workflows in FIGS. 2B-2I—may employ "off the shelf" liquid handling instrumentation such as that sold by Opentrons (OT-2™ system, Brooklyn, N.Y.); ThermoFisher Scientific (Versette™ system, Carlsbad, Calif.); Labcyte (Access™ system, San Jose, Calif.); Perkin Elmer (Janus™ system, San Jose, Calif.); Agilent Inc. (Bravo™ system, Santa Clara, Calif.); BioTek Inc. (Winoosky, Vt.); Hudson Inc. (Solo™ system, Springfield, N.J.); Andrew Alliance (Andrew™ system, Waltham, Mass.); and Hamilton Robotics (suite of tools, Reno, Nev.). Further, in workflow embodiments such as those depicted in FIGS. 2A and 2B, automated colony pickers may be employed, such as those sold by, e.g., TECAN (Pickolo™ system, Mannedorf, Switzerland); Hudson Inc. (RapidPick™, Springfield, N.J.); Molecular Devices (QPix 400™ system, San Jose, Calif.); and Singer Instruments (PIXL™ system, Somerset, UK). Further, colony growth on plates (such as shown in FIGS. 2A and 2B) can be monitored by automated devices such as those sold by JoVE (ScanLag™ system, Cambridge, Mass.) (also see Levin-Reisman, et al., Nature Methods, 7:737-39 (2010)). Cell growth for, e.g., mammalian cells may be monitored by, e.g., the growth monitor sold by IncuCyte (Ann Arbor, Mich.) (see also, Choudhry, PLos One, 11(2): e0148469 (2016)).

Figure 2C:
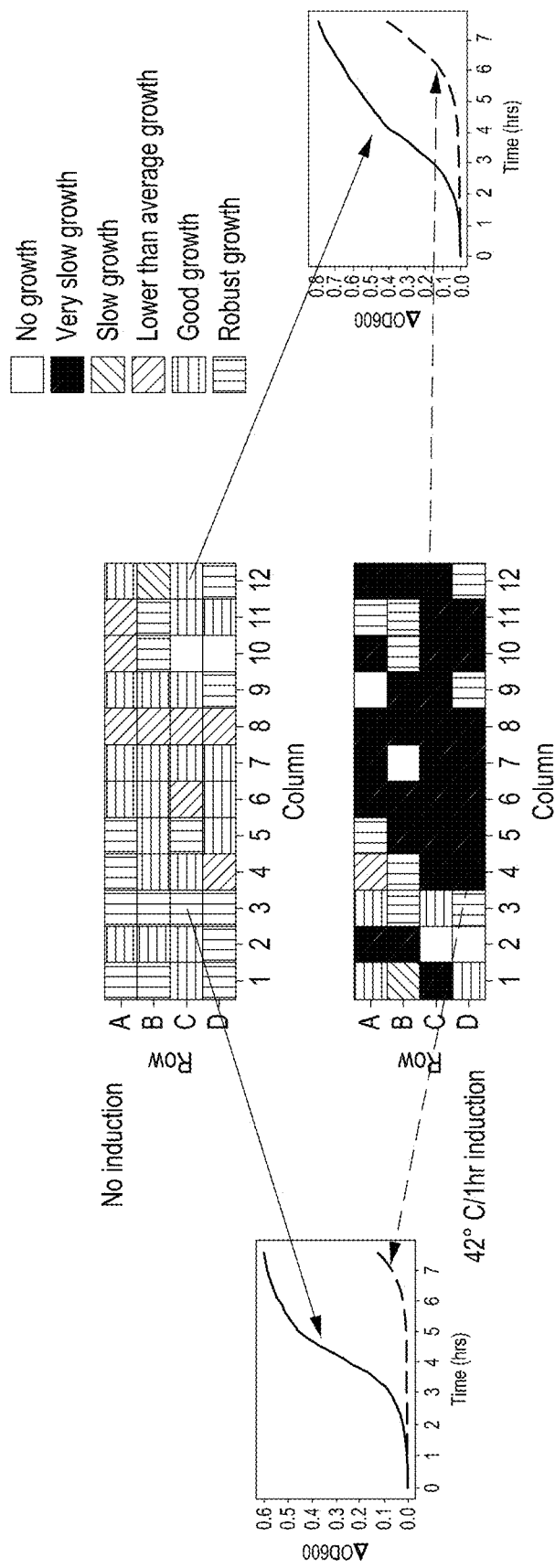
Figure 2D:
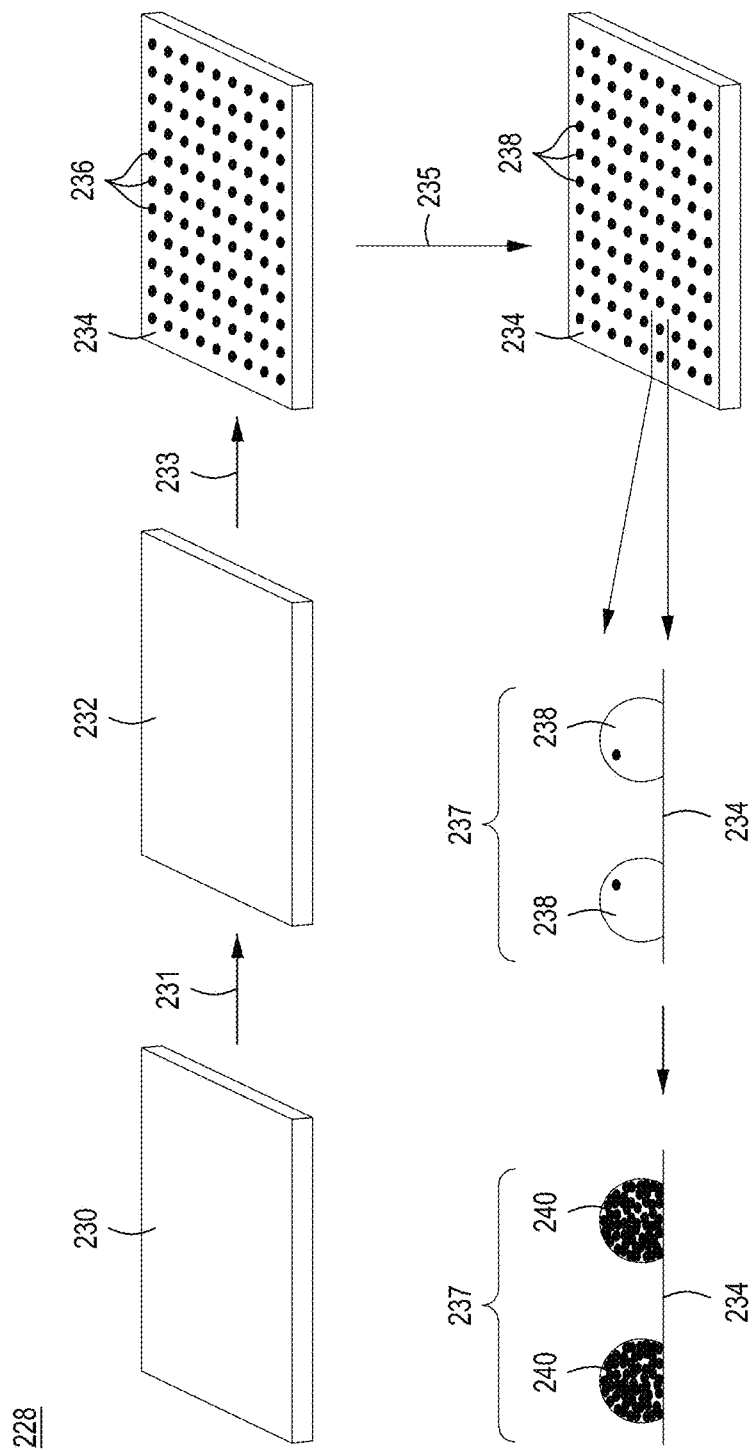
Figure 2E:
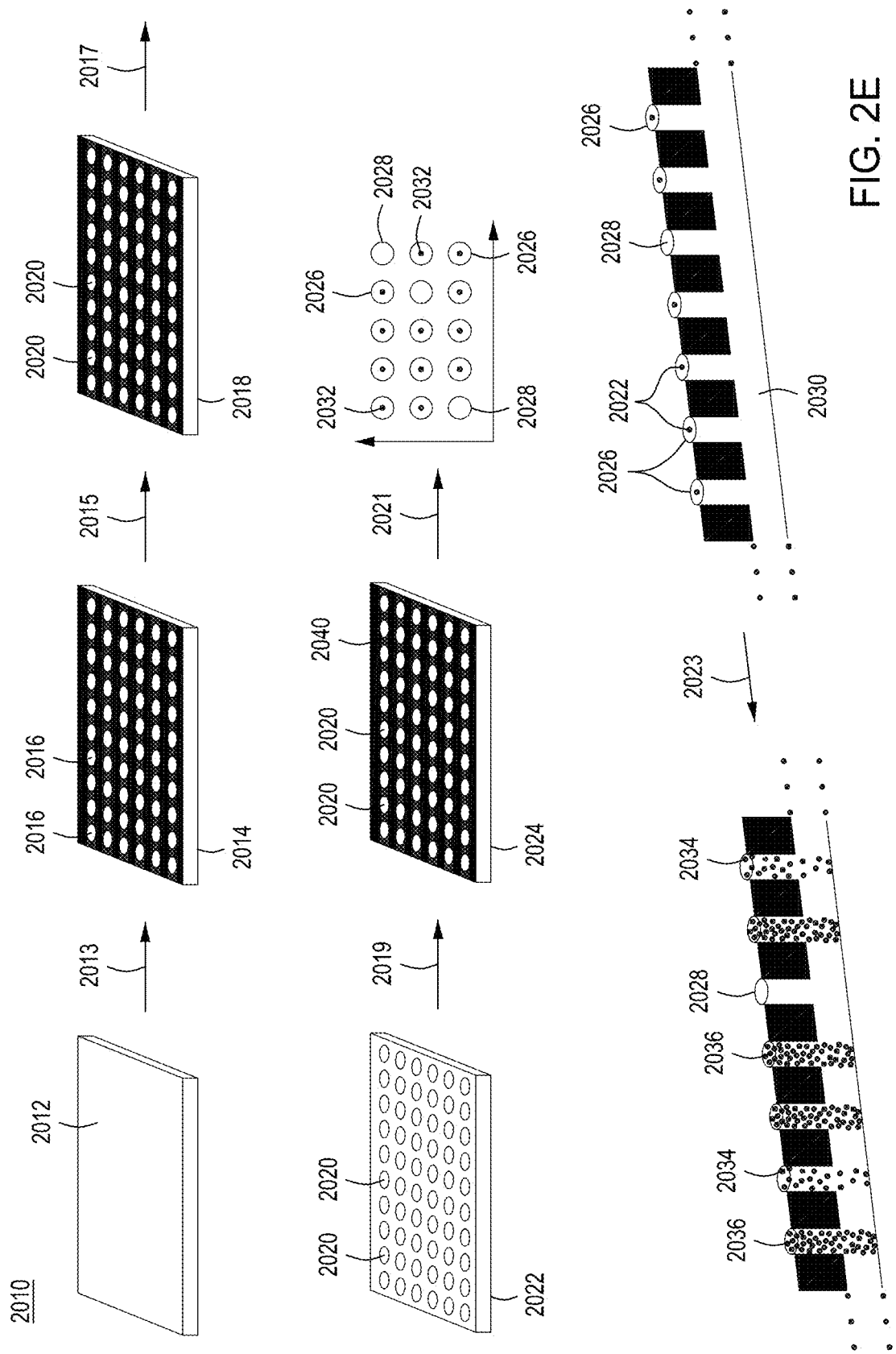
Figure 2F:
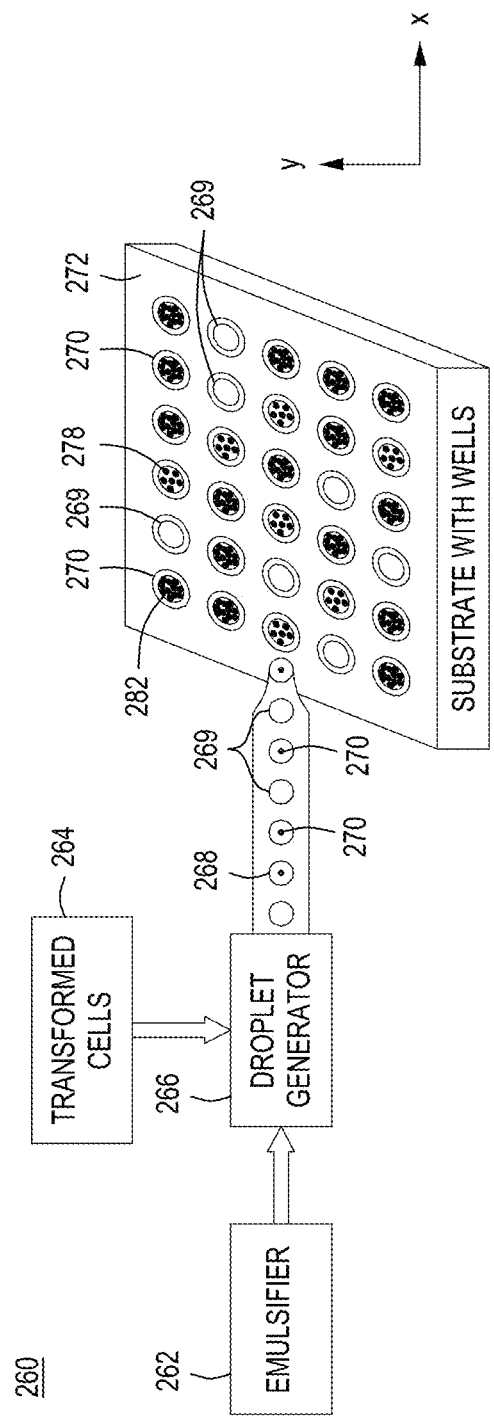
Figure 2G:
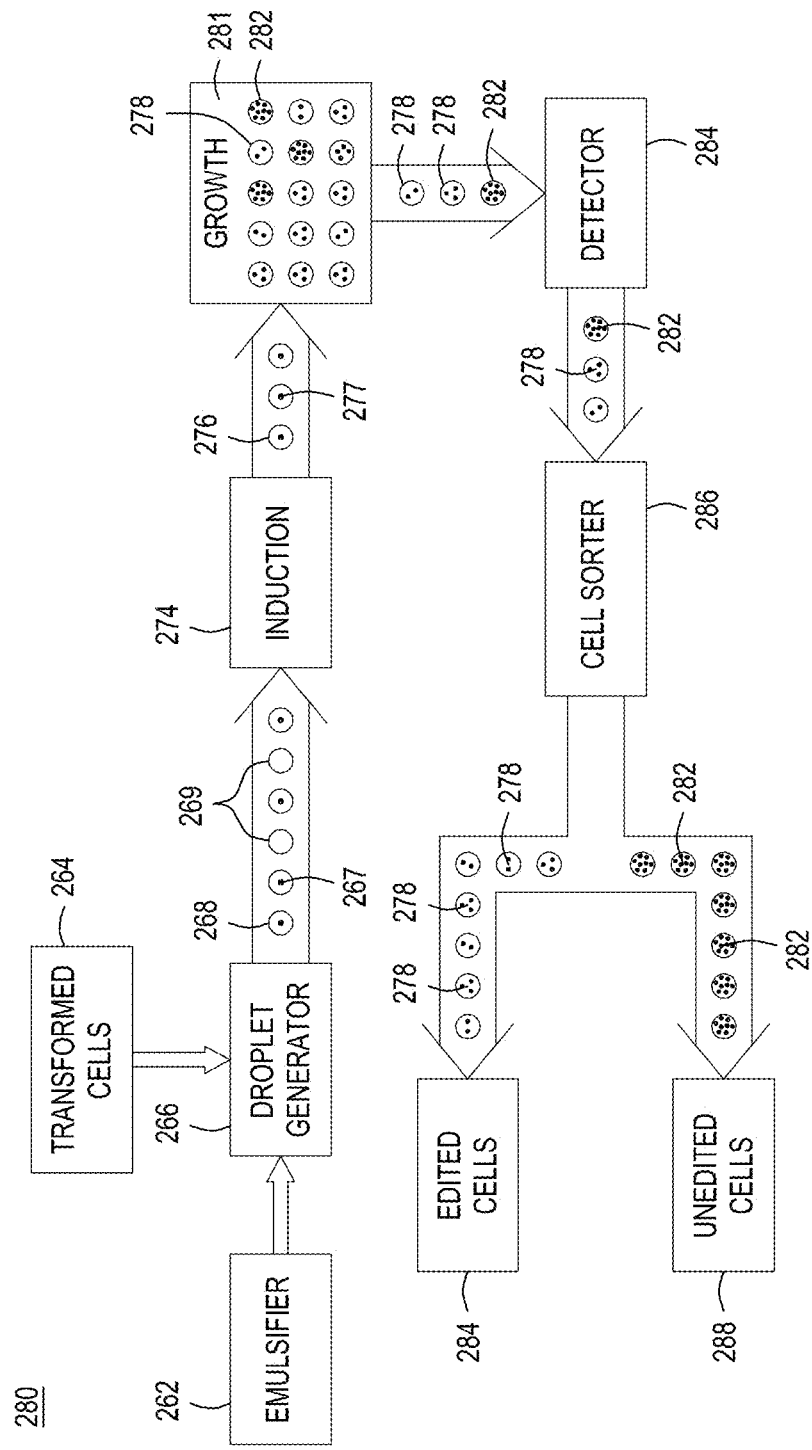

While the method for selecting for edited cells using cell growth as a proxy for editing has been described herein in the context of measuring colony size of cell colonies on a agar plate (such as in FIGS. 2A and 2B), the optical density (OD) of growing cell colonies, such as in a microtiter plate or other substrate with wells or functionalized regions, a series of tubes, or in droplets may be measured instead (as described in relation to FIGS. 2C and 2G). Additionally, other cell growth parameters may be measured in addition to or instead of cell colony size or OD, particularly if the growth parameters allow a simple readout by colorimetric (or other optically-detectable) methods. For example, spectroscopy using visible, UV, or near infrared (NIR) light allows monitoring the concentration of nutrients and/or wastes in the cell culture. Moreover, spectroscopic measurements may be used to quantify multiple chemical species simultaneously.

For example, cell proliferation assays can monitor various parameters of cell growth and functioning. One common exemplary method for assessing cell proliferation is a colorimetric assay based on DNA content in cells. New DNA synthesis provides a precise marker that may be multiplexed with other cellular markers like mitochondrial function or cell morphology. Other colorimetric assays include the BrdU, EdU, MTT, XTT, WST-1, Ki67, CFSE, Live/Dead, Trypan Blue, or β-gal assays. BrdU incorporates into newly-synthesized DNA and is detected using anti-BrdU antibody. EdU is similar to BrdU but EdU employs detection without antibodies. MTT, a yellow tetrazole, is reduced to purple formazan in living cells. The XTT assay is based on the premise that actively respiring cells convert XTT to a water-soluble, orange-colored formazan. In the WST-1 assay, WST-1 is cleaved to a soluble formazan by a complex cellular mechanism that occurs at the cell surface. For the Ki67 assay, antibodies to Ki67 nuclear protein can be used to measure cellular proliferation. In yet another colorimetric assay, CFSE, a non-fluorescent cell permeable dye, is cleaved by intracellular esterases resulting in green fluorescence. The live/dead cell assay employs simultaneous fluorescence staining of viable and dead cells using calcein-AM and propidium iodide, which stain viable and dead cells, respectively. In the trypan blue assay, dye exclusion is based on the concept that viable cells do not take up impermeable dyes but dead cells are permeable. In the β-gal assay, beta-galactosidase enzyme activity is detectable in senescent cells that do not proliferate.

Alternatively, hyperspectral imaging, such as in the near-infrared range, may be employed (see Feng, et al., Scientific Reports, 7:15934 (2017)), or coherent anti-stokes scattering hyperspectral imaging may be employed (see, e.g., Masia, et al., Anal. Chem., 90:3775-85 (2018)). Near-infrared imaging also may be applied to nonsymmetric chemical species. Conversely, symmetric chemical species can be readily quantified using Raman spectroscopy. Many critical metabolites, such as glucose, glutamine, ammonia, and lactate have distinct spectral features in the IR, such that they may be easily quantified. The amount and frequencies of light absorbed by the sample can be correlated to the type and concentration of chemical species present in the sample. Each of these measurement types provides specific advantages. FT-NIR provides the greatest light penetration depth and so can be used for thicker samples so that they provide a higher degree of light scattering. FT-mid-IR (MIR) provides information that is more easily discernible as being specific for certain analytes as these wavelengths are closer to the fundamental IR absorptions. FT-Raman is advantageous when the interference due to water is to be minimized. Other spectral properties can be measured via, e.g., dielectric impedance spectroscopy, visible fluorescence, fluorescence polarization, or luminescence. Additionally, sensors for measuring, e.g., dissolved oxygen, carbon dioxide, pH, and/or conductivity may be used to assess the rate of cell growth.

FIG. 2B depicts additional detail of the exemplary embodiment shown in FIG. 2A. FIG. 2B shows high-throughput selection 220 using colony morphology to identify and cherry pick edited cells. As described above, in edited cells cell viability is compromised in the period after editing is induced. The present method takes advantage of cell isolation and the growth lag in colonies of edited cells to identify edited cells. In FIG. 2B, transformed cells are diluted and plated on medium containing arabinose 208 and grown for a period of time at, e.g., 30° C. Thus, the workflow shown in FIG. 2B, like the workflow shown in FIG. 2A, employs dilution of cells to achieve isolation, as opposed to wells, droplets, or functionalized islands. After enough time for colonies to begin to form (e.g., approximately between 2 and 50, or between 5 and 40, or between 10 and 30 cell doublings), editing is induced by, e.g., activating an inducible promoter. In this model system, a library of editing oligos each configured to inactivate galK is exemplified. Successful editing of cells with the galK editing oligos results in white (open circles)—as opposed to red (filled circles)—colonies when plated on MacConkey agar. Colonies are allowed to grow and both small 212 and large 214 colonies result.

Colonies from plate 208 are picked 221 and arrayed on a second plate 222 containing McConkey agar, e.g., a medium to select for successful editing of galK. Note that picking small colonies 212 from the first plate results primarily in edited cells 226 (white colonies) and—at a much lower frequency—some cells in which the gRNA or nuclease is inactive 224 (red colonies, shown here as filled-in circles). Confirmation of colonies in which the gRNA is inactive is shown by picking 225 large colonies 214 from the first plate and plating them on the second plate 222 where these cells result in red colonies 224 when grown on MacConkey agar supplemented with galactose as the sole carbon source. Thus, using small and large colony morphology as a proxy for edited and non-edited cells, respectively, provides a high throughput and facile screening method for edited cells. The methods depicted in FIGS. 2A and 2B employ both isolation and cherry-picking strategies; and as noted in relation to FIGS. 2A and 2B, at least the gRNA (and also, in some embodiments, the nuclease) may be under control of an inducible promoters thus employing induction in addition to isolation and cherry picking. When induction is employed, clonal colonies of isolated cells are allowed to grow for several to many doublings before editing is induced to give the cells to be edited a chance to establish a colony before enduring the toxic effects of editing.

In an alternative embodiment, FIG. 2B also depicts replica plating 223 of plate 208; however, only the small colonies 212 are picked and plated on plate 210. Selective replica plating of only select, small colonies is accomplished by, in one embodiment, monitoring the growth of colonies 212 and 214 on plate 208 (such as, e.g., by the automated JoVE ScanLag™ device (Cambridge, Mass.)) and communicating the coordinates of the small colonies 212 to a 3D printer where a specialized replicator is fabricated (printed) and then used to transfer only the selected colonies (in this case the small colonies 212) to plate 210. Three dimensional printers are widely-available off-the-shelf from, e.g., Makergear (Beachwood, Ohio); DigiKey Electronics (Minnesota); 3D Systems (Rock Hill, S.C.); EnvisionTEC (Dearborn, Mich.); ExOne (St. Clairsville, Ohio); and StrataSys (Eden Prairie, Ill.). See Examples 1-3 below for methods and materials that may be used in this embodiment.

FIG. 2C shows the growth profiles of randomly-picked colonies of transformed cells where the gRNA is under transcriptional control of an inducible promoter. Cells were picked from an agar plate and grown up in selective medium (selecting for both the engine and editing vectors) overnight in a 96-well microtiter plate format. An aliquot of the well content of a parent microtiter plate (e.g., cell hotel or repository) was then transferred to two replica daughter microtiter plates, for example using an automatic replicator such as the QRep replicators from Molecular Devices (San Jose, Calif.) or the pin replicators from Phenix Research Products (Chandler, N.C.). One microtiter plate received no induction (top), and the other microtiter plate received gRNA induction via the pL inducible promoter for 1 hour at 42° C. (bottom). The well maps show the relative OD at 6 hours; the full growth curves are shown for reference. The replica wells represent growth observed from the same cassette design with or without gRNA induction. While the majority of the wells for the no-induction plate show varying but normal growth profiles, the induced plate shows that a large fraction of the gRNA designs is still active when induced, indicated by a large lag phase (very slow cell growth indicated by filled-in squares) before the cells reach exponential growth. That is, the actively-editing cells have reduced viability due to DNA damage such that many cells in the colonies die off, and those edited cells that do survive may grow slowly to begin with as the cellular machinery works to repair the edit and, in any case, the edited colonies take some amount of time to "catch up" with their unedited counterparts. Thus, FIG. 2C depicts an embodiment of edited cell selection using induction, solid-wall wells, isolation, and targeted, super-Poisson loading.

Note that in this embodiment, importantly, putative lethal edits can be identified. For example, if in the uninduced plate there is cell growth, but after induction of editing there is no growth (that is, not even lagging growth), it is possible that the particular edit was lethal to the cell. This concept can be tested by going back to the uninduced plate (e.g., the cell hotel or cell repository) and an aliquot of the cell colony corresponding to the putative lethal edit can be retrieved and tested.

Figure 2H:
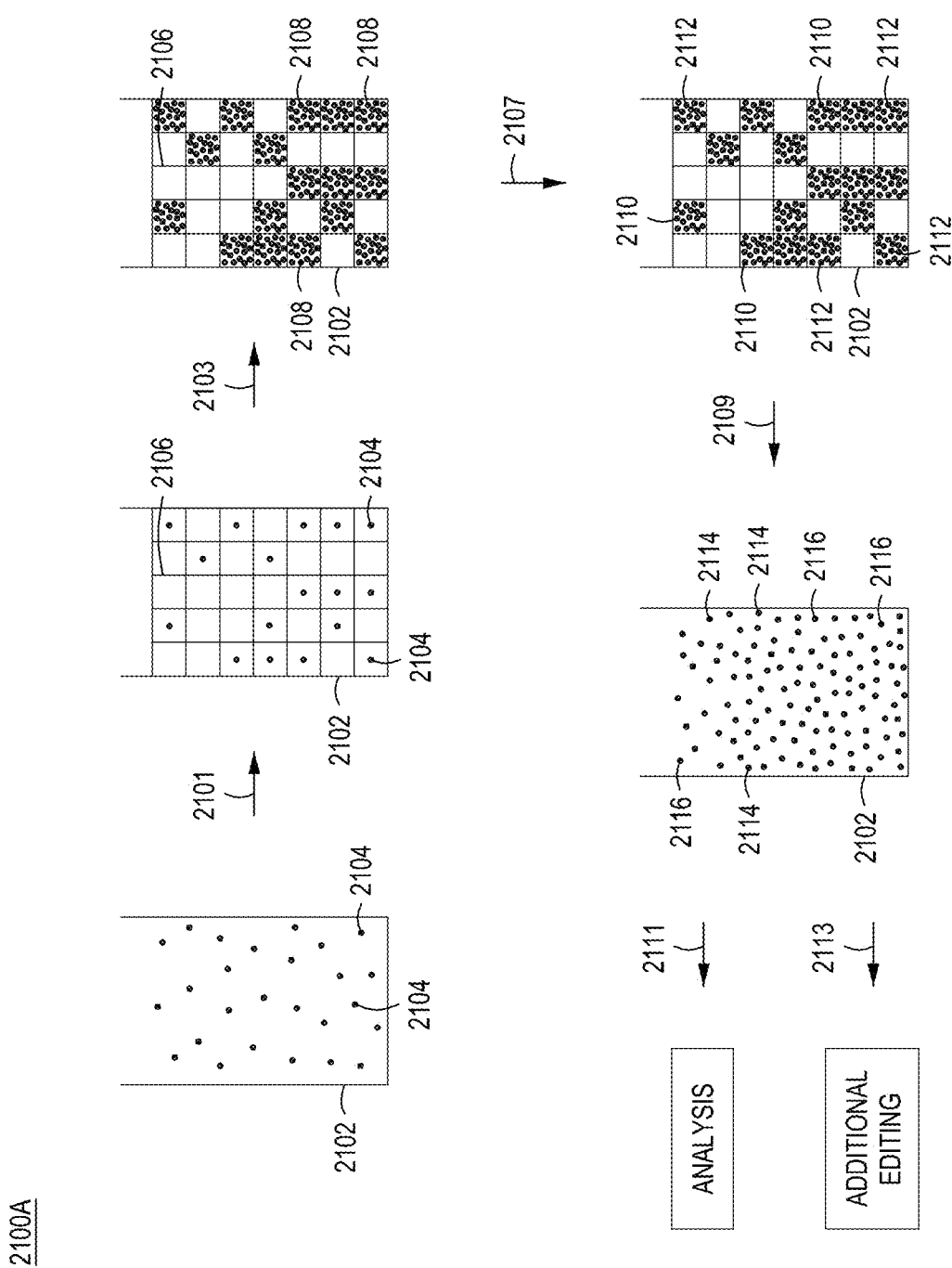
Figure 2I:
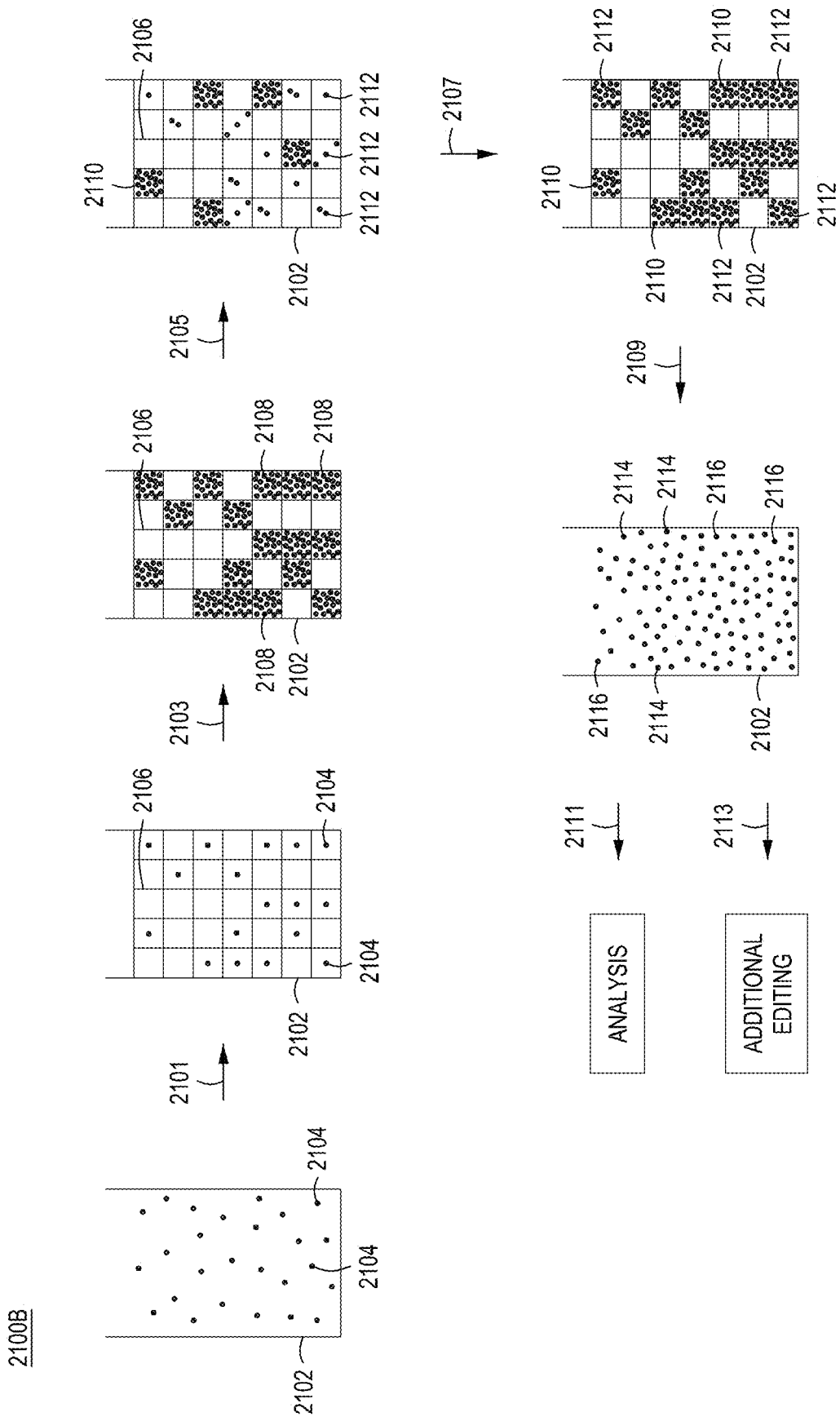
Figure 2J:
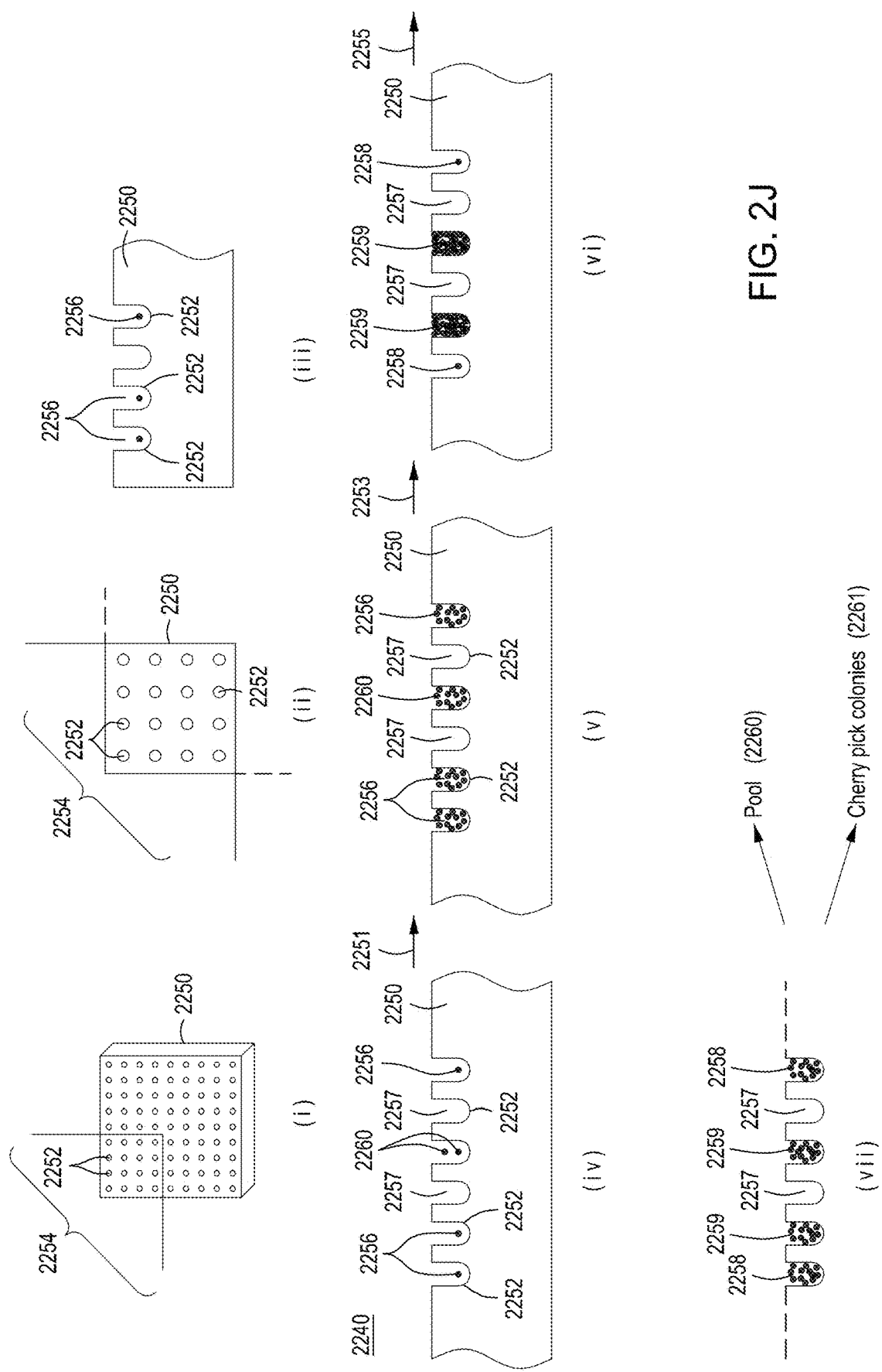
Figure 2K:
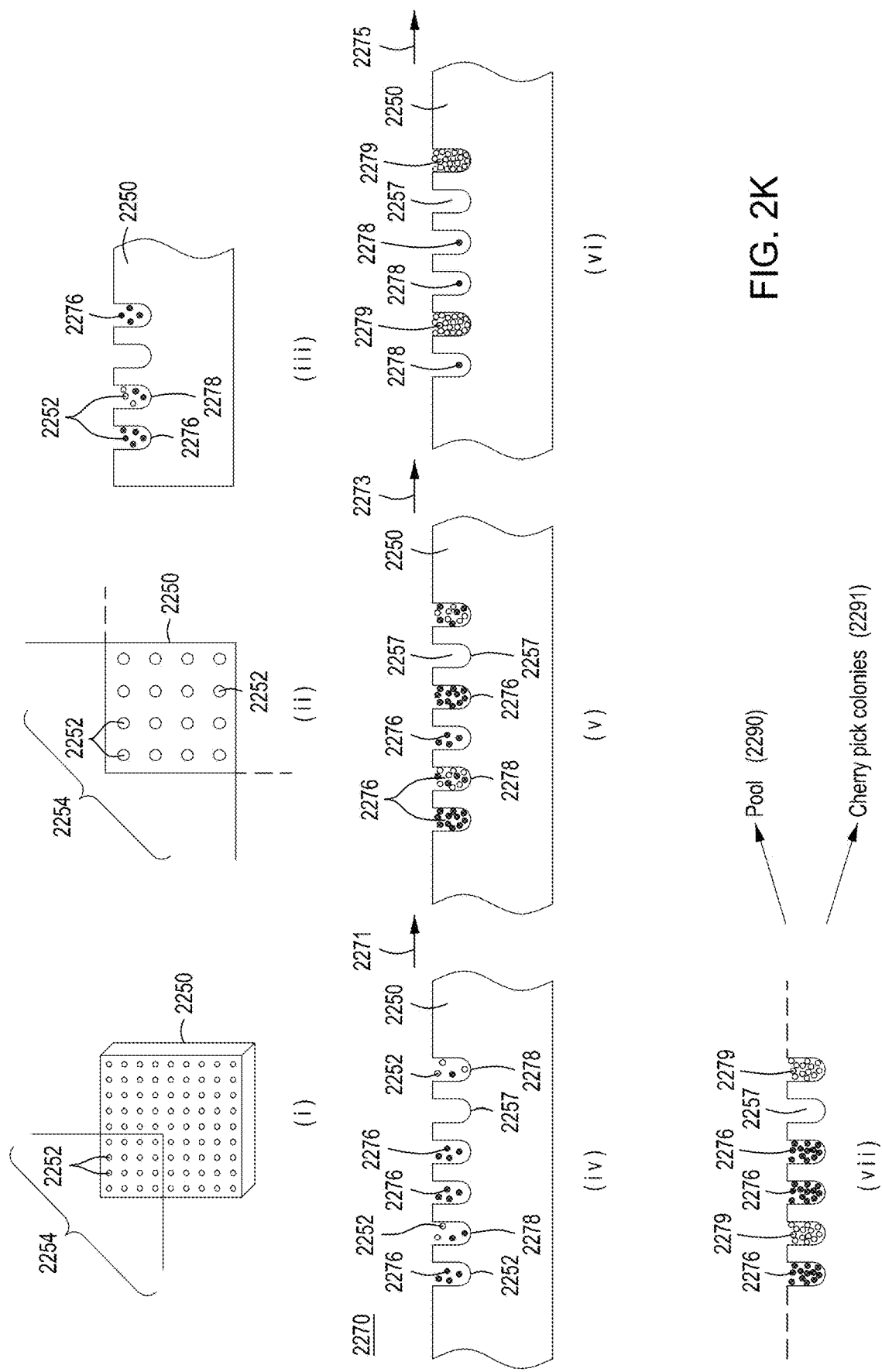

Further, though the embodiment workflow depicted in FIG. 2C describes use of 96-well plates, smaller or larger well plates can be used. It is contemplated that for induced multiplex editing (that is, where two to several edits are made to cells simultaneously), larger-well plates are needed to allow large initial colony formation (outgrowth) before editing. Again, because the double-strand cuts caused by active editing are largely toxic to the cells if not repaired, initial outgrowth of the cell colonies before editing is required—and in this case, the more edits initiated per cell, the more toxic the editing process will be. As described above, the toxicity causes both cell death in the edited colonies as well as a lag in growth for the edited cell colonies as the cells that do survive must repair and recover and catch up to the colonies of unedited cells following editing. Thus, allowing for a greater outgrowth of cells before initiating a multiplex editing process increases the odds of survival of multiplex-edited cells. This same principle can be applied to cell colonies grown on agar plates (as shown in FIGS. 2A and 2B) or in 3D agarose space (as shown in FIGS. 2H and 2I), where the colonies are plated less densely, and the colonies are allowed to grow to a bigger size. Similarly, if wells are used (as shown in FIGS. 2J and 2K), the wells are bigger to support larger cell colony growth; and if features are used to support cell growth (as shown in FIGS. 2D and 2E), the features are made larger to support growth of larger colonies. See Example 2 below for methods and materials for determining OD in plates according to this embodiment.

FIG. 2D depicts yet another workflow 228 for screening and, optionally, selecting edited cells. In FIG. 2D, a substrate 230, such as, e.g., a polystyrene or glass substrate is prepared for deposition of functionalized islands on which to grow cells. If the substrate is glass, the glass surface is prepared by oxidation, followed by deposition of polystyrene 231, where the substrate 232 is then oxidized again to render the polystyrene temporarily hydrophobic. If the substrate 230 is polystyrene, it need only be oxidized 231 to render the polystyrene hydrophobic. Once hydrophobic, collagen islands or patches are printed 233 on the hydrophobic substrate. In certain embodiments, the collagen printed may be ordinary, non-crosslinked collagen or cross-linked collagen, such as methylacrylated type-I collagen. Collagen is used routinely for cell culture, including as a matrix for growing cells for transplantation. Non-crosslinked collagen deposed on a hydrophobic substrate is stable at room temperature up to five months.

The collagen may be deposited by biologically-applied deposition and assembly devices and systems known in the art, including systems that perform direct writing, microstamping, photolithography, electroprinting, extrusion, and inkjet deposition. For example, see the system sold commercially by Arrayjet (Roslin, UK). See also Bishop, et al., Genes & Diseases, 4(4):185-95 (2017); Zheng, et al., Anal. Biochem., 410(2):171-76 (2011); and Saunders and Derby, International Materials Review, 59(8):430-48 (2014). Regardless of the device used, the collagen is printed to form "islands" 236 on hydrophobic substrate 234, then cells are flowed 235 across substrate 236 at a dilution where there is a Poisson distribution of cells on the islands (that is, such that each island has one or no cells, and the likelihood that any one island has more than one cell is low). Flowing the cells over substrate 234 results in islands of collagen with one 238 or no cell attached. A close up 237 of substrate 234 with collagen islands with one cell attached is shown. Once the cells are loaded onto the collagen islands or patches, the substrate is submerged in growth medium and the cells are allowed to proliferate into normalized colonies 240. Because the areas between the islands are hydrophobic and not functionalized with a surface upon which cells can grow, the cells are isolated (e.g., isolated) on substrate 234.

In this embodiment, the cells can be grown to terminal (normalized) growth such that the cells that have been edited and the cells that have not been edited ultimately grow to equivalent sizes. Once the cell colonies have been grown to terminal size, the cells can be pooled for further research or editing. As with other embodiments, this method enriches (screens) for edited cells by eliminating the bias from non-editing cells and fitness effects from editing; that is, isolation alone enriches for editing cells such that all isolated colonies—not only the slow-growing colonies—may be pooled into an "enriched" edited pool of cells. Alternatively, in this embodiment and particularly in bacterial systems, at least the gRNA is under the control of an inducible promoter. In this instance, isolation is carried out in the same manner (e.g., here, Poisson loading of the collagen islands); however, instead of growing the cells to colonies of terminal size, the cells are allowed to double to approximately between 2 and 200, or between 5 and 150, or between 10 and 100 times to form clonal colonies, then editing is induced by heating the substrate (e.g., for temperature-induced editing) or flowing chemicals over the substrate (e.g., sugars, antibiotics for compound-induced editing). After induction of editing, the cells are allowed to grow to continue to establish colonies, and the growth of the colonies can be normalized and the cells pooled or cell growth is monitored such that slow growing colonies can be identified and selected.

FIG. 2E depicts an exemplary substrate and workflow 2010 for isolating and selecting cells using collagen pillars isolated from one another by polyethylene glycol (PEG). In a first step, a substrate 2012 (glass or plastic) is coated with a layer of chromium, and a photolithographic mask is used to expose a pattern in the chromium 2013. Substrate 2014 thus comprises a chromium mask with features 2016 (circular areas) where the collagen will be deposited. The size of the features may vary with the type of cells that are to be isolated and cultured. For example, if bacterial cells are being cultured, the features may be on the order of 2-5 µm or larger, if yeast cells are being cultured, the features may be on the order of 3-8 µm or larger, and if mammalian cells are being cultured, the features may be on the order of 100-300 µm or larger. The chromium mask is deposited at a depth appropriate for the height of the collagen pillars. At step 2015, collagen is deposited as features 2020 on substrate 2018. In some aspects, the collagen is photo-crosslinkable collagen, such as methacrylated type-I collagen (CMA).

At step 2017, the chromium mask is removed leaving only the pillars of collagen 2020 on substrate 2022. At step 2019, polyethylene glycol (PEG) is deposited between the pillars on substrate 2024, forming an isolating barrier between the pillars 2020. At step 2021, a close up of substrate 2024 in a top view and side view depicts a substrate 2030 where cells in an appropriate dilution are flowed over the substrate 2030 such that some pillars 2026 will have a cell 2032 deposited on them and some pillars 2028 will not. Finally, in step 2023 the cells are allowed to grow and to populate the collagen pillars, growing down and into the pillars. In some pillars 2036, the cells populate the pillars quickly, whereas on other pillars the cells populate more slowly. Also seen are pillars where cells were not deposited 2028.

In some aspects of this embodiment, the cell colonies are grown to terminal size and then all cells are harvested. As described above, because isolation eliminates the bias of non-editing cells and fitness effects from editing, isolation alone enriches for editing cells such that all isolated colonies—not only the slow-growing colonies—may be pooled into an "enriched" edited pool of cells. In this aspect, editing does not need to be induced. Yet in another aspect of this embodiment, the rate of cell growth can be monitored—for example fast growing colonies 2036 can be distinguished from slow growing colonies 2034—and the slow growing colonies can be selected for further study or another round of editing. Further, it should be clear to one of ordinary skill in the art given the discussion herein that other methods and materials may be used to fabricate pillars or wells on a substrate, where collagen may be deposited to grow colonies of isolated cells. Thus, the workflow depicted in FIG. 2E employs isolation achieved by Poisson loading onto features isolated from one another by PEG (or other compound that does not allow cell growth). In this embodiment, isolation and normalization alone may be employed, or isolation and cherry picking may be employed.

FIGS. 2F and 2G depict workflows for identifying edited cells after nucleic acid-guided nuclease genome editing where cells are isolated into droplets in an emulsion and may then be selected (e.g., cherry picked). Cells are arrayed and sorted dynamically in droplets in a flow stream. A stream of an aqueous solution (cells in a cell growth medium) are introduced into a stream of carrier fluid, such as a non-polar solvent or oil, where droplets of the aqueous solution are formed. The concentration of the cells should be dilute enough that most of the droplets contain no more than a single cell with only a small statistical chance that a droplet will contain two or more cells. Dilution is effected to ensure that for the large majority of measurements, the level of reporter (colorimetric reporter or cellular density) corresponds to a single, starting cell in a droplet.

The flow stream in the main channel is typically, but not necessarily, continuous and may, in some embodiments, be stopped and started, reversed or change speed. The pressure of the flows of the carrier fluid and the aqueous solution—as well as the pressure at the droplet generation region—can be regulated by, e.g., adjusting the pressure on the carrier and aqueous fluid reservoirs. By controlling the pressure difference between the oil and aqueous sources at the droplet generation region, the size and periodicity of the droplets generated may be regulated. Alternatively, one or more valves may be coincident to either the droplet generation region or the aqueous feed to control the flow of solution. The fluids used in the exemplary modules depicted in FIGS.

2F and 2G may contain additives such as surfactants that reduce surface tension. Exemplary surfactants include Tween, Span, fluorinated oils, and other agents that are soluble in oil relative to water.

In FIG. 2F, a workflow 260 isolates cells into droplets, which are then arrayed in wells. First, a stream of an emulsifier such as a non-polar solvent (e.g., decane) or oil is flowed from reservoir 262 toward a droplet generator 266 (e.g., a T-junction, cross-junction, or flow focusing device) where the flow of the emulsifier meets the flow of transformed cells in an aqueous medium from a reservoir 264. In an automated multi-module cell processing instrument, the transformed cells may have been transferred to reservoir 264 from a transformation module (e.g., a flow-through electroporation device) as described in relation to FIGS. 3A-3D below. At the junction in the droplet generator 266 where the flow of the nonpolar solvent and the flow of the cells in aqueous medium meet, droplets 268 are formed. The concentration of the transformed cells in the aqueous medium, again, is controlled so each droplet comprises an average of one-half cell or less, such that the majority of droplets comprises either one cell or no cells. Droplets 268 each comprise a cell 270, and droplets 269 comprise no cells. The droplets proceed through a conduit until they are dispensed, one at a time, into a substrate with wells 272 containing medium. Each well in the substrate should comprise a single droplet, some droplets 268 containing a cell, and some droplets 269 without a cell.

If the editing system transformed into the cells is not an inducible system, editing may begin as soon as the necessary nucleic acid-guided nuclease editing components are delivered to and transcribed—and in some cases, translated—in the cell. That is, the editing process commences at or shortly after transformation. Alternatively, once transformation takes place, the transformed cells in reservoir 264 (and proceeding through the droplet generation device) may be cooled to prevent or slow the initiation of editing until the cells are isolated or until the cells are deposited into a well in substrate 272. The isolated cells can be grown to establish colonies, and this growth can be measured, e.g., by a spectrophotometer (not shown).

Alternatively, one or more components of the nucleic acid-guided nuclease editing system (e.g., at least the gRNA and in some embodiments the nuclease as well) may be under the control of an inducible promoter. Thus, in one embodiment, the wells of the substrate may comprise, in addition to medium, a compound that activates an inducible promoter driving the gRNA and/or nuclease, such that editing of the cellular genome is not initiated until the cell droplets are deposited into a well in the substrate 272. In yet another alternative, one or more components of the nucleic acid-guided nuclease editing system (e.g., at least the gRNA and also the nuclease) may be under the control of an inducible promoter where activity of the promoter is induced by an increase in temperature. In this instance, instead of an inducing compound in the medium in the wells, the substrate with the wells 272 is heated to an appropriate temperature to activate the inducible promoter(s). In this embodiment, the isolated cells may be grown for a period of time (e.g., 2-200 doublings) before the inducible promoters are activated. Once activated, editing commences for a period of time, then the edited cells are allowed to grow into colonies where the growth of the colonies is monitored by, e.g., the automated cell colony size monitors described above and marketed by IncuCyte (Ann Arbor, Mich.).

Further, arraying of cells in single-cell isolation as contemplated by the workflow as described in relation to FIG. 2F may be performed with "off the shelf" instrumentation, such as that sold by CellenONE (Lyon, France); Cytena (Freiberg, Germany); Cell Microsystems (the Cellraft™ technology, Research Triangle Park, N.C.); Galt, Inc. (San Carlos, Calif.); and 10× Genomics (Pleasanton, Calif.). (See also Zhang, et al., Scientific Reports, 7:41192 (2017).) Thus, the workflow depicted in FIG. 2F employs both "liquid walls" and "solid walls" for isolation and may be used to isolate and grow the isolated cells to colonies of terminal size (enrich) only, or, optionally, editing may be induced and cell growth monitored so that selection (e.g., cherry picking) may be employed.

FIG. 2G depicts another module 280 for identifying edited cells after nucleic acid-guided nuclease genome editing where cells are isolated into droplets. In FIG. 2G like FIG. 2F, a stream of an emulsifier such as a non-polar solvent (e.g., decane) or oil is flowed from reservoir 262 toward a droplet generator 266 (e.g., a T-junction, cross-junction, or flow focusing device) where the flow of the emulsifier meets the flow of transformed cells in an aqueous medium that originated in reservoir 264. At the junction in the droplet generator 266 where the flow of the nonpolar solvent and the flow of the cells in aqueous medium meet, aqueous droplets 268 are formed and transported in the nonpolar solvent (carrier phase). The concentration of the transformed cells in the aqueous medium is controlled such that an average of one-half cell is contained in each droplet; thus, the majority of droplets comprises either one cell (e.g., 268) or no cells (e.g., 269). The droplets proceed through a conduit until they reach an induction module 274.

An induction module is used if transcription of one or more components of the nucleic acid-guided nuclease editing system (e.g., at least the gRNA) is inducible. For example, if one or more components of the nucleic acid-guided nuclease editing system (e.g., one or both of the gRNA and nuclease) is under the control of an inducible promoter that is induced by a chemical compound (e.g., arabinose, rhamnose), the induction module may dispense the induction compound into the droplet, by, e.g., droplet merger. (See, e.g., U.S. Pat. No. 9,347,059 to Saxonov; U.S. Pub. No. 2011/0053798 to Hindson, et al.; and U.S. Pub. No. 2008/0014589 to Link, et al.)

Alternatively, at least the gRNA is under the control of an inducible promoter where activity of the promoter is induced by an increase in temperature, such as a pL promoter system. In this instance, instead of adding an inducing compound, the temperature of the droplets in the induction module is raised to an appropriate temperature to activate the inducible promoter(s). In cells with active gRNAs 276 editing is induced. In cells with inactive gRNAs (or other editing machinery that is inactive) 277, editing does not take place.

Once editing is initiated in the droplets, the droplets are may be transported to a growth module 281 which can maintain the droplets at the higher temperature initially to continue the editing process. Once time for editing passes, the temperature is reduced to allow the cells to grow into colonies. Colonies of edited cells, which grow slowly in relation to colonies of unedited cells, are shown at 278, and unedited cells, which grow more quickly, are shown at 282. After growth in growth module 281, the droplets containing the cells can be transported to a detector 284, where, e.g., droplets with densely grown cell colonies 282 (unedited cells) are distinguished from droplets with less densely grown cell colonies 278 (edited cells). Once each droplet is assessed for growth, the droplets proceed to the cell sorter 286 where the cells with densely grown cell colonies 282 are shuttled into a conduit leading to reservoir 288 and cells with less densely grown colonies 278 are shuttled into a conduit leading to reservoir 287. The detector measures cell growth by, e.g., a spectrophotometer (not shown) to detect optical density or the readout of a colorimetric assay. In some embodiments, the detector 284 and cell sorter 286 may be combined into a single instrument.

The detector can be any device or method for interrogating a cell as it passes through a detection region. Typically, cells (or the droplets in which the cells are contained) are sorted according to one or more predetermined characteristics that are directly or indirectly detectable, and the detector is adapted to detect the characteristic. One detector of particular use in the modules shown in FIGS. 2G and 2H is an optical detector, such as a microscope or spectrophotometer, which may be coupled to a computer and/or other image processing or enhancement device, to process images. Cells can be sorted by the optical density of cells within the droplet, or by intensity of a colorimetric assay that correlates to cell growth, such as the cell proliferation assays described above. There is no limit to the kind and/or number of cellular characteristics that may be identified or measured as long as the readout for the characteristic(s) can be sufficiently identified and detected to distinguish—e.g., as a proxy for growth of—putatively edited cells from putative nonedited cells.

The cells are analyzed and sorted based on the intensity of a signal detected as the droplets pass through a detection region or window. The signal may be collected by a microscope or spectrophotometer and measured by a photo multiplier tube. A computer digitizes the signal and controls the flow via, e.g., valve action or electroosmotic potential. Cells having a level of reporter (or OD) below a selected threshold or within a selected range are diverted into a predetermined outlet or reservoir. For example, a cell-sorting device may comprise a spectrophotometer where the optical density of each cell is read as it passes by the light beam. The optical signal is collected and projected onto a cathode of a photomultiplier tube. Optionally, part of the light may be directed onto a charge-coupled device (CCD) camera for imaging. As the cells pass by the spectrophotometer detection window, the cells are directed to conduits that lead to the reservoirs that collect edited cells and non-edited cells or empty droplets depending on voltage-potential settings. The voltages on the electrodes are provided by a pair of amplifiers powered by a power supply. The photomultiplier tube signal is digitized by a processor, which also controls the high voltage settings. In addition to optical density or colorimetric assays, cell colonies may be sorted by density; for example, see Nam, et al., BioMicrofluidics, 6:024120 (2012); and Norouzi, et al., PLoS One, 12(7):e0180520 (2017). Additionally, there are commercial single cell sorting devices available, for example from nanocellect Biomedical, Inc. (San Diego, Calif.); NanoCell Inc. (Mountain View, Calif.); and Silicon Biosystems (the DEParray™ technology, Castel, Italy).

FIG. 2H is an exemplary workflow 2100a for optimizing the observed presence of edited cells after nucleic acid-guided nuclease genome editing that may be performed in an automated isolation/growth/editing/normalization module, and, optionally, as part of an automated multi-module cell editing instrument. First, transformed cells 2104 are suspended at a pre-determined density in medium plus alginate (solidifying agent) in a vessel 2102 containing, optionally, antibiotics or other selective compounds to allow only cells that have been transformed with both the engine vector and editing vector (if two vectors are used) or a combined engine/editing vector to grow. Again, in some embodiments two vectors, an engine vector and an editing vector, are used in some embodiments a single vector comprising all necessary exogenous components for nucleic acid-guided nuclease editing is used. The medium used with depend, of course, on the type of cells being edited—e.g., bacterial, yeast or mammalian. For example, medium for bacterial growth includes LB, SOC, M9 Minimal medium, and Magic medium; medium for yeast cell growth includes TPD, YPG, YPAD, and synthetic minimal medium; and medium for mammalian cell growth includes MEM, DMEM, IMDM, RPMI, and Hanks.

Natural polymers and proteins able to form hydrogels are alginate, chitosan, hyaluronan, dextran, collagen, and fibrin; synthetic examples of synthetic polymers and proteins able to form hydrogels include polyethylene glycol, poly(hydroxyethyl methacrylate, polyvinyl alcohol, and polycaprolactone. Alginate has been used as a preferred solidifying agent in the methods described herein due to a number of advantageous properties. Alginates are polysaccharides that consist of linear (unbranched) 1,4 linked residues of D-mannuronic acid and its C5-epimer D-guluronic acid. Alginates have a high affinity for alkaline earth metals and ionic hydrogels can be formed in the presence of divalent cations except Mg+2. Chelation of the gel-forming ion occurs between two consecutive residues in the alginate chain, and an intermolecular gel network is formed as a result of a cooperative binding of consecutive residues in different alginate chains. Advantageously, ionically-gelled alginate can be dissolved by treatment with chelating agents for divalent cations such as citrate and ethylenediaminetetraacetic acid (EDTA) or hexametaphosphate. A 2% (w/v) alginate in medium was found to properly isolate cells; however appropriate ranges for the percentage of alginate in a growth medium include 0.25% to 6% (w/v) alginate, or 0.5% to 5% (w/v) alginate, or 1% to 4% (w/v) alginate, or 2% to 3% (w/v) alginate. In addition, neither of the processes of solidifying and of re-liquefying the alginate/medium (described in more detail below) impact cell viability. Moreover, induction of editing by elevating the temperature of the bulk gel to 42° C. (described in more detail below) does not impact the integrity of the solidified medium or the segregation of the isolated clonal cell colonies.

The culture of mammalian cells using hydrogels has been performed to mimic the 3D cell environments found in tissue, allowing for more biologically-relevant cellular environments. As with tissue mimetics, in the context of mammalian cell editing alginates may be chemically functionalized to alter physiochemical and biological characteristics and properties so as to better bind and promote the growth of mammalian cells once the cells have been isolated in the solidified alginate medium. As cells do not have receptors that recognize alginate, proliferation and differentiation of some mammalian cells within an alginate hydrogen require signaling molecules and matrix interaction. For example, cell attachment peptides, especially the sequence RGD (arginine-glycine-aspartic acid), have been shown to improve cellular adaptability to matricies, as is the case with alginate. Using aqueous carbodiimide chemistry, alginate can be modified by covalently grafting peptide sequence to the alginate molecule. (For a comprehensive discussion of 3D cell culture in alginate hydrogels, see Andersen, et al., Microarrays, 4:133-61 (2015).) Alternatively, as described above, mammalian cells can be grown on beads where the beads are then suspended in the alginate medium.

Once the cells are suspended at an appropriate density, the alginate in the medium is solidified 2101 by, e.g., addition of CaCl$_2$ (described below in relation to Example 7). Note that some areas of the solidified alginate have no cells 2106 and some areas have one cell 2104. Next, the cells are allowed to grow 2103 for a pre-determined approximate number of doublings. Because the cells are fixed in three-dimensional space, the resulting colonies 2108 are fixed in three-dimensional space. The colonies are grown to terminal size 2107 (that is, edited and non-edited cell colony growth is normalized), sodium citrate is added 2109 to the medium such that the solidified medium/alginate re-liquifies and the cells from the colonies 2114, 2116 (comprising to edited and unedited cells, respectively) are suspended in liquid medium once again. Once the medium is re-liquified, the cells are recovered and subjected to analysis 2111 or are used in a second round of editing 2113. Again, because the combination of the processes of isolation and normalization overcomes growth bias from unedited cells or cells exhibiting fitness effects as the result of edits made, the combination of the processes of isolation and normalization alone enriches the total population of cells with cells that have been edited; that is, isolation and normalization (e.g., growing colonies to terminal size) allows for high-throughput enrichment of edited cells.

FIG. 2I is yet another exemplary workflow 2100 for optimizing the observed presence of edited cells after nucleic acid-guided nuclease genome editing that may be performed in an automated isolation/growth/editing/normalization module, and, optionally, as part of an automated multi-module cell editing instrument. FIG. 2I, unlike FIG. 2H, employs induction of transcription of the gRNA. First, transformed cells 2104 are suspended at a pre-determined density in medium plus alginate (solidifying agent) in a vessel 2102 containing, optionally, antibiotics or other selective compounds to allow only cells that have been transformed with both the engine vector and editing vector (if two vectors are used) or a combined engine/editing vector to grow. Again, in some embodiments a single vector comprising all necessary exogenous components for nucleic acid-guided nuclease editing is used. As described above, the medium used with depend, of course, on the type of cells being edited—e.g., bacterial, yeast or mammalian. For example, medium for bacterial growth includes LB, SOC, M9 Minimal medium, and Magic medium; medium for yeast cell growth includes TPD, YPG, YPAD, and synthetic minimal medium; and medium for mammalian cell growth includes MEM, DMEM, IMDM, RPMI, and Hanks.

Once the cells 2104 are suspended at an appropriate density, the alginate in the medium is solidified 2101 by, e.g., addition of CaCl$_2$ (described below in relation to Example 7). Next, the cells are allowed to grow for a pre-determined approximate number of doublings 2103. Because the cells are fixed in three-dimensional space, the resulting colonies are fixed in three-dimensional space. After a number of doublings, editing is induced 2105 and some of the cells in the colonies where editing takes place die as a result of double-stranded breaks in the genome that are not repaired. Once editing has taken place, the colonies are allowed to grow to terminal size 2107. Once the colonies grow to terminal size (that is, edited and non-edited cell colony growth is normalized), sodium citrate 2109 is added to the medium such that the solidified medium/alginate re-liquifies and the cells from the colonies are suspended in liquid medium once again. Because the combination of the processes of isolation and normalization overcomes growth bias from unedited cells or cells exhibiting fitness effects as the result of edits made, the combination of the processes of isolation and normalization alone enriches the total population of cells with cells that have been edited; that is, isolation, optional induction, and normalization (e.g., growing colonies to terminal size) allows for high-throughput enrichment of edited cells.

FIG. 2J depicts a solid wall device 2250 and a workflow for isolating cells in microwells in the solid wall device, where in this exemplary workflow at least the gRNA is optionally be under the control of an inducible promoter, particularly if editing in bacterial cells. At the top left of the FIG. (i), there is depicted solid wall device 2250 with microwells 2252. A section 2254 of substrate 2250 is shown at (ii), also depicting microwells 2252. At (iii), a side cross-section of solid wall device 2250 is shown, and microwells 2252 have been loaded, where, in this embodiment, Poisson or substantial Poisson loading has taken place; that is, each microwell has one or no cells, and the likelihood that any one microwell has more than one cell is low. Note wells 2256 have one cell loaded. At (iv), workflow 2240 is illustrated where substrate 2250 having microwells 2252 shows microwells 2256 with one cell per microwell, microwells 2257 with no cells in the microwells, and one microwell 2260 with two cells in the microwell. In step 2251, the cells in the microwells are allowed to double approximately 2-150 times to form clonal colonies (v), then editing optionally is induced 2253 by heating the substrate (e.g., for temperature-induced editing) or flowing chemicals under or over the substrate (e.g., sugars, antibiotics for chemical-induced editing) or by moving the solid wall device to a different medium, particularly facile if the solid wall device is placed on a membrane which forms the bottom of microwells 2252 (membrane not shown). Induction of editing is optional, however. If editing is not induced, editing begins, e.g., upon transformation of the editing "machinery" into the cell or shortly thereafter.

After optional induction of editing 2253, many cells in the colonies of cells that have been edited die as a result of the double-strand cuts caused by active editing and there is a lag in growth for the edited cells that do survive but must repair and recover following editing (microwells 2258), where cells that do not undergo editing thrive (microwells 2259) (vi). All cells are allowed to continue grow to establish colonies and normalize, where the colonies of edited cells in microwells 2258 catch up in size and/or cell number with the cells in microwells 2259 that do not undergo editing (vii). Once the cell colonies are normalized, either pooling 2260 of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 2258) are identified and selected 2261 (e.g., "cherry picked") resulting in even greater enrichment of edited cells.

In growing the cells, the medium used will depend, of course, on the type of cells being edited—e.g., bacterial, yeast or mammalian. For example, medium for bacterial growth includes LB, SOC, M9 Minimal medium, and Magic medium; medium for yeast cell growth includes TPD, YPG, YPAD, and synthetic minimal medium; and medium for mammalian cell growth includes MEM, DMEM, IMDM, RPMI, and Hanks. For culture of adherent cells, cells may be disposed on beads or another type of scaffold suspended in medium. Most normal mammalian tissue-derived cells—except those derived from the hematopoietic system—are anchorage dependent and need a surface or cell culture support for normal proliferation. In the rotating growth vial described herein, microcarrier technology is leveraged.

Microcarriers of particular use typically have a diameter of 100-300 μm and have a density slightly greater than that of the culture medium (thus facilitating an easy separation of cells and medium for, e.g., medium exchange) yet the density must also be sufficiently low to allow complete suspension of the carriers at a minimum stirring rate in order to avoid hydrodynamic damage to the cells. Many different types of microcarriers are available, and different microcarriers are optimized for different types of cells. There are positively charged carriers, such as Cytodex 1 (dextran-based, GE Healthcare), DE-52 (cellulose-based, Sigma-Aldrich Labware), DE-53 (cellulose-based, Sigma-Aldrich Labware), HLX 11-170 (polystyrene-based); collagen or ECM (extracellular matrix)-coated carriers, such as Cytodex 3 (dextran-based, GE Healthcare) or HyQ-sphere Pro-F 102-4 (polystyrene-based, Thermo Scientific); non-charged carriers, like HyQspheres P 102-4 (Thermo Scientific); or macroporous carriers based on gelatin (Cultisphere, Percell Biolytica) or cellulose (Cytopore, GE Healthcare).

The solid wall devices can provide populations of cells with varying edits and/or percentages of clonality. It has been determined that flowing medium over the retentate side surface of the SWIIN, e.g., a tangential or sheer flow across the top of the perforate member of the SWIIN, will flush off the tops ("muffin tops", see FIG. 9D) of the cell colonies over-growing the wells of the SWIIN without contaminating the wells containing other cells; i.e., depositing flushed cells in wells. In one embodiment, cells are allowed to grow to a desired state, for example when some of the colonies—fast-growing colonies, which are likely to be unedited cells—have over-grown the wells, then the "muffin tops" are flushed off. In a next round, the cells again are allowed to grow again to a desired state, for example when some or many more of the colonies have over-grown the wells, then the "muffin tops" are flushed off, and additional rounds of cell growth and flushing/collection can continue as desired. After a desired number of rounds of cell growth and collection, 1) the cells can be collected and pooled, 2) certain collections may be discarded (such as the first collection of cells which are more likely to be unedited cells) and the rest of the collections pooled, or 3) each round of collection may be kept separate and analyzed for clonality, percentage of edited cells, etc. This embodiment requires monitoring of cell growth by, e.g., imaging. as described in relation to FIG. 2G or 5I.

FIG. 2K depicts a solid wall device 2250 and a workflow for substantially isolating cells in microwells in a solid wall device, where in this workflow—as in the workflow depicted in FIG. 2J—optionally at least the gRNA and nuclease is under the control of an inducible promoter, particularly in bacterial systems. At the top left of the FIG. (i), there is depicted a solid wall device 2250 with microwells 2252. A section 2254 of substrate 2250 is shown at (ii), also depicting microwells 2252. At (iii), a side cross-section of solid wall device 2250 is shown, and microwells 2252 have been loaded, where, in this embodiment, substantial Poisson loading has taken place; that is, one microwell 2257 has no cells, and some microwells 2276, 2278 have a few cells. In FIG. 2K, cells with active gRNAs are shown as solid circles, and cells with inactive gRNAs are shown as open circles. At (iv) workflow 2270 is illustrated where substrate 2250 having microwells 2252 shows three microwells 2276 with several cells all with active gRNAs, microwell 2257 with no cells, and two microwells 378 with some cells having active gRNAs and some cells having inactive gRNAs. In step 2271, the cells in the microwells are allowed to double approximately 2-150 times to form clonal colonies (v), then editing optionally is induced 2273 by heating the substrate (e.g., for temperature-induced editing) or flowing chemicals under or over the substrate (e.g., sugars, antibiotics for chemical-induced editing) or by moving the solid wall device to a different medium, particularly facile if the solid wall device is placed on a membrane which forms the bottom of microwells 2252. Again, editing need not be inducible, in which case editing commences at or shortly after transformation and is likely taking place as the cells are being deposited in the wells.

After editing 2273, many cells in the colonies of cells that have been edited die as a result of the double-strand cuts caused by active editing and there is a lag in growth for the edited cells that do survive but must repair and recover following editing (microwells 2278), where cells that do not undergo editing thrive (microwells 2279) (vi). Thus, in microwells 2278 where only cells with active gRNAs reside (cells depicted by solid circles), most cells die off; however, in microwells 2279 containing cells with inactive gRNAs (cells depicted by open circles), cells continue to grow and are not impacted by active editing. The cells in each microwell (2278 and 2279) are allowed to grow to continue to establish colonies and normalize, where the colonies of edited cells in microwells 2278 catch up in size and/or cell number with the unedited cells in microwells 2279 that do not undergo editing (vii). Note that in this workflow 2270, the colonies of cells in the microwells are not clonal; that is, not all cells in a well arise from a single cell. Instead, the cell colonies in the well may be mixed colonies, arising in many wells from two to several different cells. Once the cell colonies are normalized, either pooling 2290 of all cells in the microwells can take place, in which case the cells are enriched for edited cells by eliminating the bias from non-editing cells and fitness effects from editing or cells may be flushed from the SWIIN and collected at various time points; alternatively, colony growth in the microwells is monitored after editing, and slow growing colonies (e.g., the cells in microwells 2278) are identified and selected 2291 (e.g., "cherry picked") resulting in even greater enrichment of edited cells.

Automated Instruments Comprising Screening and Selection Modules

Figure 3A:
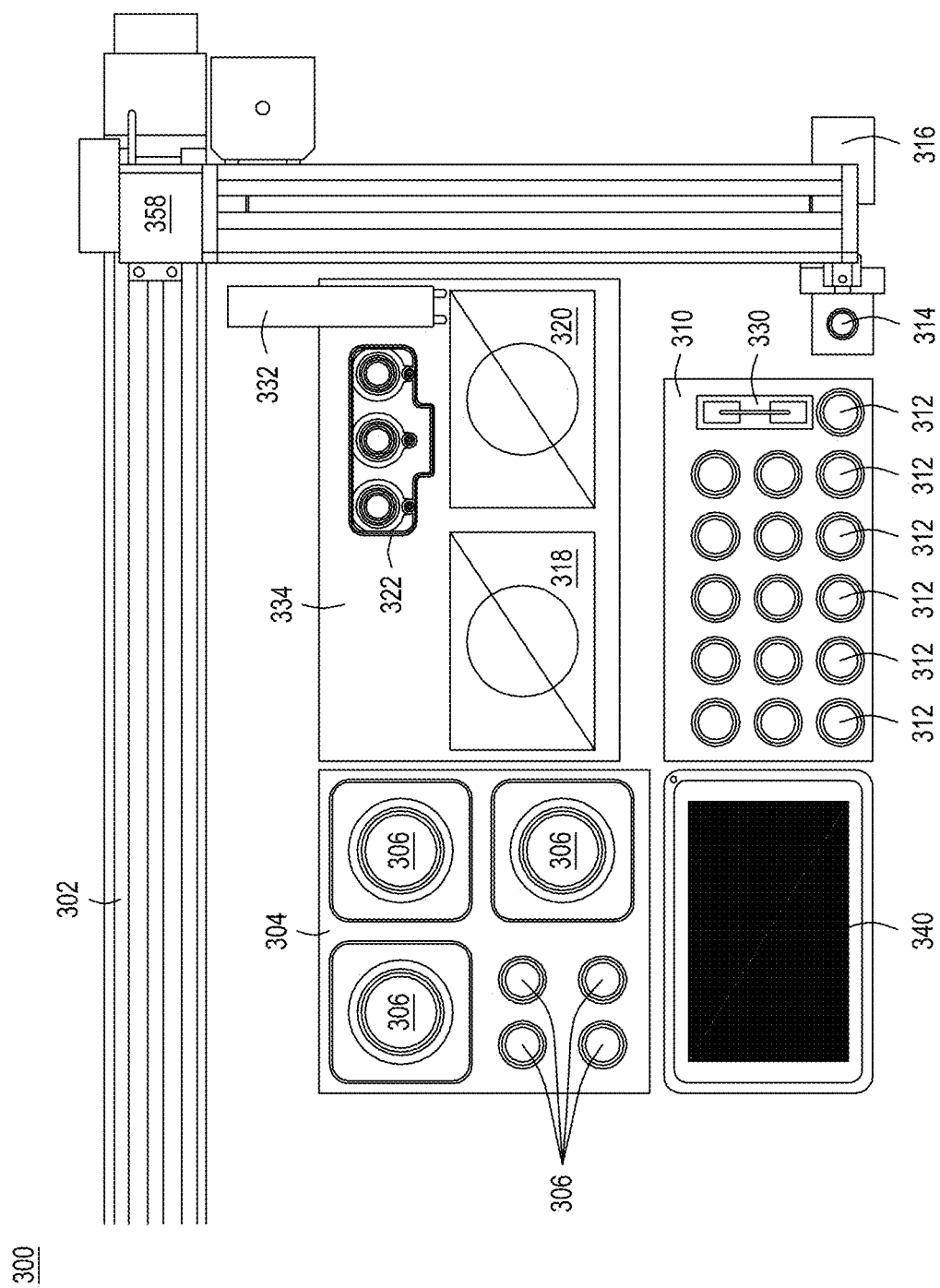
FIGS. 3A-3L depict an automated multi-module instrument and components thereof with which the enrichment/selection modules may be used.

FIG. 3A depicts an exemplary automated multi-module cell processing instrument 300 comprising a cell enrichment/selection module 340 to, e.g., perform one of the exemplary workflows described above, as well as additional exemplary modules. Illustrated is a gantry 302, providing an automated mechanical motion system (actuator) (not shown) that supplies XYZ axis motion control to, e.g., modules of the automated multi-module cell processing instrument 300, including, e.g., a liquid handling system 358 with an air displacement pipette 332. In some automated multi-module cell processing instruments, the air displacement pipettor is moved by a gantry and the various modules and reagent cartridges remain stationary; however, in other embodiments, the pipetting system may stay stationary while the various modules are moved. Also included in the automated multi-module cell processing instrument 300 is wash or reagent cartridge 304, comprising reservoirs 306. As described below in respect to FIG. 3B, wash or reagent cartridge 304 may be configured to accommodate large tubes, for example, wash solutions, or solutions that are used often throughout an iterative process. In one example, wash or reagent cartridge 304 may be configured to remain in place when two or more reagent cartridges 310 are sequentially used and replaced. Although reagent cartridge 310 and wash or reagent cartridge 304 are shown in FIG. 3A as separate cartridges, the contents of wash cartridge 304 may be incorporated into reagent cartridge 310.

The exemplary automated multi-module cell processing instrument 300 of FIG. 3A further comprises a cell growth module 334. In the embodiment illustrated in FIG. 3A, the cell growth module 334 comprises two cell growth vials 318, 320 (described in greater detail below with relation to FIG. 3E) as well as a cell concentration module 322. In alternative embodiments, the cell concentration module 322 may be separate from cell growth module 334, e.g., in a separate, dedicated module. Also illustrated as part of the automated multi-module cell processing instrument 300 of FIG. 3A is enrichment/selection module 340, served by, e.g., air displacement pipettor 332. Also seen are a waste repository (not shown), and a nucleic acid assembly/desalting module 314 comprising a reaction chamber or tube receptacle (not shown) and further comprising a magnet 316 to allow for purification of nucleic acids using, e.g., magnetic solid phase reversible immobilization (SPRI) beads (Applied Biological Materials Inc., Richmond, BC). The reagent cartridge, transformation module, and cell growth module are described in greater detail below. For additional information regarding integrated automated multi-module cell processing systems see U.S. Pat. No. 10,253,316, issued Apr. 9, 2019; U.S. Pat. No. 10,329,559, issued Jun. 25, 2019; and U.S. Pat. No. 10,323,242, issued Jun. 18, 2019; and U.S. Ser. No. 16/412,175, filed May 14, 2019; Ser. No. 16/412, 195, filed Jun. 14, 2019; and Ser. No. 16/423,289, filed May 28, 2019.

Figure 3D:
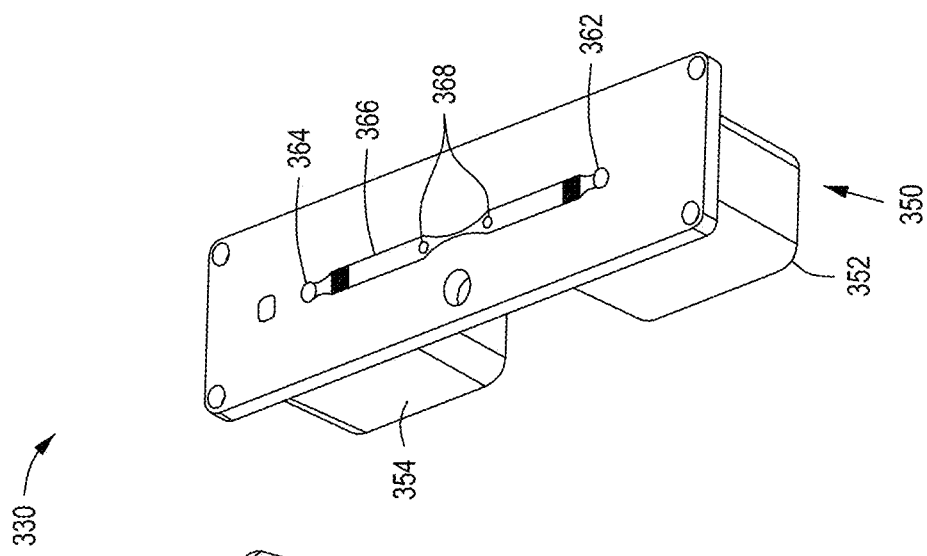
Figure 3C:
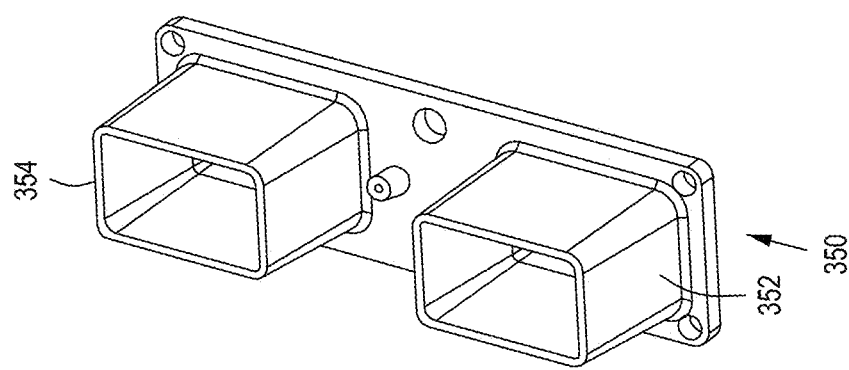
Figure 3B:
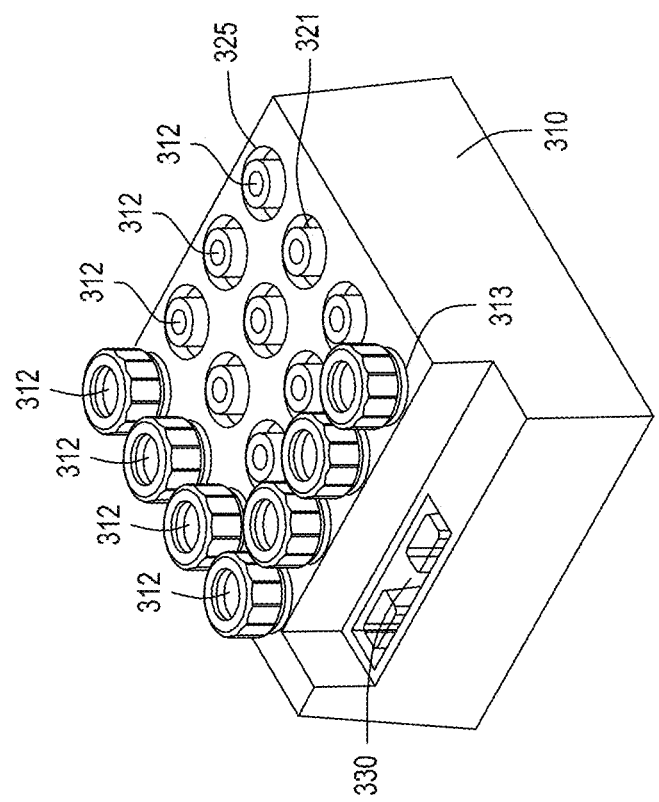

FIG. 3B depicts an exemplary combination reagent cartridge and electroporation device 310 ("cartridge") that may be used in an automated multi-module cell processing instrument along with the screening/selection module. In certain embodiments the material used to fabricate the cartridge is thermally-conductive, as in certain embodiments the cartridge 310 contacts a thermal device (not shown), such as a Peltier device or thermoelectric cooler, that heats or cools reagents in the reagent receptacles or reservoirs 312. Reagent receptacles or reservoirs 312 may be receptacles into which individual tubes of reagents are inserted as shown in FIG. 3B, or the reagent receptacles may hold the reagents without inserted tubes. Additionally, the receptacles in a reagent cartridge may be configured for any combination of tubes, co-joined tubes, and direct-fill of reagents.

In one embodiment, the reagent receptacles or reservoirs 312 of reagent cartridge 310 are configured to hold various size tubes, including, e.g., 250 ml tubes, 25 ml tubes, 10 ml tubes, 5 ml tubes, and Eppendorf or microcentrifuge tubes. In yet another embodiment, all receptacles may be configured to hold the same size tube, e.g., 5 ml tubes, and reservoir inserts may be used to accommodate smaller tubes in the reagent reservoir (not shown). In yet another embodiment—particularly in an embodiment where the reagent cartridge is disposable—the reagent reservoirs hold reagents without inserted tubes. In this disposable embodiment, the reagent cartridge may be part of a kit, where the reagent cartridge is pre-filled with reagents and the receptacles or reservoirs sealed with, e.g., foil, heat seal acrylic or the like and presented to a consumer where the reagent cartridge can then be used in an automated multi-module cell processing instrument. As one skilled in the art will appreciate given the present disclosure, the reagents contained in the reagent cartridge will vary depending on workflow; that is, the reagents will vary depending on the processes to which the cells are subjected in the automated multi-module cell processing instrument.

Reagents such as cell samples, enzymes, buffers, nucleic acid vectors, expression cassettes, proteins or peptides, reaction components (such as, e.g., $MgCl_2$, dNTPs, nucleic acid assembly reagents, gap repair reagents, and the like), wash solutions, ethanol, and magnetic beads for nucleic acid purification and isolation, etc. may be positioned in the reagent cartridge at a known position. In some embodiments of cartridge 310, the cartridge comprises a script (not shown) readable by a processor (not shown) for dispensing the reagents. Also, the cartridge 310 as one component in an automated multi-module cell processing instrument may comprise a script specifying two, three, four, five, ten or more processes to be performed by the automated multi-module cell processing instrument. In certain embodiments, the reagent cartridge is disposable and is pre-packaged with reagents tailored to performing specific cell processing protocols, e.g., genome editing or protein production. Because the reagent cartridge contents vary while components/modules of the automated multi-module cell processing instrument may not, the script associated with a particular reagent cartridge matches the reagents used and cell processes performed. Thus, e.g., reagent cartridges may be pre-packaged with reagents for genome editing and a script that specifies the process steps for performing genome editing in an automated multi-module cell processing instrument, or, e.g., reagents for protein expression and a script that specifies the process steps for performing protein expression in an automated multi-module cell processing instrument.

For example, the reagent cartridge may comprise a script to pipette competent cells from a reservoir, transfer the cells to a transformation module (such as flow through electroporation device 330 in reagent cartridge 310), pipette a nucleic acid solution comprising a vector with expression cassette from another reservoir in the reagent cartridge, transfer the nucleic acid solution to the transformation module, initiate the transformation process for a specified time, then move the transformed cells to yet another reservoir in the reagent cassette or to another module such as a cell growth module in the automated multi-module cell processing instrument. In another example, the reagent cartridge may comprise a script to transfer a nucleic acid solution comprising a vector from a reservoir in the reagent cassette, nucleic acid solution comprising editing oligonucleotide cassettes in a reservoir in the reagent cassette, and a nucleic acid assembly mix from another reservoir to the nucleic acid assembly/desalting module (314 of FIG. 3A). The script may also specify process steps performed by other modules in the automated multi-module cell processing instrument. For example, the script may specify that the nucleic acid assembly/desalting reservoir be heated to 50° C. for 30 min to generate an assembled product; and desalting and resuspension of the assembled product via magnetic bead-based nucleic acid purification involving a series of pipette transfers and mixing of magnetic beads, ethanol wash, and buffer. These processes are described in greater detail infra.

As described in relation to FIGS. 3C and 3D below, the exemplary reagent cartridges 310 for use in the automated multi-module cell processing instruments may include one or more electroporation devices 330, preferably flow-through electroporation devices. Electroporation is a widely-used method for permeabilization of cell membranes that works by temporarily generating pores in the cell membranes with electrical stimulation. Applications of electroporation include the delivery of DNA, RNA, siRNA, peptides, proteins, antibodies, drugs or other substances to a variety of cells such as mammalian cells (including human cells), plant cells, archea, yeasts, other eukaryotic cells, bacteria, and other cell types. Electrical stimulation may also be used for cell fusion in the production of hybridomas or other fused cells. During a typical electroporation procedure, cells are suspended in a buffer or medium that is favorable for cell survival. For bacterial cell electroporation, low conductance mediums, such as water, glycerol solutions and the like, are often used to reduce the heat production by transient high current. In traditional electroporation devices, the cells and material to be electroporated into the cells (collectively "the cell sample") are placed in a cuvette embedded with two flat electrodes for electrical discharge. For example, Bio-Rad (Hercules, Calif.) makes the GENE PULSER XCELL™ line of products to electroporate cells in cuvettes. Traditionally, electroporation requires high field strength; however, the flow-through electroporation devices included in the reagent cartridges such as those shown in FIGS. 3B-3D achieve high efficiency cell electroporation with low toxicity. The reagent cartridges of the disclosure allow for particularly easy integration with robotic liquid handling instrumentation that is typically used in automated instruments and systems such as air displacement pipettors. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc. as described above.

FIGS. 3C and 3D are top perspective and bottom perspective views, respectively, of an exemplary flow-through electroporation device 350 that may be part of reagent cartridge 300 in FIG. 3B or may be contained in a separate module (e.g., a transformation/transfection module). FIG. 3C depicts a flow-through electroporation unit 350. The flow-through electroporation unit 350 has wells that define cell sample inlets 352 and cell sample outlets 354. FIG. 3D is a bottom perspective view of the flow-through electroporation device 350 of FIG. 3C. An inlet well 352 and an outlet well 354 can be seen in this view. Also seen in FIG. 3D are the bottom of an inlet 362 corresponding to well 352, the bottom of an outlet 364 corresponding to the outlet well 354, the bottom of a defined flow channel 366 and the bottom of two electrodes 368 on either side of flow channel 366. Additionally, flow-through electroporation devices may comprise push-pull pneumatic means to allow multi-pass electroporation procedures; that is, cells to be electroporated may be "pulled" from the inlet toward the outlet for one pass of electroporation, then be "pushed" from the outlet end of the flow-through electroporation device toward the inlet end to pass between the electrodes again for another pass of electroporation. Further, this process may be repeated one to many times. Further, other embodiments of the reagent cartridge may provide or accommodate electroporation devices that are not configured as flow-through devices, such as those described in U.S. Ser. No. 16/147,120 filed Sep. 28, 2018; Ser. No. 16/147,353, filed Sep. 28, 2018; Ser. No. 16/426,310, filed May 30, 2019; Ser. No. 16/147,871, filed Sep. 30, 2018; and U.S. Pat. No. 10,323,258, issued Jun. 18, 2019, all of which are incorporated by reference in their entirety for all purposes.

Figure 3E:
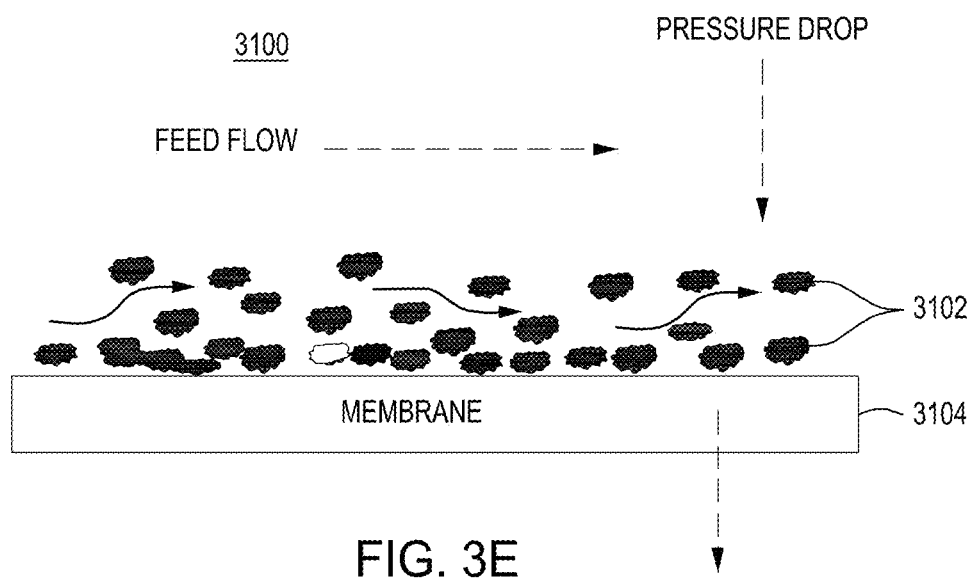

Another module useful in an automatic multi-module cell processing instrument is a cell concentration module, which also may be employed to perform buffer exchange to render cells grown in the multi-module cell processing instrument electrocompetent. FIG. 3E is a general model 3100 of tangential flow filtration. The TFF device operates using tangential flow filtration, also known as cross-flow filtration. FIG. 1A shows cells flowing over a membrane 3104, where the feed flow of the cells 3102 in medium or buffer is parallel to the membrane 3104. TFF is different from dead-end filtration where both the feed flow and the pressure drop are perpendicular to a membrane or filter.

Figure 3F:
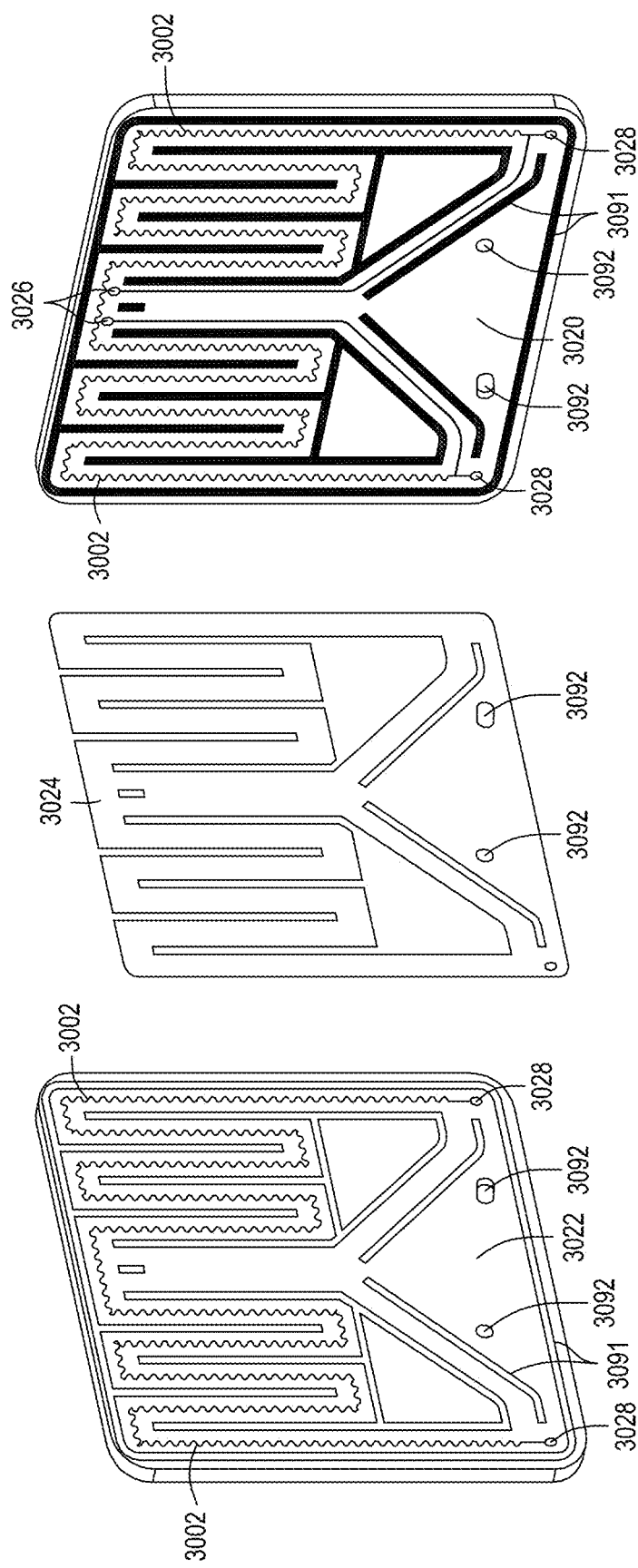

FIG. 3F depicts a configuration of a retentate member 3022 (at left), a membrane or filter 3024 (middle), and a permeate member 3020 (at right). In FIG. 3F, retentate member 3022 comprises a tangential flow channel 3002, which has a serpentine configuration that initiates at one lower corner of retentate member 3022—specifically at retentate port 3028—traverses across and up then down and across retentate member 3022, ending in the other lower corner of retentate member 3022 at a second retentate port 3028. Also seen on retentate member 3022 are energy directors 3091, which circumscribe the region where membrane or filter 3024 is seated, as well as interdigitate between areas of the channel. Energy directors 3091 in this embodiment mate with and serve to facilitate ultrasonic welding or bonding of retentate member 3022 with permeate/filtrate member 3020 via the energy director component 3091 on permeate/filtrate member 3020 (at right). Additionally, pin slot alignment elements 3092 are depicted.

Membrane or filter 3024 is seen at center in FIG. 3F, where member 3024 is configured to seat within the circumference of energy directors 3091 between the retentate member 3022 and the permeate/filtrate member 3020. Permeate/filtrate member 3020 comprises, in addition to energy director 3091, through-holes for retentate ports 3028 at each bottom corner (which mate with the through-holes for retentate ports 3028 at the bottom corners of retentate member 3022), as well as a tangential flow channel 3002 and two permeate/filtrate ports 3026 positioned at the top and center of permeate/filtrate member 3020. The tangential flow channel 3002 structure in this embodiment has a serpentine configuration and an undulating geometry, although other geometries may be used. As described above, the length of the tangential flow channel is from 10 mm to 1000 mm, from 60 mm to 200 mm, or from 80 mm to 100 mm. In some aspects the width of the channel structure is from 10 mm to 120 mm, from 40 mm to 70 mm, or from 50 mm to 60 mm. In some aspects the cross section of the tangential flow channel 3002 is rectangular, and in some aspects the cross section of the tangential flow channel 3002 is 5 µm to 1000 µm wide and 5 µm to 1000 µm high, 300 µm to 700 µm wide and 300 µm to 700 µm high, or 400 µm to 600 µm wide and 400 µm to 600 µm high. In other aspects, the cross section of the tangential flow channel 1202 is circular, elliptical, trapezoidal, or oblong, and is 100 µm to 1000 µm in hydraulic radius, 300 µm to 700 µm in hydraulic radius, or 400 µm to 600 µm in hydraulic radius.

Figure 3G:
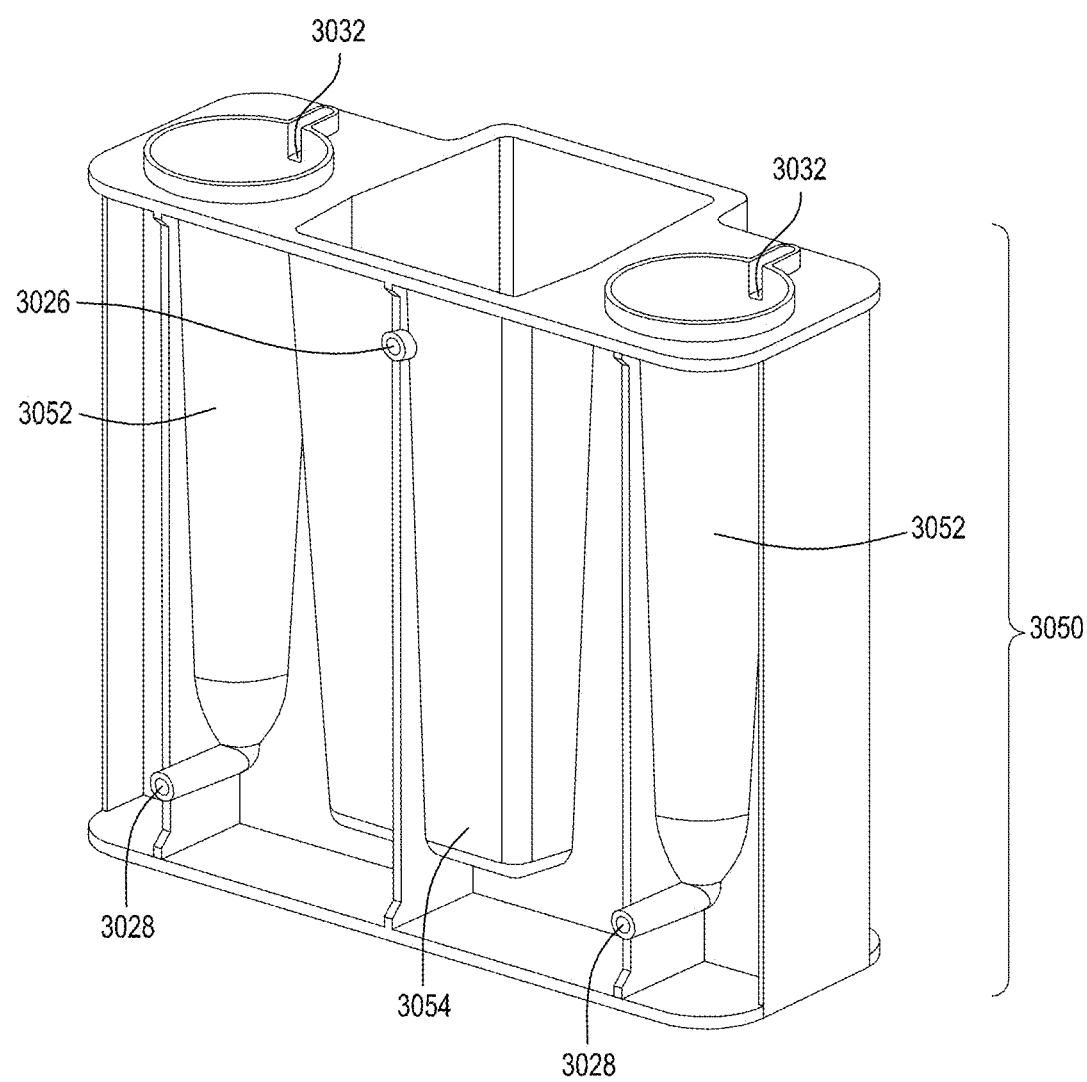

FIG. 3G is a side perspective view of a reservoir assembly 3050. Reservoir assembly 3050 comprises retentate reservoirs 3052 on either side of a single permeate reservoir 3054. Retentate reservoirs 3052 are used to contain the cells and medium as the cells are transferred through the cell concentration/growth device or module and into the retentate reservoirs during cell concentration and/or growth. Permeate/filtrate reservoir 3054 is used to collect the filtrate fluids removed from the cell culture during cell concentration, or old buffer or medium during cell growth. In this embodiment, there is not a buffer reservoir; instead, buffer or medium is supplied to the retentate member from a reagent reservoir separate from the device module. Additionally seen in FIG. 3G are grooves 3032 to accommodate pneumatic ports (not seen), a single permeate/filtrate port 3026, and retentate port through-holes 3028. The retentate reservoirs are fluidically coupled to the retentate ports 3028, which in turn are fluidically coupled to the portion of the tangential flow channel disposed in the retentate member (not shown). The permeate/filtrate reservoir is fluidically coupled to the permeate/filtrate port 3026 which in turn are fluidically coupled to the portion of the tangential flow channel disposed in permeate/filtrate member (not shown), where the portions of the tangential flow channels are bifurcated by membrane (not shown). In embodiments including the present embodiment, up to 120 mL of cell culture can be grown and/or filtered, or up to 100 mL, 90 mL, 80 mL, 70 mL, 60 mL, 50 mL, 40 mL, 30 mL or 20 mL of cell culture can be grown and/or concentrated.

Figure 3H:
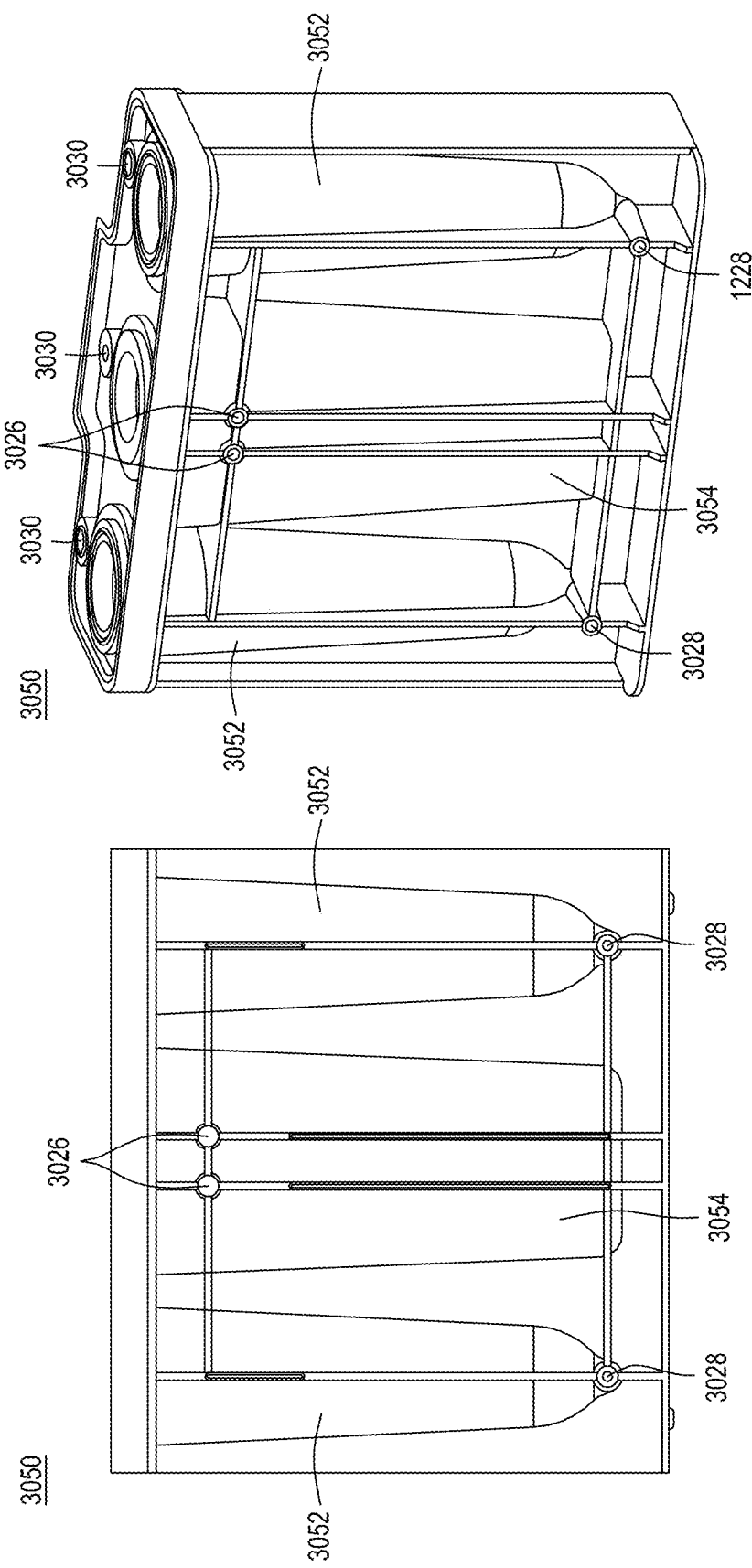

FIG. 3H is a side view (left) and a side perspective view (right) of a reservoir assembly 3050, which is similar to the reservoir assembly 3050 of FIG. 3G. In both views of reservoir assembly 3050 (views in FIGS. 3G and 3H), the reservoir assembly comprises retentate reservoirs 3052 on either side of a single permeate reservoir 3054. Retentate reservoirs 3052 are used to contain the cells and medium as the cells are transferred through the cell concentration/growth device or module and into the retentate reservoirs during cell concentration and/or growth. Permeate/filtrate reservoir 3054 is used to collect the filtrate fluids removed from the cell culture during cell concentration, or old buffer or medium during cell growth. In this embodiment, there is not a buffer reservoir; instead in this embodiment, buffer or medium is supplied to the retentate member from a reagent reservoir separate from the device module. Additionally seen in FIG. 3H are two permeate/filtrate ports 3026, and retentate port through-holes 3028. The retentate reservoirs are fluidically coupled to the retentate ports 3028, which in turn are fluidically coupled to the portion of the tangential flow channel disposed in the retentate member (not shown). The permeate/filtrate reservoirs are fluidically coupled to the permeate/filtrate ports 3026 which in turn are fluidically coupled to the portion of the tangential flow channel disposed in permeate/filtrate member (not shown), where the portions of the tangential flow channels are bifurcated by membrane 3024 (not shown). In embodiments including the present embodiment, up to 120 mL of cell culture can be grown and/or filtered, or up to 100 mL, 90 mL, 80 mL, 70 mL, 60 mL, 50 mL, 40 mL, 30 mL or 20 mL of cell culture can be grown and/or concentrated.

Figure 3I:
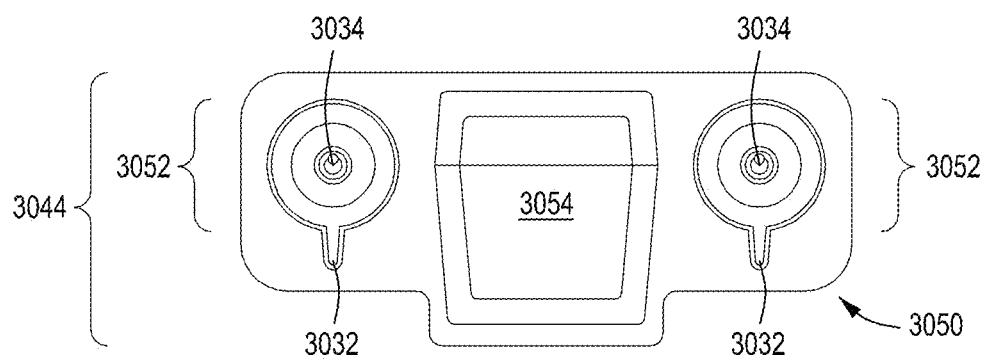
Figure 3J:
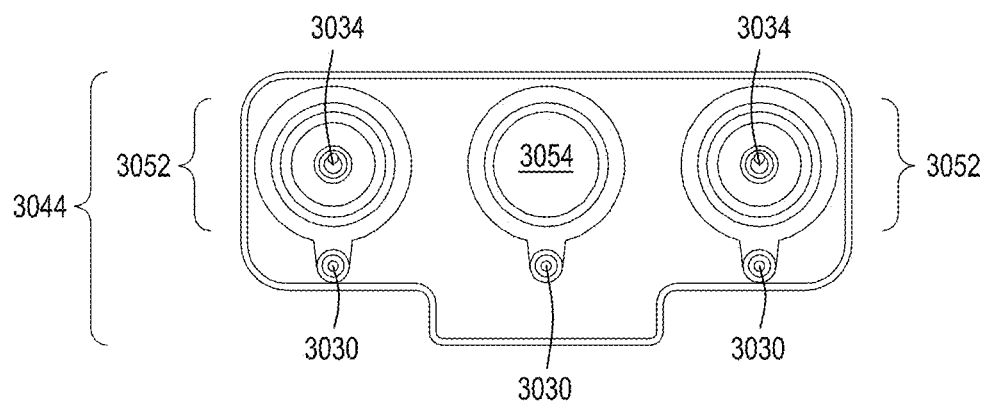
Figure 3K:
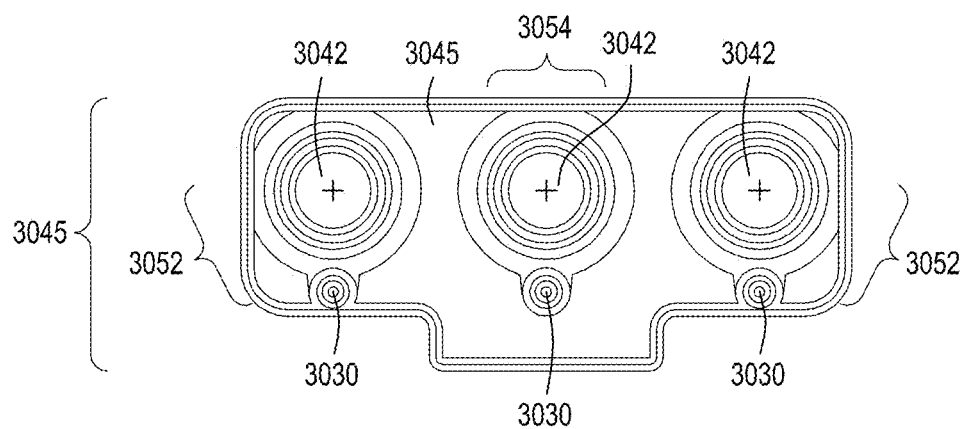

FIG. 3I depicts a top-down view of the reservoir assemblies 3050 shown in FIG. 3G and FIG. 3H. FIG. 3J depicts a cover 3044 for reservoir assembly 3050 shown in FIG. 3G and FIGS. 3H, and 3K depicts a gasket 3045 that in operation is disposed on cover 3044 of reservoir assemblies 3050 shown in FIG. 3G and FIG. 3H. FIG. 3I is a top-down view of reservoir assembly 3050, showing two retentate reservoirs 3052 (not seen in this figure but see FIG. 3H), one on either side of permeate reservoir 3054. Also seen are grooves 3032 that will mate with a pneumatic port (not shown), and fluid channels 3034 that reside at the bottom of retentate reservoirs 3052 (not seen in this figure but see FIG. 3H), which fluidically couple the retentate reservoirs 3052 (not seen in this figure but see FIG. 3H) with the retentate ports 3028 (not shown), via the through-holes for the retentate ports in permeate/filtrate member 3020 and membrane 3024 (also not shown). FIG. 3J depicts a cover 3044 that is configured to be disposed upon the top of reservoir assembly 3050. Cover 3044 has round cut-outs at the top of retentate reservoirs 3052 (not seen in this figure but see FIG. 3H) and permeate/filtrate reservoir 3054. Again, at the bottom of retentate reservoirs 3052 fluid channels 3034 can be seen, where fluid channels 3034 fluidically couple retentate reservoirs 3052 (not seen in this figure but see FIG. 3H) with the retentate ports 3028 (not shown). Also shown are three pneumatic ports 3030 for each retentate reservoir 3052 (not seen in this figure but see FIG. 3H) and permeate/filtrate reservoir 3054. FIG. 3K depicts a gasket 3045 that is configured to be disposed upon the cover 3044 of reservoir assembly 3050. Seen are three fluid transfer ports 3042 for each retentate reservoir 3052 (not seen in this figure but see FIG. 3H) and for permeate/filtrate reservoir 3054. Again, three pneumatic ports 3030, for each retentate reservoir 3052 (not seen in this figure but see FIG. 3H) and for permeate/filtrate reservoir 3054, are shown.

Figure 3L:
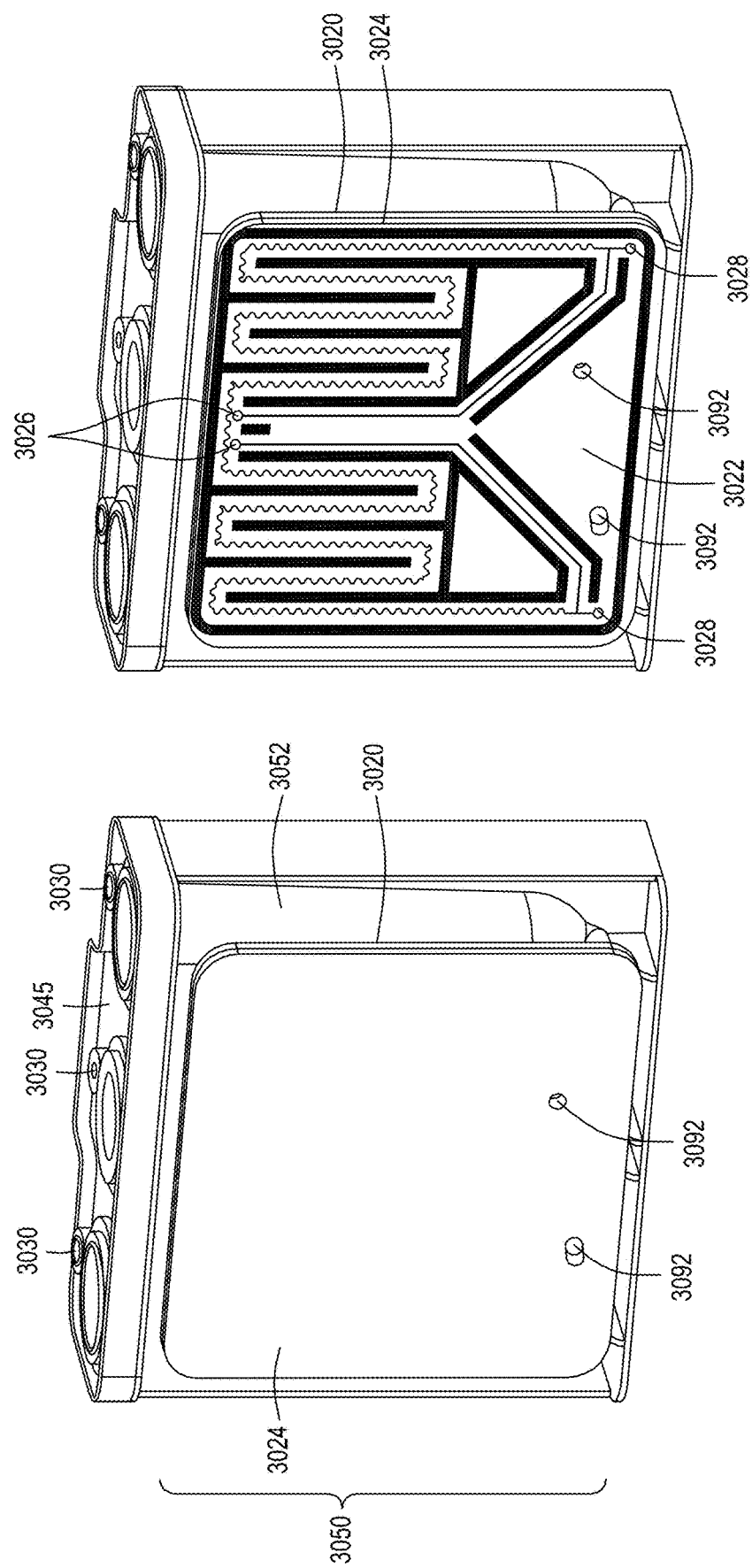

FIG. 3L depicts, on the left, an assembled view of the TFF module 3050 without retentate member 3022, and on the right, an assembled view of the TFF module 3050 with retentate member 3022. Seen are components reservoir assembly 3050, a gasket 3045 to be disposed on reservoir assembly 3050, retentate member 3022, membrane or filter 3024, and, only seen as a layer beneath membrane 3024, permeate/filtrate member 3020. Also seen are permeate/filtrate ports 3026 (seen at right), which mate with permeate/filtrate ports 3026 on permeate/filtrate reservoir 3054 (not seen), as well as two retentate ports 3028, which mate with retentate ports 3028 on retentate reservoirs 3052 (where only one retentate reservoir 3052 can be seen clearly in this FIG. 3L). Also seen are through-holes for retentate ports 3028 in permeate/filtrate member 3020. The left the assembled TFF module 3050 in FIG. 3L typically is from 50 to 175 mm in height, or from 75 to 150 mm in height, or from 90 to 120 mm in height; from 50 to 175 mm in length, or from 75 to 150 mm in length, or from 90 to 120 mm in length; and is from 30 to 90 mm in depth, or from 40 to 75 mm in depth, or from about 50 to 60 mm in depth. An exemplary TFF device is 110 mm in height, 120 mm in length, and 55 mm in depth.

The TFF device or module depicted in FIGS. 3F-3L can constantly measure cell culture growth, and in some aspects, cell culture growth is measured via optical density (OD) of the cell culture in one or both of the retentate reservoirs and/or in the flow channel of the TFF device. Optical density may be measured continuously (real-time monitoring) or at specific time intervals; e.g., every 5, 10, 15, 20, 30 45, or 60 seconds, or every 1, 2, 3, 4, 5, 6, 7, 8, 9, or 10 or so on minutes. Further, the TFF module can adjust growth parameters (temperature, aeration) to have the cells at a desired optical density at a desired time. For additional information on TFF modules, please see U.S. Ser. Nos. 62/728,365, filed Sep. 7, 2018; 62/857,599, filed Jun. 5, 2019; and 62/867,415, filed Jun. 27, 2019, all of which are incorporated in the entirety for all purposes.

Figure 4A:
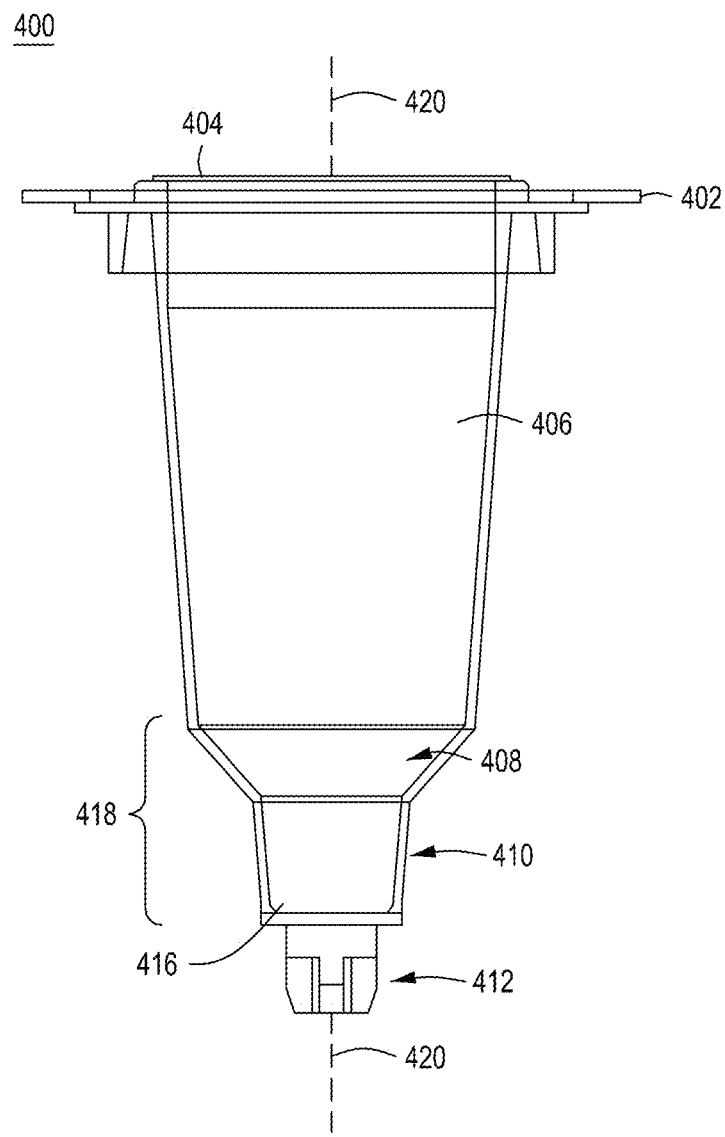
FIG. 4A is an embodiment of a rotating growth vial that may be used for growing cells in an automated multi-module cell processing instrument, as well as for cell isolation in a bulk gel environment.

FIGS. 4A-4D depict one module that is useful for both cell growth and for performing isolation or substantial isolation of cells via bulk gel, as described in relation to FIGS. 2H and 2I. FIG. 4A shows one embodiment of a rotating growth vial 400 for use with the cell growth device described in relation to FIGS. 4B-4D. The rotating growth vial 400 is an optically-transparent container having an open end 404 for receiving liquid media and cells, a central vial region 406 that defines the primary container for growing cells, a tapered-to-constricted region 418 defining at least one light path 410, a closed end 416, and a drive engagement mechanism 412. The rotating growth vial 400 has a central longitudinal axis 420 around which the vial rotates, and the light path 410 is generally perpendicular to the longitudinal axis of the vial. The first light path 410 is positioned in the lower constricted portion of the tapered-to-constricted region 418. Optionally, some embodiments of the rotating growth vial 400 have a second light path 408 in the tapered region of the tapered-to-constricted region 418. Both light paths in this embodiment are positioned in a region of the rotating growth vial that is constantly filled with the cell culture (cells+growth media) and are not affected by the rotational speed of the growth vial. The first light path 410 is shorter than the second light path 408 allowing for sensitive measurement of OD values when the OD values of the cell culture in the vial are at a high level (e.g., later in the cell growth process), whereas the second light path 408 allows for sensitive measurement of OD values when the OD values of the cell culture in the vial are at a lower level (e.g., earlier in the cell growth process).

The drive engagement mechanism 412 engages with a motor (not shown) to rotate the vial. In some embodiments, the motor drives the drive engagement mechanism 412 such that the rotating growth vial 400 is rotated in one direction only, and in other embodiments, the rotating growth vial 400 is rotated in a first direction for a first amount of time or periodicity, rotated in a second direction (i.e., the opposite direction) for a second amount of time or periodicity, and this process may be repeated so that the rotating growth vial 400 (and the cell culture contents) are subjected to an oscillating motion. Further, the choice of whether the culture is subjected to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial 400 may be oscillated at a first periodicity (e.g., every 60 seconds), and then a later stage of cell growth the rotating growth vial 400 may be oscillated at a second periodicity (e.g., every one second) different from the first periodicity.

The rotating growth vial 400 may be reusable or, preferably, the rotating growth vial is consumable. In some embodiments, the rotating growth vial is consumable and is presented to the user pre-filled with growth medium, where the vial is hermetically sealed at the open end 404 with a foil seal. A medium-filled rotating growth vial packaged in such a manner may be part of a kit for use with a stand-alone cell growth device or with a cell growth module that is part of an automated multi-module cell processing instrument. To introduce cells into the vial, a user need only pipette up a desired volume of cells and use the pipette tip to punch through the foil seal of the vial. Open end 404 may optionally include an extended lip 402 to overlap and engage with the cell growth device. In automated instruments, the rotating growth vial 400 may be tagged with a barcode or other identifying means that can be read by a scanner or camera (not shown) that is part of the automated instrument.

The volume of the rotating growth vial 400 and the volume of the cell culture (including growth medium) may vary greatly, but the volume of the rotating growth vial 400 must be large enough to generate a specified total number of cells. In practice, the volume of the rotating growth vial 400 may range from 1-250 mL, 2-100 mL, from 5-80 mL, 10-50 mL, or from 12-35 mL. Likewise, the volume of the cell culture (cells+growth media) should be appropriate to allow proper aeration and mixing in the rotating growth vial 400. Proper aeration promotes uniform cellular respiration within the growth media. Thus, the volume of the cell culture should be approximately 5-85% of the volume of the growth vial or from 20-60% of the volume of the growth vial. For example, for a 30 mL growth vial, the volume of the cell culture would be from about 1.5 mL to about 26 mL, or from 6 mL to about 18 mL.

The rotating growth vial 400 preferably is fabricated from a bio-compatible optically transparent material—or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyamide, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 4B:
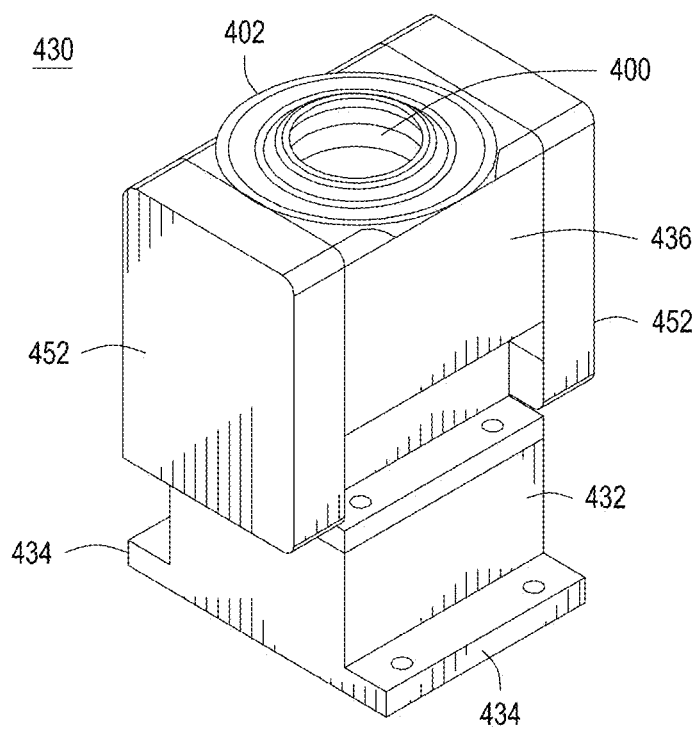
FIG. 4B illustrates a perspective view of one embodiment of a rotating growth device in a cell growth module housing.
Figure 4C:
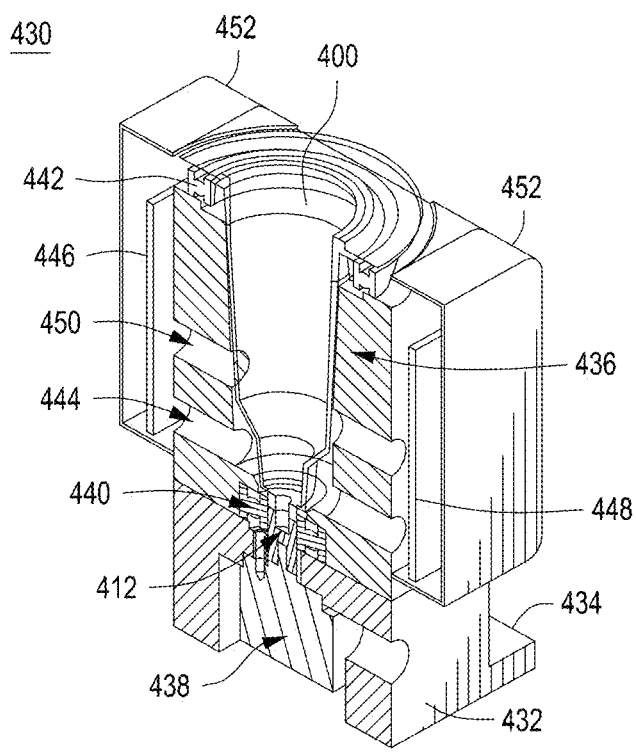
FIG. 4C depicts a cut-away view of the cell growth module from FIG. 4B.

FIG. 4B is a perspective view of one embodiment of a cell growth device 430. FIG. 4C depicts a cut-away view of the cell growth device 430 from FIG. 4B. In both FIGS., the rotating growth vial 400 is seen positioned inside a main housing 436 with the extended lip 402 of the rotating growth vial 400 extending above the main housing 436. Additionally, end housings 452, a lower housing 432 and flanges 434 are indicated in both figures. Flanges 434 are used to attach the cell growth device 430 to heating/cooling means or other structure (not shown). FIG. 4C depicts additional detail. In FIG. 4C, upper bearing 442 and lower bearing 440 are shown positioned within main housing 436. Upper bearing 442 and lower bearing 440 support the vertical load of rotating growth vial 400. Lower housing 432 contains the drive motor 438. The cell growth device 430 of FIG. 4C comprises two light paths: a primary light path 444, and a secondary light path 450. Light path 444 corresponds to light path 410 positioned in the constricted portion of the tapered-to-constricted portion of the rotating growth vial 400, and light path 450 corresponds to light path 408 in the tapered portion of the tapered-to-constricted portion of the rotating growth via 416. Light paths 410 and 408 are not shown in FIG. 4C but may be seen in FIG. 4A. In addition to light paths 444 and 440, there is an emission board 448 to illuminate the light path(s), and detector board 446 to detect the light after the light travels through the cell culture liquid in the rotating growth vial 400.

The motor 438 engages with drive mechanism 412 and is used to rotate the rotating growth vial 400. In some embodiments, motor 438 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 438 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 436, end housings 452 and lower housing 432 of the cell growth device 430 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 600 is envisioned in some embodiments to be reusable, but preferably is consumable, the other components of the cell growth device 430 are preferably reusable and function as a stand-alone benchtop device or as a module in a multi-module cell processing instrument.

The processor (not shown) of the cell growth device 430 may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor (not shown) of the cell growth device 630—may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth device 430, where the second spectrophotometer is used to read a blank at designated intervals.

Figure 4D:
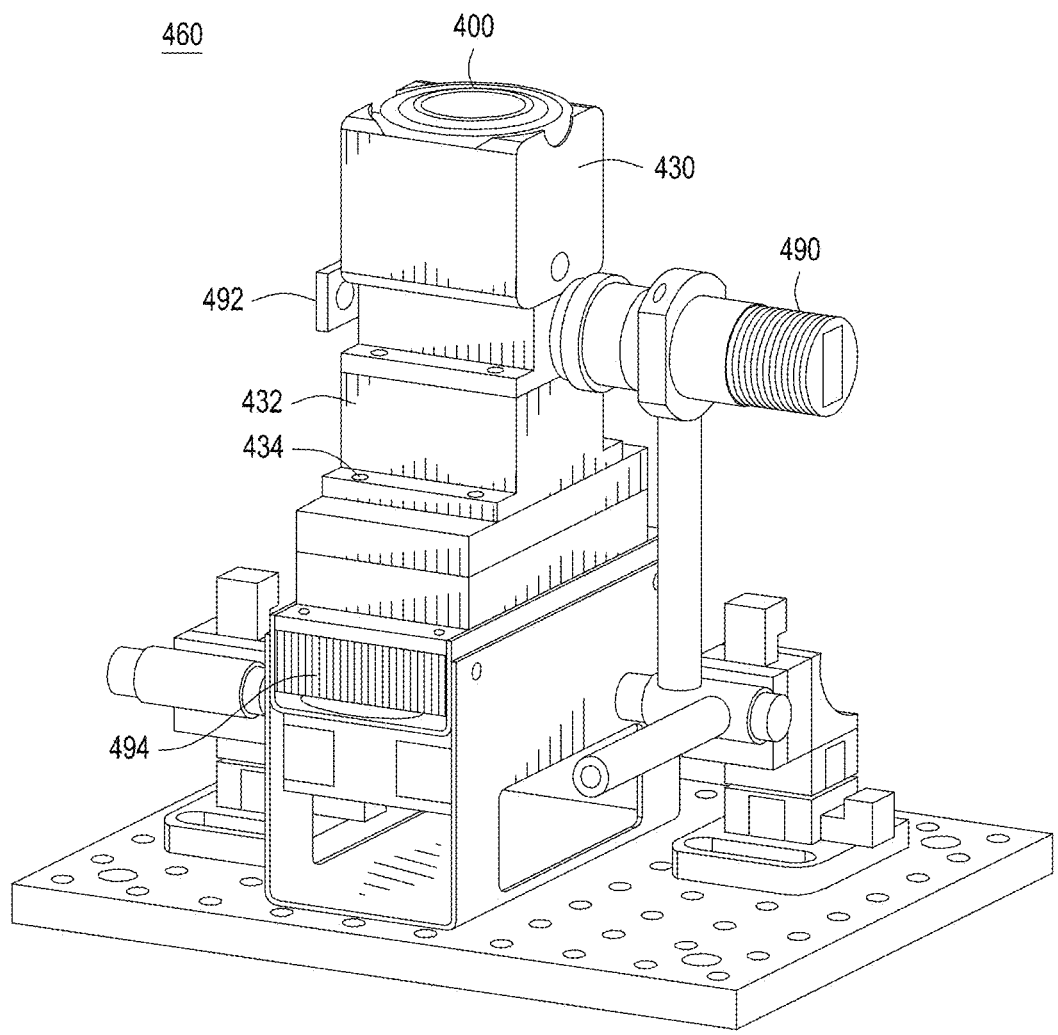
FIG. 4D illustrates the cell growth module of FIG. 4B coupled to LED, detector, and temperature regulating components.

FIG. 4D illustrates a cell growth device 430 as part of an assembly comprising the cell growth device 430 of FIG. 4B coupled to light source 490, detector 492, and thermal components 494. The rotating growth vial 400 is inserted into the cell growth device. Components of the light source 490 and detector 492 (e.g., such as a photodiode with gain control to cover 5-log) are coupled to the main housing of the cell growth device. The lower housing 432 that houses the motor that rotates the rotating growth vial 400 is illustrated, as is one of the flanges 434 that secures the cell growth device 430 to the assembly. Also, the thermal components 494 illustrated are a Peltier device or thermoelectric cooler. In this embodiment, thermal control is accomplished by attachment and electrical integration of the cell growth device 430 to the thermal components 494 via the flange 434 on the base of the lower housing 432. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 400 is controlled to approximately +/−0.5° C.

In use, cells are inoculated (cells can be pipetted, e.g., from an automated liquid handling system or by a user) into pre-filled growth media of a rotating growth vial 400 by piercing though the foil seal or film. The programmed software of the cell growth device 430 sets the control temperature for growth, typically 30° C., then slowly starts the rotation of the rotating growth vial 400. The cell/growth media mixture slowly moves vertically up the wall due to centrifugal force allowing the rotating growth vial 400 to expose a large surface area of the mixture to a normal oxygen environment. The growth monitoring module takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 430 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 minutes. While the cell growth device 430 has been described in the context of measuring the optical density (OD) of a growing cell culture, it should, however, be understood by a skilled artisan given the teachings of the present specification that other cell growth parameters can be measured in addition to or instead of cell culture OD. As with optional measure of cell growth in relation to the solid wall device or module described supra, spectroscopy using visible, UV, or near infrared (NIR) light allows monitoring the concentration of nutrients and/or wastes in the cell culture and other spectroscopic measurements may be made; that is, other spectral properties can be measured via, e.g., dielectric impedance spectroscopy, visible fluorescence, fluorescence polarization, or luminescence. Additionally, the cell growth device 430 may include additional sensors for measuring, e.g., dissolved oxygen, carbon dioxide, pH, conductivity, and the like. For additional information regarding cell growth modules incorporating a rotating growth device, see U.S. Ser. No. 16/360,404, filed Mar. 21, 2019 and Ser. No. 16/360,423, filed Mar. 21, 2019, both of which are incorporated by reference in their entirety for all purposes.

When the rotating growth vial RGV) is used as an isolation module, cells in medium containing 0.25%-6% alginate are transferred into the rotating growth vial by, e.g., a liquid handling system, where first, the cells are at an appropriate dilution to allow each cell to be isolated or substantially isolated from other cells when the medium is gelled, and second, the cell colonies that grow from the isolated cells in the gelled or solidified medium are isolated from other cell colonies. Once the cells at the proper dilution are loaded into the RGV, solidification or gelling of the medium is triggered by slowing adding an appropriate amount of, e.g., $CaCl_2$ dropwise to the RGV, preferably while the RGV is spinning at a low speed. Once the medium is solidified, the cells can be grown to colonies of terminal size (e.g., normalized) or the cells can be grown for, e.g., 2-50 doublings, editing is then induced by, e.g., raising the temperature of the RGV to 42° C. for a period of time to induce a pL promoter driving transcription of the gRNA, then the temperature is lowered and the cells are allowed to grow to terminal size. After the cells have grown to terminal size (e.g., the cells are in senescence and the cell colonies are in no longer increasing in size), the gelled or solidified medium is liquefied by adding an appropriate amount of, e.g., sodium citrate to the solidified medium dropwise preferably while the RGV is spinning at a low speed. The cells and medium may then be removed from the RGV by the liquid handling system and filtered in, e.g., a filtration module such as the TFF device as described in relation to FIGS. 3F-3L.

Figure 5A:
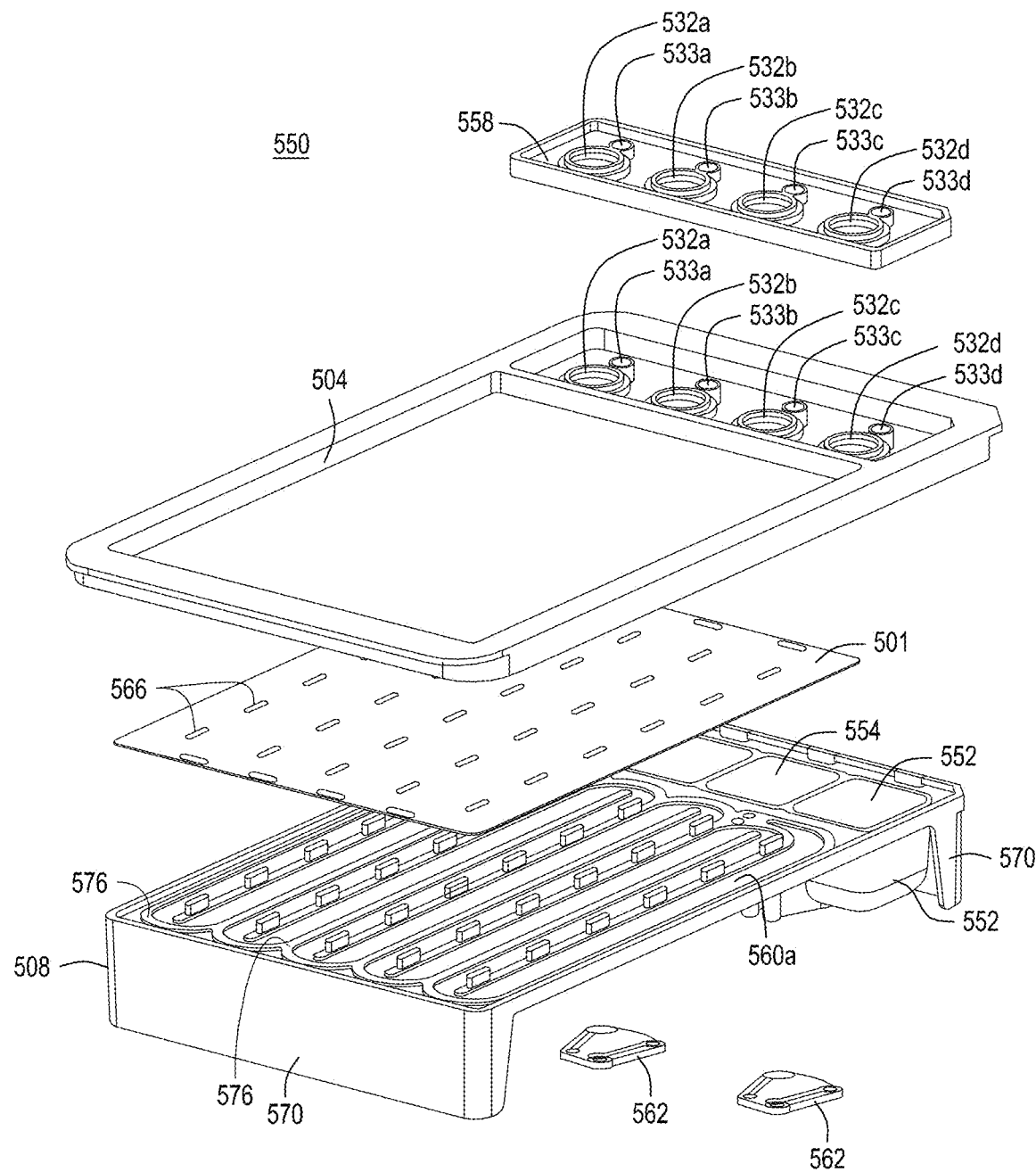
FIGS. 5A-5H depict one embodiment of a SWIIN module.

FIGS. 5A-5J depict various aspects of a solid wall module configured to perform isolation or substantial isolation of cells in an automated multi-module cell processing instrument. FIG. 5A depicts an embodiment of a SWIIN module 550 from an exploded top perspective view. The SWIIN module 550 in FIG. 5A comprises from the top down, a reservoir gasket or cover 558, a retentate member 504 (where a retentate flow channel cannot be seen in this FIG.

5A), a perforated member 501 swaged with a filter (filter not seen in FIG. 5A), a permeate member 508 comprising integrated reservoirs (permeate reservoirs 552 and retentate reservoirs 554), and two reservoir seals 562, which seal the bottom of permeate reservoirs 552 and retentate reservoirs 554. A permeate channel 560*a* can be seen disposed on the top of permeate member 508, defined by a raised portion 576 of serpentine channel 560*a*, and ultrasonic tabs 564 can be seen disposed on the top of permeate member 508 as well. The perforations that form the wells on perforated member 501 are not seen in this FIG. 5A; however, through-holes 566 to accommodate the ultrasonic tabs 564 are seen. In addition, supports 570 are disposed at either end of SWIIN module 550 to support SWIIN module 550 and to elevate permeate member 508 and retentate member 504 above reservoirs 552 and 554 and to minimize bubbles or air entering the fluid path from the permeate reservoir to serpentine channel 560*a* or the fluid path from the retentate reservoir to serpentine channel 560*b* (neither fluid path is seen in this FIG. 5A, but see FIG. 5H).

In this FIG. 5A, it can be seen that the serpentine channel 560*a* that is disposed on the top of permeate member 508 traverses permeate member 508 for most of the length of permeate member 508 except for the portion of permeate member 508 that comprises permeate reservoirs 552 and retentate reservoirs 554 and for most of the width of permeate member 508. As used herein with respect to the distribution channels in the retentate member or permeate member, "most of the length" means about 95% of the length of the retentate member or permeate member, or about 90%, 85%, 80%, 75%, or 70% of the length of the retentate member or permeate member. As used herein with respect to the distribution channels in the retentate member or permeate member, "most of the width" means about 95% of the width of the retentate member or permeate member, or about 90%, 85%, 80%, 75%, or 70% of the width of the retentate member or permeate member.

In this embodiment of a SWIIN module, the perforated member includes through-holes to accommodate ultrasonic tabs disposed on the permeate member. Thus, in this embodiment the perforated member is fabricated from 316 stainless steel, and the perforations form the walls of microwells while a filter or membrane is used to form the bottom of the microwells. Typically, the perforations (microwells) are approximately 150 μm-200 μm in diameter, and the perforated member is approximately 125 μm deep, resulting in microwells having a volume of approximately 2.5 nl, with a total of approximately 200,000 microwells. The distance between the microwells is approximately 279 μm center-to-center. Though here the microwells have a volume of approximately 2.5 nl, the volume of the microwells may be from 1 to 25 nl, or preferably from 2 to 10 nl, and even more preferably from 2 to 4 nl. As for the filter or membrane, like the filter described previously, filters appropriate for use are solvent resistant, contamination free during filtration, and are able to retain the types and sizes of cells of interest. For example, in order to retain small cell types such as bacterial cells, pore sizes can be as low as 0.10 μm, however for other cell types, the pore sizes can be as high as 0.5 μm. Indeed, the pore sizes useful in the cell concentration device/module include filters with sizes from 0.10 μm, 0.11 μm, 0.12 μm, 0.13 μm, 0.14 μm, 0.15 μm, 0.16 μm, 0.17 μm, 0.18 μm, 0.19 μm, 0.20 μm, 0.21 μm, 0.22 μm, 0.23 μm, 0.24 μm, 0.25 μm, 0.26 μm, 0.27 μm, 0.28 μm, 0.29 μm, 0.30 μm, 0.31 μm, 0.32 μm, 0.33 μm, 0.34 μm, 0.35 μm, 0.36 μm, 0.37 μm, 0.38 μm, 0.39 μm, 0.40 μm, 0.41 μm, 0.42 μm, 0.43 μm, 0.44 μm, 0.45 μm, 0.46 μm, 0.47 μm, 0.48 μm, 0.49 μm, 0.50 μm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

Figure 5B:
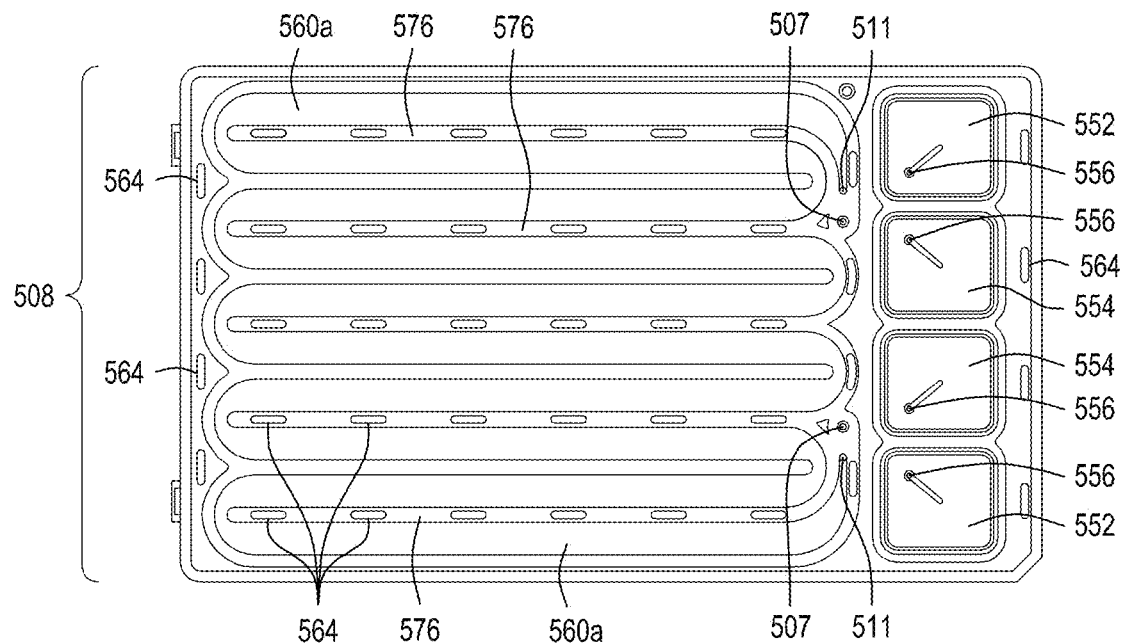

FIG. 5B is a top-down view of permeate member 508, showing serpentine channel 560*a* (the portion of the serpentine channel disposed in permeate member 508) defined by raised portion 576 of serpentine channel 560*a*, permeate reservoirs 552, retentate reservoirs 554, reservoir ports 556 (two of the four of which are labeled), ultrasonic tabs 564 disposed at each end of permeate member 508 and on the raised portion 576 of serpentine channel 560*a* of permeate member 408, and two permeate ports 511 and two retentate ports 507 are also seen.

Figure 5C:
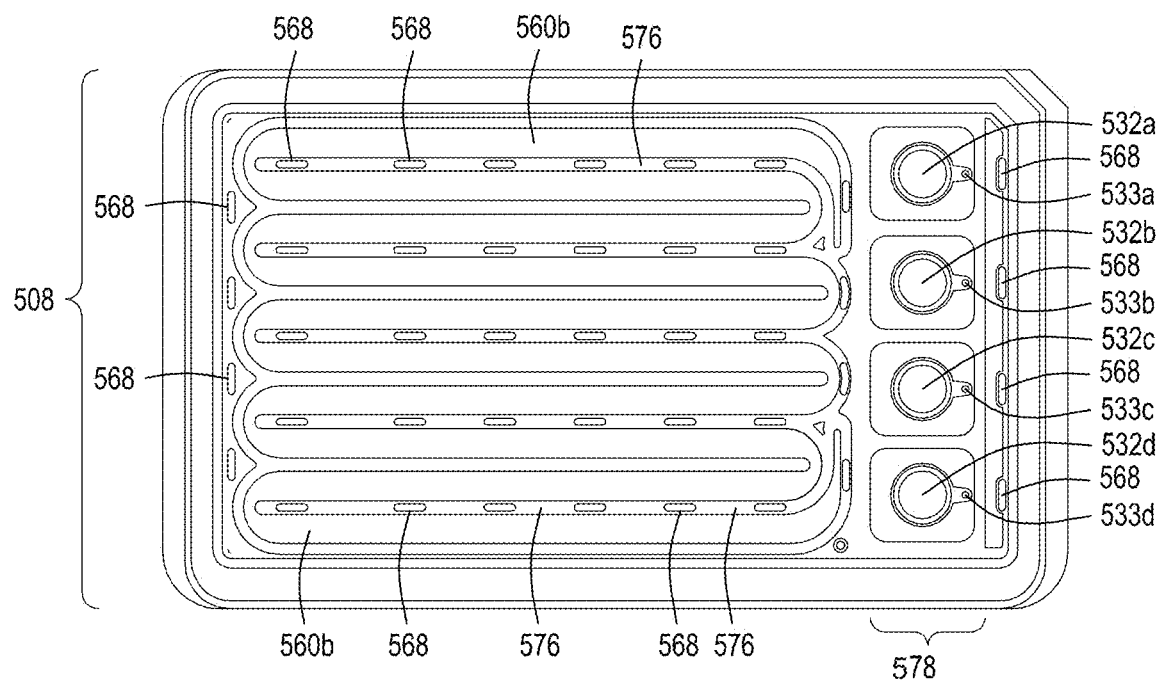

FIG. 5C is a bottom-up view of retentate member 504, showing serpentine channel 560*b* (the portion of the serpentine channel disposed in retentate member 508) defined by the raised portion 576 of the serpentine channel 560*b*. Also seen is an integrated reservoir cover 578 for the permeate and retentate reservoirs that mate with permeate reservoirs 552 and retentate reservoirs 554 on the permeate member. The integrated reservoir cover 578 comprises reservoir access apertures 532*a*, 532*b*, 532*c*, and 532*d*, as well as pneumatic ports 533*a*, 533*b*, 533*c* and 533*d*. As with previous embodiments, the serpentine channel 560*a* of permeate member 508 and the serpentine channel 560*b* of retentate member 504 mate to form the top (retentate member) and bottom (permeate member) of a mated serpentine channel. The footprint length of the serpentine channel structure is from, e.g., from 80 mm to 500 mm, from 100 mm to 400 mm, or from 150 mm to 250 mm. In some aspects, the entire footprint width of the channel structure is from 50 mm to 200 mm, from 75 mm to 175 mm, or from 100 mm to 150 mm.

The cross-section configuration of the mated serpentine channel may be round, elliptical, oval, square, rectangular, trapezoidal, or irregular. If square, rectangular, or another shape with generally straight sides, the cross section may be from about 2 mm to 15 mm wide, or from 3 mm to 12 mm wide, or from 5 mm to 10 mm wide. If the cross section of the mated serpentine channel is generally round, oval or elliptical, the radius of the channel may be from about 3 mm to 20 mm in hydraulic radius, or from 5 mm to 15 mm in hydraulic radius, or from 10 mm to 12 mm in hydraulic radius.

As in previous embodiments, disposed between serpentine channels 560*a* and 560*b* is perforated member 501 (adjacent retentate member 504) and filter 503 (adjacent permeate member 508), where filter 503 is swaged with perforated member 501. Serpentine channels 560*a* and 560*b* can have approximately the same volume or a different volume. For example, each "side" or portion 560*a*, 560*b* of the serpentine channel may have a volume of, e.g., 2 mL, or serpentine channel 560*a* of permeate member 508 may have a volume of 2 mL, and the serpentine channel 560*b* of retentate member 504 may have a volume of, e.g., 3 mL. The volume of fluid in the serpentine channel may range from about 2 mL to about 80 mL, or about 4 mL to 60 mL, or from 5 mL to 40 mL, or from 6 mL to 20 mL (note these volumes apply to a SWIIN module comprising a, e.g., 50-500K perforation member).

The serpentine channel portions 560*a* and 560*b* of the permeate member 508 and retentate member 504, respectively, are approximately 200 mm long, 130 mm wide, and 4 mm thick, though in other embodiments, the retentate and permeate members can be from 75 mm to 400 mm in length, or from 100 mm to 300 mm in length, or from 150 mm to 250 mm in length; from 50 mm to 250 mm in width, or from 75 mm to 200 mm in width, or from 100 mm to 150 mm in width; and from 2 mm to 15 mm in thickness, or from 4 mm to 10 mm in thickness, or from 5 mm to 8 mm in thickness. As in previously described embodiments the retentate (and permeate) members may be fabricated from PMMA (poly (methyl methacrylate) or other materials may be used, including polycarbonate, cyclic olefin co-polymer (COC), glass, polyvinyl chloride, polyethylene, polyamide, polypropylene, polysulfone, polyurethane, and co-polymers of these and other polymers. Preferably at least the retentate member is fabricated from a transparent material so that the cells can be visualized (see, e.g., FIG. 5I and the description thereof). For example, a video camera (as described supra in relation to FIG. 2G and infra in relation to FIG. 5I) may be used to monitor cell growth by, e.g., density change measurements based on an image of an empty well, with phase contrast, or if, e.g., a chromogenic marker, such as a chromogenic protein, is used to add a distinguishable color to the cells. Chromogenic markers such as blitzen blue, dreidel teal, virginia violet, vixen purple, prancer purple, tinsel purple, maccabee purple, donner magenta, cupid pink, seraphina pink, scrooge orange, and leor orange (the Chromogenic Protein Paintbox, all available from ATUM (Newark, Calif.)) obviate the need to use fluorescence, although fluorescent cell markers, fluorescent proteins, and chemiluminescent cell markers may also be used.

Because the retentate member preferably is transparent, colony growth in the SWIIN module can be monitored by automated devices such as those sold by JoVE (ScanLag™ system, Cambridge, Mass.) (also see Levin-Reisman, et al., Nature Methods, 7:737-39 (2010)). Cell growth for, e.g., mammalian cells may be monitored by, e.g., the growth monitor sold by IncuCyte (Ann Arbor, Mich.) (see also, Choudhry, PLos One, 11(2):e0148469 (2016)). Further, automated colony pickers may be employed, such as those sold by, e.g., TECAN (Pickolo™ system, Mannedorf, Switzerland); Hudson Inc. (RapidPick™, Springfield, N.J.); Molecular Devices (QPix 400 ™ system, San Jose, Calif.); and Singer Instruments (PIXL™ system, Somerset, UK).

Due to the heating and cooling of the SWIIN module, condensation may accumulate on the retentate member which may interfere with accurate visualization of the growing cell colonies. Condensation of the SWIIN module 550 may be controlled by, e.g., moving heated air over the top of (e.g., over the top surface of retentate member) of the SWIIN module 550, or by applying a transparent heated lid over at least the serpentine channel portion 560b of the retentate member 504. See, e.g., FIG. 5I and the description thereof infra.

As with the embodiments described previously, in SWIIN module 550 cells and medium—at a dilution appropriate for Poisson or substantial Poisson distribution of the cells in the microwells of the perforated member—are flowed into serpentine channel 560b from ports in retentate member 504, and the cells settle in the microwells while the medium passes through the filter into serpentine channel 560a in permeate member 508. The cells are retained in the microwells of perforated member 501 as the cells cannot travel through filter 503. Appropriate medium may be introduced into permeate member 508 through permeate ports 511. The medium flows upward through filter 503 to nourish the cells in the microwells (perforations) of perforated member 501. Additionally, buffer exchange can be effected by cycling medium through the retentate and permeate members. In operation, the cells are deposited into the microwells, are grown for an initial, e.g., 2-100 doublings, editing is induced by, e.g., raising the temperature of the SWIIN to 42° C. to induce a temperature inducible promoter or by removing growth medium from the permeate member and replacing the growth medium with a medium comprising a chemical component that induces an inducible promoter.

Once editing has taken place, the temperature of the SWIIN may be decreased, or the inducing medium may be removed and replaced with fresh medium lacking the chemical component thereby de-activating the inducible promoter. The cells then continue to grow in the SWIIN module 550 until the growth of the cell colonies in the microwells is normalized. For the normalization protocol, once the colonies are normalized, the colonies are flushed from the microwells by applying fluid or air pressure (or both) to the permeate member serpentine channel 560a and thus to filter 503 and pooled. Alternatively, if cherry picking is desired, the growth of the cell colonies in the microwells is monitored, and slow-growing colonies are directly selected; or, fast-growing colonies are eliminated.

Figure 5D:
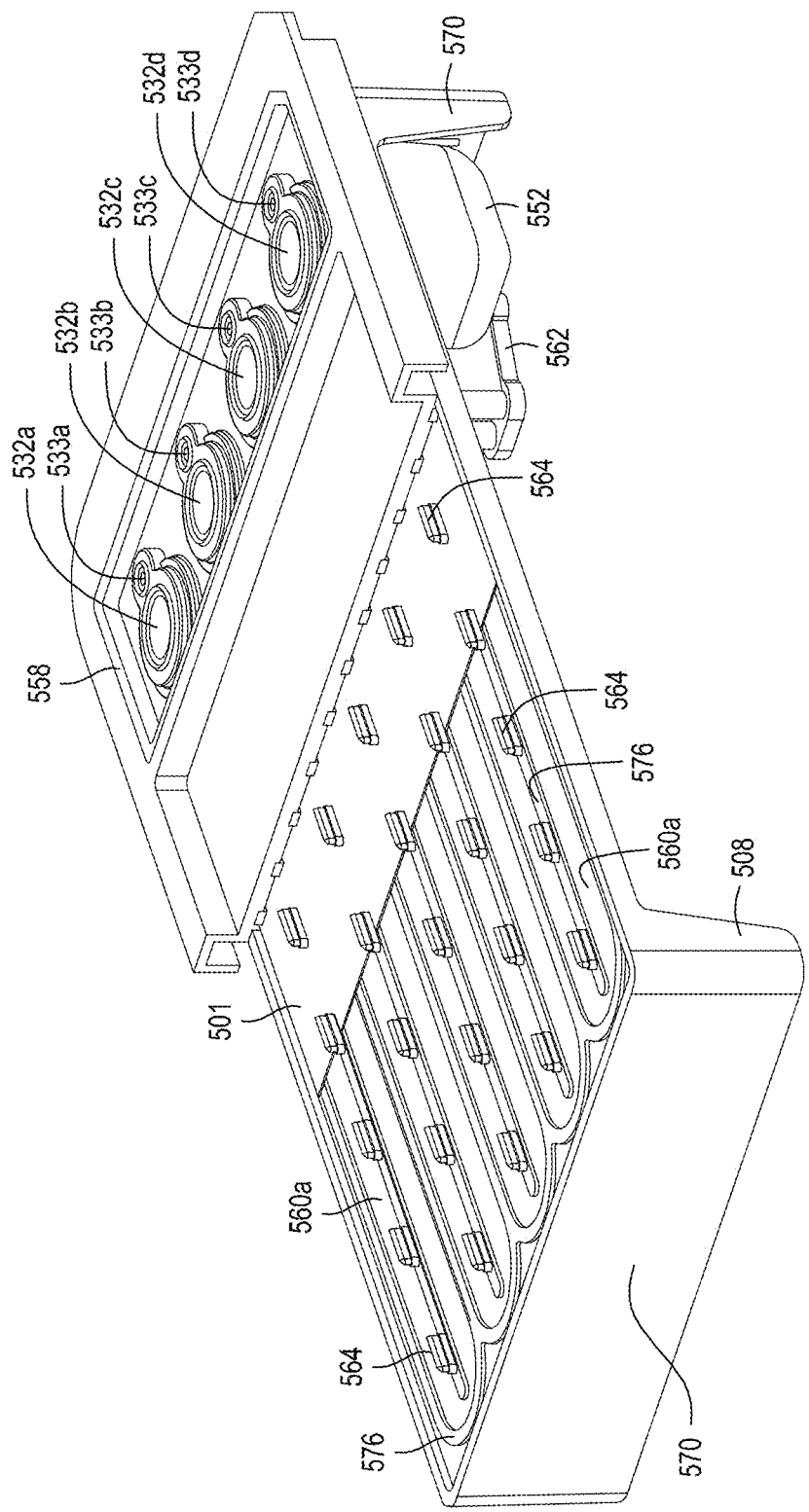

FIG. 5D is a top perspective view of a SWIIN module with the retentate and perforated members in partial cross section. In this FIG. 5D, it can be seen that serpentine channel 560a is disposed on the top of permeate member 508 is defined by raised portions 576 and traverses permeate member 508 for most of the length and width of permeate member 508 except for the portion of permeate member 508 that comprises the permeate and retentate reservoirs (note only one retentate reservoir 552 can be seen). Moving from left to right, reservoir gasket 558 is disposed upon the integrated reservoir cover 578 (cover not seen in this FIG. 5D) of retentate member 504. Gasket 558 comprises reservoir access apertures 532a, 532b, 532c, and 532d, as well as pneumatic ports 533a, 533b, 533c and 533d. Also at the far left end is support 570. Disposed under permeate reservoir 552 can be seen one of two reservoir seals 562. In addition to the retentate member being in cross section, the perforated member 501 and filter 503 (filter 503 is not seen in this FIG. 5D) are in cross section. Note that there are a number of ultrasonic tabs 564 disposed at the right end of SWIIN module 550 and on raised portion 576 which defines the channel turns of serpentine channel 560a, including ultrasonic tabs 564 extending through through-holes 566 of perforated member 501. There is also a support 570 at the end distal reservoirs 552, 554 of permeate member 508.

Figure 5E:
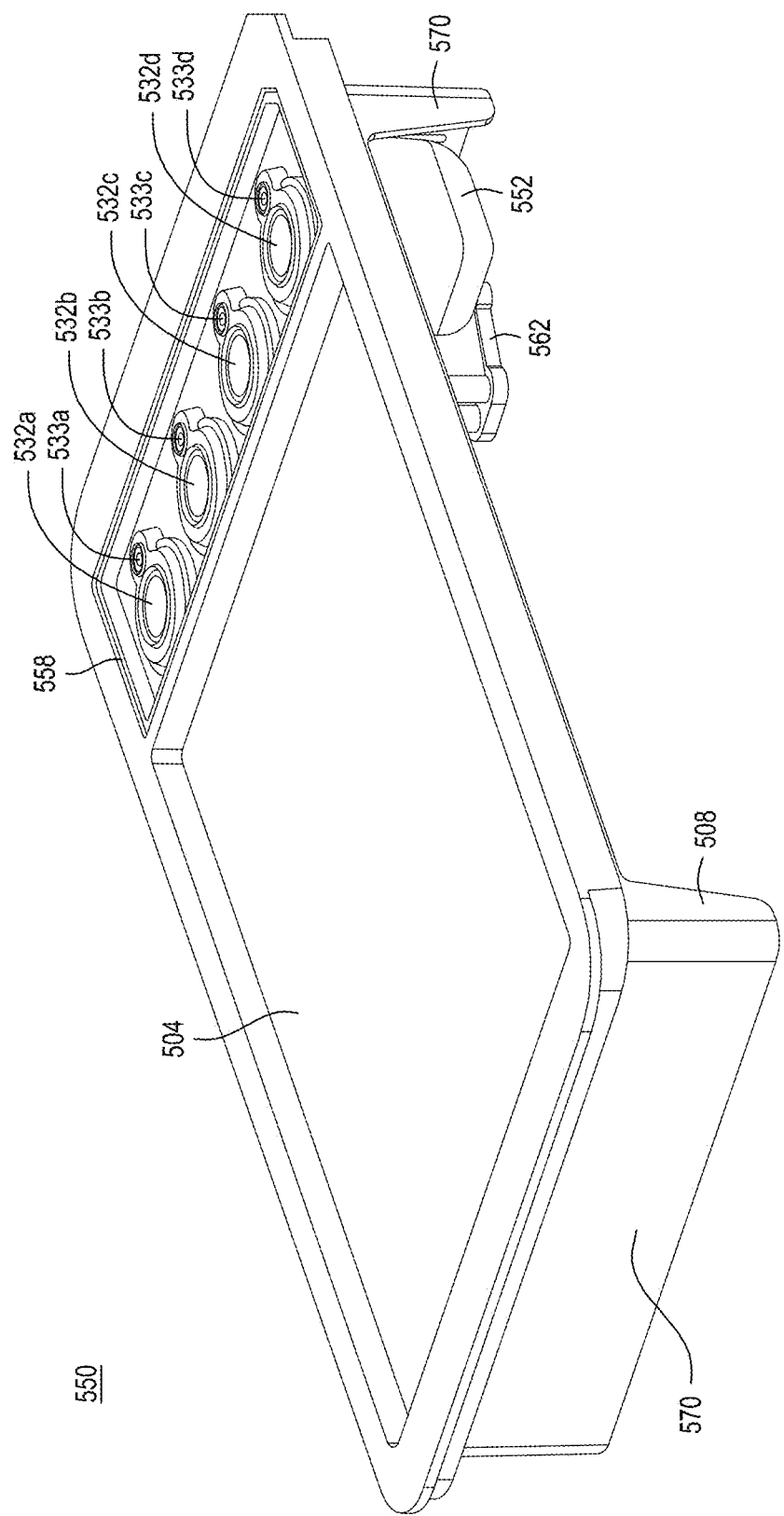

FIG. 5E is a side perspective view of an assembled SWIIN module 550, including, from right to left, reservoir gasket 558 disposed upon integrated reservoir cover 578 (not seen) of retentate member 504. Gasket 558 may be fabricated from rubber, silicone, nitrile rubber, polytetrafluoroethylene, a plastic polymer such as polychlorotrifluoroethylene, or other flexible, compressible material. Gasket 558 comprises reservoir access apertures 532a, 532b, 532c, and 532d, as well as pneumatic ports 533a, 533b, 533c and 533d. Also at the far left end is support 570 of permeate member 508. In addition, permeate reservoir 552 can be seen, as well as one reservoir seal 562. At the far right end is a second support 570.

Figure 5F:
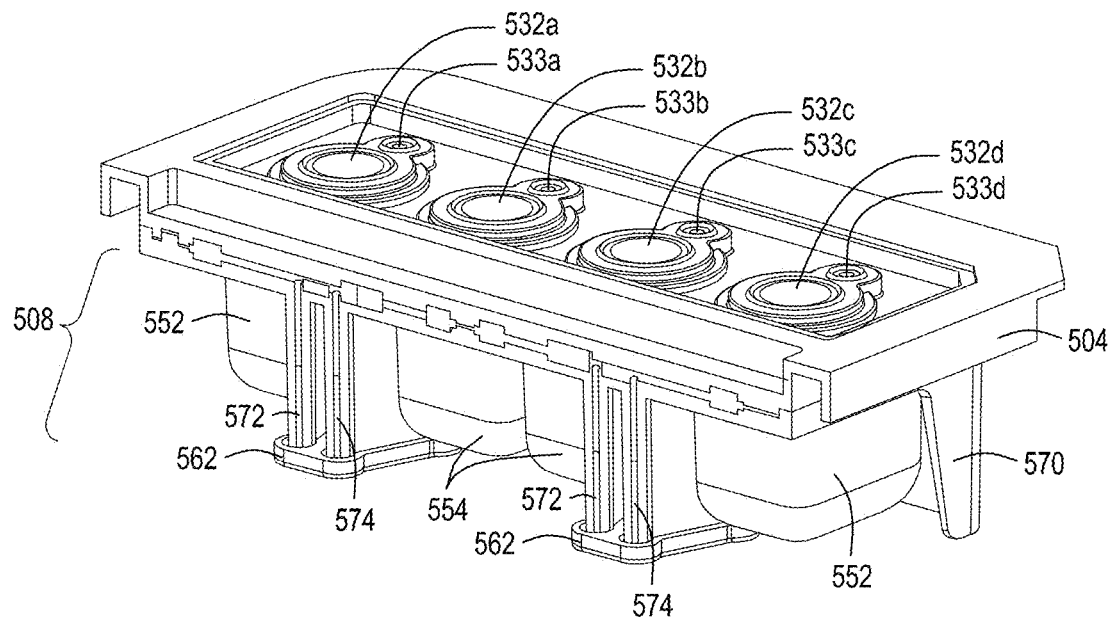

FIG. 5F is a side perspective view of the reservoir portion of permeate member 508 and retentate member 504, including gasket 558. Seen are permeate reservoirs 552 as the outside reservoirs, and retentate reservoirs 554 between permeate reservoirs 552. It should be apparent to one of ordinary skill in the art given the present description, however, that this particular configuration of reservoirs may be changed with permeate 552 and retentate 554 reservoirs alternating in position; with both permeate reservoirs 552 on one side of SWIIN module 550 and both retentate reservoirs 554 on the other side of SWIIN module 550, or the retentate reservoirs 554 may be positioned at the two sides with the permeate reservoirs 552 between the retentate reservoirs. Again, gasket 558 comprises reservoir access apertures 532a, 532b, 532c, and 532d, as well as pneumatic ports 533a, 533b, 533c and 533d. In addition, two reservoir seals 562 can be seen, each sealing one permeate reservoir 552 and one retentate reservoir 554. Also seen is support 570 at the "reservoir end" of permeate member 508.

Figure 5G:
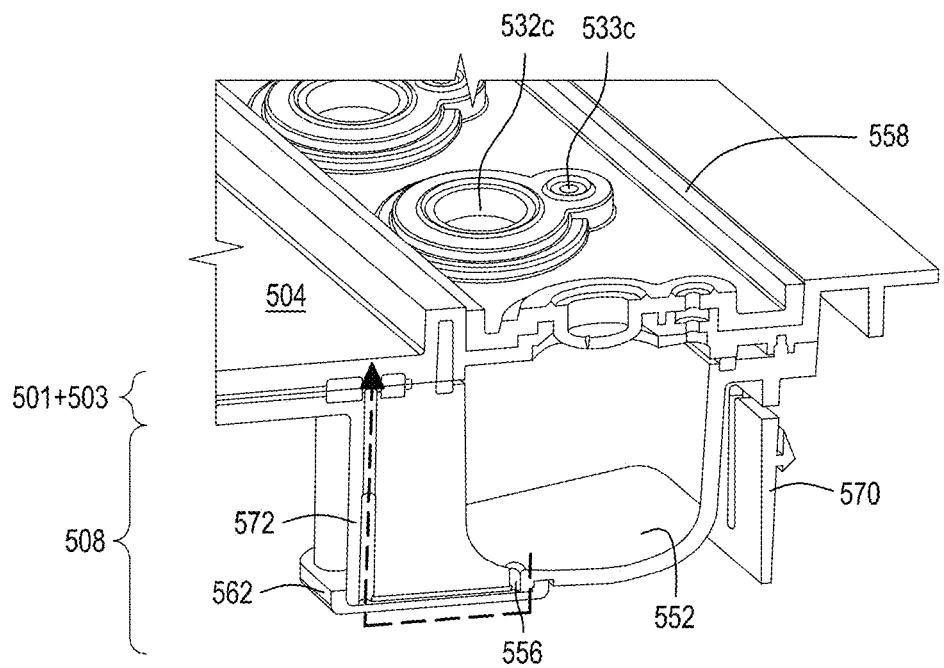

FIG. 5G is a side perspective cross sectional view of permeate reservoir 552 of permeate member 508 and retentate member 504 and gasket 558. Reservoir access aperture 532c and pneumatic aperture 533c can be seen, as well as support 570. Also seen is perforated member 501 and filter 503 (filter 503 is not seen clearly in this FIG. 5G but is sandwiched in between perforated member 501 and permeate member 508). A fluid path 572 from permeate reservoir 552 to serpentine channel 560a in permeate member 508 can be seen, as can reservoir seal 562.

Figure 5H:
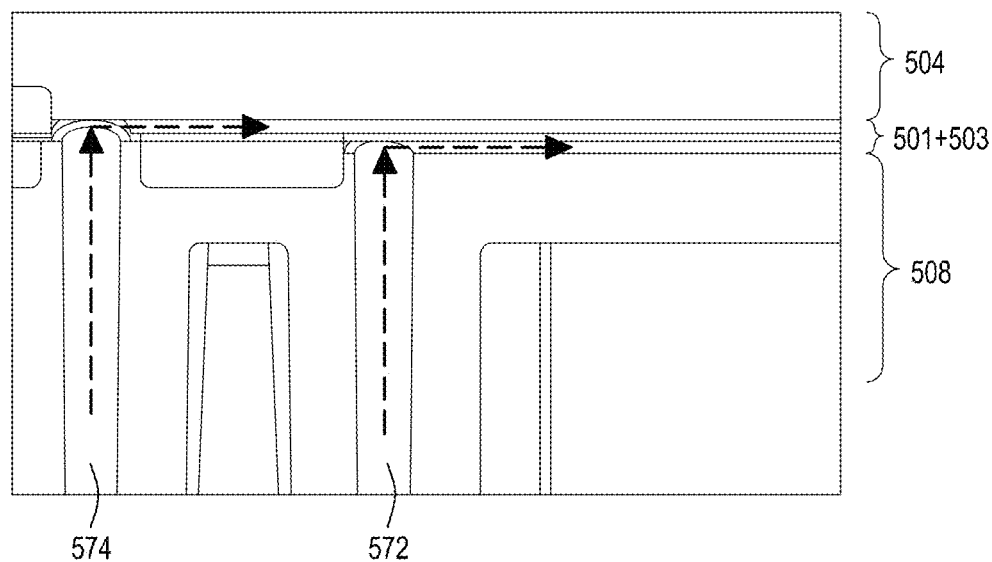

FIG. 5H is a small segment of a cross section of SWIIN module 550, showing the retentate member 504, perforated member 501, filter 503, and retentate member 508. FIG. 5H also shows a fluid path 572 from a permeate reservoir to the serpentine channel 560a disposed in permeate member 508, and a fluid path 574 from a retentate reservoir to the serpentine channel 560b disposed in permeate member 504. As mentioned previously, the reservoir architecture of this embodiment is particularly advantageous as bubbling is minimized. That is, because the reservoirs and reservoir ports are positioned below the retentate and permeate serpentine channels, there is no instantaneous flow of fluid in the reservoirs into channels that connect the reservoir ports to the retentate and permeate channels. Instead, flow is controlled by the application of pressure (positive or negative) and an appropriate time chosen by the user.

Imaging of cell colonies growing in the wells of the SWIIN is desired in most implementations for, e.g., monitoring both cell growth and device performance and imaging is necessary for cherry-picking implementations. Real-time monitoring of cell growth in the SWIIN requires backlighting, retentate plate (SWIIN top) condensation management and a system-level approach to temperature control, air flow, and thermal management. In some implementations, imaging employs a camera or CCD device with sufficient resolution to be able to image individual wells. For example, in some configurations a camera with a 9-pixel pitch is used (that is, there are 9 pixels center-to-center for each well). Processing the images may, in some implementations, utilize reading the images in grayscale, rating each pixel from low to high, where wells with no cells will be brightest (due to full or nearly-full light transmission from the backlight) and wells with cells will be dim (due to cells blocking light transmission from the backlight). After processing the images, thresholding is performed to determine which pixels will be called "bright" or "dim", spot finding is performed to find bright pixels and arrange them into blocks, and then the spots are arranged on a hexagonal grid of pixels that correspond to the spots. Once arranged, the measure of intensity of each well is extracted, by, e.g., looking at one or more pixels in the middle of the spot, looking at several to many pixels at random or pre-set positions, or averaging X number of pixels in the spot. In addition, background intensity may be subtracted. Thresholding is again used to call each well positive (e.g., containing cells) or negative (e.g., no cells in the well). The imaging information may be used in several ways, including taking images at time points for monitoring cell growth. Monitoring cell growth can be used to, e.g., remove the "muffin tops" of fast-growing cells followed by removal of all cells or removal of cells in "rounds" as described above, recover cells from specific wells (e.g., slow-growing cell colonies), or use, e.g., UV light to irradiate specific wells (e.g., fast-growing cells colonies). Imaging may also be used to assure proper fluid flow in the serpentine channel 560.

Figure 5I:
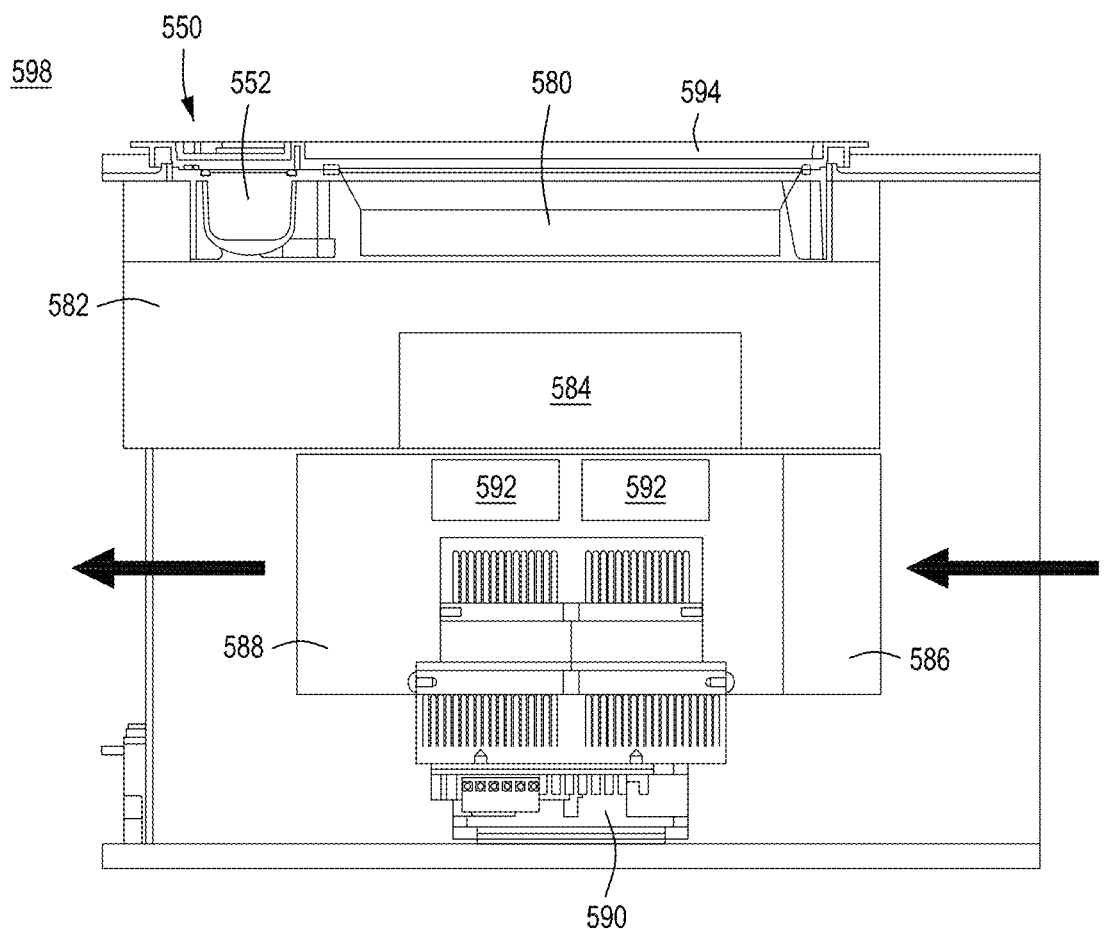
FIG. 5I depicts the embodiment of the SWIIN module in FIGS. 5A-5H further comprising a heater and a heated cover.

FIG. 5I depicts the embodiment of the SWIIN module in FIGS. 5A-5H further comprising a heat management system including a heater and a heated cover. The heater cover facilitates the condensation management that is required for imaging. Assembly 598 comprises a SWIIN module 550 seen lengthwise in cross section, where one permeate reservoir 552 is seen. Disposed immediately upon SWIIN module 550 is cover 594 and disposed immediately below SWIIN module 550 is backlight 580, which allows for imaging. Beneath and adjacent to the backlight and SWIIN module is insulation 582, which is disposed over a heatsink 584. In this FIG. 5I, the fins of the heatsink would be in-out of the page. In addition there is also axial fan 586 and heat sink 588, as well as two thermoelectric coolers 592, and a controller 590 to control the pneumatics, thermoelectric coolers, fan, solenoid valves, etc. The arrows denote cool air coming into the unit and hot air being removed from the unit. It should be noted that control of heating allows for growth of many different types of cells (prokaryotic and eukaryotic) as well as strains of cells that are, e.g., temperature sensitive, etc., and allows use of temperature-sensitive promoters. Temperature control allows for protocols to be adjusted to account for differences in transformation efficiency, cell growth and viability.

Figure 5J:
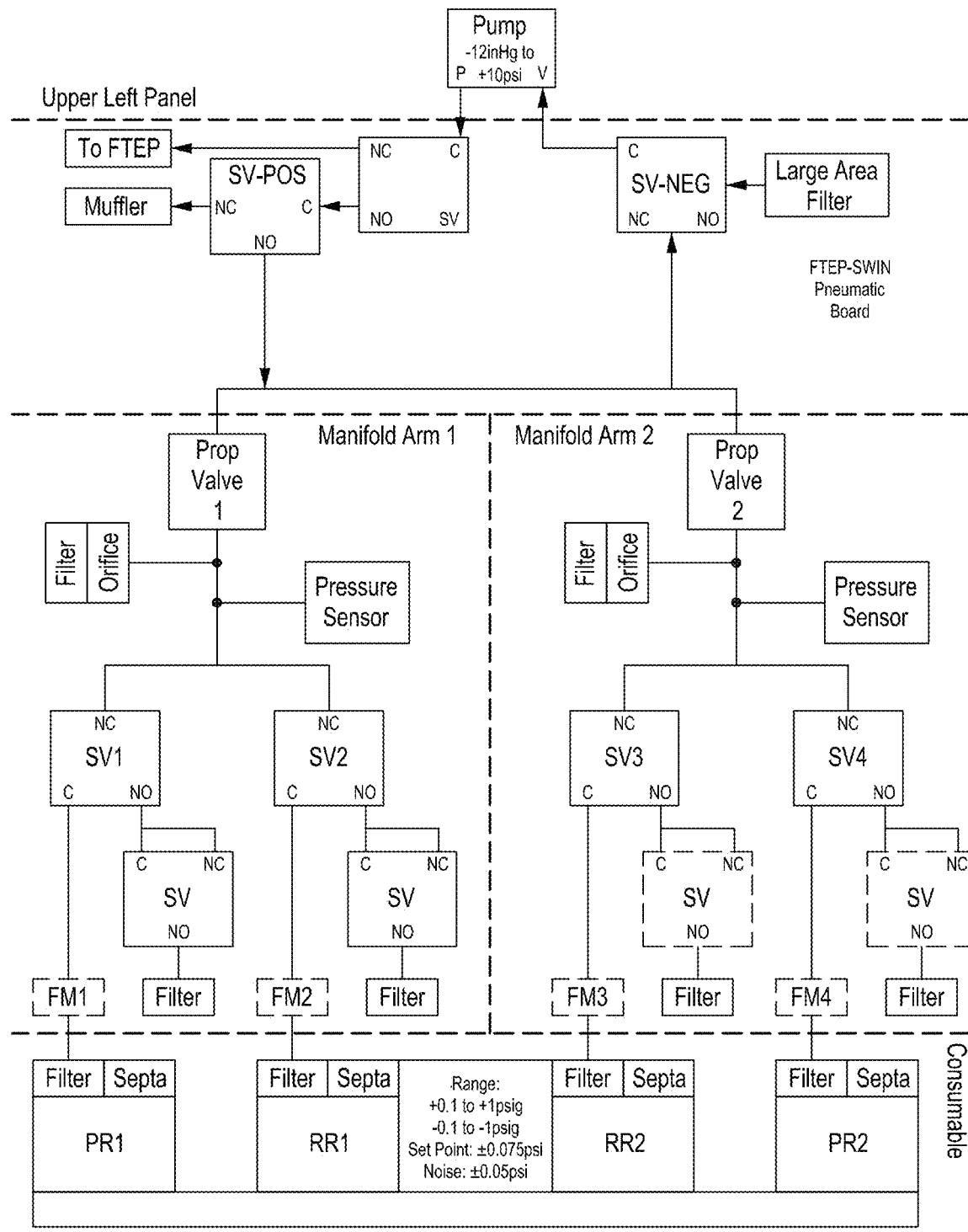
FIG. 5J is an exemplary pneumatic architecture diagram for the SWIIN module described in relation to FIGS. 5A-5I, with the status of the components for the various steps listed in Tables 1-3.

FIG. 5J is an exemplary pneumatic block diagram suitable for the SWIIN module depicted in FIGS. 5A-5I. In this configuration, there are two manifold arms that are controlled independently and there are two proportional valves, one each for the manifold arms. Tables 1-3 relate to the pneumatic diagram in FIG. 5J. Table 1 lists, for each step 1-32, the manifold arm status (open=arm open, closed=arm closed, motor engaged for pressurization); pump status (1: on, 0: off); energy status (1: energized, 0: de-energized) for each solenoid valve 1-4; and the pressure in psi for each proportional valve. Table 2 lists, for each step 1-32, the detection and threshold status for flow meters 1 and 2 as well as the duration of each step. When a change in pressure precedes a valve event, there is a delay of 1 second after reaching the set point before energizing the valves to avoid applying over- and under-shoots to the system. FALL=monitor for a falling signal, RISE=monitor for a rising signal. "Requires pLLD"=requires pressure-driven liquid level detection, such as, e.g., via air-displacement pipettor. Table 3 lists, for each step 1-32, the volumes for each reservoir, permeate reservoirs 1 and 2, and retentate reservoirs 1 and 2; the temperature of the SWIIN; and notes for operation.

Figure 6A:
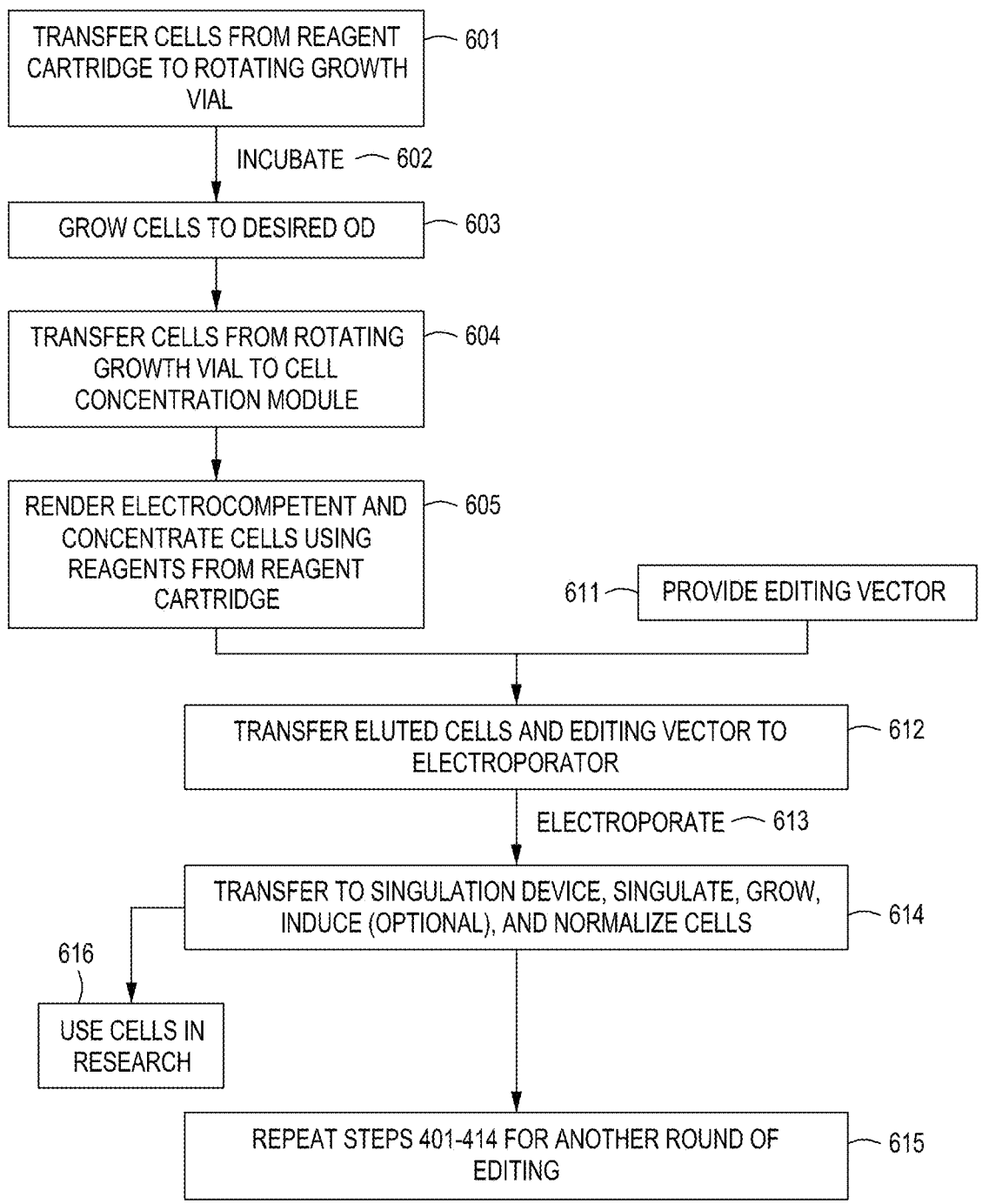
FIGS. 6A and 6B are simplified flow charts of methods for enriching or selecting edited cells using an automated multi-module cell processing instrument that includes an isolation/singulation module.

FIG. 6A is a block diagram of one embodiment of a method 400 for using the automated multi-module cell processing instrument of FIG. 3A, including the enrichment modules configured to perform the workflows described in relation to FIGS. 2A-2K. In a first step, cells are transferred 601 from reagent cartridge 310 (please refer to FIG. 3A regarding element numbers 300) to growth vial 318. The cells are incubated 602, e.g., until they grow to a desired OD 603. The cells are then transferred 604 to cell concentration module 322 to perform medium or buffer exchange and render the cells competent (e.g., electrocompetent) via medium/buffer exchange while also reducing the volume of the cell sample to a volume appropriate for electroporation, as well as to remove unwanted components, e.g., salts, from the cell sample. Once the cells have been rendered competent and suspended in an appropriate volume for transformation, the cell sample is transferred 612 to flow-through electroporation device 330 (transformation module) in reagent cartridge 310.

While cells are being processed for electroporation, automated multi-module cell processing instrument 300 may store the nucleic acids to be electroporated into the cells 611 where the editing vector is then transferred to the transformation module 612. The editing vector and the cells are thus combined in flow-through electroporation device 330 and the flow-through electroporation device is engaged 613.

After electroporation, the transformed cells optionally are transferred 614 to an isolation device 614 to, e.g., to be isolated, recover from the transformation process, be subjected to selection, and for, in this particular example, genome editing and colony normalization. Once the transformed cells have been enriched or selected, the enriched/selected cells may then be subjected to further editing 615, where all or some of steps 601-614 may be repeated, or the cells may be used in research 616.

Figure 6B:
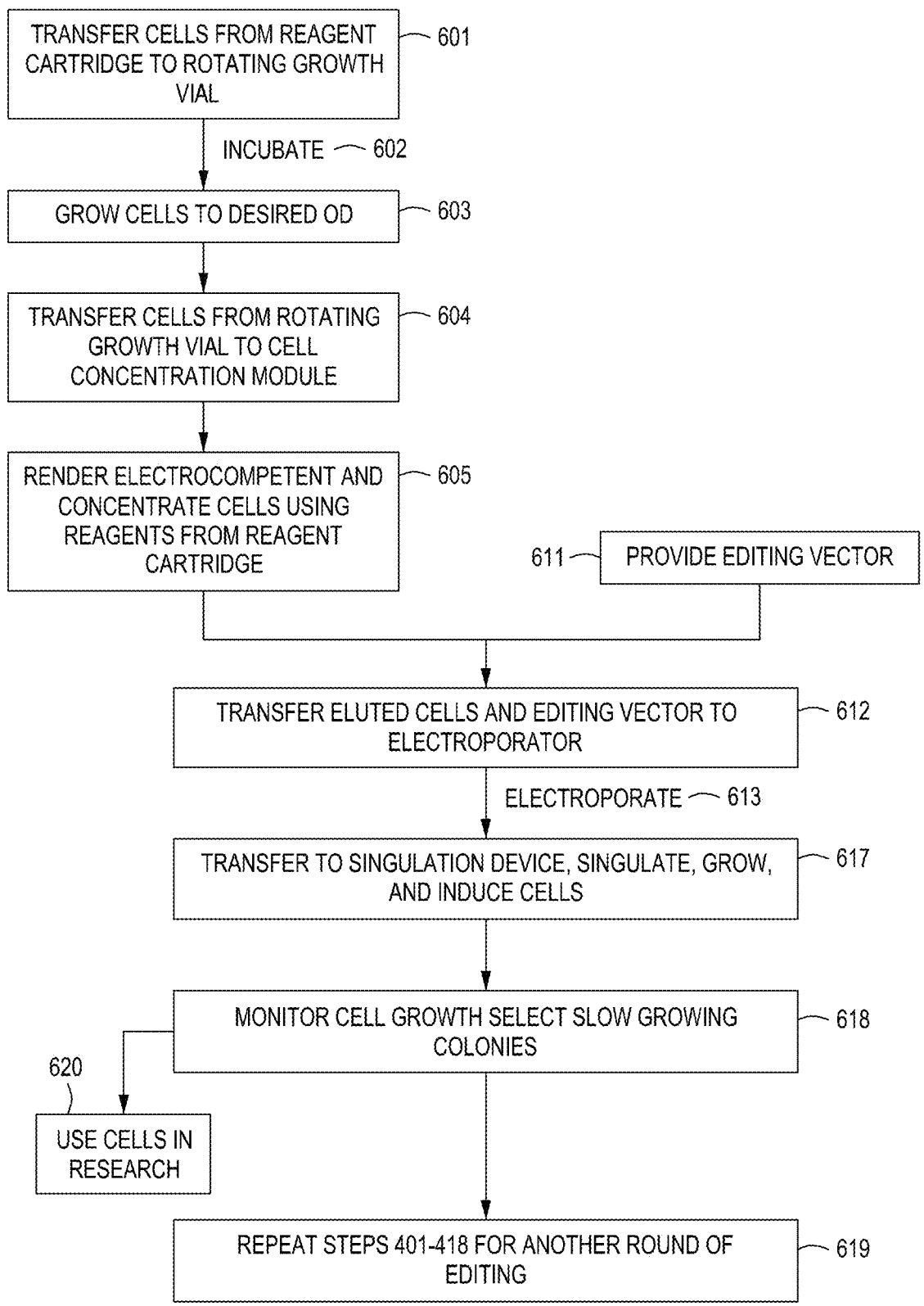

FIG. 6B is a block diagram of one embodiment of a method 606 for using the automated multi-module cell processing instrument of FIG. 3A, including the solid wall isolation/growth/editing/normalization modules configured to perform the workflow described in relation to FIGS. 2J and 2K. In a first step, cells are transferred 601 from reagent cartridge 310 (refer to FIG. 3A) to growth vial 318. The cells are incubated 602, e.g., until they grow to a desired OD 603. The cells are then transferred 604 to cell concentration module 322 (such as a cell concentration module comprising a filter) to perform medium or buffer exchange and render the cells competent (e.g., electrocompetent) via medium/buffer exchange while also reducing the volume of the cell sample to a volume appropriate for electroporation, as well as to remove unwanted components, e.g., salts, from the cell sample. Once the cells have been rendered competent and suspended in an appropriate volume for transformation, the cell sample is transferred 612 to flow-through electroporation device 330 (transformation module) in reagent cartridge 310.

While cells are being processed for electroporation, automated multi-module cell processing instrument 300 may store the nucleic acids to be electroporated into the cells 611 where the editing vector is then transferred to the transformation module 612. The editing vector and the cells are thus combined in flow-through electroporation device 330 and the flow-through electroporation device is engaged 613.

After electroporation, the transformed cells are transferred 617 to an isolation device to, e.g., recover from the transformation process, be subjected to selection, be isolated, grown, induced, and edited. Alternatively, after electroporation, the transformed cells may be transferred to a recovery module, where the cells are allowed to recover, selection may take place, and the cells can be diluted, if necessary, so that when introduced into the isolation device, the cells isolated according to a Poisson distribution or a substantial Poisson distribution. Once the transformed cells have recovered, been selected (e.g., by an antibiotic or other reagent added from the reagent cartridge), been isolated and grown a desired number of doublings. At this point, editing has been induced and the size of the colonies are monitored 618 and slow-growing colonies are selected. The cells now may be used in research 620 or the cells may then be subjected to further editing 619, where all or some of steps 601-618 may be repeated.

Figure 6C:
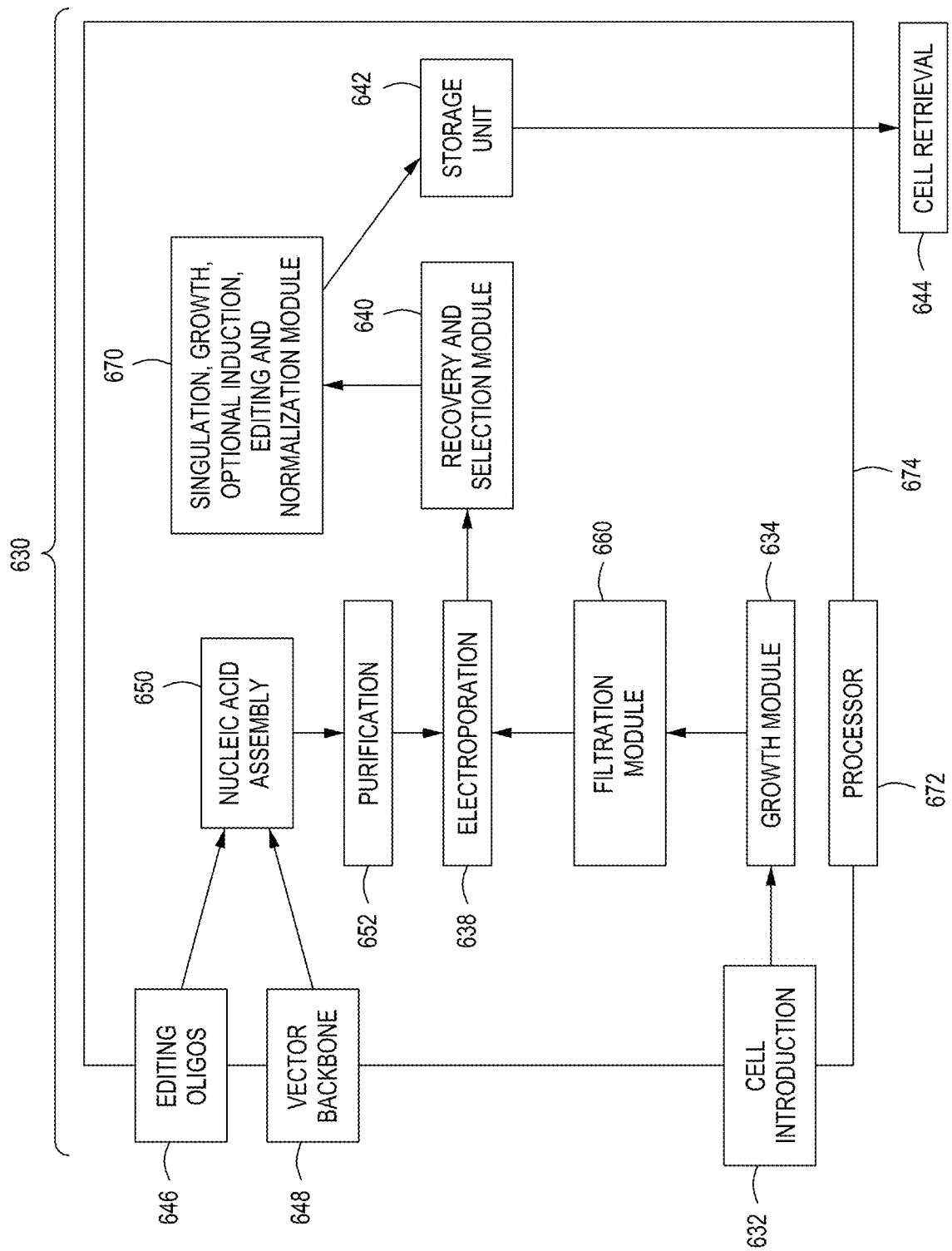
FIGS. 6C-6D are simplified block diagrams of embodiments of an exemplary automated multi-module cell processing instrument comprising an isolation and enrichment module.

FIG. 6C is a simplified block diagram of an embodiment of an exemplary automated multi-module cell processing instrument comprising a solid wall isolation/growth/editing/normalization module for enrichment for edited cells. The cell processing instrument 630 may include a housing 674, a reservoir of cells to be transformed or transfected 632, and a growth module (a cell growth device) 634. The cells to be transformed are transferred from a reservoir to the growth module to be cultured until the cells hit a target OD. Once the cells hit the target OD, the growth module may cool or freeze the cells for later processing, or the cells may be transferred to a filtration module 660 where the cells are rendered electrocompetent and concentrated to a volume optimal for cell transformation. Once concentrated, the cells are then transferred to the electroporation device 638 (e.g., transformation/transfection module). Exemplary electroporation devices of use in the automated multi-module cell processing instruments for use in the multi-module cell processing instrument include flow-through electroporation devices such as those described in U.S. Ser. No. 16/147,120, filed Sep. 28, 2018; Ser. No. 16/147,353, filed Sep. 28, 2018; Ser. No. 16/147,865, filed Sep. 30, 2018; and Ser. No. 16/147,871, filed Sep. 30, 2018 all of which are herein incorporated by reference in their entirety.

In addition to the reservoir for storing the cells, the system 630 may include a reservoir for storing editing oligonucleotide cassettes 646 and a reservoir for storing an expression vector backbone 648. Both the editing oligonucleotide cassettes and the expression vector backbone are transferred from the reagent cartridge to a nucleic acid assembly module 650, where the editing oligonucleotide cassettes are inserted into the expression vector backbone. The assembled nucleic acids may be transferred into an optional purification module 652 for desalting and/or other purification and/or concentration procedures needed to prepare the assembled nucleic acids for transformation. Alternatively, pre-assembled nucleic acids, e.g., an editing vector, may be stored within reservoir 646 or 648. Once the processes carried out by the purification module 652 are complete, the assembled nucleic acids are transferred to, e.g., an electroporation device 638, which already contains the cell culture grown to a target OD and rendered electrocompetent via filtration module 660. In electroporation device 638, the assembled nucleic acids are introduced into the cells. Following electroporation, the cells are transferred into a combined recovery/selection module 640.

Following recovery, and, optionally, selection, the cells are transferred to an isolation, growth, induction, editing, and normalization module 670, where the cells are diluted and compartmentalized such that there is an average of one cell per compartment. Isolation can entail a well (See FIGS. 2J and 2K), a droplet (see FIGS. 2F and 2G), in gel in three-dimensional space (see FIGS. 2H and 2I), or an area, e.g., cells isolated from one another on an agar plate or arrayed on a functionalized substrate (FIGS. 2A-2E). Once isolated, the cells are allowed to grow for a pre-determined number of doublings. Once these initial colonies are established, editing is induced and the edited cells are allowed to establish colonies, which are grown to terminal size (e.g., the colonies are normalized). In some embodiments, editing is induced by one or more of the editing components being under the control of an inducible promoter. In some embodiments, the inducible promoter is activated by a rise in temperature and "deactivated" by lowering the temperature.

The recovery, selection, isolation, induction, editing and growth modules may all be separate, may be arranged and combined as shown in FIG. 3A, or may be arranged or combined in other configurations. In certain embodiments, recovery and selection are performed in one module, and isolation, growth, editing, and normalization are performed in a separate module. Alternatively, recovery, selection, isolation, growth, editing, and normalization are performed in a single module.

Once the normalized cell colonies are pooled, the cells may be stored, e.g., in a storage module 642, where the cells can be kept at, e.g., 4° C. until the cells are retrieved for further study. Alternatively, the cells may be used in another round of editing. The multi-module cell processing instrument is controlled by a processor 672 configured to operate the instrument based on user input, as directed by one or more scripts, or as a combination of user input or a script. The processor 672 may control the timing, duration, temperature, and operations of the various modules of the system 630 and the dispensing of reagents. For example, the processor 672 may cool the cells post-transformation until editing is desired, upon which time the temperature may be raised to a temperature conducive of genome editing and cell growth. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module instrument.

The automated multi-module cell processing instrument 630 is a nuclease-directed genome editing instrument and can be used in single editing systems (e.g., introducing one or more edits to a cellular genome in a single editing process). The system of FIG. 6D, described below, is configured to perform sequential editing, e.g., using different nuclease-directed systems sequentially to provide two or more genome edits in a cell; and/or recursive editing, e.g. utilizing a single nuclease-directed system to introduce sequentially two or more genome edits in a cell.

Figure 6D:
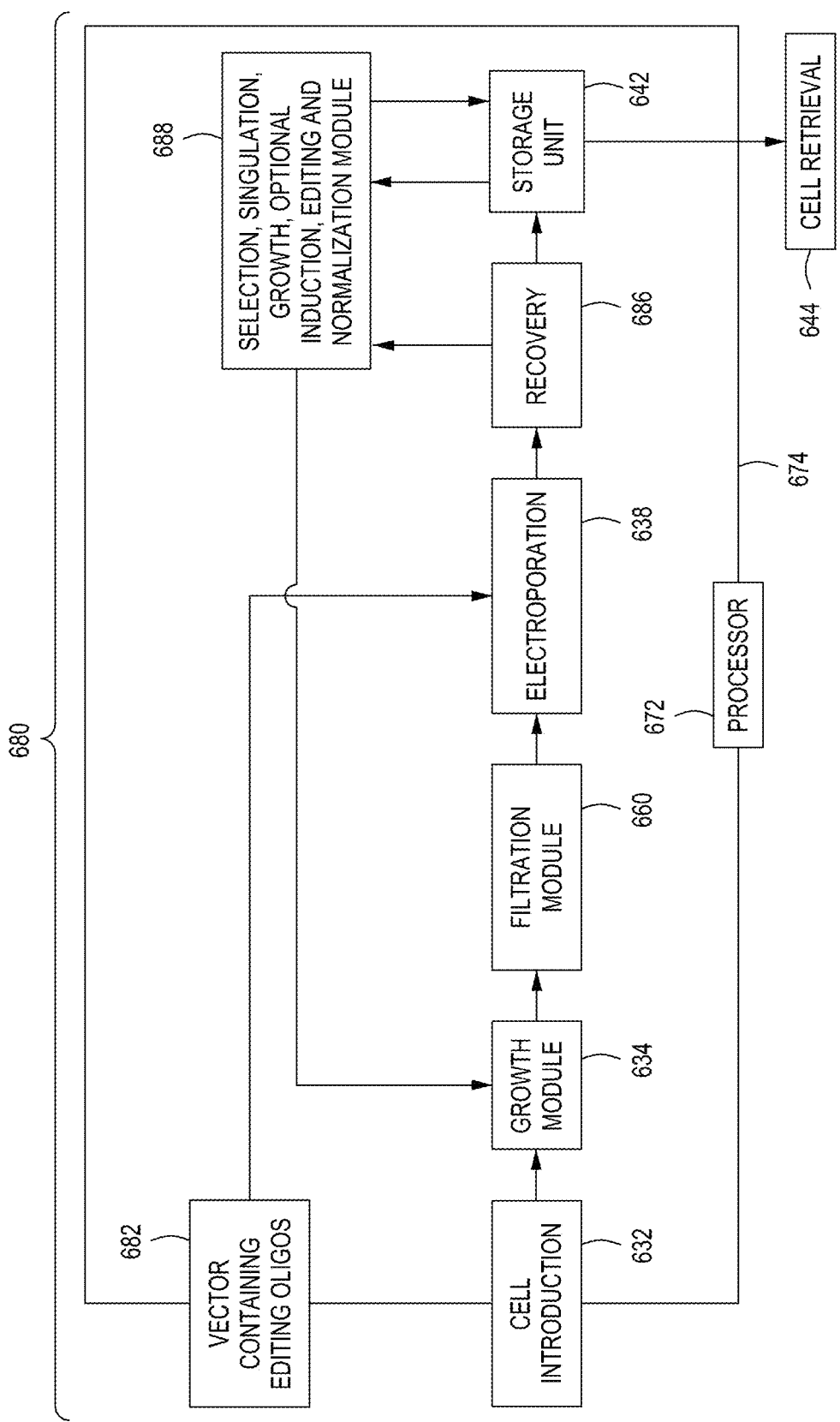

FIG. 6D illustrates another embodiment of a multi-module cell processing instrument. This embodiment depicts an exemplary system that performs recursive gene editing on a cell population. As with the embodiment shown in FIG. 6C, the cell processing instrument 680 may include a housing 674, a reservoir for storing cells to be transformed or transfected 632, and a cell growth module (comprising, e.g., a rotating growth vial) 634. The cells to be transformed are transferred from a reservoir to the cell growth module to be cultured until the cells hit a target OD. Once the cells hit the target OD, the growth module may cool or freeze the cells for later processing or transfer the cells to a filtration module 660 where the cells are subjected to buffer exchange and rendered electrocompetent, and the volume of the cells may be reduced substantially. Once the cells have been concentrated to an appropriate volume, the cells are transferred to electroporation device 638. In addition to the reservoir for storing cells, the multi-module cell processing instrument includes a reservoir for storing an editing vector pre-assembled with editing oligonucleotide cassettes 682. The pre-assembled nucleic acid vectors are transferred to the electroporation device 638, which already contains the cell culture grown to a target OD. In the electroporation device 638, the nucleic acids are electroporated into the cells.

Following electroporation, the cells are transferred into an optional recovery module 686, where the cells are allowed to recover briefly post-transformation.

After recovery, the cells may be transferred to a storage module 642, where the cells can be stored at, e.g., 4° C. for later processing, or the cells may be diluted and transferred to a selection/isolation (singulation)/growth/editing/normalization module 688. In the isolation/edit/growth module 688, the cells are arrayed such that there is an average of one cell per microwell. The arrayed cells may be in selection medium to select for cells that have been transformed or transfected with the editing vector(s). Once isolated, the cells are allowed to grow through 2-200 doublings and establish colonies. Once colonies are established, editing is induced by providing conditions (e.g., temperature, addition of an inducing or repressing chemical) to induce editing. Once editing is initiated and allowed to proceed, the cells are allowed to grow to terminal size (e.g., normalization of the colonies) and then can be flushed out of the microwells and pooled, then transferred to the storage (or recovery) unit 642 or can be transferred to a growth module 634 for another round of editing. In between pooling and transfer to a growth module, there may be one or more additional steps, such as cell recovery, medium exchange, cells concentration, etc., by, e.g., filtration. Note that the selection/isolation/growth/induction/editing and normalization modules may be the same module, where all processes are performed in the module, or selection and/or dilution may take place in a separate vessel before the cells are transferred to the isolation/growth/editing/normalization module. Once the putatively-edited cells are pooled, they may be subjected to another round of editing, beginning with growth, cell concentration and treatment to render electrocompetent, and transformation by yet another donor nucleic acid in another editing cassette via the electroporation module 638.

In electroporation device 638, the cells selected from the first round of editing are transformed by a second set of editing oligos (or other type of oligos) and the cycle is repeated until the cells have been transformed and edited by a desired number of, e.g., editing cassettes. The multi-module cell processing instrument exemplified in FIG. 6D is controlled by a processor 672 configured to operate the instrument based on user input or is controlled by one or more scripts including at least one script associated with the reagent cartridge. The processor 672 may control the timing, duration, and temperature of various processes, the dispensing of reagents, and other operations of the various modules of the system 680. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing instrument.

It should be apparent to one of ordinary skill in the art given the present disclosure that the process described may be recursive and multiplexed; that is, cells may go through the workflow described in relation to FIG. 6D, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries.

In any recursive process, it is advantageous to "cure" the previous engine and editing vectors (or single engine+ editing vector in a single vector system). "Curing" is a process in which one or more vectors used in the prior round of editing is eliminated from the transformed cells. Curing can be accomplished by, e.g., cleaving the vector(s) using a curing plasmid thereby rendering the editing and/or engine vector (or single, combined vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine plasmid.

Figure 6E:
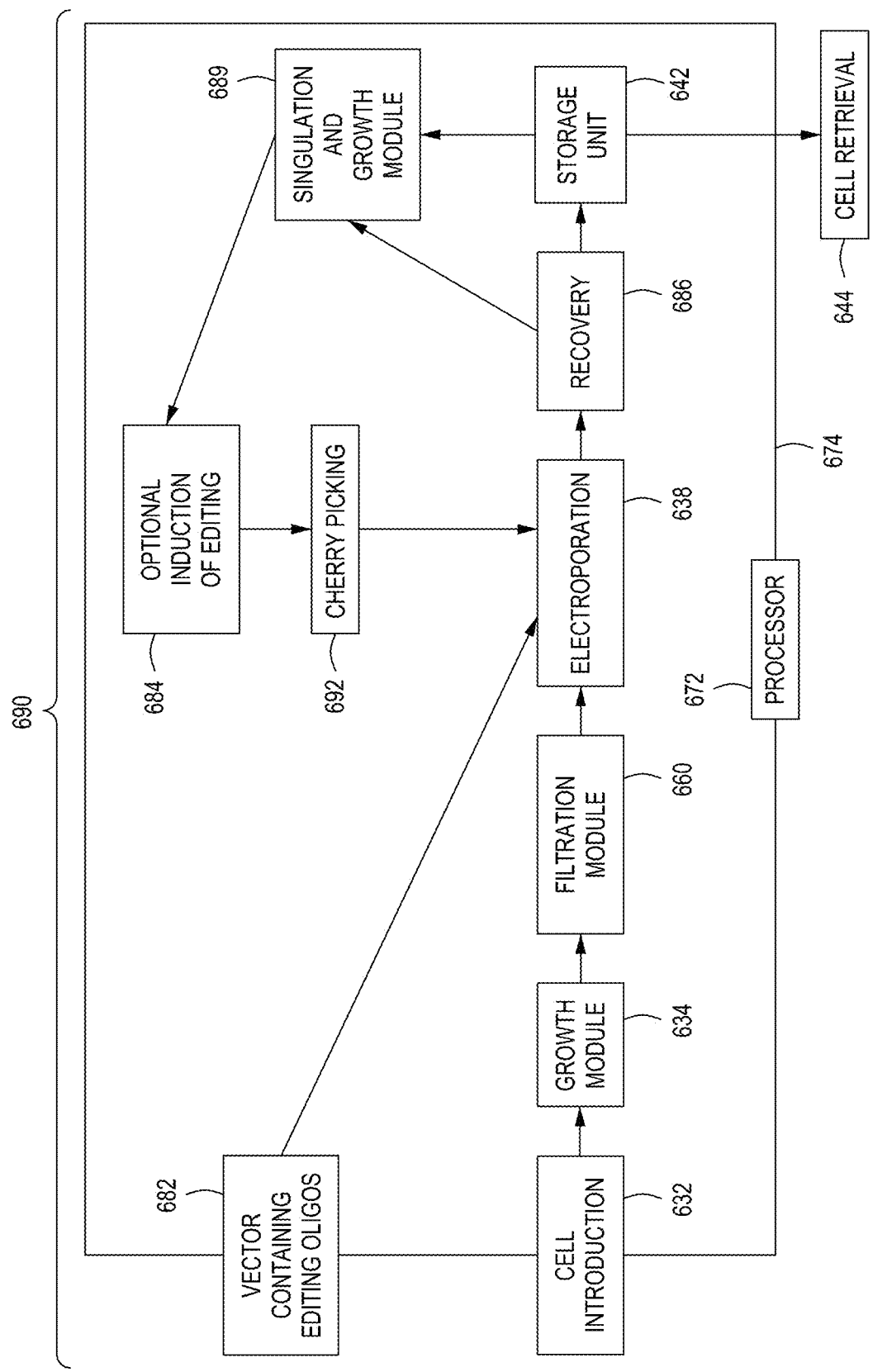
FIG. 6E is a simplified block diagram of an embodiment of an exemplary automated multi-module cell processing instrument comprising an isolation and selection module.

FIG. 6E illustrates another embodiment of a multi-module cell processing system. This embodiment depicts an exemplary system that 1) includes editing induction and cell selection in addition to enrichment, and 2) performs recursive gene editing on a cell population. As with the embodiments shown in FIGS. 6C and 6D, the cell processing system 690 may include a housing 674, a reservoir for storing cells to be transformed or transfected 632, and a cell growth module (a cell growth device) 634. The cells to be transformed are transferred from a reservoir to the cell growth module to be cultured until the cells hit a target OD. Once the cells hit the target OD, the growth module may cool or freeze the cells for later processing or transfer the cells to an optional filtration module 660 where the cells are rendered electrocompetent, and the volume of the cells may be reduced substantially. Once the cells have been concentrated to an appropriate volume, the cells are transferred to electroporation device 638. In addition to the reservoir for storing cells, the multi-module cell processing system includes a reservoir for storing the vector comprising editing oligonucleotides 682. The assembled nucleic acids are transferred to the electroporation device 638, which already contains the cell culture grown to a target OD. In the electroporation device 638, the nucleic acids are electroporated into the cells. Following electroporation, the cells are transferred into an optional recovery module 686, where the cells are allowed to recover briefly post-transformation.

After recovery, the cells may be transferred to a storage module 642, where the cells can be stored at, e.g., 4° C. until the cells are retrieved for further study, or the cells may be transferred to an isolation and growth module 634. In the isolation (e.g., singulation) and growth module 689, the cells are arrayed such that there is an average of one cell per compartment. In some embodiments, a compartment may be a well (see FIGS. 2J and 2K); a droplet (see FIGS. 2F and 2G); in gel in three-dimensional space (see FIGS. 2H and 2I); or an area, e.g., cells isolated from one another on an agar plate or arrayed on, e.g., a functionalized substrate (see FIGS. 2A, 2B, 2D, and 2E). Once isolated, the cells are allowed to grow through 2-50 doublings or more and establish colonies. Once colonies are established, the substrate with the cell colonies is transferred to an induction module, where conditions exist (temperature, addition of an inducing or repressing chemical) to induce editing. Once editing is initiated and allowed to proceed, the substrate is transferred to a cherry picking module 692, which may include, e.g., a colony measuring and picking device that selects small colonies of cells; a spectrophotometer or video camera configured to measure OD in wells or droplets and collect colonies of edited cells or ablate or irradiate colonies of unedited cells based on cell growth; or a spectrophotometer configured to measure other cellular characteristics in wells or droplets and collect colonies of edited cells based on cell characteristics that correlate with cell growth. Note that the isolation and growth module and cherry-picking module may be linked. Once the putatively-edited cells are selected (or putatively un-edited cells are eliminated), the edited cells may be subjected to another round of editing, beginning with transformation by yet another donor nucleic acid in another editing cassette via the electroporation module 638.

In electroporation device 638, the cells selected from the first round of editing are transformed by a second set of editing oligos (or other type of oligos) and the cycle is repeated until the cells have been transformed and edited by a desired number of, e.g., donor nucleic acids. The multi-module cell processing system exemplified in FIG. 6E is controlled by a processor 672 configured to operate the instrument based on user input or is controlled by one or more scripts including at least one script associated with the reagent cartridge. The processor 672 may control the timing, duration, and temperature of various processes, the dispensing of reagents, and other operations of the various modules of the system 690. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing system.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Other equivalent methods, steps and compositions are intended to be included in the scope of the invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Enrichment of Editing Cells by Growth Lag Identification

Transformation: 100 ng of the editing vector cloned library or Gibson Assembly® reaction was transformed by electroporation into 100 µL competent EC1 cells containing the engine vector. The electroporator was set to 2400 V in 2 mm cuvette. Following transformation, the cells were allowed to recover for 3 hours in SOB medium. A 10-fold dilution series of recovered cells (in $H_2O$) was spot plated and the resulting CFU counts/dilution ratios were used to calculate transformation efficiency.

Plating and Colony Arraying: 100 µL of the appropriate dilution was plated on LB medium+25 µg/mL chlor and +arabinose and grown at 30° C. for 6-8 hours. Alternatively, the cells may be grown in liquid culture in LB medium+25 µg/mL chlor at 30° C. for 6-8 hours. The temperature of the plate was adjusted to 42° C. and the plates were incubated for two hours. The temperature was then adjusted back to 30° C. and the cells were allowed to recover overnight.

Edited Cell Identification: Small-size colonies were identified. The small colony-size phenotype indicates cell viability was compromised during the induced-editing procedure. Efficient recovery of edited cells from the initial pool was accomplished by identifying and picking small colonies and arraying cells from these small colonies onto a 96-well plate to create a library of edited cells, or the cells from the colonies were pooled generating highly-edited cell populations for recursive editing. Editing was assessed/validated by sequencing. It was found that 85% of the small colonies were edited cells (data not shown).

Example 2

Assessing Editing by Optical Density

FIG. 2C is a depiction of the growth profiles of randomly-picked variants from a silent PAM mutation (SPM) library. This 500-member library targets regions located across the entire E. coli genome and integrated synonymous mutations that have no expected fitness effects. Colonies were picked from agar plates of uninduced transformed cells. Cells were picked from an agar plate and grown up in 200 µL LB+chlor/carb overnight in a 96-well microtiter plate format. 10 µL of the well content of the parent microtiter plate was then transferred to two replica daughter microtiter plates that received either no induction (top) or gRNA and nuclease induction (via the pL inducible promoter) for 1 hour at 42° C. (bottom). The well maps show the relative OD at 6 hours; the full growth curves are shown for reference. The replica wells represent growth observed from the same cassette design with or without gRNA induction. While the majority of the wells for the no-induction plate show normal growth profiles, the induced plate shows that a large fraction of the gRNA designs are still active when induced, indicated by a large lag phase before the cells reach exponential growth. That is, the actively-editing cells have reduced viability due to DNA damage such that many cells in the colonies die off, and those edited cells that do survive take longer to re-establish colonies. This characteristic of edited cells can be exploited to screen for active editing in a high-throughput manner.

Example 3

Editing Cassette and Backbone Amplification and Assembly

Editing Cassette Preparation: 5 nM of oligonucleotides synthesized on a chip were amplified using Q5 polymerase in 50 µL volumes. The PCR conditions were 95° C. for 1 minute; 8 rounds of 95° C. for 30 seconds/60° C. for 30 seconds/72° C. for 2.5 minutes; with a final hold at 72° C. for 5 minutes. Following amplification, the PCR products were subjected to SPRI cleanup, where 30 µL SPRI mix was added to the 50 µL PCR reactions and incubated for 2 minutes. The tubes were subjected to a magnetic field for 2 minutes, the liquid was removed, and the beads were washed 2× with 80% ethanol, allowing 1 minute between washes. After the final wash, the beads were allowed to dry for 2 minutes, 50 µL 0.5× TE pH 8.0 was added to the tubes, and the beads were vortexed to mix. The slurry was incubated at room temperature for 2 minutes, then subjected to the magnetic field for 2 minutes. The eluate was removed and the DNA quantified.

Following quantification, a second amplification procedure was carried out using a dilution of the eluate from the SPRI cleanup. PCR was performed under the following conditions: 95° C. for 1 minute; 18 rounds of 95° C. for 30 seconds/72° C. for 2.5 minutes; with a final hold at 72° C. for 5 minutes. Amplicons were checked on a 2% agarose gel and pools with the cleanest output(s) were identified. Amplification products appearing to have heterodimers or chimeras were not used.

Backbone Preparation: A 10-fold serial dilution series of purified backbone was performed, and each of the diluted backbone series was amplified under the following conditions: 95° C. for 1 minute; then 30 rounds of 95° C. for 30 seconds/60° C. for 1.5 minutes/72° C. for 2.5 minutes; with a final hold at 72° C. for 5 minutes. After amplification, the amplified backbone was subjected to SPRI cleanup as described above in relation to the cassettes. The backbone was eluted into 100 µL dd$H_2O$ and quantified before isothermal nucleic acid assembly.

Isothermal Nucleic Acid Assembly: 150 ng backbone DNA was combined with 100 ng cassette DNA. An equal volume of 2× isothermal nucleic acid assembly master mix was added, and the reaction was incubated for 45 minutes at 50° C. After assembly, the assembled backbone and cassettes were subjected to SPRI cleanup, as described above.

Transformation of Editing Vector into E Cloni®: 20 µL of the prepared editing vector isothermal assembly reaction was added to 30 µL chilled water along with 10 µL E Cloni® (Lucigen, Middleton, Wis.) supreme competent cells. An aliquot of the transformed cells were spot plated to check the transformation efficiency, where >100× coverage was required to continue. The transformed E Cloni® cells were outgrown in 25 mL SOB+100 µg/mL carbenicillin (carb). Glycerol stocks were generated from the saturated culture by adding 500 µL 50% glycerol to 1000 µL saturated overnight culture. The stocks were frozen at −80° C. This step is optional, providing a ready stock of the cloned editing library. Alternatively, Gibson or another assembly of the editing cassettes and the vector backbone can be performed before each editing experiment.

Creation of New Cell Line Transformed with Engine Vector: Transformation: 1 µL of the engine vector DNA (comprising a coding sequence for MAD7 nuclease under the control of the pL inducible promoter, a chloramphenicol resistance gene, and the λ Red recombineering system) was added to 50 µL EC1 strain *E. coli* cells. The transformed cells were plated on LB plates with 25 µg/mL chloramphenicol (chlor) and incubated overnight to accumulate clonal isolates. The next day, a colony was picked, grown overnight in LB+25 µg/mL chlor, and glycerol stocks were prepared from the saturated overnight culture by adding 500 µL 50% glycerol to 1000 µL culture. The stocks of EC1 comprising the engine vector were frozen at −80° C.

Preparation of Competent Cells: A 1 mL aliquot of a freshly-grown overnight culture of EC1 cells transformed with the engine vector was added to a 250 mL flask containing 100 mL LB/SOB+25 µg/mL chlor medium. The cells were grown to 0.4-0.7 OD, and cell growth was halted by transferring the culture to ice for 10 minutes. The cells were pelleted at 8000× g in a JA-18 rotor for 5 minutes, washed 3× with 50 mL ice cold ddH$_2$O or 10% glycerol and pelleted at 8000× g in JA-18 rotor for 5 minutes. The washed cells were resuspended in 5 mL ice cold 10% glycerol and aliquoted into 200 µL portions. Optionally at this point the glycerol stocks could be stored at −80° C. for later use.

Example 4

Exemplary Workflow for Diversity Generation

First, a library was designed, taking approximately 1-4 weeks. The reagents were manufactured (approximately 2 weeks) and received. Optionally, the engine and editing vectors are pre-assembled, although in some workflows, the engine vector is pre-assembled and used to transform the cells to be edited in advance, while the editing vector is transformed into the cells in the automated multi-module cell processing instrument. Yet another option is to combine the engine and editing vectors into a single vector. In this example, both the nuclease and the guide nucleic acid were under the control of the pL inducible promoter, which is induced by temperature.

Transformation in the automated transformation module employing an electroporation device took approximately 5 minutes. At this point, the transformed cells may optionally be stored in a freezer for later experiments, or the cells can proceed to editing. The cells were outgrown to saturation (approximately 12 hours) and then diluted and plated to agar, such as on 3-4 Q trays. The plated cells were allowed to grow for 6-12 hours, and then are induced by raising the temperature to 42° C. In one option, the cells were grown to colonies of terminal size, and then the colonies were harvested and an aliquot of the cells is prepared for sequencing to QC the library. The cells on the Q trays were then picked into 96-well plates. In one option, all colonies were picked. In an alternative option, only small colonies were picked. Once picked, the colonies are allowed to grow overnight, and aliquots from these colonies are replica plated into a different 96-well plate. At this point, assays can be run to identify edits.

Alternatively, the cells on the Q trays may be scraped and pooled into a tube. A glycerol stock can be made of this library, and another aliquot can be used to run selections on, e.g., Q trays. The results of the editing process are then analyzed using amplicon verification or genome validation.

Example 5

Exemplary Workflow for Combinatorial Edit Generation

As with the diversity workflow, a library was designed, taking approximately 1-4 weeks. The reagents were manufactured (approximately 2 weeks) and received. Optionally, the engine and editing vectors are pre-assembled, although in some workflows, the engine vector is pre-assembled and used to transform the cells to be edited in advance, while the editing vector is transformed into the cells in the automated multi-module cell processing instrument. Yet another option is to combine the engine and editing vectors into a single vector. In this embodiment, both the nuclease and the guide nucleic acid are under the control of the pL inducible promoter, which is induced by temperature.

Transformation in the automated transformation module employing an electroporation device took approximately 5 minutes. At this point, the transformed cells may optionally be stored in a freezer for later experiments, or the cells can proceed to editing. The cells can then be outgrown to saturation (approximately 12 hours) and then diluted and plated to agar, such as on 3-4 QTRAYS™ (Molecular Devices, San Jose, Calif.). The plated cells were allowed to grow for 6-12 hours, and then were induced by raising the temperature to 42° C. In one option, the cells are grown to colonies of terminal size. Next, the cells are subjected to an optional recursion step, in which the plates are scraped, pooled, cured, made electrocompetent, and transformed with another set of editing vectors.

In one option, the cells were grown to colonies of terminal size, and then the colonies were harvested and an aliquot of the cells was prepared for sequencing to QC the library. The cells on the QTRAYS™ are then picked into 96-well plates. In one option, all colonies are picked. In an alternative option, only small colonies are picked. Once picked, the colonies are allowed to grow overnight and aliquots from these colonies are replica plated into a different 96-well plate. At this point, assays can be run to identify edits.

Alternatively, the cells on the QTRAYS™ may be scraped and pooled into a tube. A glycerol stock can be made of this library, and another aliquot can be used to run selections on, e.g., QTRAYS™. The results of the editing process are then analyzed using amplicon verification or genome validation.

Example 6

Exemplary Workflow for Diversity Generation with Cell Printing

As in the workflows described above, first a library was designed, taking approximately 1-4 weeks. The reagents were manufactured (approximately 2 weeks) and received. Optionally, the engine and editing vectors are pre-assembled, although in some workflows, the engine vector is pre-assembled and used to transform the cells to be edited in advance, while the editing vector is transformed into the cells in the automated multi-module cell processing instrument. Yet another option is to combine the engine and editing vectors. In this embodiment, both the nuclease and the guide nucleic acid were under the control of the pL inducible promoter, which is induced by temperature.

Transformation in the automated transformation module employing an electroporation device took approximately 5 minutes. At this point, the transformed cells may optionally be stored in a freezer for later experiments, or the cells can proceed to editing. The cells can then be outgrown to saturation (approximately 12 hours). Once grown, the cells are printed 100×96-well or 25×384-well plates. The number of plates grows with lower basal editing efficiency (e.g., 50% editing efficiency requires 200×96-well plates). The cells are allowed to grow for several to many doublings and are then the promoters driving both transcription of the nuclease and guide nucleic acid are induced with temperature. After induction, the temperature is lowered and the edited cells are allowed to grow for some time. If wells have high degree of polyclonality they optionally can be repooled and run back through cell printer.

To characterize the cells, the library may be QC'd, and assays are run. In another option, all cell colonies are pooled, a glycerol stock library is made, and selections are run on aliquots of the pooled cells. Finally, the cells are analyzed using amplicon verification or genome validation.

Example 7

Bulk Cell 3D Isolation, Colony Normalization, and Processing within a Rotating Growth Vial Editing Bulk Cell Culture: This protocol describes a standard bulk culture protocol using alginate as the solidifying agent. Alginate both solidifies and re-liquifies at a temperature appropriate for enriching for nucleic acid-guided nuclease editing of bacterial and yeast cells by isolation, growth, editing, and normalization. This protocol was used to leverage the inducible system for both the nuclease and gRNAs to allow for a phenotypic difference in colonies. Alginate (Alginate, A1112 Sigma-Aldrich (St. Louis, Mo.), Alginic acid sodium salt from brown algae, low viscosity).
Solutions:

TABLE 4

LB Alginate

| | 1L | 500 ml | 250 ml | units | notes |
|---|---|---|---|---|---|
| LB powder | 25 | 12.5 | 6.25 | g | LB Miller version of LB Broth powder (Teknova Cat. No. L9135) |
| DI H$_2$O | 1000 | 500 | 250 | ml | |
| Alginate | 20 | 10 | 5 | g | Alginic acid sodium salt from brown algae, low viscosity (A1112 Sigma); 2% final conc |

LB and DI H$_2$O in desired quantities as listed in Table 4 were combined in a flask. A stir bar was added to the flask and the alginate was added slowly while the LB/alginate mixture was stirred on a stir plate. The LB/alginate mixture was then sterilized by autoclavation using standard conditions (e.g., 121° C., 20 min, liquid cycle). After autoclavation, the solution was immediately cooled on ice. Before using the LB/alginate solution, cells and desired antibiotics were added to the appropriate concentration.

TABLE 5

LB Alginate, composition for arabinose induction (1% final conc)

| | 1L | 500 ml | 250 ml | units | notes |
|---|---|---|---|---|---|
| LB powder | 25 | 12.5 | 6.25 | g | LB Miller version of LB Broth powder (Teknova Cat. No. L9135) |

TABLE 5-continued

LB Alginate, composition for arabinose induction (1% final conc)

| | 1L | 500 ml | 250 ml | units | notes |
|---|---|---|---|---|---|
| DI H$_2$O | 950 | 475 | 237.5 | ml | |
| alginate | 20 | 10 | 5 | g | Alginic acid sodium salt from brown algae, low viscosity (A1112 Sigma); 2% final conc |
| 20% arabinose | 50 | 25 | 12.5 | ml | From 20% Arabinose Solution, 1 Liter, Sterile. (Teknova Cat.No. A2100); 1% final conc, to be added after autoclavation, just before use |

LB and DI H$_2$O in desired quantities as listed in Table 5 were combined in a bottle. A stir bar was added to the bottle and the alginate was added slowly while the LB/alginate mixture was stirred on a stir plate. The LB/alginate mixture was then sterilized by autoclavation using standard conditions (e.g., 121° C., 20 min, liquid cycle). After autoclavation, the solution was immediately cooled on ice. Before using the LB/alginate solution, cells and desired antibiotics were added to the appropriate concentration, and 1 ml of 20% arabinose also was added to 19 ml of the LB alginate solution to obtain a 1% arabinose final concentration. Next, calcium chloride (1M) solution was prepared, using calcium chloride dihydrate, MW=147.01 g/mol, and this calcium chloride solution was filter sterilized. Also, a 1M sodium citrate solution was prepared, using sodium citrate tribasic dihydrate, MW=294.10 g/mol, which was also filter sterilized.

Editing was performed following the above protocols to make LB Alginate (25 ml per sample) and LB Alginate+1% arabinose (25 ml per sample). 10 ml of alginate+1% arabinose solution was added to each 50 ml conical tube. The conical tubes were kept at 30° C., to be ready for use after transformation protocol was complete. Transformation was performed using 500 ng of the nucleic acid assembly (vector+editing cassette library) into ec83 (recombineering competent cells) using the Nepagene electroporator settings for *E. coli*. The cells were allowed to recover in 3000 μl of SOB in 15 ml conical tubes while shaking at 30° C. for 3 hours. After 3 hours, the alginate tubes and the transformation tubes were removed from the 30° C. incubator, and 250 μl of cells was added to each tube with the 25 ml of Alginate solution (1:10). The Alginate solution was solidified by slowly transferring 20 ml of the alginate+cells solution into 30 ml of 100 mM CaCl$_2$ solution. The alginate slurry was then centrifuged for 10 min at 4000× g. The supernatant was decanted, and the bulk gel was incubated at 30° C. for 9 hours. After the 9-hour 30° C. incubation, the temperature was shifted to 42° C. for 2 hours for induction of editing.

After editing, the temperature was shifted back to 30° C. for growth overnight. To re-liquify (dissolve) the alginate, 40 ml DI water was added to each conical tube, and 10 ml of 1M sodium citrate was added. The tubes were then shaken at 30° C. for 30-45 minutes. FIG. 6 is a photograph of *E. coli* cells expressing green fluorescent protein in 2.0% alginate and medium that has been solidified showing isolated colonies (left) and a photograph of *E. coli* cells expressing green fluorescent protein in 2.0% alginate and medium after the medium has been re-liquified (right). For singleplex recovery, the libraries were recovered by diluting the cells and plating the cells on selective media plates. Various dilutions were plated and plates also were spotted to get colony counts. The cells were grown on the selective medium for 12-24 hours, and colonies were picked into a 96-well plate with each well containing 750 ml LB. The picked colonies were grown for 24 hours, and each sample was prepped for DNA extraction and next-gen sequencing. For amplicon recovery, the cells were spun at 5,000× g for 10 minutes. The supernatant was removed and the cells were resuspended in 500 µl of 0.8 NaCl. A Zyppy™ Plasmid Miniprep kit (Zymo Research, Bath, UK) was used to extract the plasmid DNA from the library, and the samples were prepped for PCR of the inserts, and for assaying the amplicons via next-gen sequencing.

Figure 7A:
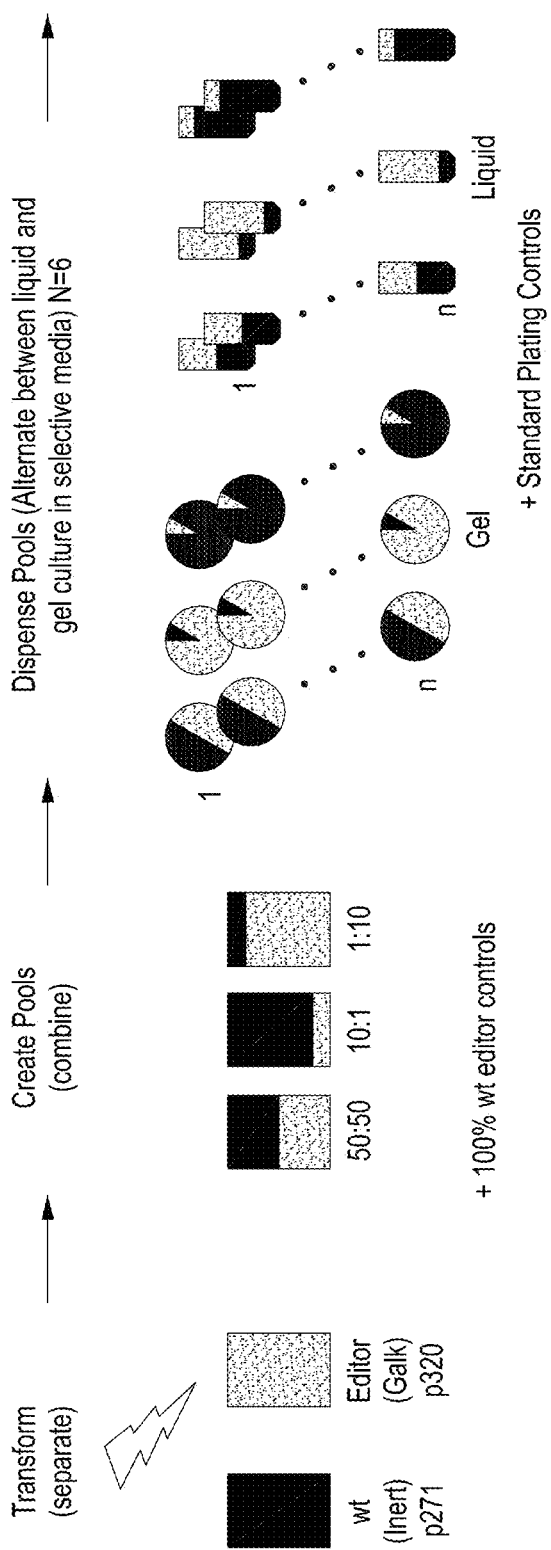
FIGS. 7A-7C together show a graphic of an experiment performed to demonstrate that normalization is achieved in bulk cell culture.
Figure 7B:
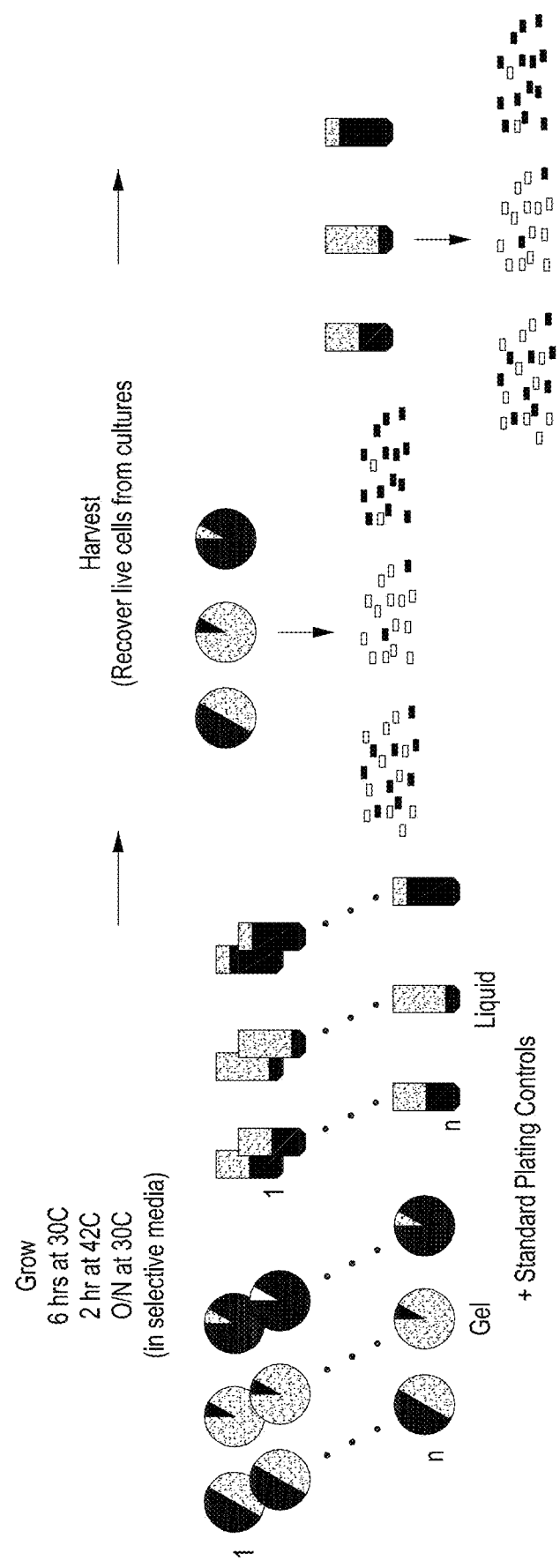
Figure 7C:
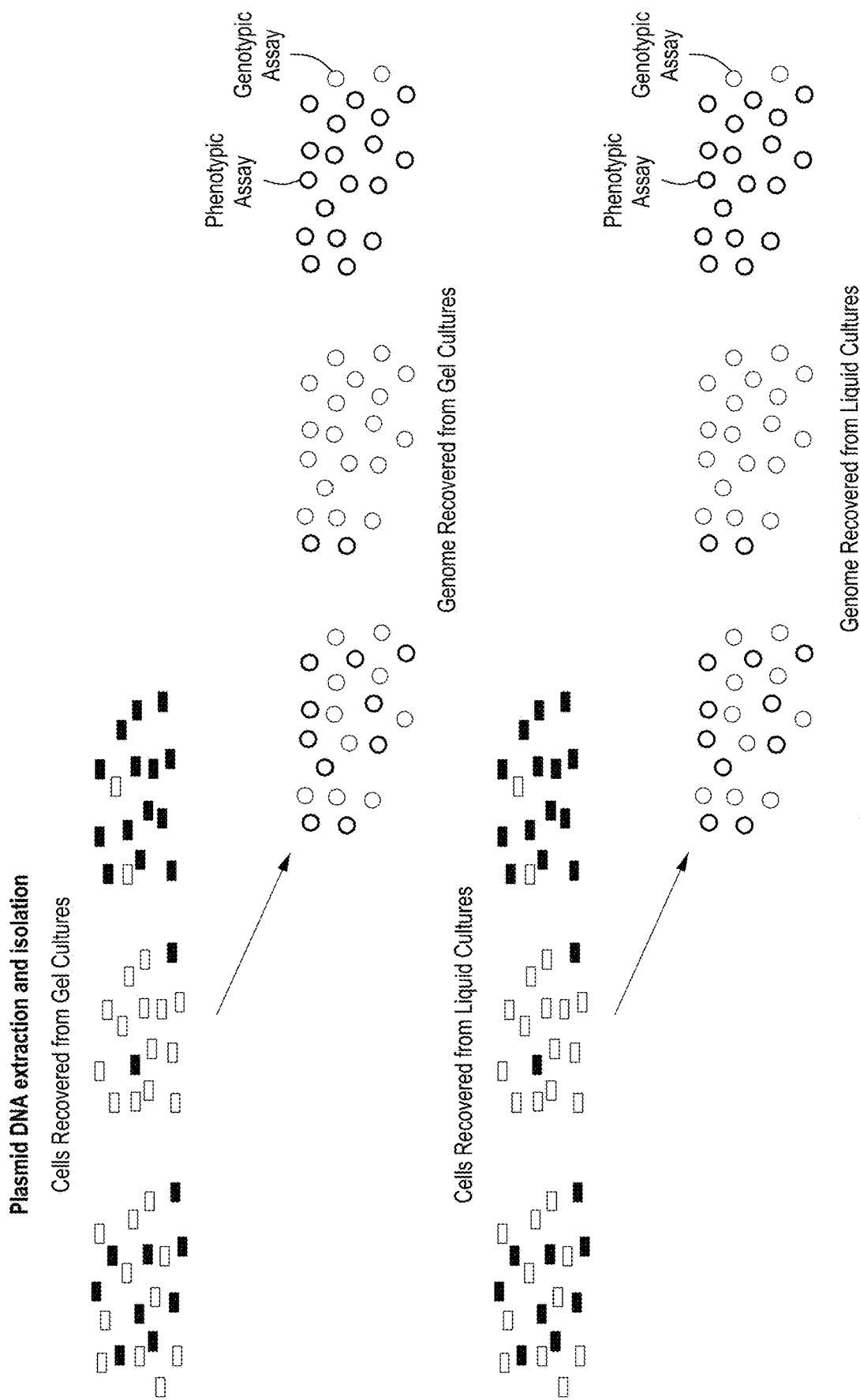
Figure 7D:
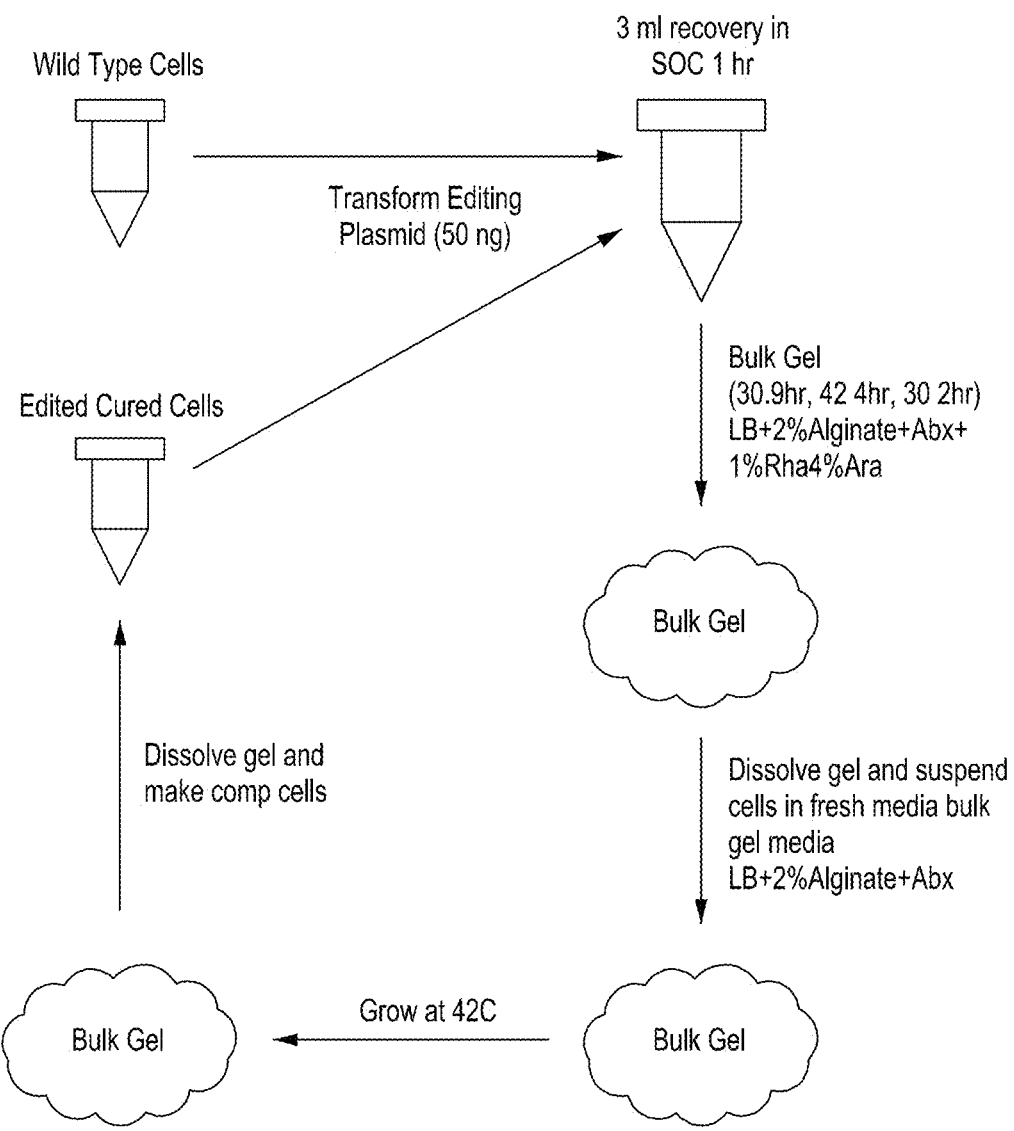
FIG. 7D is a graphic of a recursive workflow using bulk gel cell culture with curing.

FIGS. 7A-7C are a depiction of an experiment performed to demonstrate that normalization is achieved in bulk culture, which compares the quantity of wildtype (inert) plasmid and editing plasmid (GalK) in bulk gel versus liquid cell culture (see Example 9 below). In a first step (shown in FIG. 7A), the wildtype plasmid was used to transform an $E.\ coli$ cell line, and separately, an editing plasmid was used to transform the $E.\ coli$ cell line. Once transformed, pools of the transformed cells were combined in the following ratios: 50:50, 10:1, and 1:10 (wildtype to editing cells, respectively) and dispensed between both bulk culture and liquid culture, where six replicates were prepared for each. Controls included 100% wildtype and 100% editing cells, and standard plating controls. In FIG. 7B, the bulk and liquid cultures (experimental and controls) were grown at 30° C. for 6 hours, 42° C. for 2 hours, and at 30° C. overnight. Next, live cells were recovered from each culture (e.g., six experimental cultures and controls for each of the bulk and liquid cultures). FIG. 7C depicts plasmid extraction and isolation of the cells recovered from the bulk gel cultures and from the liquid cultures (shown) as well as the controls (not shown). Phenotypic assessment was used to determine whether normalization takes place in the bulk gel culture. The phenotypic read out comprised red/white screening on MacConkey agar. The results obtained demonstrated cells edited in bulk gel match most closely the loaded ratio of the 50:50 mix of cells edited at 25% in alginate and 7% liquid and on a plate. FIG. 7D depicts the bulk gel process with recursive cell editing.

Figure 7E:
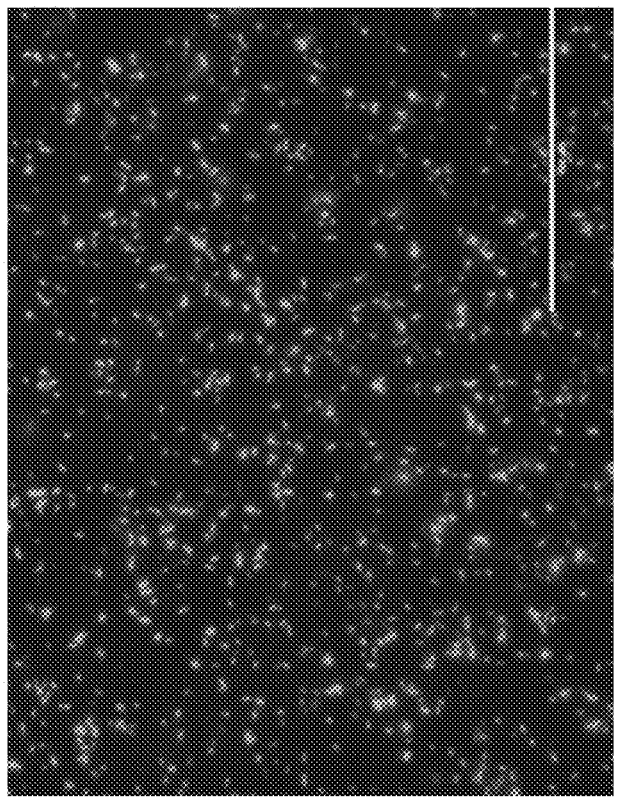
FIG. 7E is a photograph of E. coli cells expressing green fluorescent protein in 2.0% alginate and medium that has been solidified showing singulated colonies (left) and a photograph of E. coli cells expressing green fluorescent protein in 2.0% alginate and medium after the medium has been re-liquified.
Figure 7E:
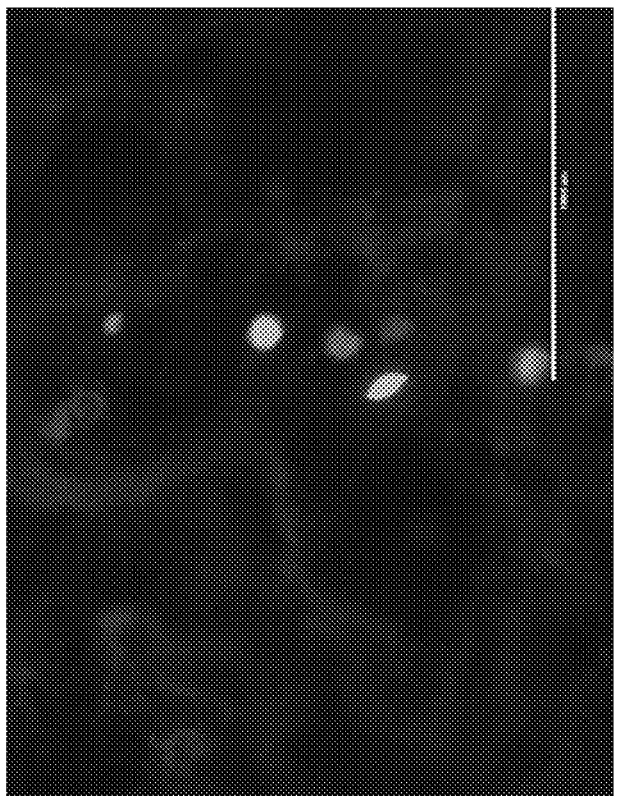

FIG. 7E is a photograph of $E.\ coli$ cells expressing green fluorescent protein in 2.0% alginate and medium that has been solidified showing singulated colonies (left) and a photograph of $E.\ coli$ cells expressing green fluorescent protein in 2.0% alginate and medium after the medium has been re-liquified.

Figure 7F:
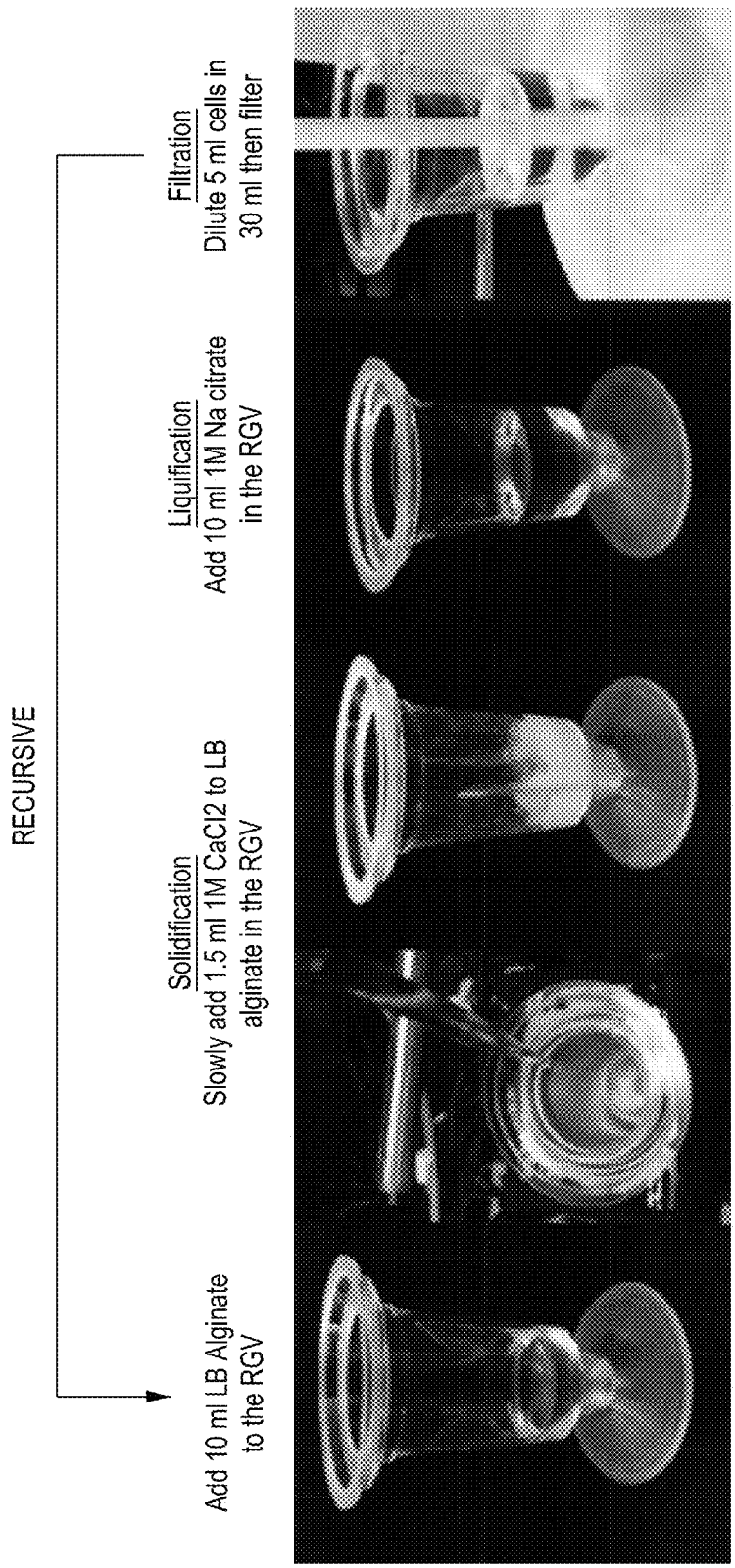
FIG. 7F is a depiction of a bulk cell culture workflow for automation in an isolation/growth/editing/normalization module utilizing a rotating growth vial (such as that shown in FIG. 4A), which in turn may be a part of a multi-module cell editing instrument.

FIG. 7F depicts the workflow for bulk alginate isolation, growth, induction, editing, and normalization in a rotating growth vial (as shown in FIG. 4A and described above), which can be used in a multi-module cell editing instrument (as shown in FIG. 3A and described above). In a first step, 10 ml LB medium comprising alginate was added to the rotating growth vial, which already contained the transformed cells to be edited. In addition to the alginate, the medium also comprises antibiotics to select for the cells that have been properly transformed. The medium was then solidified by slowly adding 1.5 ml of 1M $CaCl_2$ to the LB alginate cell culture in the rotating growth vial. The cells were allowed to grow for 6 hours at 30° C. to establish cell colonies, 2 hours at 42° C. (which induces editing), then overnight at 30° C. to normalize the edited and unedited cell colonies. After normalization, the solidified LB alginate medium was liquified by adding 10 ml 1 M sodium citrate to the solidified medium, and the liquified normalized cell culture was filtered in a filtration module allowing for buffer exchange, cell concentration, and, if desired, rendering the cells electrocompetent for an additional round of editing. Liquefaction disperses all cells throughout the culture. Alternatively, the cells were diluted and plated, and slow-growing colonies were "cherry picked" (e.g., small colonies were picked and larger colonies were not), to select for edited cells.

Example 8

Standard Plating for Comparison to Bulk Culture or Solid Wall Isolation

This protocol describes a standard plating protocol for enriching for nucleic acid-guided nuclease editing of bacterial cells by isolation, growth, editing, and normalization. This protocol was used to leverage the inducible system for both the nuclease and gRNAs to allow for a phenotypic difference in colonies. From the resulting agar plates, it is possible to select edited cells with a high degree (~80%) of confidence. Though clearly this protocol can be employed for enriching for edited cells, in the experiments described herein this "standard plating protocol" of "SPP" was used to compare efficiencies of isolation, editing, and normalization with the bulk cell culture. The protocols for liquid cell culture described in Example 7 were used for the same purpose.

Materials: Outside of standard molecular biology tools, the following will be necessary:

TABLE 6

| Product | Vendor |
| --- | --- |
| SOB | Teknova |
| LB | Teknova |
| LB agar plate with chloramphenicol/carbenicillin and 1% arabinose | Teknova |

Protocol: Inputs for this protocol are frozen electrocompetent cells and purified nucleic acid assembly product. Immediately after electroporation, the cell/DNA mixture was transferred to a culture tube containing 2.7 mL of SOB medium. Preparing 2.7 mL aliquots in 14 mL culture tubes prior to electroporation allowed for a faster recovery of cells from the electroporation cuvette; the final volume of the recovery was 3 mL. All culture tubes were placed into a shaking incubator set to 250 RPM and 30° C. for three hours. While the cultures were recovering, the necessary number of LB agar plates with chloramphenicol and carbenicillin+1% arabinose were removed from the refrigerator and warmed to room temperature. Multiple dilutions were used for each plating so as to have countable and isolated colonies on the plates. Plating suggestions:

TABLE 7

| Sequencing type | Dilution(s) suggested | Volume to plate |
| --- | --- | --- |
| SinglePlex | $10^{-1}$ through $10^{-3}$ | 300 uL |
| Amplicon | None | 300 uL (=1/10$^{th}$ recovery) |

After three hours, the culture tubes were removed from the shaking incubator. First, plating for amplicon sequencing was performed by following the above table. Plating beads were used to evenly distribute the culture over the agar. The beads were removed from the plate the plate was allowed to dry uncovered in a flow hood. While the plates were drying, the remaining culture was used to perform serial dilutions, where the standard dilutions were 50 µL of culture into 450 uL of sterile, 0.8% NaCl. The plate/tubes used for these dilutions (as well as the original culture) were maintained at 4° C. in case additional dilutions were needed to be performed based on colony counts. Plating for SinglePlex was performed according to the Table 7. Additional or fewer dilutions may be used based on library/competent cell knowledge. The cultures were evenly spread across the agar using sterile, plating beads. The beads were then removed from the plate and the plates were allowed to dry uncovered in the flow hood. While the plates were drying, an incubator was programmed according to the following settings: 30° C. for 9 hours→42° C. for 2 hours→30° C. for 9 hours. The agar plates were placed in the pre-set incubator, and after the temperature cycling was complete (~21 hours), the agar plates were removed from the incubator. If induction of editing has been successful, size differences in the colonies will be visible.

Example 9

Liquid Cell Culture Procedure for Comparison to Bulk Culture

Liquid culture process for control: The editing cassette libraries were transformed via electroporation into specific strains of E. coli expressing Mad7 (nuclease) and Lambda Red (recombination) proteins. Transformation of process control vectors—alongside the editing cassette libraries—is essential to calculate the transformation efficiency and editing efficiency (sgRNA efficiency). Immediately post-transformation, the electroporated cells were transferred to medium for recovery.

TABLE 8

Summary of Related QC Assays/M-Tools

| Module | QC Assay Description | What is being measured | Input | Output |
|---|---|---|---|---|
| Transformation (supercoiled plasmids) | Live/dead flow after transformation | #starting cells, live cells with plasmid | # live/dead stain, cells after transf. | # live/dead cells, selective/non-selective conditions |
| Transformation (direct to test) | Live/dead flow after transformation | #starting cells, live cells with plasmid | # live/dead stain, cells after transf. | # live/dead cells, selective/non-selective conditions |

Following electroporation and recovery, cells from these process control transformations were spread on LB agar plates with the appropriate antibiotics. After overnight growth on plates, cells are scraped and then plated on the selective MacConkey phenotypic agar plates for the sugar edits that are tested: Xylose, Galactose, or Lactose, or scraped and replated on LB agar to determine clonality of the individual cells from plates. In more detail, after a 3-hour incubation (recovery), the culture tubes were removed from the shaking incubator. While the culture tubes were incubating, 250 mL baffled shake flasks were prepared with 25 mL of LB+100 ug/mL carbenicillin and 25 ug/mL chloramphenicol and 1% arabinose. After incubation, 250 µL of undiluted culture from each transformation was transferred into the prepared 250 mL shake flasks. An incubator was set to the following temperature settings: 30° C. for 9 hours→42° C. for 2 hours→30° C. for 9 hours. This temperature regime was used to allow for additional recovery during the first nine hours followed by induction of the nuclease during the two-hour step. The lambda (recombineering system) induction was triggered by arabinose in the medium. The flasks were incubated/shaken at 250 RPM. After the temperature cycling was complete (~21 hours), the flasks were removed from the incubator/shaker.

Serial dilutions of each culture were prepared with 0.8% NaCl, where the standard dilutions were 50 µL of culture into 450 µL of sterile, 0.8% NaCl, and dilutions of $10^{-5}$ to $10^{-7}$ were made to produce isolated colonies. 300 uL of each dilution of each culture was plated onto LB agar plates with standard concentrations of chloramphenicol and carbenicillin. Arabinose was not used in the agar plates as all editing should have occurred in the incubation/shaking process. The plates were placed in a 30° C. incubator for overnight growth where colonies formed overnight and were picked for singleplex next-gen sequencing the following day using 250 µL of culture as the input for a plasmid extraction protocol.

Example 10

Results

Figure 8A:
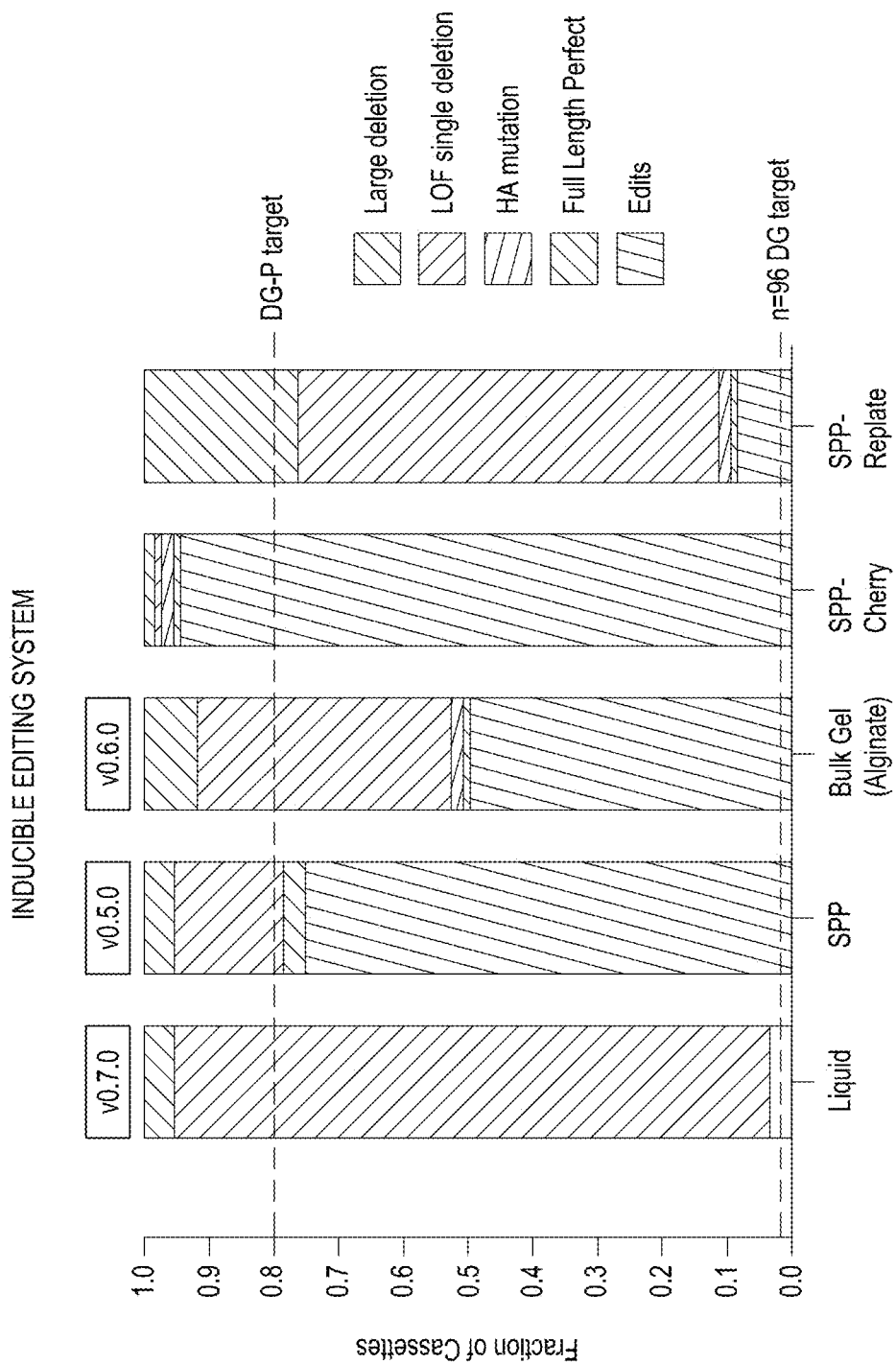
FIGS. 8A, 8B and 8C depict a graph, table, and two graphs, respectively, of the results obtained from editing experiments performed with liquid cell culture employing no isolation or normalization, but employing inducible editing; bulk cell gel culture employing isolation, inducible editing, and normalization; solid agar plating (SPP) employing isolation, inducible editing, and normalization; solid agar plating (SPP-Cherry) employing isolation, inducible editing, and cherry picking; and solid agar plating (SPP) employing isolation, inducible editing, and normalization but without cherry picking and simply scraping the colonies from the plate and re-plating.
Figures 8B, 8C:
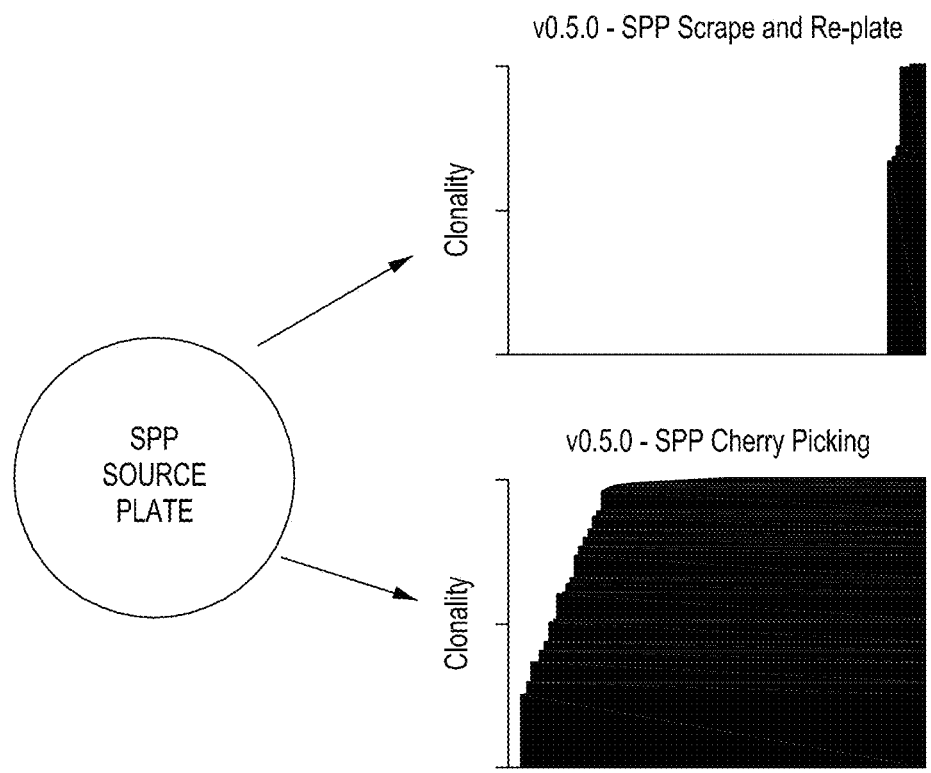

FIGS. 8A, 8B, and 8C show the results of the editing rates and clonality resulting from editing experiments performed with liquid cell culture employing no isolation or normalization, but employing inducible editing; bulk cell gel culture, employing isolation, inducible editing, and normalization; solid agar plating (SPP) employing isolation, inducible editing, and normalization; solid agar plating (SPP-Cherry) employing isolation, inducible editing, and cherry picking; and solid agar plating (SPP) employing only isolation and inducible editing and simply scraping the colonies from the plate and re-plating.

FIG. 8A shows that liquid culture results in a very low rate of observed editing, at about 1-2%; the standard plating procedure (SPP) results in an approximate 75% rate of observed editing; the bulk alginate cell culture protocol results in an approximate 50% rate of observed editing; the standard plating procedure plus cherry picking (SPP-cherry) (e.g., manual picking of only small colonies from the plated cells, where the presumption is that small colonies represent colonies of cells that have been edited) protocol results in an approximate 95% rate of observed editing; and the standard plating procedure (SPP) without normalization or cherry picking results in an approximate 8% of observed editing. Thus, it is clear that SPP+cherry picking produces the highest rate of observed editing. In addition, SPP without cherry picking—but including isolation, induced editing, and normalization—results in a high (75%) rate of observed editing, and the easily-automatable bulk gel cell culture process resulted in an approximate 50% rate of observed editing.

FIG. 8B provides the observed clonality for the standard plating procedure (SPP), the standard plating procedure+cherry picking (SPP cherry), the standard plating procedure+scraping the plate comprising the colonies where editing has been induced (but also comprising unedited cells), and for the bulk procedure. The first column gives the fraction of colonies examined with more than half the reads being called edits. The second column gives the fraction of colonies that have more than 90% of the reads being called edit reads. The higher fraction here shows how complete the edits are if there are some colonies examined between the 50% and 90% cut offs that demonstrate that not all of the cells in the colony that is being picked are edited. That is when one cell hits the plate and begins growing into a clonal colony for, e.g., ~100 cells—then editing is induced—some of the cells are edited but not all, and the cells that are not edited cause this incomplete editing in the colony (e.g., less than 100% clonality). The third column provides the number of unique edits for the colonies in the >50% clonal colonies. Note that SPP-cherry provides the highest clonality and number of unique edits, but that the bulk gel cell culture provides good clonality (44/95 at >50%) and a high proportion of the clonal colonies consist of unique edits (42/44).

Finally, FIG. 8C provides a graph of the data in FIG. 8B. This graph indicates the extent of incomplete editing.

Example 11

Solid Wall Embodiment

Figure 9A:
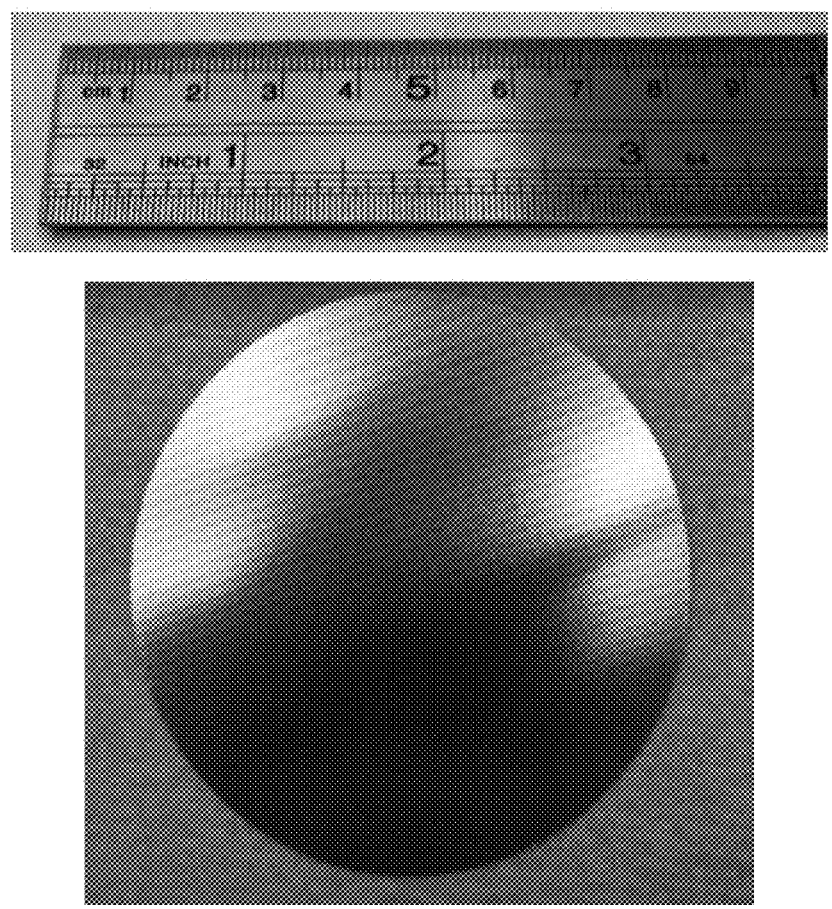
FIG. 9A is a photograph of one embodiment of a perforated member to be used in a solid wall device.

FIG. 9A is a photograph of one embodiment of a solid wall device comprising microwells for isolating cells. As can be seen from the photo, the solid wall device is approximately 2 inches (~47 mm) in diameter. The solid device seen in this photograph is essentially a perforated disk of 316 stainless steel, where the perforations form the walls of the microwells, and a filter or membrane is used to form the bottom of the microwells. Use of a filter or membrane (such as a 0.22µ PVDF Duropore™ woven membrane filter) allows for medium and/or nutrients to enter the microwells but prevents the cells from flowing down and out of the microwells. Filter or membrane members that may be used in the solid wall isolation/growth/editing/normalization devices and modules are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 20 µm or larger. Indeed, the pore sizes useful in the cell concentration device/module include filters with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

In the photograph shown in FIG. 9A, the perforations are approximately 152 nM in diameter, resulting in the microwells having a volume of approximately 2.5 nL, with a total of approximately 30,000 wells. The distance between the microwells is approximately 279 nM center-to-center. Though here the microwells have a volume of approximately 2.5 nL, the volume of the microwells may be from 1 to 25 nL, or preferably from 2 to 10 nL, and even more preferably from 2 to 4 nL. The preferred size/volume of the microwells will depend of cell type (e.g., bacterial, yeast, mammalian). The perforated disk shown here is made of 316 stainless steel; however other bio-compatible metals and materials may be used. The solid wall device may be disposable or it may be reusable. The solid wall device shown in FIG. 9A is round, but can be of any shape, for example, square, rectangular, oval, etc. (See, e.g., the rectangular perforated member in the SWIIN depicted in FIGS. 5A-5I.) Round solid wall devices are useful if petri dishes are used to supply the solid wall device with nutrients via solid medium. The filters used to form the bottom of the wells of the solid wall device include 0.22µ PVDF Duropore™ woven membrane filters. Further, though a 2-inch (~47 mm) diameter solid wall device is shown, the solid wall devices may be smaller or larger as desired and the configuration of the solid wall device will depend on how nutrients are supplied to the solid wall device, and how media exchange is performed (see, e.g., the solid wall device described in relation to Example 18, FIGS. 14A and 14B).

Figure 9B:
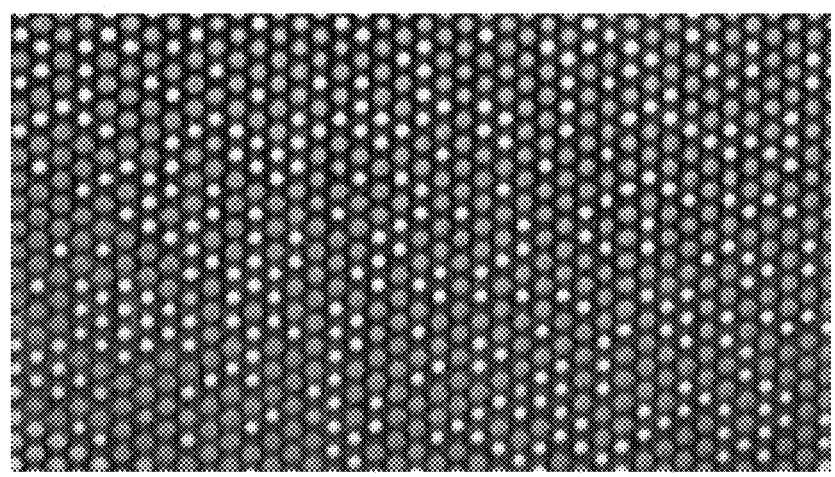
FIGS. 9B-9D are photographs of E. coli cells isolated (via Poisson distribution) and grown into colonies in microwells in a solid wall device with a permeable bottom at low, medium, and high magnification, respectively.
Figure 9C:
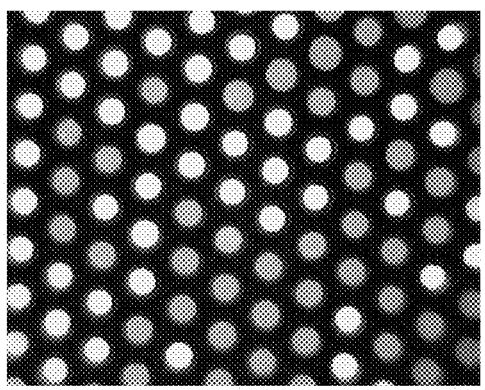
Figure 9D:
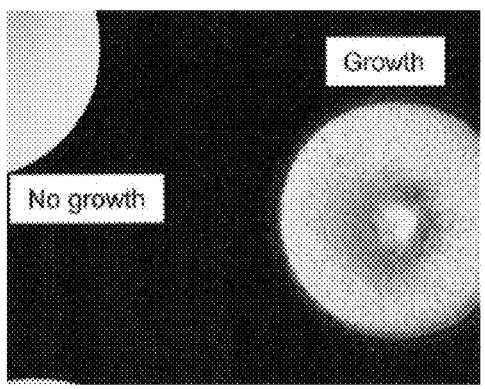
Figure 9D:
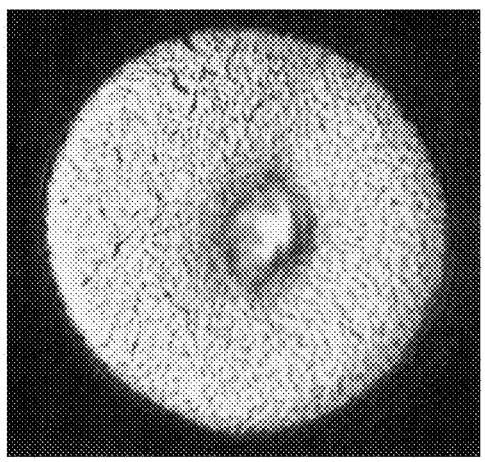

FIGS. 9B-9D are photographs of E. coli cells isolated via Poisson distribution in microwells in a solid wall device with a membrane bottom at low, medium and high magnification, respectively. FIG. 9B shows digital growth at low magnification where the darker microwells are microwells where cells are growing. FIG. 9C is a top view of microwells in a solid wall device where the darker microwells are microwells where cells are growing. FIG. 9D is a photograph of microwells where the membrane (e.g., the permeable membrane that forms the bottom of the microwells) has been removed, where unpatterned (smooth) microwells are microwells where cells are not growing, and microwells with irregular pigment/patterned are microwells where cells are growing, and, in this photograph, have filled the microwells in which they are growing. In these photographs, a 0.2 µm filter (membrane) was pressed against the perforated metal sold wall device such as the round solid wall device depicted in FIG. 9A. The perforated metal solid wall device formed the walls of the microwells, and the 0.2 µm filter formed the bottom of the microwells. To load the solid wall device, the E. coli cells were pulled into the microwells using a vacuum. The solid wall device+filter was then placed on an LB agar plate membrane-side down, and the cells were grown overnight at 30° C., then two days at room temperature. The membrane was removed and the bottomless microwells were photographed by light microscopy. Note the ease with which different selective media can be used to select for certain cell phenotypes; that is, one need only transfer the solid wall device+filter to a different plate or petri dish comprising a desired selective medium.

Example 12

Isolation and Culture of E. coli in a Solid Wall Device

Electrocompetent E. coli cells were transformed with a cloned library, an isothermal assembled library, or a process control sgRNA plasmid (escapee surrogate) as described in Example 3 above. The E. coli strain carried the appropriate endonuclease and lambda red components and editing induction system (e.g., on an engine plasmid or integrated into the bacterial genome or a combination). Transformations routinely used 150 ng of plasmid DNA (or Gibson Assembly reactions) with 150 ng of pL sgRNA backbone DNA. Following electroporation, the cells were allowed to recover in 3 ml SOB and incubated at 30° C. with shaking for 3 hours. In parallel with processing samples through the solid wall device, samples were also processed with the solid plating protocol (see Example 8 above), so as to compare "normalization" in the sold wall device with the standard benchtop process. Immediately before cells the cells were introduced to the permeable-bottom solid wall device, the 0.2 µm filter forming the bottom of the microwells was treated with a 0.1% TWEEN solution to effect proper spreading/distribution of the cells into the microwells of the solid wall device. The filters were placed into a Swinnex Filter Holder (47 mm, Millipore®, SX0004700) and 3 ml of a solution with 0.85% NaCl, and 0.1% TWEEN was pulled through the solid wall device and filter through using a vacuum. Different TWEEN concentrations were evaluated, and it was determined that for a 47 mm diameter solid wall device with a 0.21M filter forming the bottom of the microwells, a pre-treatment of the solid wall device+filter with 0.1% TWEEN was preferred (data not shown).

After the 3-hour recovery in SOB, the transformed cells were diluted and a 3 ml volume of the diluted cells was processed through the TWEEN-treated solid wall device and filter, again using a vacuum. The number of successfully transformed cells was expected to be approximately 1.0 E+06 to 1.0 E+08, with the goal of loading approximately 10,000 transformed cells into the current 47 mm permeable-bottom solid wall device (having ~30,000 wells). Serial dilutions of $10^{-1}$, $10^{-2}$, and $10^{-3}$ were prepared, then 100 µL volumes of each of these dilutions were combined with 3 ml 0.85% NaCl, and the samples were loaded onto solid wall devices. Each permeable-bottom solid wall device was then removed from the Swinnex filter holder and transferred to an LB agar plate containing carbenicillin (100 µg/ml), chloramphenicol (25 µg/ml) and arabinose (1% final concentration). The solid wall devices were placed metal side "up," so that the permeable-bottom membrane was touching the surface of the agar such that the nutrients from the plate could travel up through the filter "bottom" of the wells. The solid wall devices on the LB agar plates were incubated for 9 hours at 30° C., at 42° C. for 2 hours, then returned to incubation at 30° C., for 12-16 hour, and, in another experiment for 36-40 hours.

At the end of the incubation the perforated disks and filters (still assembled) were removed from the supporting nutrient source (in this case an agar plate) and were photographed with a focused, "transilluminating" light source so that the number and distribution of loaded microwells on the solid wall device could be assessed (data not shown). To retrieve cells from the permeable-bottom solid wall device, the filter was transferred to a labeled sterile 100 mm petri dish which contained 15 ml of sterile 0.85% NaCl, then the petri dish was placed in a shaking incubator set to 30° C./80 RPM to gently remove the cells from the filter and resuspend the cells in the 0.85% NaCl. The cells were allowed cells to shake for 15 minutes, then were transferred to a sterile tube, e.g., a 50 ml conical centrifuge tube. The OD600 of the cell suspension was measured and at this point, the cells can be processed in different ways depending on the purpose of the study. For example, if the plasmids or libraries are designed to target a sugar metabolism pathway gene such as galK, then the resuspended cells can be spread onto MacConkey agar plates containing galactose (1% final concentration) and the appropriate antibiotics. On this differential medium, colonies that are the result of successfully-edited cells are expected to be phenotypically white in color, whereas unedited colonies are red in color. This red/white phenotype can then be used to assess the percentage of edited cells and the extent of normalization of edited and unedited cells. The results of one experiment are shown below in Table 9. In all replicates, the transformed cells were allowed to grow in the solid wall devices for 9 hours at 30° C., 2 hours at 42° C., and overnight at 30° C.

TABLE 9

| Tween? | Dilution counted | Red colonies | White colonies | % edit |
|---|---|---|---|---|
| No tween | $10^{-4}$ | 72 | 5 | 6% |
| No tween | $10^{-4}$ | 89 | 3 | 3% |
| No tween | $10^{-3}$ | 64 | 5 | 7% |
| Pre-treatment tween | $10^{-4}$ | 71 | 5 | 7% |
| Pre-treatment tween | $10^{-3}$ | 443 | 29 | 6% |
| Pre-treatment tween | $10^{-3}$ | 149 | 12 | 7% |
| Pre-treatment tween | $10^{-3}$ | 83 | 21 | 20% |
| Pre-treatment tween | $10^{-2}$ | 318 | 112 | 26% |
| Pre-treatment tween + tween in cell loading buffer | $10^{-3}$ | 163 | 25 | 13% |
| Pre-treatment tween + tween in cell loading buffer | $10^{-4}$ | 132 | 10 | 7% |
| Pre-treatment tween + tween in cell loading buffer | $10^{-4}$ | 31 | 9 | 23% |
| Pre-treatment tween + tween in cell loading buffer | $10^{-3}$ | 147 | 18 | 10.9% |
| Pre-treatment tween + tween in cell loading buffer | $10^{-2}$ | 720 | 150 | 17% |
| Pre-treatment tween + tween in cell loading buffer | $10^{-3}$ | 55 | 15 | 21% |

Figure 9E:
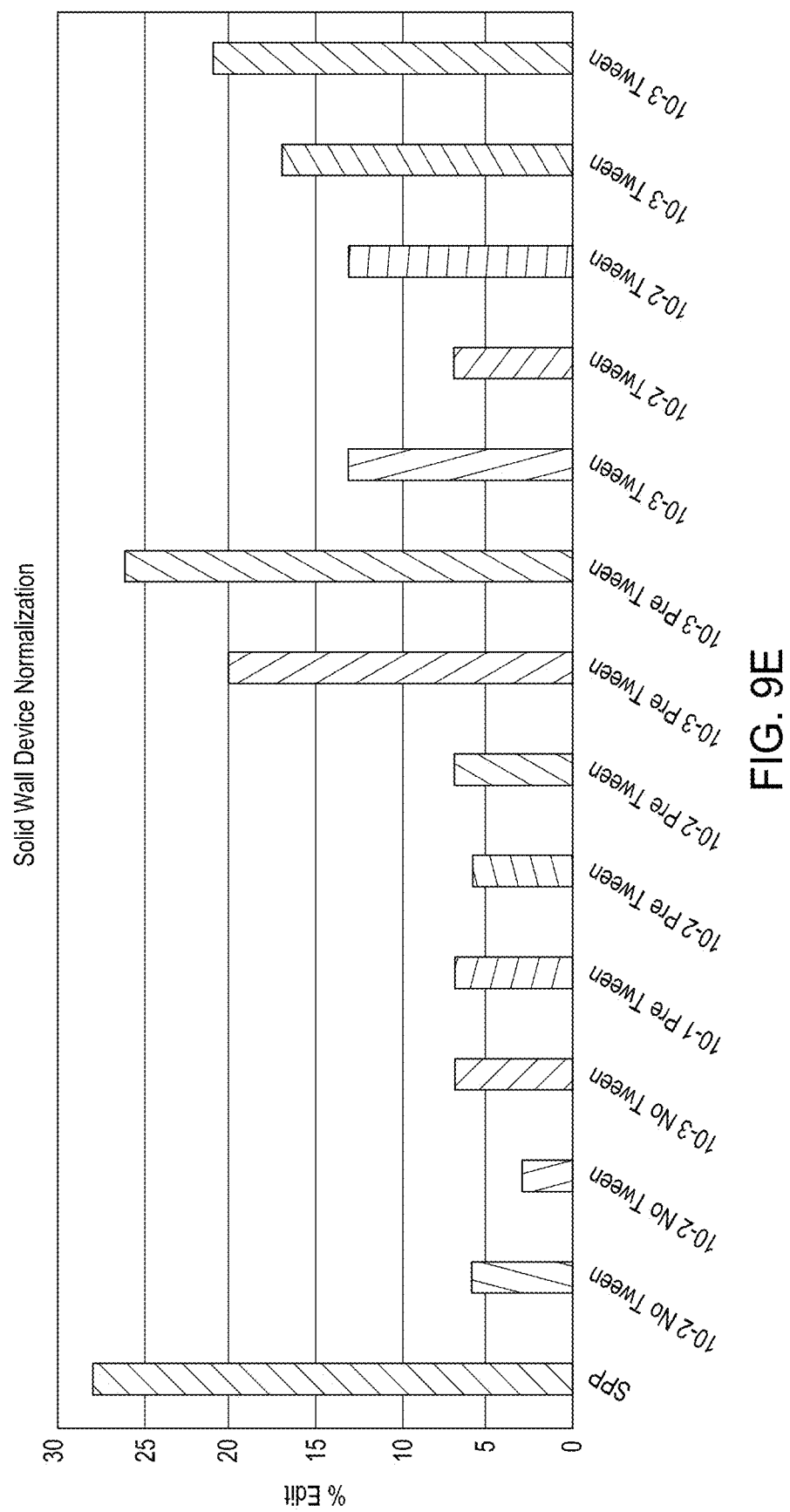
FIG. 9E shows the results of cell colony normalization for E. coli cells under various conditions.

The solid wall device+filter was pre-treated with 0.1% TWEEN to assist in dispersing the cells on the solid wall device, and a $10^{-3}$ dilution of the transformed cells was introduced to the solid wall device. FIG. 9E is a graph showing the extent of normalization of cells (% edited cells) for different dilutions of transformed cells, and no treatment with TWEEN vs. pre-treatment with TWEEN vs. pre-treatment with TWEEN+TWEEN in the buffer when loading the cells into the microwells of the solid wall device. A standard plating protocol (SPP) was conducted in parallel with the solid wall isolation experiments as a benchmark (first bar on the left in the graph). Note that the percentage of edits for the standard plating protocol was approximately 27.5%, and the percentage of edits for two replicates of the $10^{-3}$ dilution of cells with pre-treatment with TWEEN was approximately 20% and 26%, respectively.

Example 13

Isolation of Yeast Colonies in a Solid Wall Device

Electrocompetent yeast cells were transformed with a cloned library, an isothermal assembled library, or a process control sgRNA plasmid (escapee surrogate) as described in Example 3 above. Electrocompetent *Saccharomyces cerevisiae* cells were prepared as follows: The afternoon before transformation was to occur, 10 mL of YPAD was inoculated with the selected *S. cerevisiae* strain. The culture was shaken at 250 RPM and 30° C. overnight. The next day, 100 mL of YPAD was added to a 250-mL baffled flask and inoculated with the overnight culture (around 2 mL of overnight culture) until the OD600 reading reached 0.3+/−0.05. The culture was placed in the 30° C. incubator shaking at 250 RPM and allowed to grow for 4-5 hours, with the OD checked every hour. When the culture reached an OD600 of approximately 1.5, 50 mL volumes were poured into two 50-mL conical vials, then centrifuged at 4300 RPM for 2 minutes at room temperature. The supernatant was removed from all 50 ml conical tubes, while avoiding disturbing the cell pellet. 50 mL of a Lithium Acetate/Dithiothreitol solution was added to each conical tube and the pellet was gently resuspended. Both suspensions were transferred to a 250 mL flask and placed in the shaker; then shaken at 30° C. and 200 RPM for 30 minutes. After incubation was complete, the suspension was transferred to two 50-mL conical vials. The suspensions then were centrifuged at 4300 RPM for 3 minutes, then the supernatant was discarded. Following the Lithium Acetate/Dithiothreitol treatment step, cold liquids were used and the cells were kept on ice until electroporation.

Figure 9F:
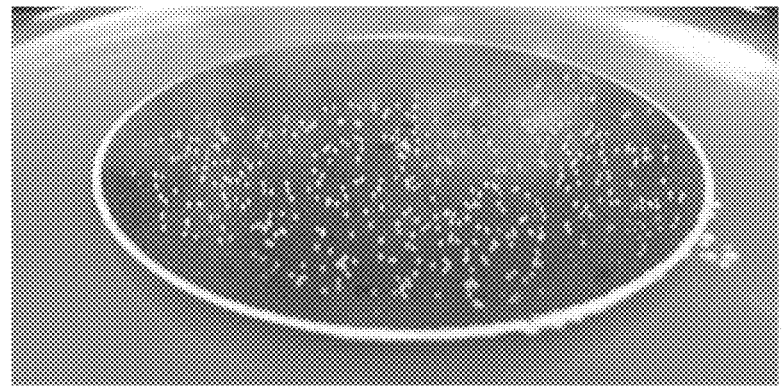
FIG. 9F is a photograph of a solid wall device with a permeable bottom on agar, on which yeast cells have been isolated and grown into clonal colonies.
Figure 9G:
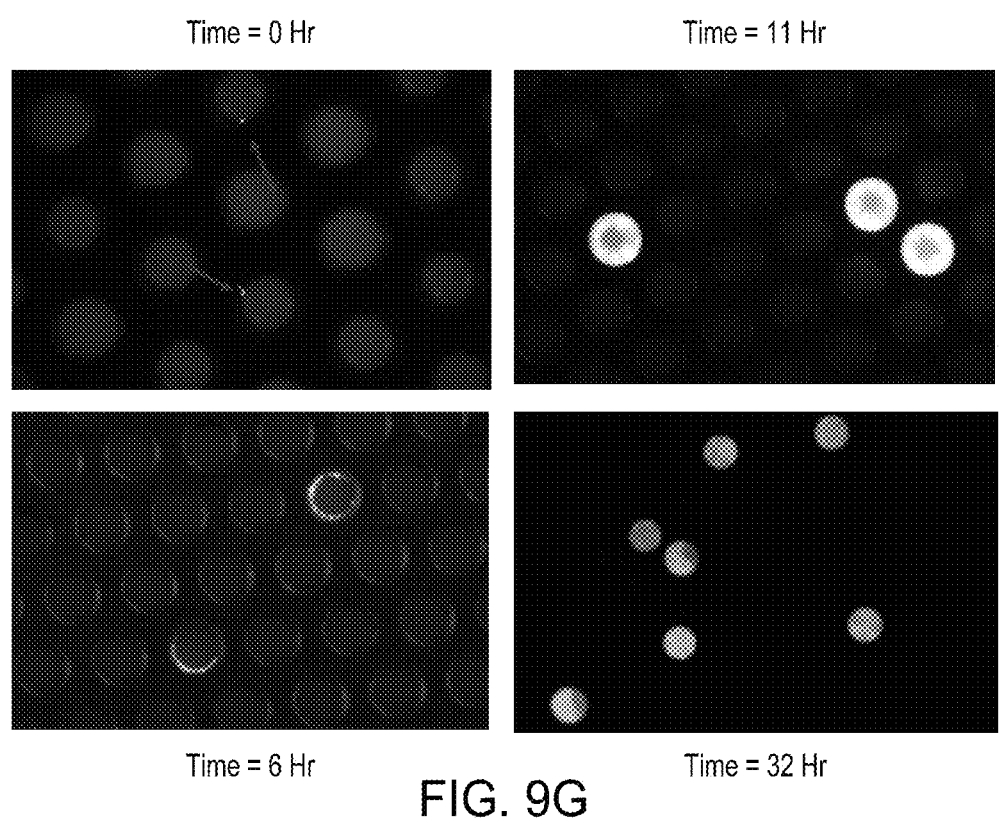
FIG. 9G presents photographs of yeast colony growth at various time points.

50 mL of 1 M sorbitol was added and the pellet was resuspended, then centrifuged at 4300 RPM, 3 minutes, 4° C., after which the supernatant was discarded. The 1M sorbitol wash was repeated twice for a total of three washes. 50 µL of 1 M sorbitol was added to one pellet, cells were resuspended, then transferred to the other tube to suspend the second pellet. The volume of the cell suspension was measured and brought to 1 mL with cold 1 M sorbitol. At this point the cells were electrocompetent and could be transformed with a cloned library, an isothermal assembled library, or process control sgRNA plasmids. In brief, a required number of 2-mm gap electroporation cuvettes were prepared by labeling the cuvettes and then chilling on ice. The appropriate plasmid—or DNA mixture—was added to each corresponding cuvette and placed back on ice. 100 µL of electrocompetent cells was transferred to each labelled cuvette, and each sample was electroporated using appropriate electroporator conditions. 900 uL of room temperature YPAD Sorbitol media was then added to each cuvette. The cell suspension was transferred to a 14 ml culture tube and then shaken at 30° C., 250 RPM for 3 hours. After a 3 hr recovery, 9 ml of YPAD containing the appropriate antibiotic, e.g., geneticin or Hygromycin B, was added. At this point the transformed cells were processed in parallel in the solid wall device and the standard plating protocol (see Example 8 above), so as to compare "normalization" in the sold wall device with the standard benchtop process. FIG. 9F is a photograph of a solid wall device with a permeable bottom on agar, on which yeast cells have been isolated and grown into clonal colonies. FIG. 9G presents photographs of yeast colony growth at various time points. Immediately before cells the cells were introduced to the permeable-bottom solid wall device, the 0.45 µM filter forming the bottom of the microwells was treated with a 0.1% TWEEN solution to effect proper spreading/distribution of the cells into the microwells of the solid wall device. The filters were placed into a Swinnex Filter Holder (47 mm, Millipore®, SX0004700) and 3 ml of a solution with 0.85% NaCl and 0.1% TWEEN was pulled through the solid wall device and filter through using a vacuum. Different TWEEN concentrations were evaluated, and it was determined that for a 47 mm diameter solid wall device with a 0.45 µM filter forming the bottom of the microwells, a pre-treatment of the solid wall device+filter with 0.1% TWEEN was preferred (data not shown).

After the 3-hour recovery in SOB, the transformed cells were diluted and a 3 ml volume of the diluted cells was processed through the TWEEN-treated solid wall device and filter, again using a vacuum. The number of successfully transformed cells was expected to be approximately 1.0 E+06 to 1.0 E+08, with the goal of loading approximately 10,000 transformed cells into the current 47 mm permeable-bottom solid wall device (having ~30,000 wells). Serial dilutions of $10^{-1}$, $10^{-2}$, and $10^{-3}$ were prepared, then 100 µL volumes of each of these dilutions were combined with 3 ml 0.85% NaCl, and the samples were loaded onto solid wall devices. Each permeable-bottom solid wall device was then removed from the Swinnex filter holder and transferred to an LB agar plate containing carbenicillin (100 m/ml), chloramphenicol (25 m/ml) and arabinose (1% final concentration). The solid wall devices were placed metal side "up," so that the permeable-bottom membrane was touching the surface of the agar such that the nutrients from the plate could travel up through the filter "bottom" of the wells. The solid wall devices on the YPD agar plates were incubated for 2-3 days at 30° C.

At the end of the incubation the perforated disks and filters (still assembled) were removed from the supporting nutrient source (in this case an agar plate) and were photographed with a focused, "transilluminating" light source so that the number and distribution of loaded microwells on the solid wall device could be assessed (data not shown). To retrieve cells from the permeable-bottom solid wall device, the filter was transferred to a labeled sterile 100 mm petri dish which contained 15 ml of sterile 0.85% NaCl, then the petri dish was placed in a shaking incubator set to 30° C./80 RPM to gently remove the cells from the filter and resuspend the cells in the 0.85% NaCl. The cells were allowed cells to shake for 15 minutes, then were transferred to a sterile tube, e.g., a 50 ml conical centrifuge tube. The OD600 of the cell suspension was measured; at this point the cells can be processed in different ways depending on the purpose of the study. For example, if an ADE2 stop codon mutagenesis library is used, successfully-edited cells should result in colonies with a red color phenotype when the resuspended cells are spread onto YPD agar plates and allowed to grow for 4-7 days. This phenotypic difference allows for a quantification of percentage of edited cells and the extent of normalization of edited and unedited cells.

Example 14

Isolation, Growth and Editing of *E. coli* in 200K SWIIN

Singleplex automated genomic editing using MAD7 nuclease, a library with 94 different edits in a single gene (yagP) and employing a 200K SWIIN module such as that exemplified in FIGS. 5A-5I was successfully performed. The engine vector used had MAD7 under the control of the pL inducible promoter and the Red system under the control of a pBAD promoter), and the editing vector used comprised an editing cassette (gRNA and donor DNA) being under the control of the pL inducible promoter. Two SWIIN workflows were compared, and further were benchmarked against the standard plating protocol (see Example 8). The SWIIN protocols different from one another that in one set of replicates LB medium containing arabinose was used to distribute the cells in the SWIIN (arabinose was used to induce the λ Red recombineering system (which allows for repair of double-strand breaks in *E. coli* that are created during editing), and in the other set of replicates SOB medium without arabinose was used to distribute the cells in the SWIIN and for initial growth, with medium exchange performed to replace the SOB medium without arabinose with SOB medium with arabinose. Approximately 70K cells were loaded into the 200K SWIIN.

Figure 10:
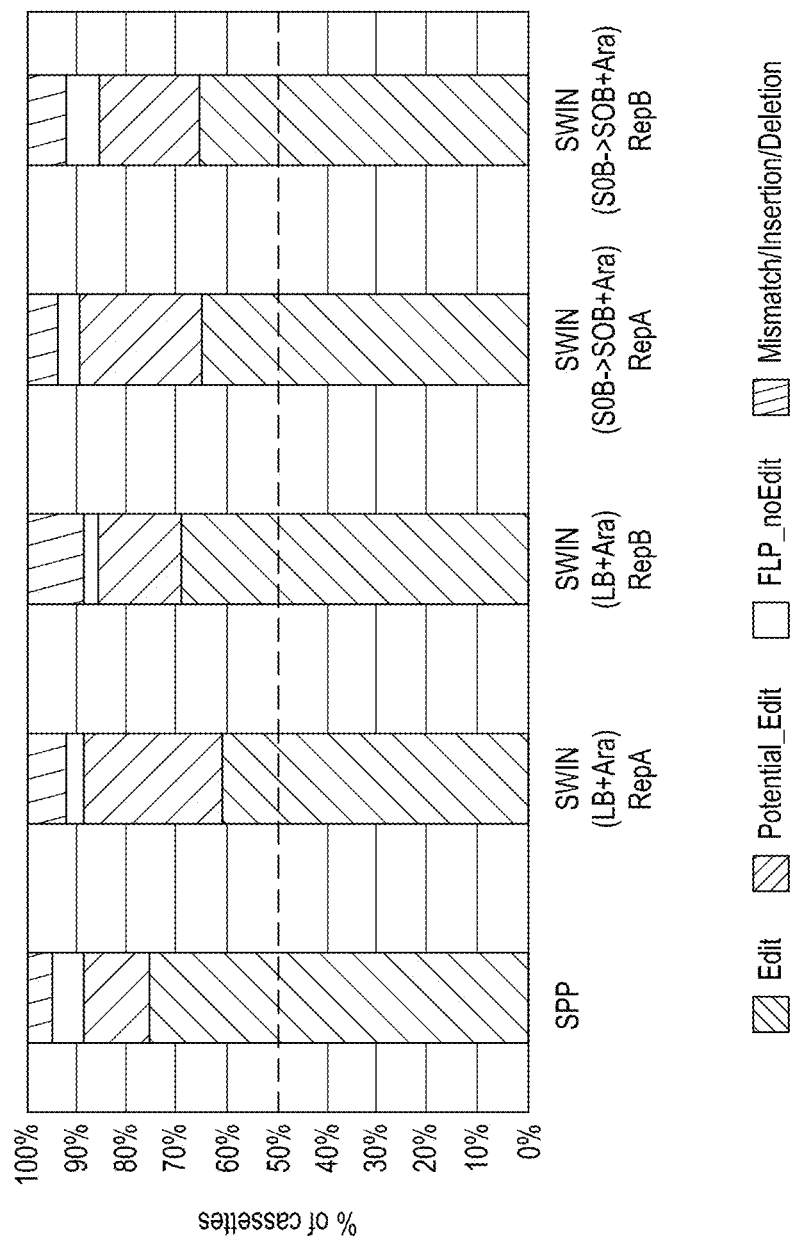
FIG. 10 is a graph comparing the percentage of editing obtained for a standard plating protocol (SPP), and replicate samples using two different conditions in a solid wall isolation, incubation, and normalization device (SWIIN): the first with LB+arabinose; and the second with SOB followed by SOB+arabinose.

In all protocols (standard plating, LB-SWIIN, and SOB-SWIIN), the cells were allowed to grow at 30° C. for 9 hours and editing was induced by raising the temperature to 42° C. for 2.5 hours, then the temperature was returned to 30° C. and the cells were grown overnight. The results of this experiment are shown in FIG. 10 and in Table 10 below. Note that similar editing performance was observed with the four replicates of the two SWIIN workflows, indicating that the performance of SWIIN plating with and without arabinose in the initial medium is similar. Editing percentage in the standard plating protocol was approximately 77%, in bulk liquid was approximately 67%, and for the SWIIN replicates ranged from approximately 63% to 71%. Note that the percentage of unique edit cassettes divided by the total number of edit cassettes was similar for each protocol.

TABLE 10

|  | Standard Plating | SWIIN LB/Ara Rep. A | SWIIN LB/Ara Rep. B | SWIIN SOB then SOB/Ara Rep. A | SWIIN SOB then SOB/Ara Rep. B |
|---|---|---|---|---|---|
| 40006 edit calls/ identified wells | 0.777 | 0.633 | 0.719 | 0.663 | 0.695 |
| Unique edit cassettes/ total edit cassettes | 0.49 | 0.49 | 0.43 | 0.50 | 0.51 |

Example 15

Protocol Flow from mTFF to FTEP to SWIIN mTFF module, E. coli workflow: Approximately 20 ml of E. coli was transferred from a rotating growth vial (RGV) in a cell growth module. Specially, the E. coli was EC83, an E. coli MG1655 strain comprising an engine vector coding for the Red recombineering system and a MAD7 coding sequence. In the RGV, the EC83 was grown in LB growth medium to an OD600 ~0.6 and having a conductivity of ~16,500 µS/cm. In the mTFF the cells were washed with a low-conductivity solution (10% glycerol) and concentrated in a small volume (approximately 0.80 ml) in the same low-conductivity solution. Both the input and output cell counts were determined by plating on solid media. The cell input was approximately 3.1 E+09 and the cell output was approximately 2.3 E+09. The output of the mTFF was used as input for the flow-through electroporation (FTEP) module.

FTEP module, E. coli workflow: Approximately 500 µl of the concentrated EC83 cells in 10% glycerol—e.g., an aliquot of the output of the mTFF—was combined with 100 µl of the assembled editing vector (see, e.g., FIG. 11B) and a TWEEN solution (see Example 12 above). The cells and DNA were mixed and passed through the FTEP at a very high field strength in a high resistance solution. After transformation in the FTEP, the cells were transferred back to the cell growth module into a fresh RGV containing 3 ml SOB with chloramphenicol. The cells were incubated at 30° C. for 1 hour. The input CFU was approximately 2.3 E+09 and the output CFU was approximately 9.8 E+08 survival and 8.5 E+05 uptake.

SWIIN module, E. coli workflow: Subsequent to the 1 hour recovery in the cell growth module, the cells were combined with a PBS/TWEEN solution and approximately 0.35 ml was loaded onto the SWIIN. Once cells were loaded and growth medium (was LB with 1% arabinose, 25 ug/ml chloramphenicol and 100 µg/ml carbenicillin) was added to the permeate chamber of the SWIIN, the SWIIN was placed in a programmable incubator for the induction and editing stages. The script for the SWIIN protocol was set for a 9 hour incubation at 30° C., a 2.5 hour incubation at 42° C., then 9 additional hours at 30° C. The CFU input into the SWIIN was approximately 7.5 E+04 and the CFU output was approximately 6.5 E+06 in a 7.0 ml volume.

Amplicon and Singleplex sequencing: Cells were recovered from the SWIIN with a PBS solution, and 100 µl of the undiluted cell suspension was spread on an LB chlor/carb agar plate and incubated overnight at 30° C. This plate was then "scraped" and used as the amplicon DNA input. Dilutions were also prepared from the PBS/cell suspension and then plated on an LB chlor/carb agar plate and incubated overnight at 30° C.; isolated colonies were selected and used for singleplex sequencing.

Example 16

Loading and Performing Editing on a SWIIN

Figure 11A:
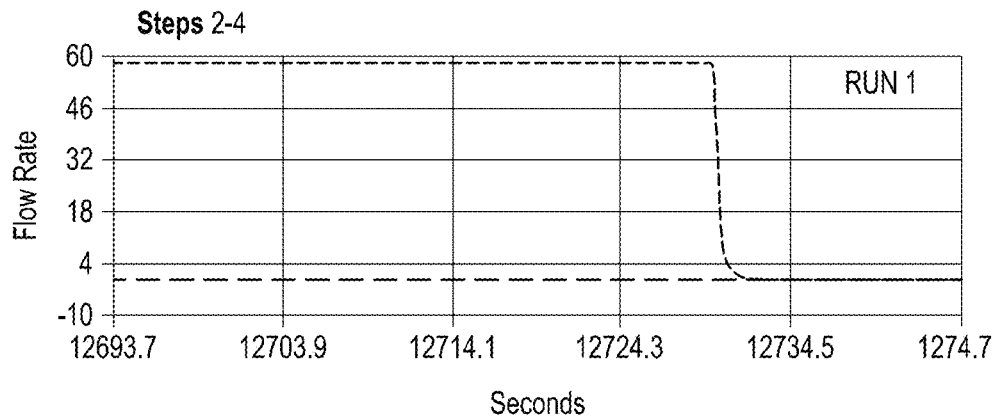
FIGS. 11A-11C are simplified depictions of the status of pressure and volume for each reservoir in the SWIIN depicted in relation to FIGS. 5A-5I commensurate with the pneumatic diagram of FIG. 5J.
Figure 11A:
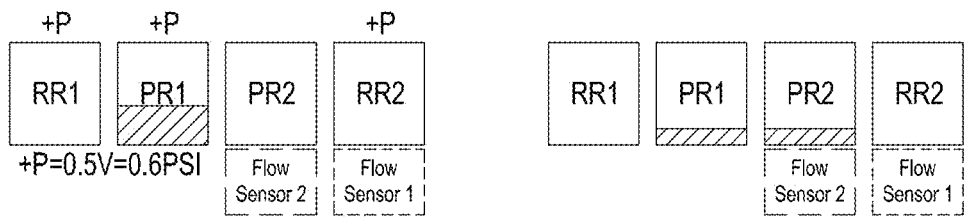
Figure 11A:
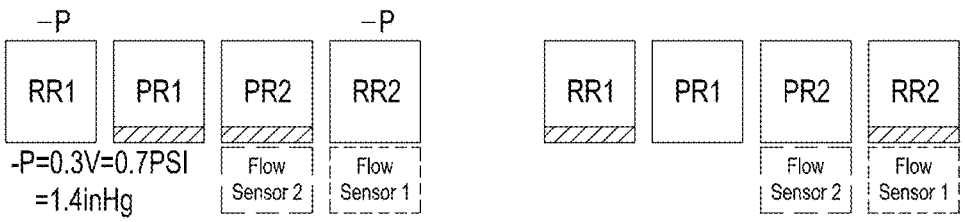
Figure 11A:
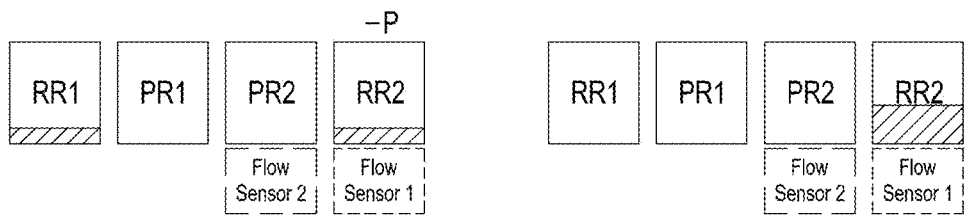
Figure 11B:
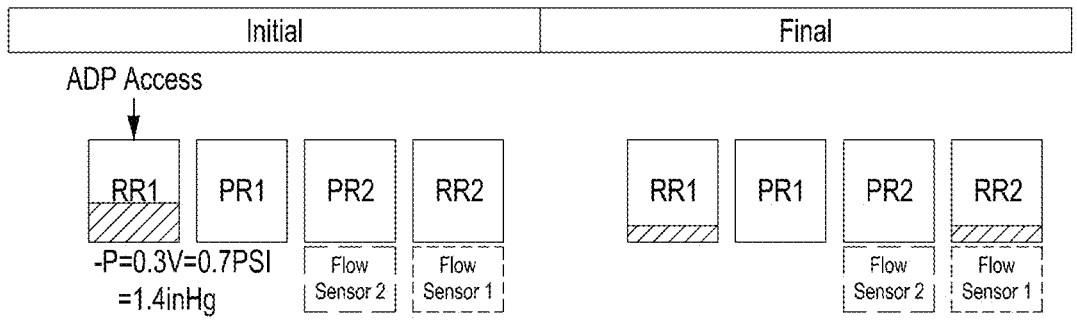
Figure 11B:
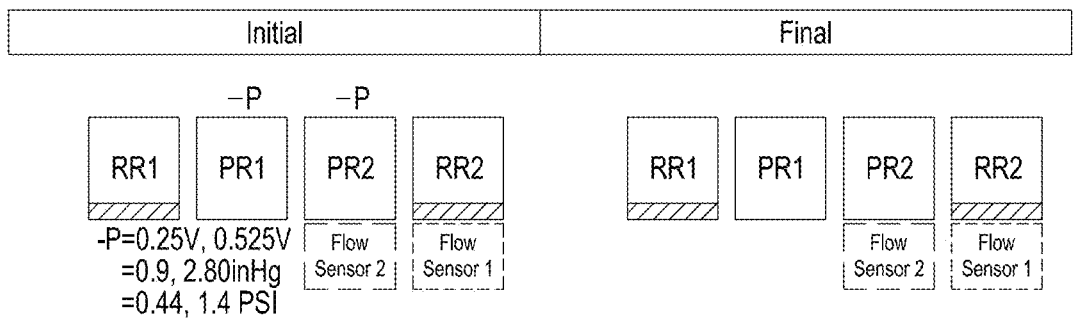
Figure 11B:
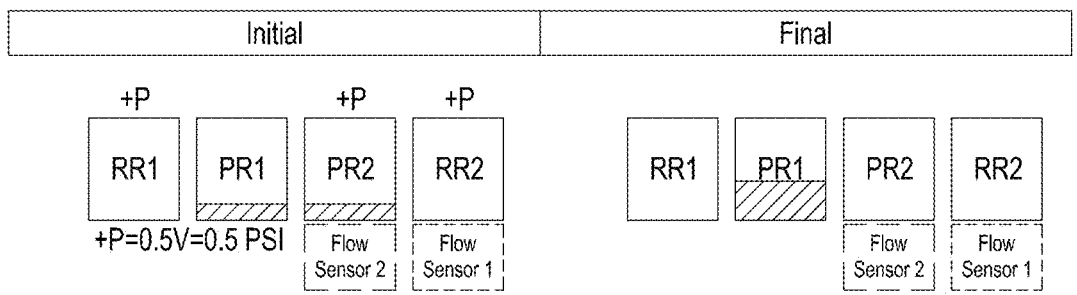
Figure 11B:
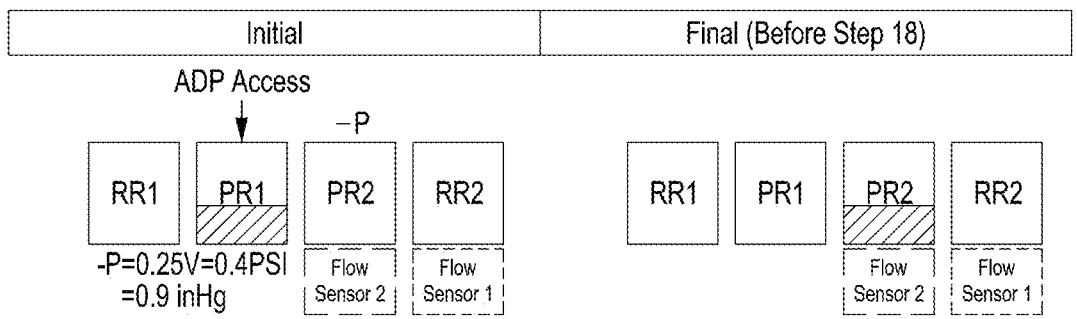
Figure 11C:
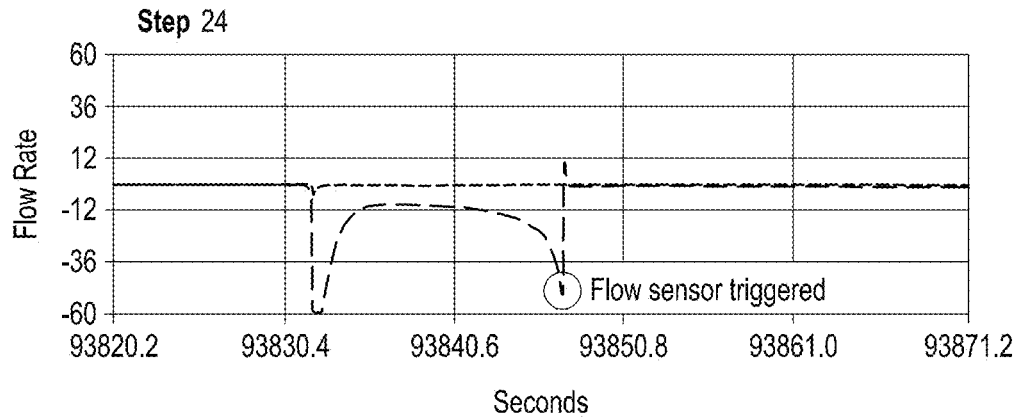
Figure 11C:
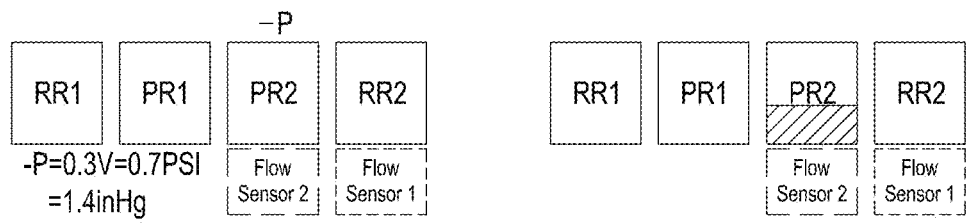
Figure 11C:
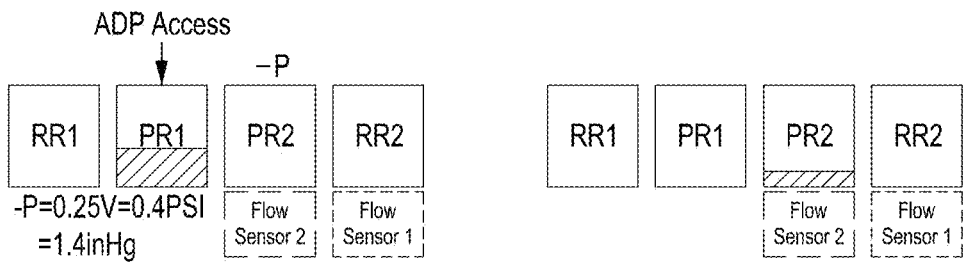

FIGS. 11A-11C are simplified overviews of various parameters for loading cells onto a SWIIN module, performing editing, and removing or recovering the edited cells from the SWIIN module. The steps of FIGS. 11A-11C correspond to the steps listed in Tables 1-3, with the exception that step 1 (loading the SWIIN module into the automated multi-module cell processing instrument) and step 32 (unloading the SWIIN from the automated multi-module cell processing instrument) are not represented on FIGS. 11A-11C. FIG. 11A begins with step 2, where 10 mL of PBS/0.01% Tween80 was transferred from a reagent cartridge to permeate reservoir 1. At this initial step, retentate reservoir 1, retentate reservoir 2, and permeate reservoir 1 were under positive pressure, flow sensor 1 detected a high flow rate and flow sensor 2 detected a low flow rate. At step 3, additional PBS/0.01% Tween80 was loaded into the permeate channel and a bubble flush was performed. At step 4, more PBS/0.01% Tween80 was loaded into the permeate channel to fill the permeate channel. Step 4 ended with a flow meter trigger, and flow sensor 1 returned to baseline once the permeate channel was filled with liquid.

At step 5, a vacuum was applied at retentate reservoirs 1 and 2, and the retentate channel was flooded. Once the retentate channel was flooded (and there was minimal fluid remaining in the permeate reservoirs), the negative pressure (vacuum) was removed. At step 6, negative pressure was applied to retentate reservoir 2, thereby sweeping all liquid to retentate reservoir 2. At step 7, the liquid in retentate reservoirs 1 and 2 was removed by, e.g., an air displacement pipette. At step 8, 9.5 mL of PBS/0.01% Tween80 was transferred from the reagent cartridge to retentate reservoir 1, and at step 9, 0.5 mL of transformed cells were transferred from the transformation module (the flow-through electroporation device) to retentate reservoir 1. At step 10, the cell-containing liquid was pipetted up and down in retentate reservoir 1, and at step 11, the cell-containing liquid was pulled from retentate reservoir 1 into the retentate channel leaving minimal fluid in retentate reservoirs 1 and 2. Step 11 is sensitive to timing and was thus controlled via air displacement pipette liquid level detection in retentate reservoir 1.

FIG. 11B begins with step 12, in which the fluid in the serpentine channel in the retentate member was pulled through the membrane or filter member on low vacuum; that is, negative pressure was applied to both permeate reservoirs 1 and 2. At step 13, the fluid in the serpentine channel in the retentate member was pulled through the filter member on high vacuum, with fluid pulled into the serpentine channel in the permeate member and then into permeate reservoirs 1 and 2. At step 14, all fluid was swept to permeate reservoir 1 by applying positive pressure to retentate reservoirs 1 and 2 and permeate reservoir 2. Remaining liquid was aspirated out of permeate reservoirs 1 and 2 at step 5, with the air displacement pipette accessing permeate reservoir 1. At step 16, 10 mL medium was transferred from the reagent cartridge to permeate reservoir 1, and at step 17, the medium was transferred from permeate reservoir 1 into the permeate channel. Step 17 is sensitive to timing and thus was controlled via liquid level detection via a air displacement pipette in retentate reservoir 1. At the end of step 17, some amount of liquid resided in permeate reservoir 2, and at step 18, liquid (permeate) was aspirated out of permeate reservoirs 1 and 2.

Steps 19-23 are not represented in FIGS. 11A-11C. At step 19, the SWIIN module was incubated at 30° C. with intermittent airflow and medium rinses/exchanges, as deemed necessary. In step 20, the temperature of the SWIIN module was raised to 42° C., and at step 21 the SWIIN module was incubated for 2 hours. At step 22, the temperature of the SWIIN module was ramped down from 42° C. to 30° C., and the SWIIN was then incubated at 30° C. for 9 hours. During this incubation the manifold arms of the SWIIN assembly may be unsealed and resealed to effect airflow. In addition, media rinses or exchanges may be performed.

FIG. 11C begins with step 24, where medium was pulled out of the permeate channel into permeate reservoir 2, by applying negative pressure to permeate reservoir 2. During this time, the flow rate for flow sensor 1 and flow sensor 2 are roughly the same at 0, then flow sensor 2 spiked to 0, rebounded, then spiked to 0 again triggering flow sensor 2. Step 24 ended with fluid in permeate reservoir 2. At step 25, the liquid was aspirated out of permeate reservoir 2 by applying a vacuum to permeate reservoir 2, and at step 26, 10 mL of medium containing 10% glycerol was transferred from the reagent cartridge to permeate reservoir 1. At step 27 the medium/10% glycerol was pulled from permeate reservoir 1 into the permeate channel, and at the end of this step, a minimal amount of fluid remains in permeate reservoir 2. At step 28, the retentate channel was flooded to dislodge the cells with positive pressure applied to permeate reservoirs 1 and 2, thus pushing fluid from the permeate reservoirs into the retentate reservoirs. Next at step 29, all fluid was swept to retentate reservoir 2 by applying a vacuum to retentate reservoir 2. Step 29 is controlled by the trigger of flow sensor 1. Step 30 involved aspirating the cell solution from retentate reservoir 2 into a vial, and step 31 involved aspirating all liquid out of both retentate reservoirs. The final step, step 32, is not represented on FIG. 11C, but involved removing the SWIIN from the automated multi-module cell processing instrument.

Example 17

Fully-Automated Singleplex RGN-Directed Editing Run

Singleplex automated genomic editing using MAD7 nuclease was successfully performed with an automated multi-module instrument such as that shown in FIG. 5A-5D. See U.S. Pat. No. 9,982,279, issued May, 29, 2018 and U.S. Pat. No. 10/240,167, issued Apr. 9, 2019.

An ampR plasmid backbone and a lacZ_F172* editing cassette were assembled via isothermal nucleic acid assembly into an "editing vector" in an isothermal nucleic acid assembly module included in the automated instrument. lacZ_F172 functionally knocks out the lacZ gene. "lacZ_F172*" indicates that the edit happens at the 172 nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent *E. Coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0\ \mathrm{E}^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example 18

Fully-Automated Recursive Editing Run

Recursive editing was successfully achieved using the automated multi-module cell processing system. An ampR plasmid backbone and a lacZ_V10* editing cassette were assembled via isothermal nucleic acid assembly into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent *E. Coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154 th amino acid residue, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent *E. Coli* cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers are performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. An automated stand-alone multi-module cell editing instrument comprising:
   a housing configured to house all or some of the modules;
   a receptacle configured to receive cells;
   a receptacle configured to receive editing nucleic acids;
   a growth module for growing cells;
   a selection module;
   a transformation module configured to introduce the editing nucleic acids into the cells;
   a singulation and editing module configured to isolate the transformed cells and allow the editing nucleic acids to edit nucleic acids in the cells wherein the singulation and editing module comprises a device for emulsion formation, comprising: a microfluidic device having an emulsion formation unit including a sample well configured to receive cells in aqueous medium; a carrier fluid well configured to receive a fluid that is immiscible with the cells in aqueous medium; a collection substrate to collect aqueous droplets formed in the immiscible fluid; a sample channel extending from the sample well to a channel intersection; a carrier fluid channel extending from the carrier fluid well to the channel intersection; a droplet channel extending from the channel intersection to the collection substrate; and a pneumatic assembly having a pressure source and a pressure sensor, wherein the pneumatic assembly is configured (a) to apply pressure to the emulsion formation unit to drive generation of droplets at the channel intersection of the emulsion formation unit and collect droplets in the collection substrate, (b) to monitor the pressure with the pressure sensor, and (c) to stop application of the pressure to the emulsion formation unit when the pressure sensor detects a change in pressure indicative of air entering the sample channel from the sample well;
   a processor configured to operate the automated multi-module cell editing instrument based on user input and/or selection of a pre-programmed script; and
   an automated liquid handling system to move liquids from the cell receptacle to the growth module, from the growth module to the transformation module, from the nucleic acid receptacle to the transformation module, from the transformation module to the selection module and/or from the singulation and editing module; and from the transformation module to the singulation and editing module without user intervention.

2. The automated stand-alone multi-module cell editing instrument of claim 1, wherein the singulation and editing module further comprises a detection station downstream from the channel intersection but before the collection substrate.

3. The automated stand-alone multi-module cell editing instrument of claim 2, wherein the detection station comprises a camera.

4. The automated stand-alone multi-module cell editing instrument of claim 2, further comprising a temperature-controlled editing reservoir positioned between the channel intersection and the detection station.

5. The automated stand-alone multi-module cell editing instrument of claim 4, wherein the detection station detects the optical density of cells in the aqueous droplets.

6. The automated stand-alone multi-module cell editing instrument of claim 5, further comprising a droplet sorter positioned between the detection station and the collection substrate.

7. The automated stand-alone multi-module cell editing instrument of claim 6, wherein the collection substrate comprises two receptacles.

8. The automated stand-alone multi-module cell editing instrument of claim 1, wherein the collection substrate comprises wells, and is configured to collect one droplet per well.

9. The automated stand-alone multi-module cell editing instrument of claim 8, wherein the collection substrate is temperature-controlled.

10. The automated stand-alone multi-module cell editing instrument of claim 9, further comprising a detection station configured to detect droplets in the collection substrate.

11. A method for isolating and editing cells in the automated stand-alone multi-module cell editing instrument of claim 1, comprising the steps of:

providing live cells in the receptacle configured to receive the live cells;
providing editing nucleic acids the receptacle configured to receive editing nucleic acids;
growing the live cells in a growth module to a desired optical density to produce grown cells;
transforming the grown cells in a transformation module configured to introduce the editing nucleic acids into the filtered cells to produce transformed cells;
selecting for transformed cells to produce selected cells;
generating droplets in the microfluidic device by providing the selected cells in an aqueous medium in the sample well; providing the fluid immiscible with the selected cells in the aqueous medium in the carrier fluid well; flowing the immiscible fluid from the carrier fluid well through the carrier channel to the channel intersection; flowing the selected cells in aqueous medium from the sample well through the sample channel to the channel intersection; generating aqueous droplets in the immiscible fluid; and collecting the aqueous droplets in wells in the collection substrate;
incubating the aqueous droplets in the collection substrate to allow the editing nucleic acids to edit the selected cells;
pooling the aqueous droplets; and
using an automated liquid handling system to 1) transfer the editing nucleic acids from the receptacle configured to receive nucleic acids to the transformation module, 2) transfer the live cells from the receptacle configured to receive the live cells to the growth module, 3) transfer the grown cells from the growth module to the transformation module; 4) transfer the transformed cells from the transformation module to the selection module, 5) transfer the selected cells to the sample well, and 6) transfer the cells from the collection substrate to a vessel without user intervention.

12. The method of claim 11, wherein the fluid immiscible with the cells in the aqueous medium is decane.

13. The method of claim 11, wherein the generated aqueous droplets comprise cells in a Poisson distribution.

14. The method of claim 11, wherein the cells are bacterial cells.

15. The method of claim 11, after the pooling step, filtering the edited cells in a filtration module.

16. A method for isolating and editing cells in the automated stand-alone multi-module cell editing instrument of claim 2, comprising the steps of:
providing live cells in the receptacle configured to receive the live cells;
providing editing nucleic acids the receptacle configured to receive editing nucleic acids;
growing the live cells in a growth module to a desired optical density to produce grown cells;
transforming the grown cells in a transformation module configured to introduce the editing nucleic acids into the grown cells to produce transformed cells;
selecting the transformed cells in a selection module to produce selected cells;
generating droplets in the microfluidic device by providing the selected cells in an aqueous medium in the sample well; providing the fluid immiscible with the selected cells in the aqueous medium in the carrier fluid well; flowing the immiscible fluid from the carrier fluid well through the carrier channel to the channel intersection; flowing the selected cells in aqueous medium from the sample well through the sample channel to the channel intersection; generating aqueous droplets in the immiscible fluid; and collecting the aqueous droplets one at a time in wells in the collection substrate;
incubating the aqueous droplets in the collection substrate to allow the editing nucleic acids to edit the selected cells thereby producing edited cells;
monitoring edited cell growth in the droplets via the detection station;
sorting the aqueous droplets based on rapidity of edited cell growth;
pooling the aqueous droplets with slow-growing edited cells in a vessel; and
using an automated liquid handling system to 1) transfer the editing nucleic acids from the receptacle configured to receive nucleic acids to the transformation module, 2) transfer the live cells from the receptacle configured to receive the live cells to the growth module, 3) transfer the grown cells from the growth module to the transformation module; 4) transfer the transformed cells from the transformation module to the selection module, 5) transfer the selected cells to the sample well, and 6) transfer the edited cells from the collection substrate to a vessel without user intervention.

17. The method of claim 16, wherein the fluid immiscible with the cells in the aqueous medium is decane.

18. The method of claim 16, wherein the generated aqueous droplets comprise cells in a Poisson distribution.

19. The method of claim 16, wherein the cells are bacterial cells.

20. The method of claim 16, after the pooling step, filtering the edited cells in the filtration module.

* * * * *